United States Patent
Labadie et al.

(10) Patent No.: US 10,654,867 B2
(45) Date of Patent: May 19, 2020

(54) HETEROARYL ESTROGEN RECEPTOR MODULATORS AND USES THEREOF

(71) Applicant: Genentech, Inc., South San Francisco, CA (US)

(72) Inventors: Sharada Labadie, Sunnyvale, CA (US); Jun Li, Foster City, CA (US); Jun Liang, Los Altos Hills, CA (US); Daniel Fred Ortwine, San Ramon, CA (US); Xiaojing Wang, Foster City, CA (US); Jason Zbieg, South San Francisco, CA (US); Birong Zhang, Union City, CA (US); Nicholas Charles Ray, Harlow Essex (GB); Simon Goodacre, Harlow Essex (GB); Jiangpeng Liao, Shanghai (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/565,041

(22) Filed: Sep. 9, 2019

(65) Prior Publication Data
US 2020/0002353 A1 Jan. 2, 2020

Related U.S. Application Data

(62) Division of application No. 15/623,904, filed on Jun. 15, 2017, now abandoned.
(Continued)

(51) Int. Cl.
*A61K 31/4985* (2006.01)
*A61K 31/397* (2006.01)
(Continued)

(52) U.S. Cl.
CPC .......... *C07D 495/04* (2013.01); *A61K 31/437* (2013.01); *A61K 31/4355* (2013.01); *A61K 31/4365* (2013.01); *A61K 31/4375* (2013.01); *A61K 31/4985* (2013.01); *A61K 31/55* (2013.01); *A61K 31/695* (2013.01); *A61K 45/06* (2013.01); *C07D 471/04* (2013.01); *C07D 471/14* (2013.01); *C07D 487/04* (2013.01);
(Continued)

(58) Field of Classification Search
CPC ........................ A61K 31/4985; A61K 31/397
See application file for complete search history.

(56) References Cited

U.S. PATENT DOCUMENTS 5,206,377 A   4/1993  McAfee
6,774,122 B2  8/2004  Evans
(Continued)

FOREIGN PATENT DOCUMENTS

WO        0151056       7/2001
WO    2002/062339 A1    8/2002
(Continued)

OTHER PUBLICATIONS

International Search Report Issued in counterpart International application No. PCT/EP2015/080119.
(Continued)

*Primary Examiner* — Samira J Jean-Louis
(74) *Attorney, Agent, or Firm* — Kevin M. Clark

(57) ABSTRACT

Described herein are heteroaryl compounds with estrogen receptor modulation activity or function having the Formula I, II, and III structures:

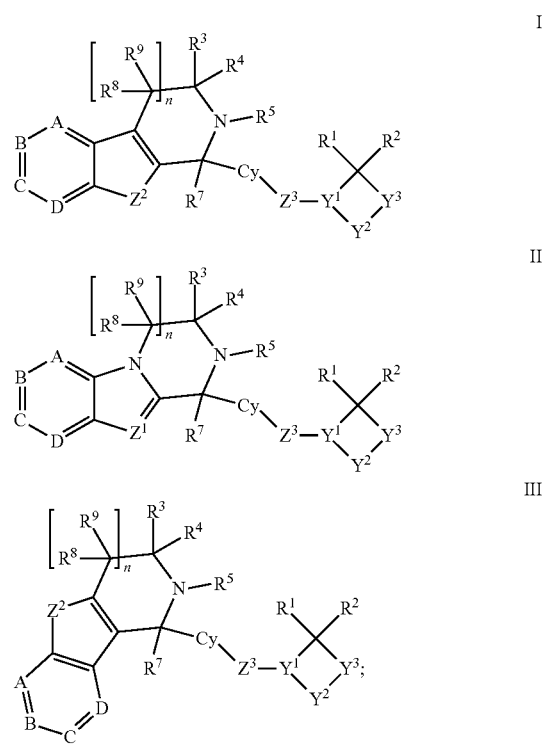

and
stereoisomers, tautomers, or pharmaceutically acceptable salts thereof, and with the substituents and structural features described herein. Also described are pharmaceutical compositions and medicaments that include the Formula I, II, and III compounds, as well as methods of using such estrogen receptor modulators, alone and in combination with other therapeutic agents, for treating diseases or conditions that are mediated or dependent upon estrogen receptors.

5 Claims, No Drawings

Related U.S. Application Data

(60) Provisional application No. 62/350,885, filed on Jun. 16, 2016.

(51) Int. Cl.

| | | |
|---|---|---|
| *C07D 495/04* | (2006.01) | |
| *C07D 491/048* | (2006.01) | |
| *A61K 31/4355* | (2006.01) | |
| *A61K 45/06* | (2006.01) | |
| *A61K 31/4365* | (2006.01) | |
| *C07D 487/04* | (2006.01) | |
| *C07F 7/18* | (2006.01) | |
| *C07D 471/04* | (2006.01) | |
| *A61K 31/437* | (2006.01) | |
| *C07D 471/14* | (2006.01) | |
| *A61K 31/4375* | (2006.01) | |
| *A61K 31/695* | (2006.01) | |
| *A61K 31/55* | (2006.01) | |

(52) U.S. Cl.
CPC ........ *C07D 491/048* (2013.01); *C07F 7/1804* (2013.01)

(56) References Cited

U.S. PATENT DOCUMENTS

| | | |
|---|---|---|
| 7,456,160 B2 | 11/2008 | Evans |
| 8,329,680 B2 | 11/2012 | Evans |
| 8,466,139 B2 | 6/2013 | Evans |
| 8,703,810 B2 | 4/2014 | Kahraman et al. |
| 8,853,423 B2 | 7/2014 | Govek |
| 9,187,460 B2 | 11/2015 | Smith et al. |
| 9,193,714 B2 | 11/2015 | Smith |
| 2005/0282849 A1 | 12/2005 | Moon |
| 2007/0254878 A1 | 1/2007 | Cao |
| 2008/0064683 A1 | 3/2008 | Cao |
| 2010/0249153 A1 | 9/2010 | Tandon |
| 2013/0137746 A1 | 5/2013 | Govek |
| 2013/0116232 A1 | 9/2013 | Kahraman |
| 2014/0364427 A1 | 11/2014 | Smith |
| 2016/0090377 A1 | 3/2016 | Govek |
| 2016/0090378 A1 | 3/2016 | Kahraman |
| 2016/0175284 A1 | 6/2016 | Labadie |

FOREIGN PATENT DOCUMENTS

| | | | |
|---|---|---|---|
| WO | 2002/064590 A2 | 8/2002 | |
| WO | 2005/089764 A1 | 9/2005 | |
| WO | 2006/015035 A1 | 2/2006 | |
| WO | 2007/002051 A1 | 1/2007 | |
| WO | 2007/006688 | 1/2007 | |
| WO | 2008/127714 A1 | 10/2008 | |
| WO | 2008/127715 A1 | 10/2008 | |
| WO | 2010/107485 A1 | 9/2010 | |
| WO | 2010/138652 A1 | 12/2010 | |
| WO | 2010/138659 A1 | 12/2010 | |
| WO | 2010/138685 A1 | 12/2010 | |
| WO | 2010/138695 A1 | 12/2010 | |
| WO | 2010/138706 A1 | 12/2010 | |
| WO | 2010/138758 | 12/2010 | |
| WO | WO-2010138758 A1 * | 12/2010 | ............ A61K 31/44 |
| WO | 2015/082990 A1 | 6/2011 | |
| WO | 2011/150162 A1 | 12/2011 | |
| WO | 2011/156518 | 12/2011 | |
| WO | 2011/159769 A2 | 12/2011 | |
| WO | 2013/090829 A1 | 6/2013 | |
| WO | 2013/090836 A1 | 6/2013 | |
| WO | 2014/083529 A1 | 6/2014 | |
| WO | 2014/205136 A1 | 12/2014 | |
| WO | 2014/205138 A1 | 12/2014 | |
| WO | 2015/136016 A2 | 9/2015 | |
| WO | 2015/136017 A1 | 9/2015 | |
| WO | 2015161373 | 10/2015 | |
| WO | 2015/197861 A1 | 12/2015 | |
| WO | 2016/097071 A1 | 6/2016 | |
| WO | 2016/097073 A1 | 6/2016 | |

OTHER PUBLICATIONS

Dan R Robinson et al., "Activating ESR1 mutations in hormone-resistant metastatic breast cancer" Nature Genetics 45(12):1446-1451 (Nov. 3, 2013).
Howell, "Pure oestrogen antagonists for the treatment of advanced breast cancer" Endocr Relat Cancer 13(3):689-706 (Sep. 2006).
ISR for PCT/EP2017/064650.
Jeselsohn et al., "Emergence of constitutively active estrogen receptor-α mutations in pretreated advanced estrogen receptor-positive breast cancer" Clin Cancer Res. 20(7):1757-1767 (Apr. 2014).
Li et al., "Endocrine-therapy-resistant ESR1 variants revealed by genomic characterization of breast-cancer-derived xenografts" Cell Rep. 4(6):1116-30 (Sep. 2013).
Mark J. Thompson et al., "Synthesis and Evaluation of 1-Amino-6-halo-B-carbolines as Antimalarial and Antiprion Agents" ChemMedChem 7:578-586 (Jan. 2012).
Merenbakh-Lamin et al., "D538G mutation in estrogen receptor-α: A novel mechanism for acquired endocrine resistance in breast cancer" Cancer Res. 73(23):6856-64 (Dec. 2013).
Puhalla et al., "Hormonal therapy in breast cancer: a model disease for the personalization of cancer care" Mol Oncol. 6(2):222-36 (Apr. 2012).
Reid et al., "Cyclic, Proteasome-Mediated Turnover of Unliganded and Liganded ERα on Responsive Promoters is an Integral Feature of Estrogen Signaling" Molecular Cell 11:695-707 ( 2003).
Tamrazi et al., "Molecular sensors of estrogen receptor conformations and dynamics" Mol Endocrinol. 17(12):2593-602 (Dec. 2003).
Welboren et al., "Genomic actions of estrogen receptor α: what are the targets and how are they regulated?" Endocrine-Related Cancer, 16:1073-1089 ( 2009).

* cited by examiner

HETEROARYL ESTROGEN RECEPTOR MODULATORS AND USES THEREOF

CROSS REFERENCE TO RELATED APPLICATIONS

This application is a divisional application of U.S. patent application Ser. No. 15/623,904, filed 15 Jun. 2017, which claims priority to U.S. Provisional Application Ser. No. 62/350,885 filed on 16 Jun. 2016, and International Application No. PCT/CN2017/087241 filed on 6 Jun. 2017, each of which are incorporated by reference in their entirety and for all purposes.

FIELD OF THE INVENTION

Described herein are compounds, including pharmaceutically acceptable salts, solvates, metabolites, prodrugs thereof, pharmaceutical compositions comprising such compounds, and methods of using such compounds to treat, prevent or diagnose diseases or conditions that are estrogen sensitive, estrogen receptor dependent or estrogen receptor mediated in combination with other therapeutic agents.

BACKGROUND OF THE INVENTION

The estrogen receptor ("ER") is a ligand-activated transcriptional regulatory protein that mediates induction of a variety of biological effects through its interaction with endogenous estrogens. Endogenous estrogens include 17β (beta)-estradiol and estrones. ER has been found to have two isoforms, ER-α (alpha) and ER-β (beta). Estrogens and estrogen receptors are implicated in a number of diseases or conditions, such as breast cancer, lung cancer, ovarian cancer, colon cancer, prostate cancer, endometrial cancer, uterine cancer, as well as others diseases or conditions. There is a need for new ER-α targeting agents that have activity in the setting of metastatic disease and acquired resistance.

SUMMARY OF THE INVENTION

The invention relates generally to heteroaryl compounds with estrogen receptor modulation activity or function having the Formulas I, II, and III structures:

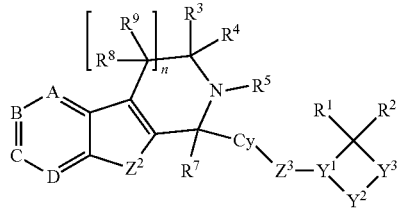

I

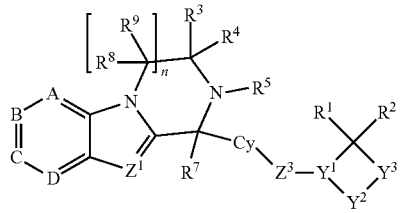

II

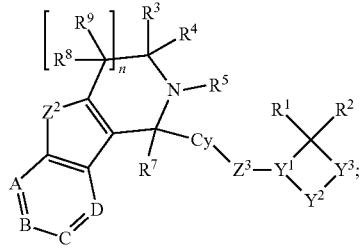

III stereoisomers, tautomers, or pharmaceutically acceptable salts thereof, and with the substituents and structural features described herein.

An aspect of the invention is a pharmaceutical composition of a Formula I, II, and III compound and a pharmaceutically acceptable carrier, glidant, diluent, or excipient.

An aspect of the invention is a process for making a Formula I, II, and III compound or a pharmaceutical composition comprising a Formula I, II, and III compound.

An aspect of the invention is a method of treating an ER-related disease or disorder in a patient comprising administering a therapeutically effective amount of the pharmaceutical composition to a patient with an ER-related disease or disorder.

An aspect of the invention is a kit for treating a condition mediated by an estrogen receptor, comprising:
 a) a pharmaceutical composition comprising a Formula I, II, or III compound; and
 b) instructions for use.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

Definitions

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkyldiyl" as used herein refers to a saturated linear or branched-chain divalent hydrocarbon radical of about one to twelve carbon atoms ($C_1$-$C_{12}$), wherein the alkyldiyl radical may be optionally substituted independently with one or more substituents described below. In another embodiment, an alkyldiyl radical is one to eight carbon atoms ($C_1$-$C_8$), or one to six carbon atoms ($C_1$-$C_6$). Examples of alkyldiyl groups include, but are not limited to, methylene (—$CH_2$—), ethylene (—$CH_2CH_2$—), propylene (—$CH_2CH_2CH_2$—), and the like. An alkyldiyl group may also be referred to as an "alkylene" group.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—$CH=CH_2$), allyl (—$CH_2CH=CH_2$), and the like.

The terms "alkenylene" or "alkenyldiyl" refer to a linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—$CH=CH$—), allyl (—$CH_2CH=CH$—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—$C\equiv CH$), propynyl (propargyl, —$CH_2C\equiv CH$), and the like.

The term "alkynylene" or "alkynyldiyl" refer to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—$C\equiv C$—), propynylene (propargylene, —$CH_2C\equiv C$—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

The term "carbocyclyldiyl" refers to a divalent non-aromatic, saturated or partially unsaturated ring having 3 to 12 carbon atoms ($C_3$-$C_{12}$) as a monocyclic ring or 7 to 12 carbon atoms as a bicyclic ring.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

The terms "arylene" or "aryldiyl" mean a divalent aromatic hydrocarbon radical of 6-20 carbon atoms ($C_6$-$C_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents as described.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or 3-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA™, APCI-32765, Pharmacyclics Inc./Janssen Biotech Inc.; CAS Reg. No. 936563-96-1, U.S. Pat. No. 7,514,444), idelalisib (ZYDELIG®, CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (Platinol®, (SP-4-2)-diamminedichloroplatinum(II), cis-diamine, dichloroplatinum (II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®, CAS No. 23214-92-8), Akti-1/2, HPPD, and rapamycin.

Chemotherapeutic agents include inhibitors of B-cell receptor targets such as BTK, Bcl-2 and JAK inhibitors.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), palbociclib, (IBRANCE®, Pfizer), imatinib mesylate (GLEEVEC®, Novartis), cobimetinib (COTELLIC™, XL-518, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidamine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate) and selective estrogen receptor modulators (SERDs) such as fulvestrant (FASLODEX®, Astra Zeneca); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors, such as cobimetinib (WO 2007/044515); (v) lipid kinase inhibitors, such as taselisib (GDC-0032, Genentech Inc.); (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (PERJETA™, 2C4, Genentech), trastuzumab (HERCEPTIN®, Genentech), trastuzumab emtansine (KADCYLA®, Genentech Inc.), and tositumomab (BEXXAR, Corixia).

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I, II, and III compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities.

Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate (EtOAc), acetic acid (AcOH), and ethanolamine.

The term "$EC_{50}$" is the half maximal effective concentration and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I, II, and III" include compounds of Formulas I, II, and III, and stereoisomers, geometric isomers, tautomers, solvates, metabolites, and pharmaceutically acceptable salts and prodrugs thereof.

Any formula or structure given herein, including Formula I, II, and III compounds, is also intended to represent hydrates, solvates, and polymorphs of such compounds, and mixtures thereof.

Any formula or structure given herein, including Formula I, II, and III compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Estrogen Receptor

Estrogen receptor alpha (ER-α; NR3A1) and estrogen receptor beta (ER-β; NR3A2) are steroid hormone receptors, which are members of the large nuclear receptor superfamily. Nuclear receptors share a common modular structure, which minimally includes a DNA binding domain (DBD) and a ligand binding domain (LBD). Steroid hormone receptors are soluble, intracellular proteins that act as ligand-regulated transcription factors. Vertebrates contain five closely related steroid hormone receptors (estrogen receptor, androgen receptor, progesterone receptor, glucocorticoid receptor, mineral corticoid receptor), which regulate a wide spectrum of reproductive, metabolic and developmental activities. The activities of ER are controlled by the binding of endogenous estrogens, including 17 β-estradiol and estrones.

The ER-α (alpha) gene is located on 6q25.1 and encodes a 595 AA protein. The ER-β gene resides on chromosome 14q23.3 and produces a 530 AA protein. However, due to alternative splicing and translation start sites, each of these genes can give rise to multiple isoforms. In addition to the DNA binding domain (called C domain) and ligand binding domain (E domain) these receptors contain an N-terminal (A/B) domain, a hinge (D) domain that links the C and E domains, and a C-terminal extension (F domain) (Gronemeyer and Laudet; Protein Profile 2: 1173-1308, 1995). While the C and E domains of ER-α and ER-β are quite conserved (95% and 55% amino acid identity, respectively), conservation of the A/B, D and F domains is poor (below 30% amino acid identity). Both receptors are involved in the regulation and development of the female reproductive tract but also play various roles in the central nervous system, cardiovascular systems and bone metabolism.

The ligand binding pocket of steroid hormone receptors is deeply buried within the ligand binding domain. Upon binding, the ligand becomes part of the hydrophobic core of this domain. Consequently most steroid hormone receptors are instable in the absence of hormone and require assistance from chaperones, such as Hsp90, in order to maintain hormone-binding competency. The interaction with Hsp90 also controls nuclear translocation of these receptors. Ligand-binding stabilizes the receptor and initiates sequential conformational changes that release the chaperones, alter the interactions between the various receptor domains and remodel protein interaction surfaces that allow these receptors to translocate into the nucleus, bind DNA and engage in interactions with chromatin remodeling complexes and the transcriptional machinery. Although ER can interact with Hsp90, this interaction is not required for hormone binding and, dependent on the cellular context, apo-ER can be both cytoplasmic and nuclear. Biophysical studies indicated that DNA binding rather than ligand binding contributes to the stability of the receptor (Greenfield et al., Biochemistry 40: 6646-6652, 2001).

ER can interact with DNA either directly by binding to a specific DNA sequence motif called estrogen response element (ERE) (classical pathway), or indirectly via protein-protein interactions (nonclassical pathway) (Welboren et al., Endocrine-Related Cancer 16: 1073-1089, 2009). In the nonclassical pathway, ER has been shown to tether to other transcription factors including SP-1, AP-1 and NF-κB. These interactions appear to play critical roles in the ability of ER to regulate cell proliferation and differentiation.

Both types of ER DNA interactions can result in gene activation or repression dependent on the transcriptional coregulators that are recruited by the respective ER-ERE complex (Klinge, Steroid 65: 227-251, 2000). The recruitment of coregulators is primarily mediated by two protein interaction surfaces, the AF2 and AF1. AF2 is located in the ER E-domain and its conformation is directly regulated by the ligand (Brzozowski et al., (1997) Nature 389: 753-758). Full agonists appear to promote the recruitment of co-activators, whereas weak agonists and antagonists facilitate the binding of co-repressors. The regulation of protein with the AF1 is less well understood but can be controlled by serine phosphorylation (Ward and Weigel, (2009) Biofactors 35: 528-536). One of the involved phosphorylation sites (S118) appears to control the transcriptional activity of ER in the presence of antagonists such as tamoxifen, which plays an important role in the treatment of breast cancer. While full agonists appear to arrest ER in certain conformation, weak agonists tend to maintain ER in equilibrium between different conformations, allowing cell-dependent differences in co-regulator repertoires to modulate the activity of ER in a cell-dependent manner (Tamrazi et al., Mol. Endocrinol. 17: 2593-2602, 2003). Interactions of ER with DNA are dynamic and include, but are not limited to, the degradation of ER by the proteasome (Reid et al., Mol Cell 11: 695-707, 2003). The degradation of ER with ligands provides an attractive treatment strategy for diseases or conditions that are estrogen-sensitive and/or resistant to available anti-hormonal treatments. ER signaling is crucial for the development and maintenance of female reproductive organs including breasts, ovulation and thickening of the endometrium. ER signaling also has a role in bone mass, lipid metabolism, cancers, etc. About 70% of breast cancers express ER-☐ (ER-☐ positive) and are dependent on estrogens for growth and survival. Other cancers also are thought to be dependent on ER-α signaling for growth and survival, such as for example ovarian and endometrial cancers. The ER-α antagonist tamoxifen has been used to treat early and advanced ER-α positive breast cancer in both pre- and post-menopausal women. Fulvestrant (FASLODEX®, AstraZeneca) a steroid-based ER antagonist is used to treat breast cancer in women which have progressed despite therapy with tamoxifen (Howell A. (2006) Endocr Relat Cancer; 13:689-706; U.S. Pat. Nos. 6,774,122; 7,456,160; 8,329,680; 8,466,139). Steroidal and non-steroidal aromatase inhibitors are also used to treat cancers in humans. In some embodiments, the steroidal and non-steroidal aromatase inhibitors block the production of estrogen from androstenedione and testosterone in post-menopausal women, thereby blocking ER dependent growth in the cancers. In addition to these anti-hormonal agents, progressive ER positive breast cancer is treated in some cases with a variety of other chemotherapeutics, such as for example, the anthracyclines, platins, taxanes. In some cases, ER positive breast cancers that harbor genetic amplification of the ERB-B/HER2 tyrosine kinase receptor are treated with the monoclonal antibody trastuzumab (Herceptin®, Genentech Inc.) or the small molecule pan-ERB-B inhibitor lapatinib (TYKERB®, GlaxoSmith Kline Corp.). Despite this battery of anti-hormonal, chemotherapeutic and small-molecule and antibody-based targeted therapies, many women with ER-α positive breast develop progressive metastatic disease and are in need of new therapies. Importantly, the majority of ER positive tumors that progress on existing anti-hormonal, as well as and other therapies, are thought to remain dependent on ER-α for growth and survival. Thus, there is a need for new ER-α targeting agents that have activity in the setting of metastatic disease and acquired resistance. In one aspect, described herein are compounds that are selective estrogen receptor modulators (SERMs). In specific embodiments, the SERMs described herein are selective estrogen receptor degraders (SERDs). In some embodiments, in cell-based assays the compounds described herein result in a reduction in steady state ER-α levels (i.e. ER degradation) and are useful in the treatment of estrogen sensitive diseases or conditions and/or diseases or conditions that have developed resistant to anti-hormonal therapies.

Most breast cancer patients are treated with agents that either block estrogen synthesis (e.g., aromatase inhibitors; AIs) or antagonize the effects of estradiol via competitive ER binding (e.g., tamoxifen) (Puhalla S, et al Mol Oncol 2012; 6(2):222-236). Despite the well documented therapeutic utility of these agents in various stages of disease, many ER+ breast cancers recur and patients eventually succumb. Recently, next generation whole genome and targeted sequencing has identified ESR1 (estrogen receptor alpha gene) mutations in up to 20% of tumors from patients with advanced breast cancer who have progressed on endocrine therapies, largely aromatase inhibitors (Li S, et al. Cell Rep (2013); 4(6): 1116-1130; Merenbakh-Lamin K, et al. Cancer Res (2013); 73(23): 6856-6864; Robinson D R, et al. Nat Genet (2013); 45(12): 1446-1451; Toy W, et al. Nat Genet (2013); 45(12): 1439-1445; Jeselsohn R, et al. Clin Cancer Res (2014); 20: 1757-1767). These ligand-binding domain (LBD) mutations confer high basal activity of the apo-receptor rendering them ligand-independent and thus active in the setting of low estradiol. There is a need for therapies that target ER signaling with robust activity in the setting of progressive disease post AI or tamoxifen treatment including the subset of patients harboring ESR1 mutant tumors.

In some embodiments, Formula I, II, and III compounds disclosed herein are used in methods for treating a hormone resistant-estrogen receptor (ER) positive breast cancer in a patient characterized as having a mutation in the ESR1 gene, comprising administering a therapeutically-effective amount of a Formula I, II, or III compound. In some embodiments, the mutation in the ESR1 gene results in an ER polypeptide having an amino acid substitution at a position selected from among amino acids positions 6, 118, 269, 311, 341, 350, 380, 392, 394, 433, 463, 503, 534, 535, 536, 537, 538 and 555 of SEQ ID NO:2. In some embodiments, the mutation results in an ER polypeptide having an amino acid substitution selected from among H6Y, S118P, R269C, T311M, S341L, A350E, E380Q, V392I, R394H, S433P, S463P, R503W, V534E, P535H, L536R, L536P, L536Q, Y537N, Y537C, Y537S, D538G, and R555C. In some embodiments, the patient has two or more mutations in the ESR1 gene.

Given the central role of ER-α in breast cancer development and progression, compounds disclosed herein are useful in the treatment of breast cancer, either alone or in combination with other agents that can modulate other critical pathways in breast cancer, including but not limited to those that target IGF1R, EGFR, CDK 4/6, erB-B2 and 3, the PI3K/AKT/mTOR axis, HSP90, PARP or histone deacetylases.

Given the central role of ER-α in breast cancer development and progression, Formula I, II, and III compounds disclosed herein are useful in the treatment of breast cancer, either alone or in combination with other agent used to treat breast cancer, including but not limited to aromatase inhibitors, anthracyclines, platins, nitrogen mustard alkylating agents, taxanes. Illustrative agent used to treat breast cancer, include, but are not limited to, PI3K inhibitors such as taselisib (GDC-0032, Genentech Inc.), brilanestrant (GDC-0810, Genentech Inc.), paclitaxel, anastrozole, exemestane, cyclophosphamide, epirubicin, fulvestrant, letrozole (FEMARA®, Novartis, Corp.), gemcitabine, trastuzumab, pegfilgrastim, filgrastim, tamoxifen, docetaxel, toremifene, vinorelbine, capecitabine (XELODA®, Roche), ixabepilone, as well as others described herein.

ER-related diseases or conditions include ER-α dysfunction is associated with cancer (bone cancer, breast cancer, lung cancer, colorectal cancer, endometrial cancer, prostate cancer, ovarian and uterine cancer), central nervous system (CNS) defects (alcoholism, migraine), cardiovascular system defects (aortic aneurysm, susceptibility to myocardial infarction, aortic valve sclerosis, cardiovascular disease, coronary artery disease, hypertension), hematological system defects (deep vein thrombosis), immune and inflammation diseases (Graves' Disease, arthritis, multiple sclerosis, cirrhosis), susceptibility to infection (hepatitis B, chronic liver disease), metabolic defects (bone density, cholestasis, hypospadias, obesity, osteoarthritis, osteopenia, osteoporosis), neurological defects (Alzheimer's disease, Parkinson's disease, migraine, vertigo), psychiatric defects (anorexia nervosa, attention deficit hyperactivity disorder (ADHD), dementia, major depressive disorder, psychosis) and reproductive defects (age of menarche, endometriosis, infertility).

In some embodiments, compounds disclosed herein are used in the treatment of an estrogen receptor dependent or estrogen receptor mediated disease or condition in mammal.

In some embodiments, compounds disclosed herein are used to treat cancer in a mammal. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, compounds disclosed herein are used to treat hormone receptor positive metastatic breast cancer in a postmenopausal woman with disease progression following anti-estrogen therapy.

In some embodiments, compounds disclosed herein are used to treat a hormonal dependent benign or malignant disease of the breast or reproductive tract in a mammal. In some embodiments, the benign or malignant disease is breast cancer.

In some embodiments, the compound used in any of the methods described herein is an estrogen receptor degrader; is an estrogen receptor antagonist; has minimal or negligible estrogen receptor agonist activity; or combinations thereof.

In some embodiments, methods of treatment with compounds described herein include a treatment regimen that includes administering radiation therapy to the mammal.

In some embodiments, methods of treatment with compounds described herein include administering the compound prior to or following surgery.

In some embodiments, methods of treatment with compounds described herein include administering to the mammal at least one additional anti-cancer agent.

In some embodiments, compounds disclosed herein are used to treat cancer in a mammal, wherein the mammal is chemotherapy-nave.

In some embodiments, compounds disclosed herein are used in the treatment of cancer in a mammal. In some embodiments, compounds disclosed herein are used to treat cancer in a mammal, wherein the mammal is being treated for cancer with at least one anti-cancer agent. In one embodiment, the cancer is a hormone refractory cancer.

In some embodiments, compounds disclosed herein are used in the treatment or prevention of diseases or conditions of the uterus in a mammal. In some embodiments, the disease or condition of the uterus is leiomyoma, uterine leiomyoma, endometrial hyperplasia, or endometriosis. In some embodiments, the disease or condition of the uterus is a cancerous disease or condition of the uterus. In some other embodiments, the disease or condition of the uterus is a non-cancerous disease or condition of the uterus.

In some embodiments, compounds disclosed herein are used in the treatment of endometriosis in a mammal.

In some embodiments, compounds disclosed herein are used in the treatment of leiomyoma in a mammal. In some embodiments, the leiomyoma is a uterine leiomyoma, esophageal leiomyoma, cutaneous leiomyoma, or small bowel leiomyoma. In some embodiments, compounds disclosed herein are used in the treatment of fibroids in a mammal.

In some embodiments, compounds disclosed herein are used in the treatment of uterine fibroids in a mammal.

Heteroaryl Compounds

The present invention provides heteroaryl compounds of Formulas I, II, and III including subgeneric formulas and pharmaceutical formulations thereof, which are potentially useful in the treatment of diseases, conditions and/or disorders modulated by Estrogen Receptor alpha (ERa).

Formulas I, II, and III compounds have the structures:

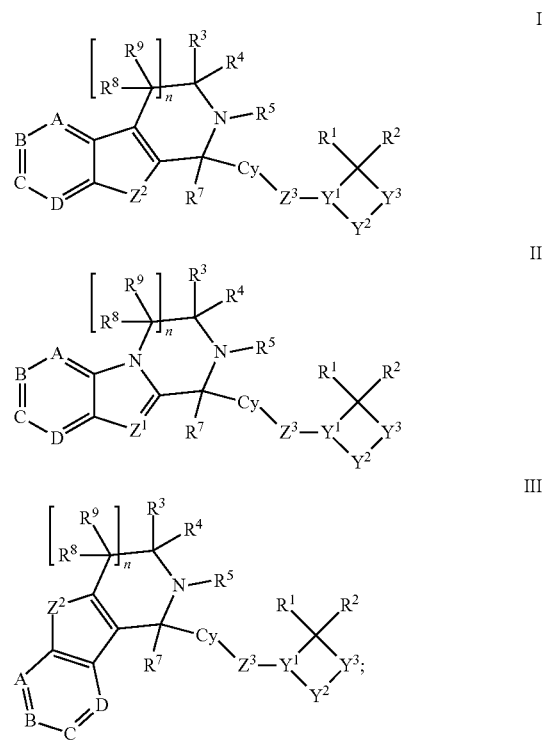

stereoisomers, tautomers, or pharmaceutically acceptable salts thereof, wherein:

A, B, C, and D are independently selected from $CR^6$ and N;

$Y^1$ is $CR^b$ or N;

$Y^2$ is —($CH_2$)—, —($CH_2CH_2$)—, or $NR^a$;

$Y^3$ is $NR^a$ or $C(R^b)_2$;

where one of $Y^1$, $Y^2$ and $Y^3$ is N or $NR^a$;

$R^a$ is selected from H, $C_1$-$C_6$ alkyl, $C_2$-$C_8$ alkenyl, propargyl, $C_3$-$C_6$ cycloalkyl, and $C_3$-$C_6$ heterocyclyl, optionally substituted with one or more groups independently selected from F, Cl, Br, I, CN, OH, $OCH_3$, and $SO_2CH_3$;

$R^b$ is independently selected from H, —O($C_1$-$C_3$ alkyl), $C_1$-$C_6$ alkyl, $C_2$-$C_8$ alkenyl, propargyl, —($C_1$-$C_6$ alkyldiyl)-($C_3$-$C_6$ cycloalkyl), $C_3$-$C_6$ cycloalkyl, and $C_3$-$C_6$ heterocyclyl, optionally substituted with one or more groups independently selected from F, Cl, Br, I, CN, —$CH_2F$, —$CHF_2$, —$CF_3$, —$CH_2CF_3$, —$CH_2CHF_2$, —$CH_2CH_2F$, OH, $OCH_3$, and $SO_2CH_3$;

$R^c$ is selected from H, $C_1$-$C_6$ alkyl, allyl, propargyl, optionally substituted with one or more groups independently selected from F, Cl, Br, I, CN, OH, $OCH_3$, and $SO_2CH_3$;

Cy is selected from $C_6$-$C_{20}$ aryldiyl, $C_3$-$C_{12}$ carbocyclyldiyl, $C_2$-$C_{20}$ heterocyclyldiyl, and $C_1$-$C_{20}$ heteroaryldiyl;

$Z^1$ is selected from $CR^a$ and N;

$Z^2$ is selected from O, S, and $NR^a$ $Z^3$ is selected from O, S, $NR^a$, $C_1$-$C_6$ alkyldiyl, $C_1$-$C_6$ fluoroalkyldiyl, O—($C_1$-$C_6$ alkyldiyl), O—($C_1$-$C_6$ fluoroalkyldiyl), C(O), and a bond;

$R^1$, $R^2$, $R^3$, $R^4$, $R^8$, and $R^9$ are independently selected from H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino; or $R^3$ and $R^8$ form a 4, 5, 6, or 7-membered carbocylic or heterocyclic ring;

$R^5$ is selected from H, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, —($C_1$-$C_6$ alkyldiyl)-($C_3$-$C_9$ cycloalkyl), —($C_1$-$C_6$ alkyldiyl)-($C_3$-$C_9$ heterocycle), C(O)$R^b$, C(O)$NR^a$, SO$_2R^a$, and SO$_2NR^a$, optionally substituted with one or more of halogen, CN, $OR^a$, $N(R^a)_2$, $C_1$-$C_9$ alkyl, $C_3$-$C_9$ cycloalkyl, $C_3$-$C_9$ heterocycle, $C_6$-$C_9$ aryl, $C_6$-$C_9$ heteroaryl, C(O)$R^b$, C(O)$NR^a$, SO$_2R^a$, and SO$_2NR^a$; or $R^3$ and $R^5$ form a 4, 5, 6, or 7-membered heterocyclic ring; or Cy and $R^5$ form a 4, 5, 6, or 7-membered heterocyclic ring;

$R^6$ is selected from H, F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CH$_2$NH$_2$, —CH$_2$NHSO$_2$CH$_3$, —CH$_2$NHCH$_3$, —CH$_2$N(CH$_3$)$_2$, —CF$_3$, —CH$_2$CF$_3$, —CH$_2$CHF$_2$, —CH$_2$CH$_2$F, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CONHCH$_2$CH$_3$, —CONHCH(CH$_3$)$_2$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;

$R^7$ is selected from H, $C_1$-$C_6$ alkyl, $C_2$-$C_8$ alkenyl, and propargyl; or $R^7$ and Cy form a spiro, 4, 5, 6, or 7-membered carbocyclic or heterocyclic ring; and n is selected from 1 and 2;

where alkyldiyl, fluoroalkyldiyl, aryldiyl, carbocylyldiyl, heterocyclyldiyl, and heteroaryldiyl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH$_2$CH$_2$F, —CH(CH$_3$)CN, —C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, cyclopropylamide, cyclobutyl, oxetanyl, azetidinyl, 1-methylazetidin-3-yl)oxy, N-methyl-N-oxetan-3-ylamino, azetidin-1-ylmethyl, benzyloxyphenyl, pyrrolidin-1-yl, pyrrolidin-1-yl-methanone, piperazin-1-yl, morpholinomethyl, morpholino-methanone, and morpholino;

with the proviso that for a Formula I compound when n is 1; A, B, C, and D are each $CR^6$; and $Z^2$ is N; then $R^7$ is not H.

Exemplary embodiments of Formulas I, II, and III compounds include wherein A, B, C, and D are each $CR^6$.

Exemplary embodiments of Formulas I, II, and III compounds include wherein one or two of A, B, C, and D are N.

Exemplary embodiments of Formula I compounds include wherein $Z^2$ is O.

Exemplary embodiments of Formula I compounds include wherein $Z^2$ is S.

Exemplary embodiments of Formula I compounds include wherein $Z^2$ is $NR^a$.

Exemplary embodiments of Formula II compounds include wherein $Z^1$ is $CR^a$.

Exemplary embodiments of Formula II compounds include wherein $Z^1$ is N.

Exemplary embodiments of Formula II compounds include wherein $Z^2$ is O.

Exemplary embodiments of Formula III compounds include wherein $Z^2$ is S.

Exemplary embodiments of Formula III compounds include wherein $Z^2$ is $NR^a$.

Exemplary embodiments of Formula I, II, and III compounds include wherein Cy is phenyldiyl, substituted with one or more F.

Exemplary embodiments of Formula I, II, and III compounds include wherein $Z^3$ is O or $NR^a$.

Exemplary embodiments of Formula I, II, and III compounds include wherein $Z^3$ is NH.

Exemplary embodiments of Formula I, II, and III compounds include wherein $Z^3$ is O—($C_1$-$C_6$ alkyldiyl), $Y^1$ is N, $Y^2$ is —(CH$_2$)—, and $Y^3$ is C($R^b$)$_2$.

Exemplary embodiments of Formula I, II, and III compounds include wherein $Y^3$ is CH(CH$_2$F).

Exemplary embodiments of Formula I, II, and III compounds include wherein $Y^1$ is $CR^b$, $Y^2$ is —(CH$_2$)—, and $Y^3$ is $NR^a$.

Exemplary embodiments of Formula I, II, and III compounds include wherein $Y^3$ is NCH$_2$CH$_2$F.

Exemplary embodiments of Formula I, II, and III compounds include wherein $R^5$ is $C_1$-$C_9$ alkyl, substituted with one or more F.

Exemplary embodiments of Formula I, II, and III compounds are selected from Tables 1a and 1b.

Biological Evaluation

The relative efficacies of Formula I, II, and III compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Cell proliferation, cytotoxicity, and cell viability of the Formula I, II, and III compounds can be measure by the CellTiter-Glo® Luminescent Cell Viability Assay (Promega Corp.). The CellTiter-Glo® Luminescent Cell Viability Assay is a homogeneous method of determining the number of viable cells in culture based on quantitation of the ATP present, an indicator of metabolically active cells. The CellTiter-Glo® Assay is designed for use with multiwell formats, making it ideal for automated high-throughput screening (HTS), cell proliferation and cytotoxicity assays. The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

All of the exemplary Formula I, II, and III compounds in Tables 1a and 1b were made and characterized by LCMS $[M+H]^+$ (liquid chromatography mass spectroscopy) with detection of parent ion. All of the exemplary Formula I, II, and III compounds in Tables 1a and 1b were tested for binding to ERa (Estrogen Receptor alpha) and biological activity according to the assays, protocols, and procedures of Examples 901-907. ER-alpha MCF7 HCS $S_{inf}$(%) values in Tables 1a and 1b were measured by the Breast Cancer Cell ERa High Content Fluorescence Imaging Degradation Assay of Example 901. ER-alpha MCF7 HCS $EC_{50}$ (µM) values in Tables 1a and 1b were measured by the in vitro cell proliferation assays described in Examples 902 and 903. The rat uterine wet weight assays of Examples 906 and 907 allow rapid determination of compound antagonist activity in an ER responsive tissue (immature rat uterus) while competing against the native ER ligand estradiol, i.e. antagonist mode (Ashby, J.; et al (1997) Regulatory toxicology and pharmacology: RTP, 25 (3):226-31). Exemplary Formula I, II, and III compounds in Tables 1a and 1b have the following structures, corresponding names (ChemBioDraw, Version 12.0.2, CambridgeSoft Corp., Cambridge Mass.), and biological activity. Where more than one name is associated with a Formula I, II, and III compound or intermediate, the chemical structure shall define the compound.

TABLE 1a

| No. | Structure | Name | LCMS $[M + H]^+$ or $[M − H]^−$ | ER-alpha MCF7HCS $EC_{50}$ (µM) | ER-alpha MCF7HCS $S_{inf}$(%) |
|---|---|---|---|---|---|
| 101 | 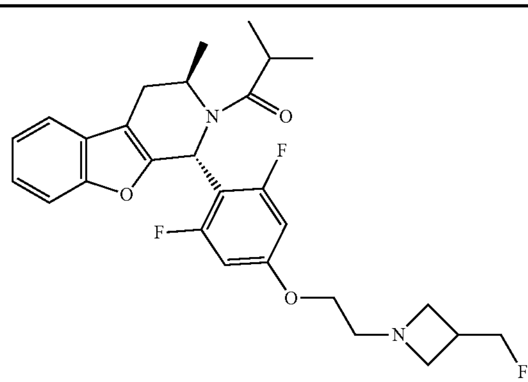 | 1-((1R,3R)-1-(2,6-difluoro-4-(2-(3-(fluoromethyl)azetidin-1-yl)ethoxy)phenyl)-3-methyl-3,4-dihydrobenzofuro[2,3-c]pyridin-2(1H)-yl)-2-methylpropan-1-one | 501.2 | 0.000275 | −94.5 |
| 102 | 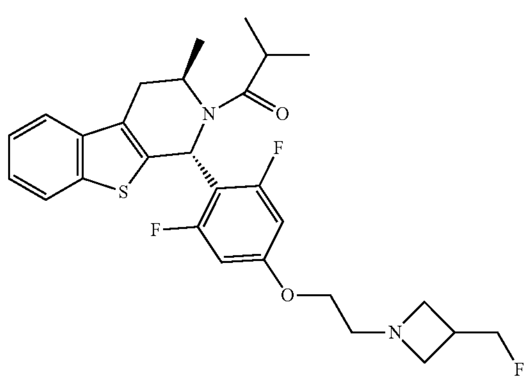 [SMILES: CC(C)C(=O)N1[C@H](c2c(F)cc(OCCN3CC(CF)C3)cc2F)c2sc3ccccc3c2C[C@H]1C] | 1-((1,3-trans)-1-(2,6-difluoro-4-(2-(3-(fluoromethyl)azetidin-1-yl)ethoxy)phenyl)-3-methyl-3,4-dihydrobenzo[4,5]thieno[2,3-c]pyridin-2(1H)-yl)-2-methylpropan-1-one | 517.2 | 0.058 | −64.5 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$(%) |
|---|---|---|---|---|---|
| 103 | 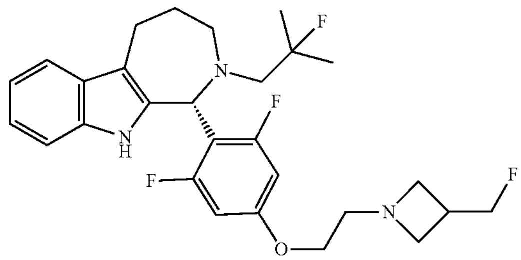 [SMILES: CC(C)(F)CN1CCCc2c([nH]c3ccccc23)[C@H]1c1c(F)cc(OCCN2CC(CF)C2)cc1F] | (R)-1-(2,6-difluoro-4-(2-(3-(fluoromethyl)azetidin-1-yl)ethoxy)phenyl)-2-(2-fluoro-2-methylpropyl)-1,2,3,4,5,10-hexahydroazepino[3,4-b]indole | 504.2 | 0.000128 | −96.7 |
| 104 | 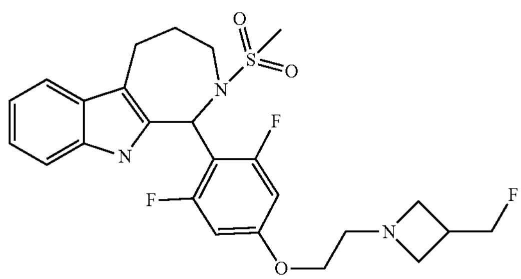 [SMILES: CS(=O)(=O)N1CCCc2c([nH]c3ccccc23)C1c1c(F)cc(OCCN2CC(CF)C2)cc1F] | (±)-1-(2,6-difluoro-4-(2-(3-(fluoromethyl)azetidin-1-yl)ethoxy)phenyl)-2-(methylsulfonyl)-1,2,3,4,5,10-hexahydroazepino[3,4-b]indole | 508.6 | >0.10 | |
| 105 | 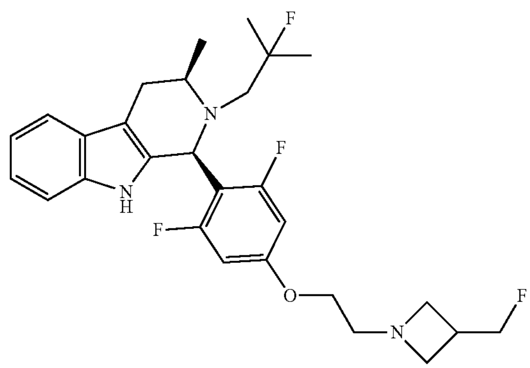 [SMILES: C[C@@H]1Cc2c([nH]c3ccccc23)[C@H](c2c(F)cc(OCCN3CC(CF)C3)cc2F)N1CC(C)(C)F] | (1S,4R)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole | 504.2 | 0.0434 | −45 |
| 106 | 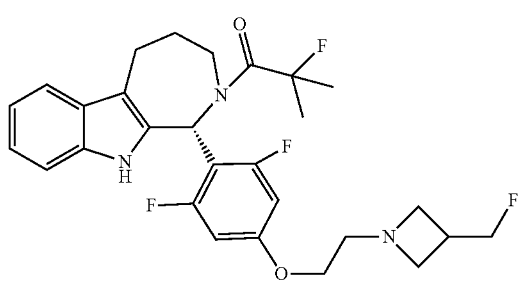 [SMILES: CC(C)(F)C(=O)N1CCCc2c([nH]c3ccccc23)[C@H]1c1c(F)cc(OCCN2CC(CF)C2)cc1F] | (R)-1-(1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-one | 518.2 | 0.0534 | −35 |
| 107 | 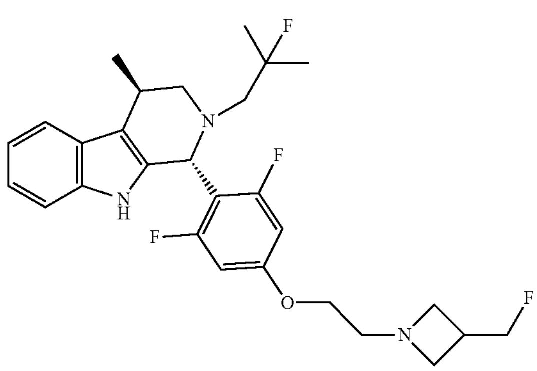 [SMILES: C[C@H]1CN(CC(C)(C)F)[C@H](c2c(F)cc(OCCN3CC(CF)C3)cc2F)c2[nH]c3ccccc3c21] | (1R,4R)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole | 504.2 | 0.000731 | −97.8 |

TABLE 1a-continued

| No. | Structure | Name | LCMS [M + H]+ or [M − H]− | ER-alpha MCF7HCS EC50 (μM) | ER-alpha MCF7HCS S$_{inf}$ (%) |
|---|---|---|---|---|---|
| 108 | 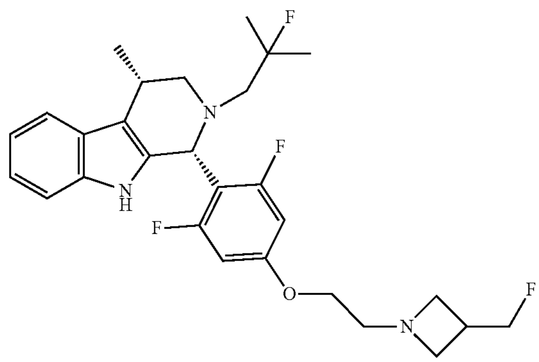 [SMILES: C[C@@H]1CN(CC(C)(C)F)[C@H](c2c(F)cc(OCCN3CC(CF)C3)cc2F)c2[nH]c3ccccc3c21] | (1R,4S)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole | 504.2 | 0.000731 | −92.4 |
| 109 | 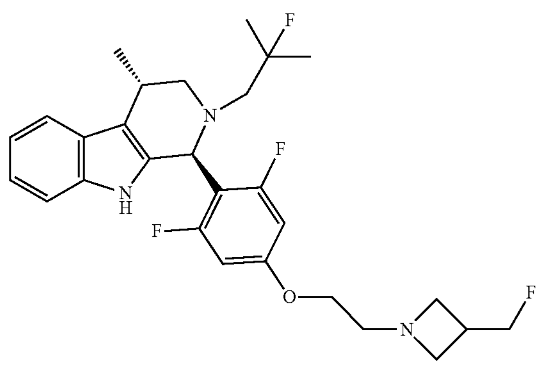 [SMILES: C[C@@H]1CN(CC(C)(C)F)[C@@H](c2c(F)cc(OCCN3CC(CF)C3)cc2F)c2[nH]c3ccccc3c21] | (1S,4S)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole | 504.2 | 0.0234 | −74.6 |
| 110 | 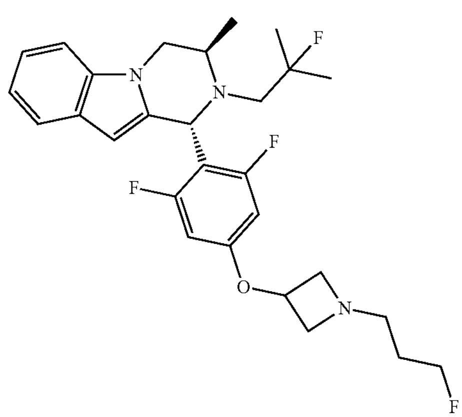 [SMILES: C[C@@H]1Cn2c(cc3ccccc32)[C@@H](c2c(F)cc(OC3CN(CCCF)C3)cc2F)N1CC(C)(C)F] | (1R,3R)-1-(2,6-Difluoro-4-((1-(3-(fluoropropyl)azetidin-3-yl)oxy)phenyl)-2-(2-fluoro-2-methylpropyl)-3-methyl-1,2,3,4-tetrahydropyrazino[1,2-a]indole | 504.3 | 0.00054 | −100 |
| 111 | 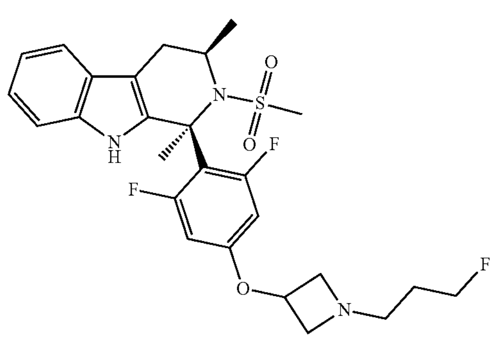 [SMILES: C[C@@H]1Cc2c([nH]c3ccccc23)[C@](C)(c2c(F)cc(OC3CN(CCCF)C3)cc2F)N1S(C)(=O)=O] | (1S,3R)-1-(2,6-Difluoro-4-((1-(3-(fluoropropyl)azetidin-3-yl)oxy)phenyl)-1,3-dimethyl-2-(methylsulfonyl)-2,3,4,9-tetrahydro-1H-pyrido[3,4-b]indole | 522.1 | 0.1 | |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$(%) |
|---|---|---|---|---|---|
| 112 | 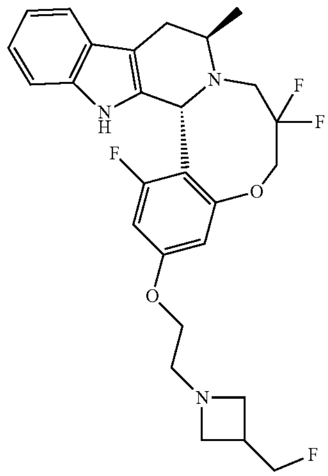 [SMILES: C[C@@H]1Cc2c([nH]c3ccccc23)[C@H]2c3c(F)cc(OCCN4CC(CF)C4)cc3OCC(F)(F)CN21] | (10R,16bR)-1,7,7-Trifluoro-3-(2-(3-(fluoromethyl)azetidin-1-yl)ethoxy)-10-methyl-7,8,10,11,16,16b-hexahydro-6H-benzo[2',3'][1,5]oxazocino[5',4':1,2]pyrido[3,4-b]indole | 504.1 | 0.033 | −50 |
| 113 | 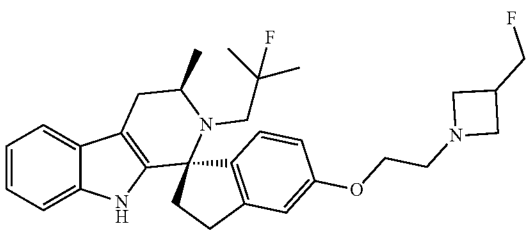 [SMILES: C[C@@H]1Cc2c([nH]c3ccccc23)[C@]2(CCc3cc(OCCN4CC(CF)C4)ccc32)N1CC(C)(C)F] | (1R,3'R)-2'-(2-fluoro-2-methylpropyl)-5-(2-(3-(fluoromethyl)azetidin-1-yl)ethoxy)-3'-methyl-2,2',3,3',4',9'-hexahydrospiro[indene-1,1'-pyrido[3,4-b]indole] | 494.4 | 0.0044 | −94.7% |
| 114 | 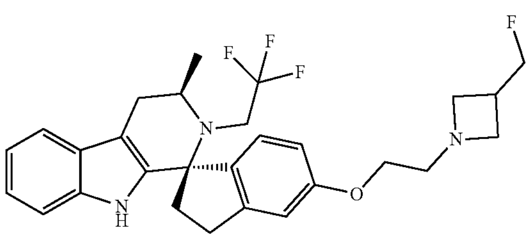 [SMILES: C[C@@H]1Cc2c([nH]c3ccccc23)[C@]2(CCc3cc(OCCN4CC(CF)C4)ccc32)N1CC(F)(F)F] | (1R,3'R)-5-(2-(3-(fluoromethyl)azetidin-1-yl)ethoxy)-3'-methyl-2'-(2,2,2-trifluoroethyl)-2,2',3,3',4',9'-hexahydrospiro[indene-1,1'-pyrido[3,4-b]indole] | 502.3 | 0.0002 | −96.6% |
| 115 | 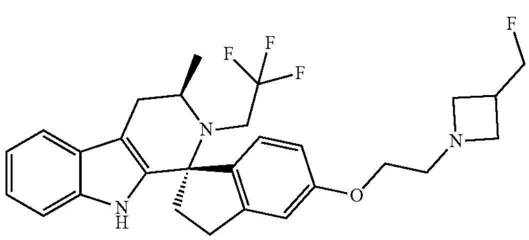 [SMILES: C[C@@H]1Cc2c([nH]c3ccccc23)[C@@]2(CCc3cc(OCCN4CC(CF)C4)ccc32)N1CC(F)(F)F] | (1S,3'R)-5-(2-(3-(fluoromethyl)azetidin-1-yl)ethoxy)-3'-methyl-2'-(2,2,2-trifluoroethyl)-2,2',3,3',4',9'-hexahydrospiro[indene-1,1'-pyrido[3,4-b]indole] | 502.3 | 0.0007 | −98% |
| 116 | 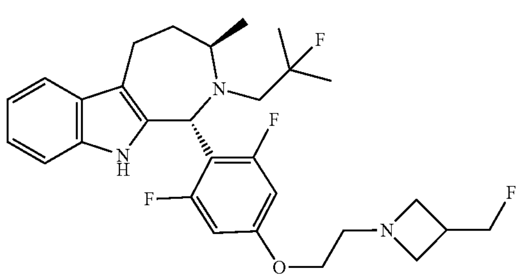 [SMILES: C[C@@H]1CCc2c([nH]c3ccccc23)[C@@H](c2c(F)cc(OCCN3CC(CF)C3)cc2F)N1CC(C)(C)F] | (1R,3R)-1-(2,6-difluoro-4-(2-(3-(fluoromethyl)azetidin-1-yl)ethoxy)phenyl)-2-(2-fluoro-2-methylpropyl)-3-methyl-1,2,3,4,5,10-hexahydrospiro[3,4-b]indole | 518.3 | 0.00129 | −93.5 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$ (%) |
|---|---|---|---|---|---|
| 117 | 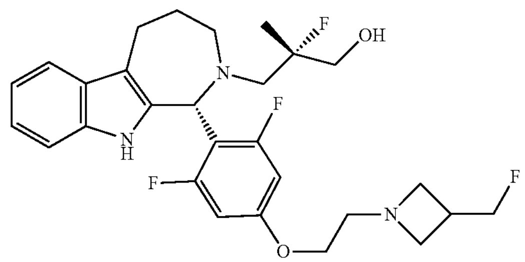 [SMILES: C[C@@](F)(CO)CN1CCCc2c([nH]c3ccccc23)[C@H]1c1c(F)cc(OCCN2CC(CF)C2)cc1F] | (S)-3-((R)-1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-ol | 520.3 | 0.000047 | −93.8 |
| 118 | 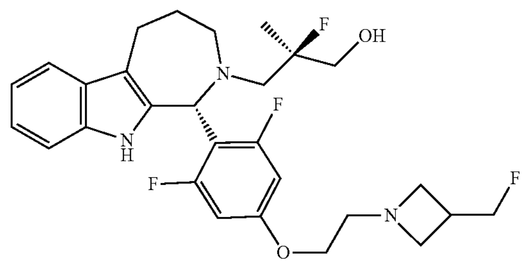 [SMILES: C[C@](F)(CO)CN1CCCc2c([nH]c3ccccc23)[C@H]1c1c(F)cc(OCCN2CC(CF)C2)cc1F] | (R)-3-((R)-1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-ol | 520.3 | 0.000068 | −95.9 |
| 119 | 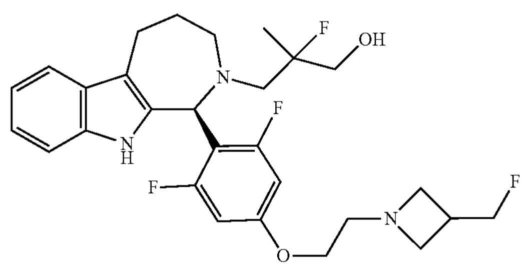 [SMILES: CC(F)(CO)CN1CCCc2c([nH]c3ccccc23)[C@@H]1c1c(F)cc(OCCN2CC(CF)C2)cc1F] | 3-((S)-1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-ol | 520.3 | 0.000531 | −95.6 |
| 120 | 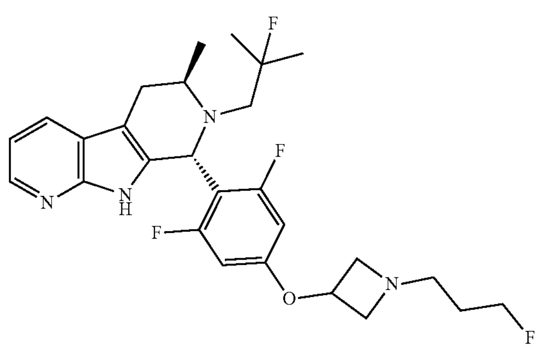 [SMILES: C[C@@H]1Cc2c([nH]c3ncccc23)[C@@H](c2c(F)cc(OC3CN(CCCF)C3)cc2F)N1CC(C)(C)F] | (6R,8R)-8-(2,6-difluoro-4-((1-(3-(fluoropropyl)azetidin-3-yl)oxy)phenyl)-7-(2-fluoro-2-methylpropyl)-6-methyl-6,7,8,9-tetrahydro-5H-pyrrolo[2,3-b:5,4-c']dipyridine | 505.3 | 0.0002 | −88.0 |
| 121 | 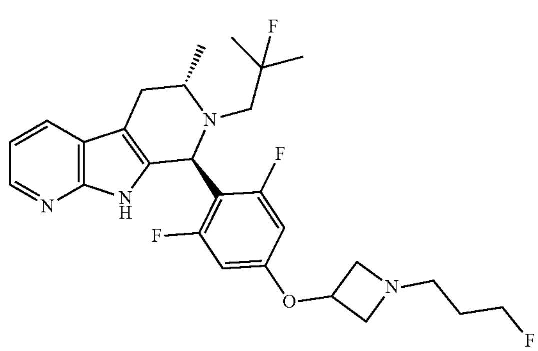 [SMILES: C[C@H]1Cc2c([nH]c3ncccc23)[C@H](c2c(F)cc(OC3CN(CCCF)C3)cc2F)N1CC(C)(C)F] | (6S,8S)-8-(2,6-difluoro-4-((1-(3-(fluoropropyl)azetidin-3-yl)oxy)phenyl)-7-(2-fluoro-2-methylpropyl)-6-methyl-6,7,8,9-tetrahydro-5H-pyrrolo[2,3-b:5,4-c']dipyridine | 505.3 | >0.10 | — |

TABLE 1a-continued

| No. | Structure | Name | LCMS [M + H]⁺ or [M − H]⁻ | ER-alpha MCF7HCS EC$_{50}$ (μM) | ER-alpha MCF7HCS S$_{inf}$ (%) |
|---|---|---|---|---|---|
| 122 | 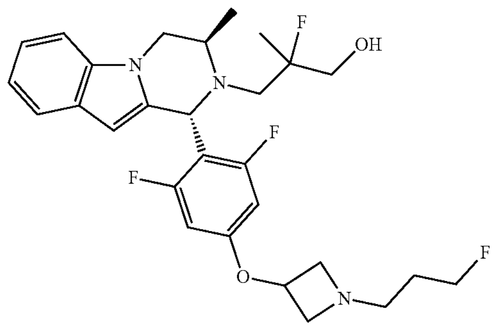 [SMILES: C[C@@H]1Cn2c(cc3ccccc32)[C@@H](c2c(F)cc(OC3CN(CCCF)C3)cc2F)N1CC(C)(F)CO] | 3-((1R,3R)-1-(2,6-Difluoro-4-((1-(3-fluoropropyl)azetidin-3-yl)oxy)phenyl)-3-methyl-3,4-dihydropyrazino[1,2-a]indol-2(1H)-yl)-2-fluoro-2-methylpropan-1-ol | 520.2 | 0.00014 | −97 |
| 123 | 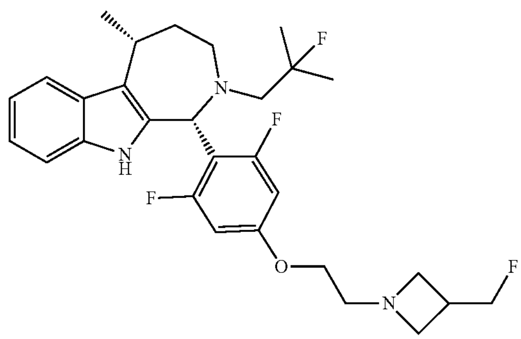 [SMILES: C[C@@H]1CCN(CC(C)(C)F)[C@H](c2c(F)cc(OCCN3CC(CF)C3)cc2F)c2[nH]c3ccccc3c21] | (1R,5R)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole | 518.3 | 0.000351 | −96.9 |
| 124 | 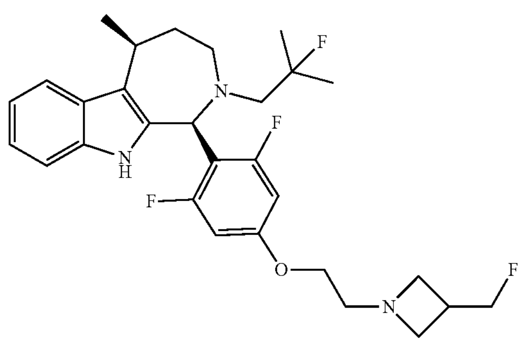 [SMILES: C[C@H]1CCN(CC(C)(C)F)[C@@H](c2c(F)cc(OCCN3CC(CF)C3)cc2F)c2[nH]c3ccccc3c21] | (1S,5S)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole | 518.3 | 0.00268 | −75 |
| 125 | 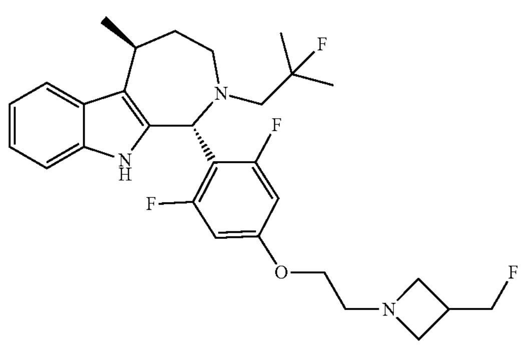 [SMILES: C[C@H]1CCN(CC(C)(C)F)[C@H](c2c(F)cc(OCCN3CC(CF)C3)cc2F)c2[nH]c3ccccc3c21] | (1R,5S)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole | 518.3 | 0.00115 | −101 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$(%) |
|---|---|---|---|---|---|
| 126 | 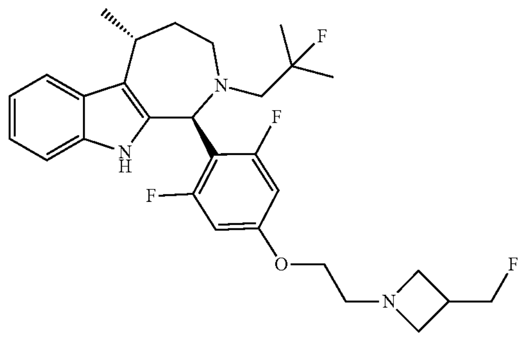 [SMILES: C[C@@H]1CCN(CC(C)(C)F)[C@@H](c2c(F)cc(OCCN3CC(CF)C3)cc2F)c2[nH]c3ccccc3c21] | (1S,5R)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole | 518.3 | 0.0457 | −50 |
| 127 | 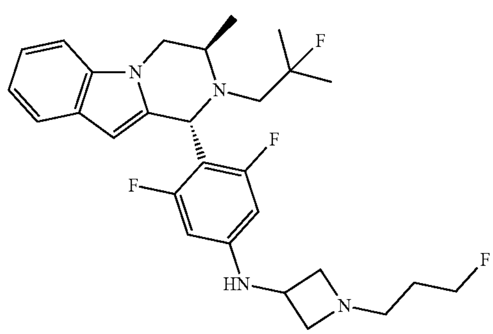 [SMILES: C[C@@H]1Cn2c(cc3ccccc32)[C@@H](c2c(F)cc(NC3CN(CCCF)C3)cc2F)N1CC(C)(C)F] | N-(3,5-Difluoro-4-((1R,3R)-2-(2-fluoro-2-methylpropyl)-3-methyl-1,2,3,4-tetrahydroazepino[1,2-a]indol-1-yl)phenyl)-1-(3-fluoropropyl)azetidin-3-amine | 503.3 | 0.00016 | −100 |
| 128 | 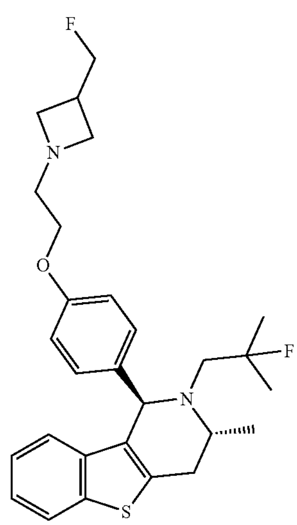 [SMILES: C[C@@H]1Cc2sc3ccccc3c2[C@@H](c2ccc(OCCN3CC(CF)C3)cc2)N1CC(C)(C)F] | (1R,3R)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine | 485.2 | 0.000132 | −101 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$(%) |
|---|---|---|---|---|---|
| 129 | 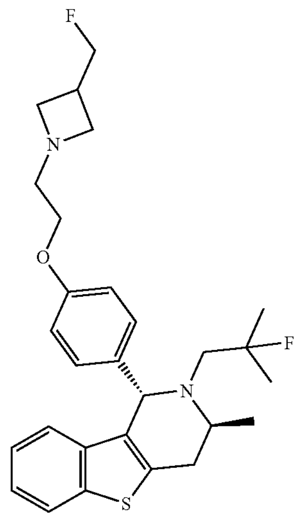 [SMILES: C[C@H]1Cc2sc3ccccc3c2[C@H](c2ccc(OCCN3CC(CF)C3)cc2)N1CC(C)(C)F] | (1S,3S)-2-(2-Fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine | 485.2 | 0.0145 | −43.8 |
| 130 | 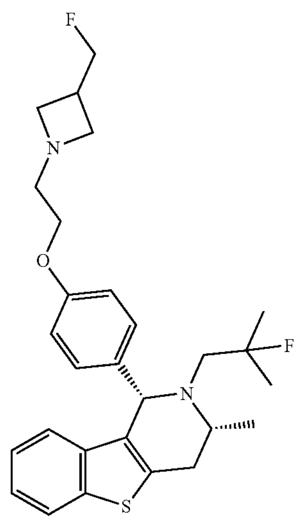 [SMILES: C[C@@H]1Cc2sc3ccccc3c2[C@H](c2ccc(OCCN3CC(CF)C3)cc2)N1CC(C)(C)F] | (1S,3R)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine | 485.2 | 0.0249 | −76.8 |
| 131 | 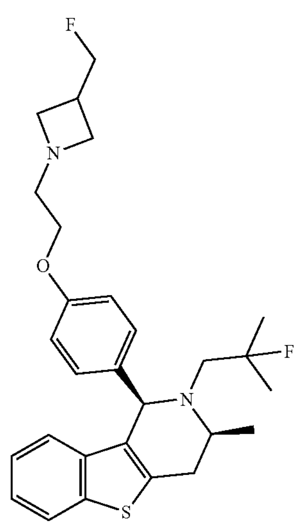 [SMILES: C[C@H]1Cc2sc3ccccc3c2[C@@H](c2ccc(OCCN3CC(CF)C3)cc2)N1CC(C)(C)F] | (1S,3S)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine | 485.2 | 0.00105 | −99 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$ (%) |
|---|---|---|---|---|---|
| 132 | 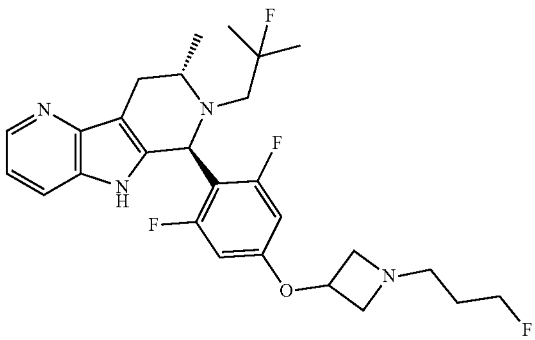 [SMILES: C[C@H]1Cc2c([nH]c3cccnc23)[C@H](c2c(F)cc(OC3CN(CCCF)C3)cc2F)N1CC(C)(C)F] | (6S,8S)-8-{2,6-Difluoro-4-[2-(3-fluoromethyl-azetidin-1-yl)-ethoxy]-phenyl}-7-(2-fluoro-2-methyl-propyl)-6-methyl-6,7,8,9-tetrahydro-5H-dipyrido[2,3-b;4',3'-d]pyrrole | 505.3 | 0.0086 | −30 |
| 133 | 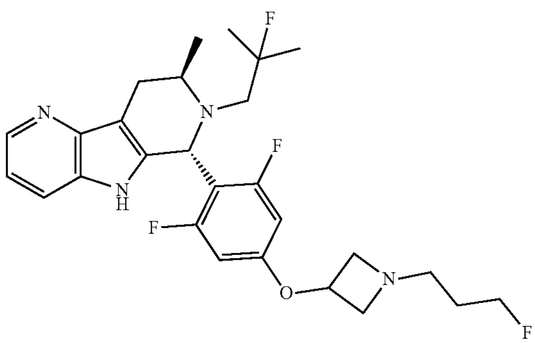 [SMILES: C[C@@H]1Cc2c([nH]c3cccnc23)[C@@H](c2c(F)cc(OC3CN(CCCF)C3)cc2F)N1CC(C)(C)F] | (6R,8R)-6-{2,6-Difluoro-4-[2-(3-fluoromethyl-azetidin-1-yl)-ethoxy]-phenyl}-7-(2-fluoro-2-methyl-propyl)-8-methyl-6,7,8,9-tetrahydro-5H-dipyrido[2,3-b;4',3'-d]pyrrole | 505.3 | 0.0003 | −94.5 |
| 134 | 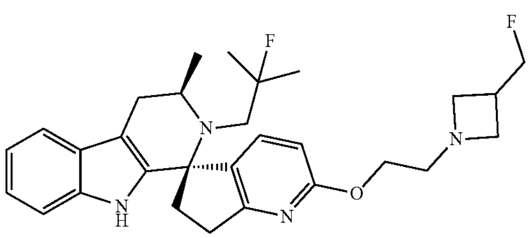 [SMILES: C[C@@H]1Cc2c([nH]c3ccccc23)[C@]2(CCc3nc(OCCN4CC(CF)C4)ccc32)N1CC(C)(C)F] | (3'R,5R)-2-(2-(3-(fluoromethyl)azetidin-1-yl)ethoxy)-3'-methyl-2'-(2,2,2-trifluoroethyl)-2',3',4',6,7,9'-hexahydrospiro[cyclopenta[b]pyridine-5,1'-pyrido[3,4-b]indole] | 503.3 | 0.0003 | −96.5% |
| 135 | 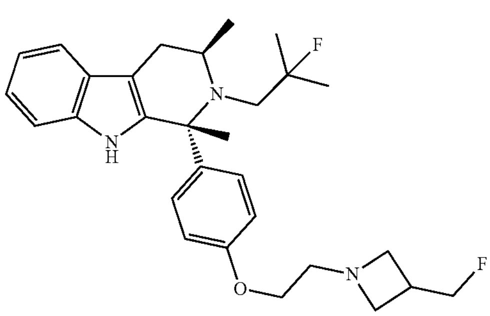 [SMILES: C[C@@H]1Cc2c([nH]c3ccccc23)[C@@](C)(c2ccc(OCCN3CC(CF)C3)cc2)N1CC(C)(C)F] | (1R,3R)-2-(2-Fluoro-2-methylpropyl)-1-(4-(2-(3-(fluoromethyl)azetidin-1-yl)ethoxy)-phenyl)-1,3-dimethyl-2,3,4,9-tetrahydro-1H-pyrido[3,4-b]indole | 482.3 | 0.00035 | −95 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$(%) |
|---|---|---|---|---|---|
| 136 | 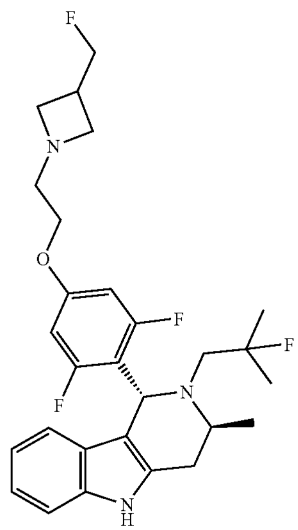 [SMILES: C[C@H]1Cc2[nH]c3ccccc3c2[C@H](c2c(F)cc(OCCN3CC(CF)C3)cc2F)N1CC(C)(C)F] | (1R,3S)-1-(2-6-difluoro-4-(2-(3-(fluoromethyl)azetidin-1-yl)ethoxy)phenyl)-2-(2-fluoro-2-methylpropyl)-3-methyl-2,3,4,5-tetrahydro-1H-pyrido[3,4-b]indole | 504.3 | 0.0337 | −51 |
| 137 | 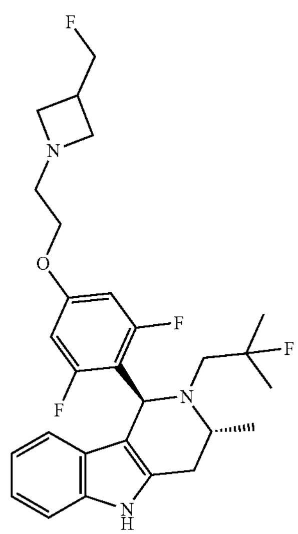 [SMILES: C[C@@H]1Cc2[nH]c3ccccc3c2[C@@H](c2c(F)cc(OCCN3CC(CF)C3)cc2F)N1CC(C)(C)F] | (1S,3R)-1-(2-6-difluoro-4-(2-(3-(fluoromethyl)azetidin-1-yl)ethoxy)phenyl)-2-(2-fluoro-2-methylpropyl)-3-methyl-2,3,4,5-tetrahydro-1H-pyrido[4,3-b]indole | 504.3 | 0.000125 | −94.2 |
| 138 | 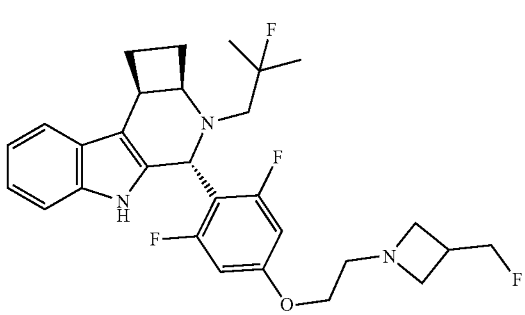 [SMILES: CC(C)(F)CN1[C@H](c2c(F)cc(OCCN3CC(CF)C3)cc2F)c2[nH]c3ccccc3c2[C@H]2CC[C@H]21] | (2aR,4R,9cR)-4-(2-6-difluoro-4-(2-(3-(fluoromethyl)azetidin-1-yl)ethoxy)phenyl)-3-(2-fluoro-2-methylpropyl)-2,2a,3,4,5,9c-hexahydro-1H-cyclobuta[5,6]pyrido[3,4-b]indole | 516.3 | 0.0002 | −68% |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$(%) |
|---|---|---|---|---|---|
| 139 | 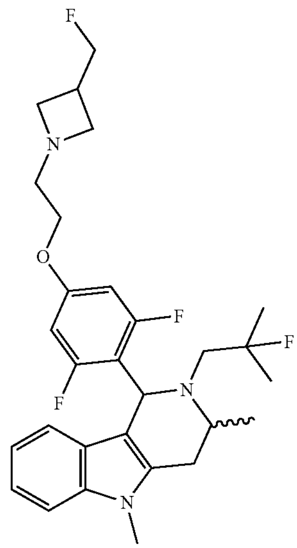 [SMILES: CC1Cc2c(c3ccccc3n2C)C(c2c(F)cc(OCCN3CC(CF)C3)cc2F)N1CC(C)(C)F] | (±)-1-(2-6-difluoro-4-(2-(3-(fluoromethyl)azetidin-1-yl)ethoxy)phenyl)-2-(2-fluoro-2-methylpropyl)-3,5-dimethyl-2,3,4,5-tetrahydro-1H-pyrido[4,3-b]indole | 518.3 | 0.00141 | −88.6 |
| 140 | 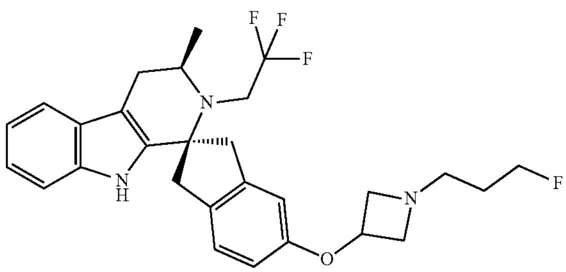 [SMILES: C[C@@H]1Cc2c([nH]c3ccccc23)[C@]2(Cc3ccc(OC4CN(CCCF)C4)cc3C2)N1CC(F)(F)F] | (2R,3'R)-5-((1-(3-(fluoropropyl)azetidin-3-yl)oxy)-3'-methyl-2'-(2,2,2-trifluoroethyl)-1,2',3,3',4',9'-hexahydrospiro[indene-2,1'-pyrido[3,4-b]indole] | 502.3 | 0.035 | −15% |
| 141 | 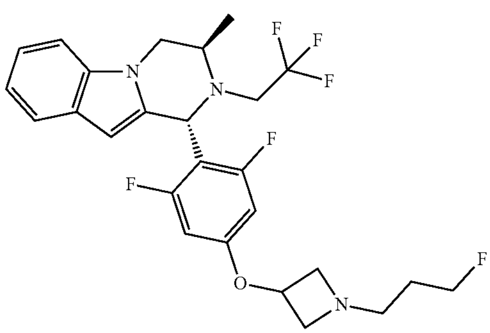 [SMILES: C[C@@H]1Cn2c(cc3ccccc32)[C@@H](c2c(F)cc(OC3CN(CCCF)C3)cc2F)N1CC(F)(F)F] | (1R,3R)-1-(2-6-difluoro-4-((1-(3-(fluoropropyl)azetidin-3-yl)oxy)phenyl)-3-methyl-2-(2,2,2-trifluoroethyl)-1,2,3,4-tetrahydropyrazino[1,2-a]indole | 512.3 | 0.00022 | −103 |
| 142 | 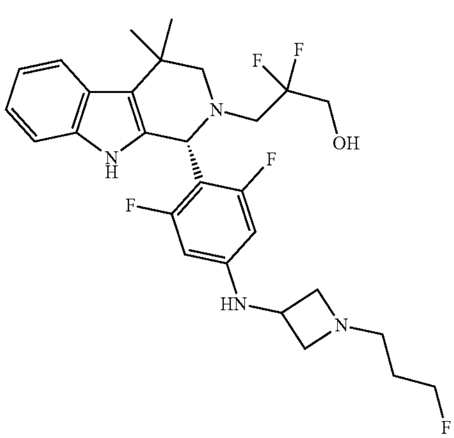 [SMILES: CC1(C)CN(CC(F)(F)CO)[C@H](c2c(F)cc(NC3CN(CCCF)C3)cc2F)c2[nH]c3ccccc3c21] | (R)-3-(1-(2,6-difluoro-4-(1-(3-(fluoropropyl)azetidin-3-ylamino)phenyl)-4,4-dimethyl-3,4-dihydro-1H-pyrido[3,4-b]indol-2(9H)-yl)-2,2-difluoropropan-1-ol | 537.2 | 0.00577 | −96 |

TABLE 1a-continued

| No. | Structure | Name | LCMS [M + H]+ or [M − H]− | ER-alpha MCF7HCS EC₅₀ (μM) | ER-alpha MCF7HCS S$_{inf}$(%) |
|---|---|---|---|---|---|
| 143 | 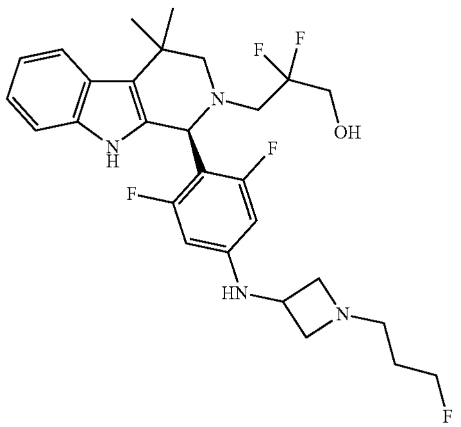 [SMILES: CC1(C)CN(CC(F)(F)CO)[C@@H](c2c(F)cc(NC3CN(CCCF)C3)cc2F)c2[nH]c3ccccc3c21] | (S)-3-(1-(2,6-difluoro-4-(1-(3-(fluoropropyl)azetidin-3-ylamino)phenyl)-4,4-dimethyl-3,4-dihydro-1H-pyrido[3,4-b]indol-2(9H)-yl)-2,2-difluoropropan-1-ol | 537.2 | >0.1 | |
| 144 | 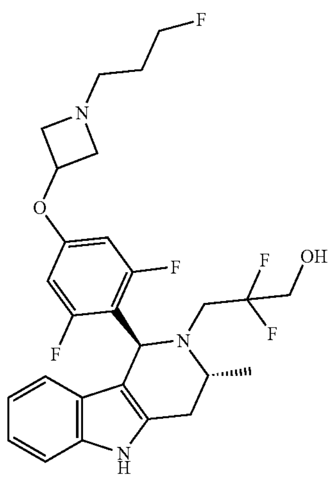 [SMILES: C[C@@H]1Cc2[nH]c3ccccc3c2[C@@H](c2c(F)cc(OC3CN(CCCF)C3)cc2F)N1CC(F)(F)CO] | trans-3-(1-(2,6-difluoro-4-(1-(3-fluoropropyl)azetidin-3-yloxy)phenyl)-3-methyl-3,4-dihydro-1H-pyrido[4,3-b]indol-2(5H)-yl)-2,2-difluoropropan-1-ol | 524.2 | 0.0028 | −98.8 |
| 145 | 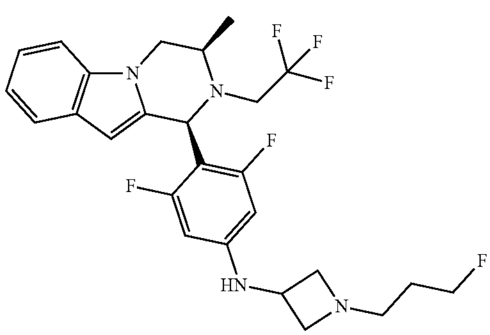 [SMILES: C[C@@H]1Cn2c(cc3ccccc32)[C@H](c2c(F)cc(NC3CN(CCCF)C3)cc2F)N1CC(F)(F)F] | N-(3,5-Difluoro-4-((1S,3R)-3-methyl-2-(2,2,2-trifluoroethyl)-1,2,3,4-tetrahydropyrazino[1,2-a]indol-1-yl)phenyl)-1-(3-fluoropropyl)azetidin-3-amine | 511.2 | 0.012 | −87 |
| 146 | 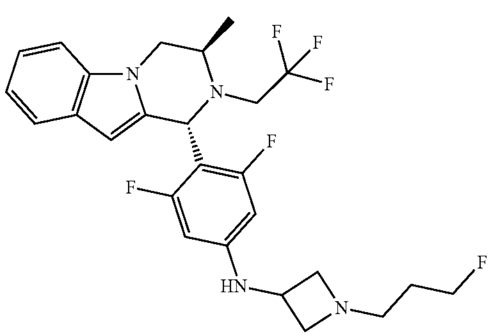 [SMILES: C[C@@H]1Cn2c(cc3ccccc32)[C@@H](c2c(F)cc(NC3CN(CCCF)C3)cc2F)N1CC(F)(F)F] | N-(3,5-Difluoro-4-((1R,3R)-3-methyl-2-(2,2,2-trifluoroethyl)-1,2,3,4-tetrahydropyrazino[1,2-a]indol-1-yl)phenyl)-1-(3-fluoropropyl)azetidin-3-amine | 511.2 | 0.00011 | −100 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$ (%) |
|---|---|---|---|---|---|
| 147 | 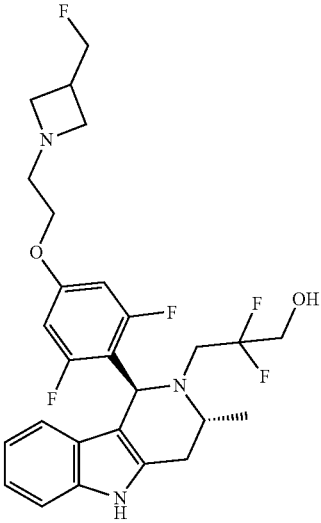 [SMILES: C[C@@H]1Cc2[nH]c3ccccc3c2[C@@H](c2c(F)cc(OCCN3CC(CF)C3)cc2F)N1CC(F)(F)CO] | 3-[(1S,3R)-1-[2,6-difluoro-4-[2-[3-(fluoromethyl)azetidin-1-yl]ethoxy]phenyl]-3-methyl-1,3,4,5-tetrahydropyrido[4,3-b]indol-2-yl]-2,2-difluoro-propan-1-ol | 524.2 | 0.000391 | −95.7 |
| 148 | 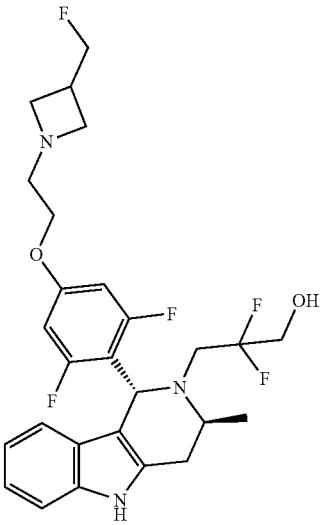 [SMILES: C[C@H]1Cc2[nH]c3ccccc3c2[C@H](c2c(F)cc(OCCN3CC(CF)C3)cc2F)N1CC(F)(F)CO] | 3-[(1R,3S)-1-[2,6-difluoro-4-[2-[3-(fluoromethyl)azetidin-1-yl]ethoxy]phenyl]-3-methyl-1,3,4,5-tetrahydropyrido[4,3-b]indol-2-yl]-2,2-difluoro-propan-1-ol | 524.2 | 0.0197 | −79 |
| 149 | 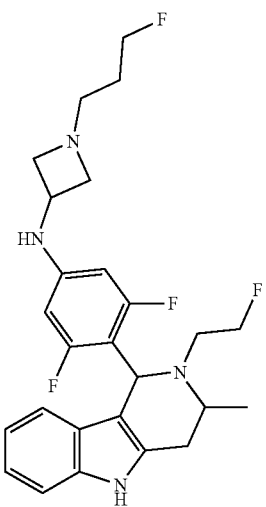 [SMILES: CC1Cc2[nH]c3ccccc3c2C(c2c(F)cc(NC3CN(CCCF)C3)cc2F)N1CCF] | (□)-N-(3,5-difluoro-4-(2-(2-fluoroethyl)-3-methyl-2,3,4,5-tetrahydro-1H-pyrido[4,3-b]indol-1-yl)phenyl)-1-(3-fluoropropyl)azetidin-3-amine | 475.2 | 0.0429 | −75 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$ (%) |
|---|---|---|---|---|---|
| 150 | 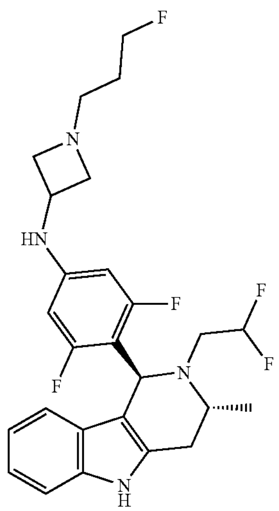 [SMILES: C[C@@H]1Cc2[nH]c3ccccc3c2[C@@H](c2c(F)cc(NC3CN(CCCF)C3)cc2F)N1CC(F)F] | N-(4-((1S,3R)-2-(2,2-difluoroethyl)-3-methyl-2,3,4,5-tetrahydro-1H-pyrido[4,3-b]indol-1-yl)-3,5-difluorophenyl)-1-(3-fluoropropyl)azetidin-3-amine | 493.2 | 0.0011 | −99.4 |
| 151 | 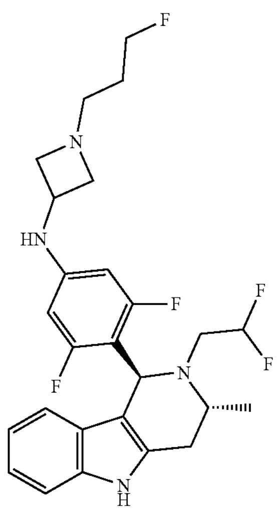 [SMILES: C[C@@H]1Cc2[nH]c3ccccc3c2[C@@H](c2c(F)cc(NC3CN(CCCF)C3)cc2F)N1CC(F)F] | N-(4-((1S,3R)-2-(2,2-difluoroethyl)-3-methyl-2,3,4,5-tetrahydro-1H-pyrido[4,3-b]indol-1-yl)-3,5-difluorophenyl)-1-(3-fluoropropyl)azetidin-3-amine | 493.2 | >0.10 | |
| 152 | 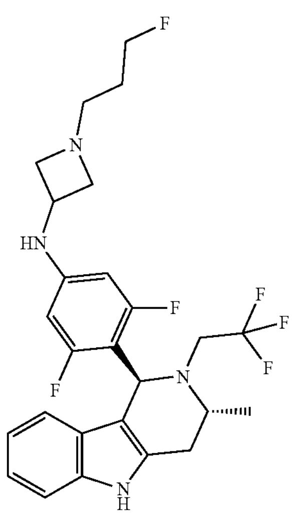 [SMILES: C[C@@H]1Cc2[nH]c3ccccc3c2[C@@H](c2c(F)cc(NC3CN(CCCF)C3)cc2F)N1CC(F)(F)F] | N-(3,5-difluoro-4-((1S,3R)-3-methyl-2-(2,2,2-trifluoroethyl)-2,3,4,5-tetrahydro-1H-pyrido[4,3-b]indol-1-yl)-phenyl)-1-(3-fluoropropyl)azetidin-3-amine | 511.2 | 0.0010 | −99 |

TABLE 1a-continued

| No. | Structure | Name | LCMS [M + H]⁺ or [M − H]⁻ | ER-alpha MCF7HCS EC$_{50}$ (μM) | ER-alpha MCF7HCS S$_{inf}$ (%) |
|---|---|---|---|---|---|
| 153 | 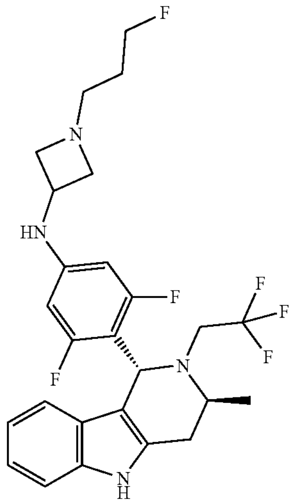 [SMILES: C[C@H]1Cc2[nH]c3ccccc3c2[C@H](c2c(F)cc(NC3CN(CCCF)C3)cc2F)N1CC(F)(F)F] | N-(3,5-difluoro-4-((1R,3S)-3-methyl-2-(2,2,2-trifluoroethyl)-2,3,4,5-tetrahydro-1H-pyrido[4,3-b]indol-1-yl)-phenyl)-1-(3-fluoropropyl)azetidin-3-amine | 511.2 | 0.00301 | −30 |
| 154 | 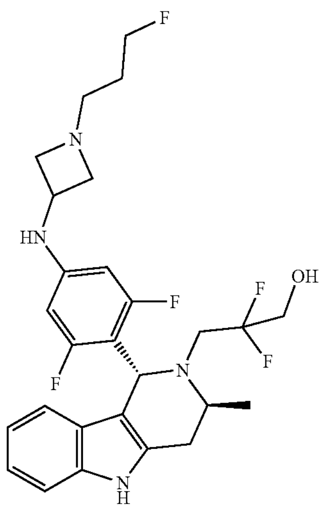 [SMILES: C[C@H]1Cc2[nH]c3ccccc3c2[C@H](c2c(F)cc(NC3CN(CCCF)C3)cc2F)N1CC(F)(F)CO] | 3-((1R,3S)-1-(2,6-difluoro-4-((1-(3-fluoropropyl)azetidin-3-yl)amino)phenyl)-3-methyl-1,3,4,5-tetrahydro-2H-pyrido[4,3-b]indol-2-yl)-2,2-difluoropropan-1-ol | 523.2 | 0.00224 | −30 |
| 155 | 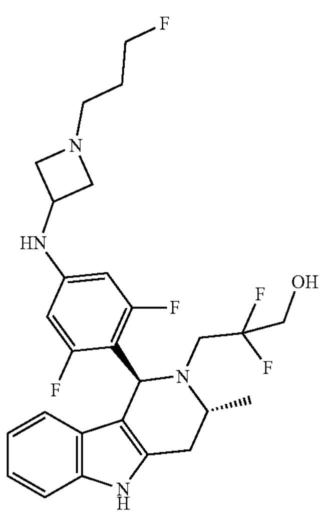 [SMILES: C[C@@H]1Cc2[nH]c3ccccc3c2[C@@H](c2c(F)cc(NC3CN(CCCF)C3)cc2F)N1CC(F)(F)CO] | 3-((1S,3R)-1-(2,6-difluoro-4-((1-(3-fluoropropyl)azetidin-3-yl)amino)phenyl)-3-methyl-1,3,4,5-tetrahydro-2H-pyrido[4,3-b]indol-2-yl)-2,2-difluoropropan-1-ol | 523.2 | 0.000214 | −97.4 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$ (%) |
|---|---|---|---|---|---|
| 156 | 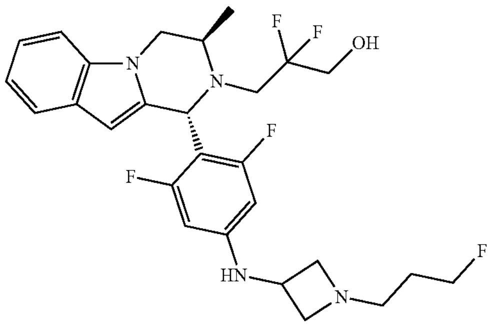 [SMILES: C[C@@H]1Cn2c(cc3ccccc32)[C@@H](c2c(F)cc(NC3CN(CCCF)C3)cc2F)N1CC(F)(F)CO] | 3-[(1R,3R)-1-(2,6-difluoro-4-((1-(3-fluoropropyl)azetidin-3-yl)amino)phenyl)-3-methyl-3,4,-dihydro-1H-pyrazino[1,2-a]indol-2-yl]-2,2-difluoro-propan-1-ol | 523.4 | | |
| 157 | 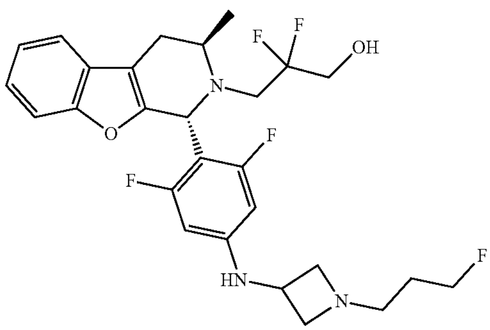 | 3-((1R,3R)-1-(2,6-Difluoro-4-((1-(3-fluoropropyl)azetidin-3-yl)amino)phenyl)-3-methyl-3,4-dihydrobenzofuro[2,3-c]pyridin-2(1H)-yl)-2,2-difluoropropan-1-ol | 524.2 | 0.000011 | −102 |
| 158 | 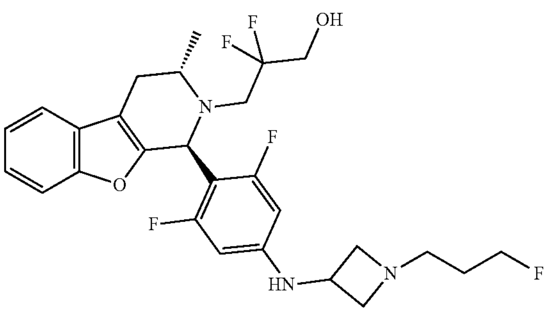 | 3-((1S,3S)-1-(2,6-Difluoro-4-((1-(3-fluoropropyl)azetidin-3-yl)amino)phenyl)-3-methyl-3,4-dihydrobenzofuro[2,3-c]pyridin-2(1H)-yl)-2,2-difluoropropan-1-ol | 524.2 | 0.00389 | −88.8 |
| 159 | 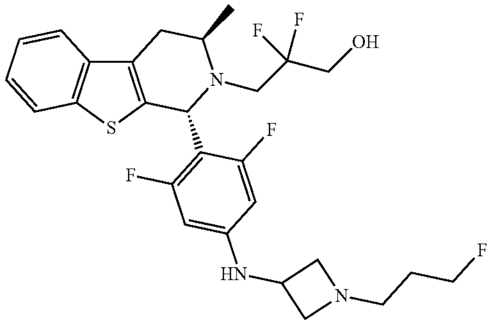 [SMILES: C[C@@H]1Cc2c(oc3ccccc23)[C@@H](c2c(F)cc(NC3CN(CCCF)C3)cc2F)N1CC(F)(F)CO] | 3-((1R,3R)-1-(2,6-difluoro-4-((1-(3-fluoropropyl)azetidin-3-yl)amino)phenyl)-3-methyl-3,4-dihydrobenzo[4,5]thieno[2,3-c]pyridin-2(1H)-yl)-2,2-difluoropropan-1-ol | 540.1 | 0.00023 | −102 |

TABLE 1a-continued

| No. | Structure | Name | LCMS [M + H]+ or [M − H]− | ER-alpha MCF7HCS EC$_{50}$ (μM) | ER-alpha MCF7HCS S$_{inf}$ (%) |
|---|---|---|---|---|---|
| 160 | 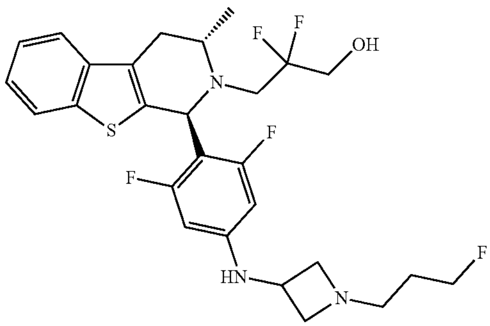 [SMILES: C[C@H]1Cc2c(sc3ccccc23)[C@H](c2c(F)cc(NC3CN(CCCF)C3)cc2F)N1CC(F)(F)CO] | 3-((1S,3S)-1-(2,6-difluoro-4-((1-(3-fluoropropyl)azetidin-3-yl)amino)phenyl)-3-methyl-3,4-dihydrobenzo[4,5]thieno[2,3-c]pyridin-2(1H)-yl)-2,2-difluoropropan-1-ol | 540.1 | 0.0131 | −96.9 |

TABLE 1b

| No. | Structure | IUPAC Name | ERalpha (WT) MCF7HCS (EC50) (μMol) | ERalpha (WT) MCF7HCS (Sinf) | Mass Spec. [M + H]+ |
|---|---|---|---|---|---|
| 161 | 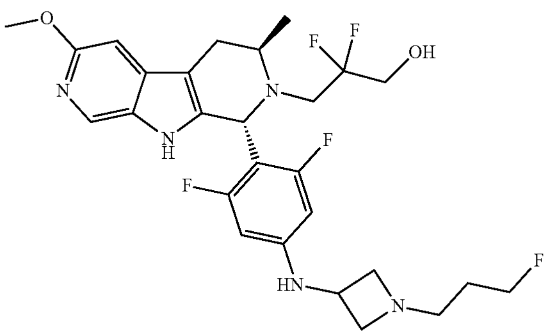 [SMILES: COc1cc2c3c([nH]c2cn1)[C@@H](c1c(F)cc(NC2CN(CCCF)C2)cc1F)N(CC(F)(F)CO)[C@H](C)C3] | 3-((1R,3R)-1-(2,6-Difluoro-4-((1-(3-fluoropropyl)azetidin-3-yl)amino)phenyl)-6-methoxy-3-methyl-3,4-dihydro-1H-pyrrolo[2,3-c:5,4-c']dipyridin-2(9H)-yl)-2,2-difluoropropan-1-ol | 0.00113 | −97.3 | 554.2 |
| 162 | 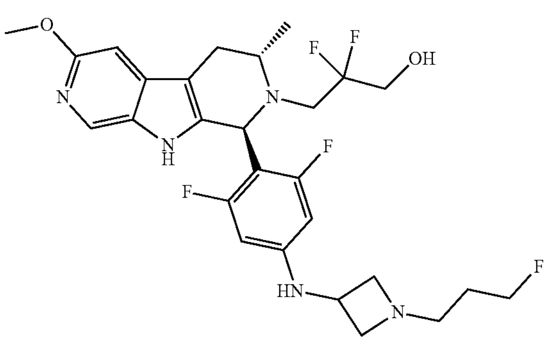 [SMILES: COc1cc2c3c([nH]c2cn1)[C@H](c1c(F)cc(NC2CN(CCCF)C2)cc1F)N(CC(F)(F)CO)[C@@H](C)C3] | 3-((1S,3S)-1-(2,6-Difluoro-4-((1-(3-fluoropropyl)azetidin-3-yl)amino)phenyl)-6-methoxy-3-methyl-3,4-dihydro-1H-pyrrolo[2,3-c:5,4-c']dipyridin-2(9H)-yl)-2,2-difluoropropan-1-ol | >0.10 | | 554.2 |

TABLE 1b-continued

| No. | Structure | IUPAC Name | ERalpha (WT) MCF7HCS (EC50) (μMol) | ERalpha (WT) MCF7HCS (Sinf) | Mass Spec. [M + H]+ |
|---|---|---|---|---|---|
| 163 | 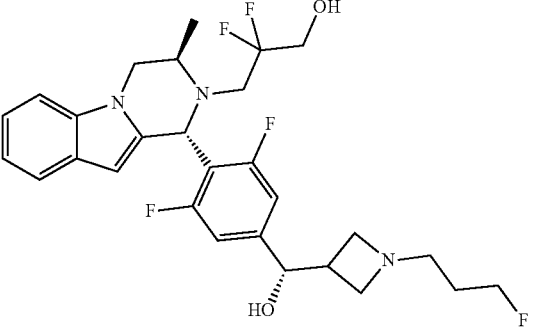 [SMILES: C[C@@H]1Cn2c(cc3ccccc32)[C@@H](c2c(F)cc([C@@H](O)C3CN(CCCF)C3)cc2F)N1CC(F)(F)CO] | 3-[(1R,3R)-1-[2,6-difluoro-4-[(S)-[1-(3-fluoropropyl)azetidin-3-yl]-hydroxy-methyl]phenyl]-3-methyl-3,4-dihydro-1H-pyrazino[1,2-a]indol-2-yl]-2,2-difluoro-propan-1-ol | 0.000032 | −100 | 538.2 |
| 164 | 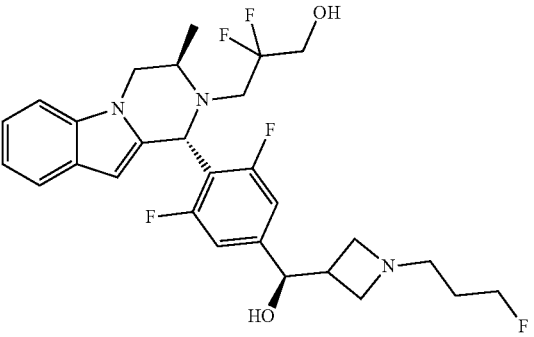 [SMILES: C[C@@H]1Cn2c(cc3ccccc32)[C@@H](c2c(F)cc([C@H](O)C3CN(CCCF)C3)cc2F)N1CC(F)(F)CO] | 3-[(1R,3R)-1-[2,6-difluoro-4-[(R)-[1-(3-fluoropropyl)azetidin-3-yl]-hydroxy-methyl]phenyl]-3-methyl-3,4-dihydro-1H-pyrazino[1,2-a]indol-2-yl]-2,2-difluoro-propan-1-ol | 0.000056 | −98.6 | 538.2 |
| 165 | 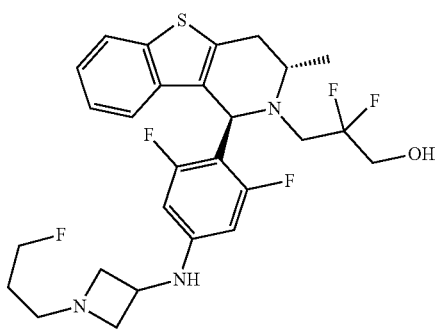 [SMILES: C[C@H]1Cc2sc3ccccc3c2[C@H](c2c(F)cc(NC3CN(CCCF)C3)cc2F)N1CC(F)(F)CO] | 3-((1S,3S)-1-(2,6-difluoro-4-((1-(3-fluoropropyl)azetidin-3-yl)amino)phenyl)-3-methyl-3,4-dihydrobenzo[4,5]thieno[3,2-c]pyridin-2(1H)-yl)-2,2-difluoropropan-1-ol | 0.00794 | −92.3 | 540.2 |
| 166 | 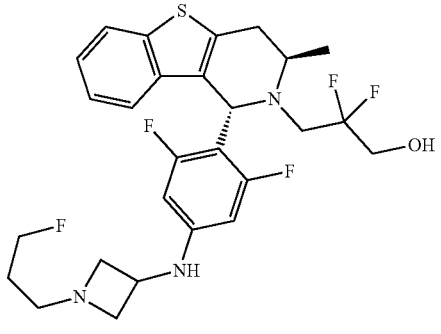 [SMILES: C[C@@H]1Cc2sc3ccccc3c2[C@@H](c2c(F)cc(NC3CN(CCCF)C3)cc2F)N1CC(F)(F)CO] | 3-((1R,3R)-1-(2,6-difluoro-4-((1-(3-fluoropropyl)azetidin-3-yl)amino)phenyl)-3-methyl-3,4-dihydrobenzo[4,5]thieno[3,2-c]pyridin-2(1H)-yl)-2,2-difluoropropan-1-ol | 0.000041 | −101 | 540.2 |

TABLE 1b-continued

| No. | Structure | IUPAC Name | ERalpha (WT) MCF7HCS (EC50) (μMol) | ERalpha (WT) MCF7HCS (Sinf) | Mass Spec. [M + H]+ |
|---|---|---|---|---|---|
| 167 | 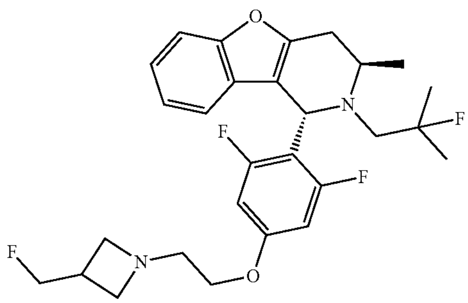 [SMILES: C[C@@H]1Cc2oc3ccccc3c2[C@@H](c2c(F)cc(OCCN3CC(CF)C3)cc2F)N1CC(C)(C)F] | 1-(2,6-difluoro-4-(2-(3-(fluoromethyl)azetidin-1-yl)ethoxy)phenyl)-2-(2-fluoro-2-methylpropyl)-3-methyl-1,2,3,4-tetrahydrobenzofuro[3,2-c]pyridine | 0.00017 | −96 | 505.2 |
| 168 | 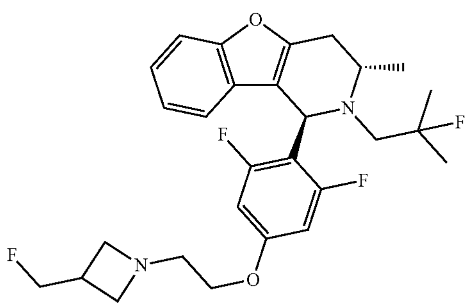 [SMILES: C[C@H]1Cc2oc3ccccc3c2[C@H](c2c(F)cc(OCCN3CC(CF)C3)cc2F)N1CC(C)(C)F] | 1-(2,6-difluoro-4-(2-(3-(fluoromethyl)azetidin-1-yl)ethoxy)phenyl)-2-(2-fluoro-2-methylpropyl)-3-methyl-1,2,3,4-tetrahydrobenzofuro[3,2-c]pyridine | 0.00275 | −97 | 505.2 |
| 169 | 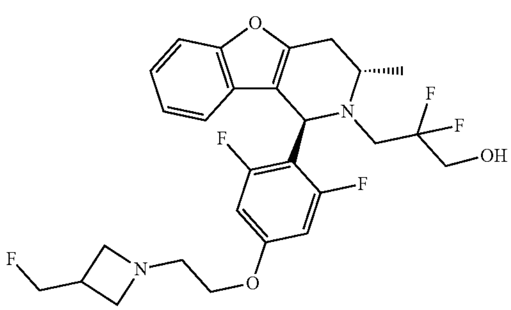 [SMILES: C[C@H]1Cc2oc3ccccc3c2[C@H](c2c(F)cc(OCCN3CC(CF)C3)cc2F)N1CC(F)(F)CO] | 3-(1(2,6-difluoro-4-(2-(3-(fluoromethyl)azetidin-1-yl)ethoxy)phenyl)-3-methyl-3,4-dihydrobenzofuro[3,2-c]pyridin-2(1H)-yl)-2,2-difluoropropan-1-ol | >0.1 | | 525.2 |
| 170 | 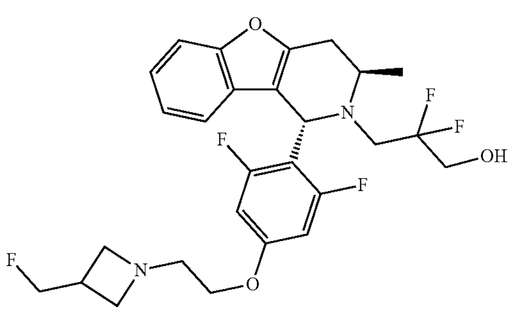 [SMILES: C[C@@H]1Cc2oc3ccccc3c2[C@@H](c2c(F)cc(OCCN3CC(CF)C3)cc2F)N1CC(F)(F)CO] | 1-(2,6-difluoro-4-(2-(3-(fluoromethyl)azetidin-1-yl)ethoxy)phenyl)-2-(2-fluoro-2-methylpropyl)-3-methyl-1,2,3,4-tetrahydrobenzofuro[3,2-c]pyridine | 0.000045 | −93 | 525.2 |

Administration of Formula I, II, and III Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I, II, or III compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I, II, and III Compounds

Formula I, II, and III compounds of the present invention are useful for treating a human or animal patient suffering from a disease or disorder arising from abnormal cell growth, function or behavior associated with USP7 such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I, II, and III having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I, II, and III may be prepared. Suitable examples of sustained-release preparations include semipermeable matrices of solid hydrophobic polymers containing a compound of Formula I, II, and III, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(-)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I, II, and III suitable for oral administration may be prepared as discrete units such as pills, capsules, cachets or tablets each containing a predetermined amount of a compound of Formula I, II, and III. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I, II, and III intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I, II, and III compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I, II, and III may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I, II, and III may be employed alone or in combination with additional therapeutic agents for the treatment of a disease or disorder described herein, such as inflammation or a hyperproliferative disorder (e.g., cancer). In certain embodiments, a compound of Formula I, II, and III is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, a PI3K inhibitor, an mTOR inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I, II, and III such that they do not adversely affect each other. Such compounds are suitably present in combination in amounts that are effective for the purpose intended. In one embodiment, a composition of this invention comprises a compound of Formula I, II, and III, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, II, and III, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, II, and III, or a stereoisomer, tautomer, solvate, metabolite, or pharmaceutically acceptable salt or prodrug thereof, and the use of at least one other cancer treatment method. The amounts of the compound(s) of Formula I, II, and III and the other pharmaceutically active therapeutic agent(s) and the relative timings of administration will be selected in order to achieve the desired combined therapeutic effect.

In some embodiments, a compound of Formula I, II, and III, or a pharmaceutically acceptable salt thereof, is used in combination with an aromatase inhibitor, a phosphoinositide 3-kinase (PI3K)/mTOR pathway inhibitor, a CDK 4/6 inhibitor, a HER-2 inhibitor, an EGFR inhibitor, a PD-1 inhibitor, poly ADP-ribose polymerase (PARP) inhibitor, a histone deacetylase (HDAC) inhibitor, an HSP90 inhibitor, a VEGFR inhibitor, an AKT inhibitor, chemotherapy, or any combination thereof.

In some embodiments, a pharmaceutical composition comprising a compound of Formula I, II, and III, or a pharmaceutically acceptable salt thereof, is administered in combination with a therapeutic agent selected from paclitaxel, anastrozole, exemestane, cyclophosphamide, epirubicin, fulvestrant, letrozole, palbociclib, gemcitabine, trastuzumab (HERCEPTIN®, Genentech), trastuzumab emtansine (KADCYLA®, Genentech), pegfilgrastim, filgrastim, tamoxifen, docetaxel, toremifene, vinorelbine, capecitabine, and ixabepilone.

In some embodiments, a compound of Formula I, II, and III, or a pharmaceutically acceptable salt thereof, is used in combination with hormone blocking therapy, chemotherapy, radiation therapy, monoclonal antibodies, or combinations thereof.

Hormone blocking therapy includes the use of agents that block the production of estrogens or block the estrogen receptors. In some embodiments, hormone blocking therapy includes the use of estrogen receptor modulators and/or aromatase inhibitors. Estrogen receptor modulators include triphenylethylene derivatives (e.g. tamoxifen, toremifene, droloxifene, 3-hydroxytamoxifen, idoxifene, TAT-59 (a phosphorylated derivative of 4-hydroxytamoxifen) and GW5638 (a carboxylic acid derivative of tamoxifen)); non-steroidal estrogen receptor modulators (e.g. raloxifene, LY353381 (SERM3) and LY357489); steroidal estrogen receptor modulators (e.g. ICI-182,780). Aromatase inhibitors include steroidal aromatase inhibitors and non-steroidal aromatase inhibitors. Steroidal aromatase inhibitors include, but are not limited to, such exemestane. Non-steroidal aromatase inhibitors include, but are not limited to, as anastrozole, and letrozole.

In some embodiments, a compound of Formula I, II, and III, or a pharmaceutically acceptable salt thereof, is administered in combination with a CDK 4/6 inhibitor. In some embodiments, the CDK 4/6 inhibitor is palbociclib (IBRANCE®, PD-0332991, Pfizer), ribociclib (LEE011) or LY283519. In some embodiments, the CDK 4/6 inhibitor is LEE011. In some embodiments, ribociclib (LEE011) is administered at a dose of about 10 mg per day to about 1000 mg per day. In some embodiments, LEE011 is administered at a dose of about 400 mg per day, about 500 mg per day or about 600 mg per day. In some embodiments, the daily dose of LEE011 is orally administered. In some embodiments, the daily dose of ribociclib (LEE011) is orally administered once a day for three weeks followed by a one week drug holiday where ribociclib (LEE011) is not administered.

In some embodiments, a compound of Formula I, II, and III, or a pharmaceutically acceptable salt thereof, is administered in combination with a phosphoinositide 3-kinase (PI3K)/mTOR pathway inhibitor. In some embodiments, the a phosphoinositide 3-kinase (PI3K)/mTOR pathway inhibitor is everolimus, temsirolimus, BEZ235 (dactolisib), BYL719 (alpelisib), GDC0032 (taselisib), BKM120 (buparlisib), BGT226, GDC0068 (ipatasertib), GDC-0980 (apitolisib), GDC0941 (pictilisib), INK128 (MLN0128), INK1117, OSI-027, CC-223, AZD8055, SAR245408, SAR245409, PF04691502, WYE125132, GSK2126458, GSK-2636771, BAY806946, PF-05212384, SF1126, PX866, AMG319, ZSTK474, Cal101 (idelalisib), PWT33597, CU-906, AZD-2014 or CUDC-907. In some embodiments, the phosphoinositide 3-kinase (PI3K)/mTOR pathway inhibitor is everolimus. In some embodiments, everolimus is administered at a dose of about 1 mg per day to about 20 mg per day. In some embodiments, everolimus is administered at a dose of about 2.5 mg per day, about 5 mg per day, or about 10 mg per day. In some embodiments, the daily dose of everolimus is administered once a day. In some embodiments, the phosphoinositide 3-kinase (PI3K)/mTOR pathway inhibitor is BKM120 (buparlisib). In some embodiments, BKM120 (buparlisib) is administered at a dose of about 5 mg per day to about 500 mg per day. In some embodiments, BKM120 is administered at a dose of about 50 mg per day to about 100 mg per day. In some embodiments, BKM120 is administered at a dose of about 100 mg per day. In some embodiments, the daily dose of BKM120 is administered once a day. In some embodiments, the phosphoinositide 3-kinase (PI3K)/mTOR pathway inhibitor is BYL719. In some embodiments, BYL719 is administered at a dose of about 25 mg per day to about 1000 mg per day. In some embodiments, BYL719 is administered at a dose of about 250 mg per day or about 350 mg per day. In some embodiments, the daily dose of BYL719 is administered once a day.

Metabolites of Compounds of Formula I, II, and III

Also falling within the scope of this invention are the in vivo metabolic products of Formula I, II, and III described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, II, and III, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, II, and III, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I, II, and III or a formulation thereof which is effective for treating the condition and may have a sterile access port (for example, the container may be an intravenous solution bag or a vial having a stopper pierceable by a hypodermic injection needle). At least one active agent in the composition is a compound of Formula I, II, and III. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I, II, and III can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I, II, and III and, if present, the second pharmaceutical formulation. For example, if the kit comprises a first composition comprising a compound of Formula I, II, and III and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, II, and III, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I, II, and III contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I, II, and III and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I, II, and III Compounds

Compounds of Formula I, II, and III may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I, II, and III compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I, II, and III may be prepared singly or as compound libraries comprising at least 2, for example 5 to 1,000 compounds, or 10 to 100 compounds. Libraries of compounds of Formula I, II, and III may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Examples provide exemplary methods for preparing Formula I, II, and III compounds. Those skilled in the art will appreciate that other synthetic routes may be used to synthesize the Formula I, II, and III compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing Formula I, II, and III compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, β-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Formula I, II, and III compounds can be prepared by the General Procedures of Schemes 1-8, where R groups are as described in Formulas I, II, and III, or precursors thereof.

Scheme 1

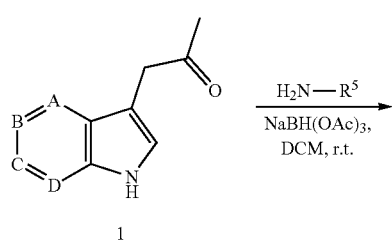

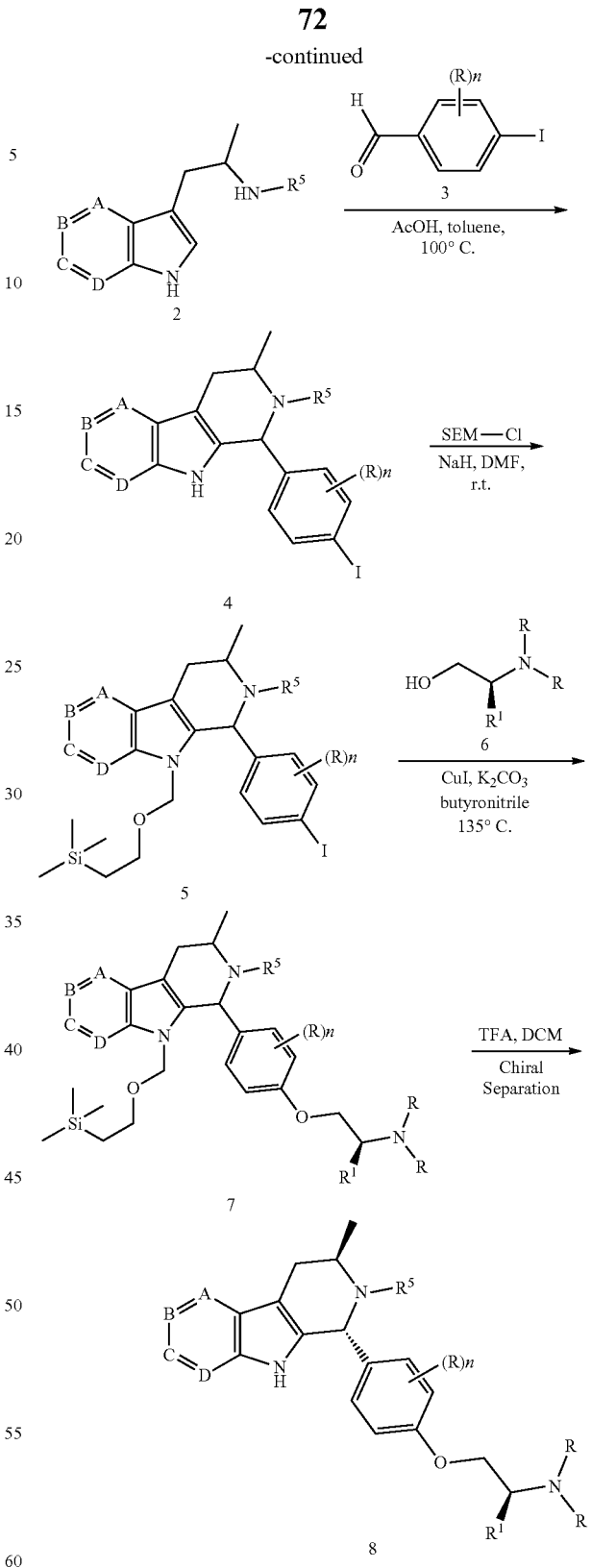

A, B, C, D = carbon or nitrogen

A general synthesis of compound 8 is shown is Scheme 1. A methyl ketone 1 was converted to 2 through reductive amination. Pictet-Spengler cyclization of 2 with a para-iodo, benzaldehyde 3 afforded cyclized intermediate 4. Protection of the indole NH in intermediate 4, followed by Ullmann coupling with an alcohol 6 provided 7. Deprotection and then chiral separation afforded 8.

Spengler cyclization gave 13. Subsequent Ullmann coupling of 13 with an alcohol 6 afforded 14.

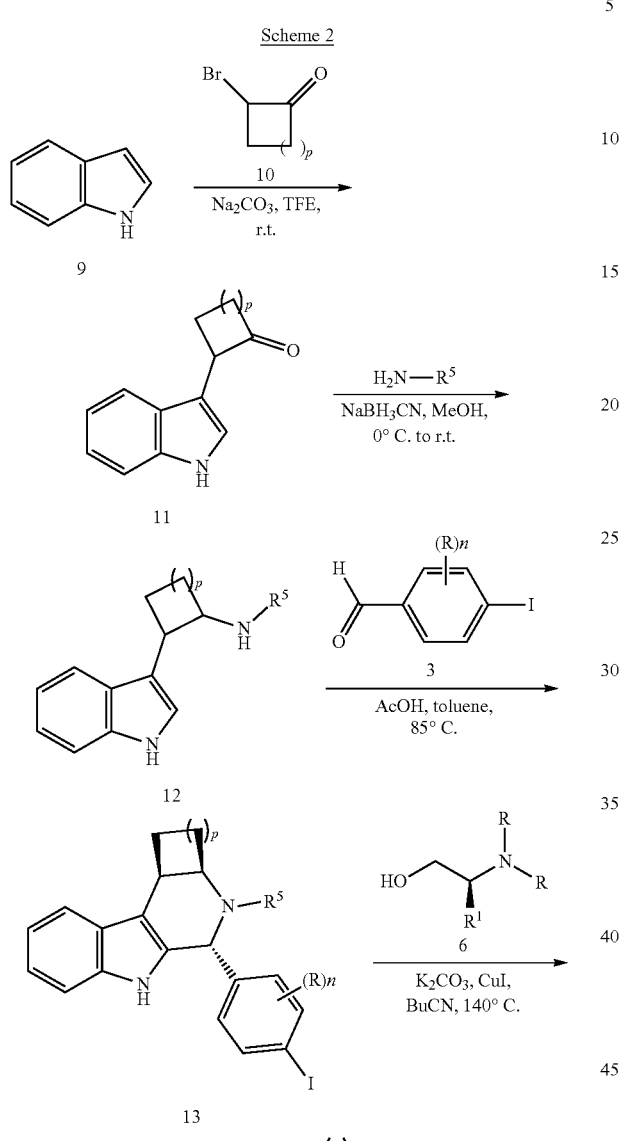

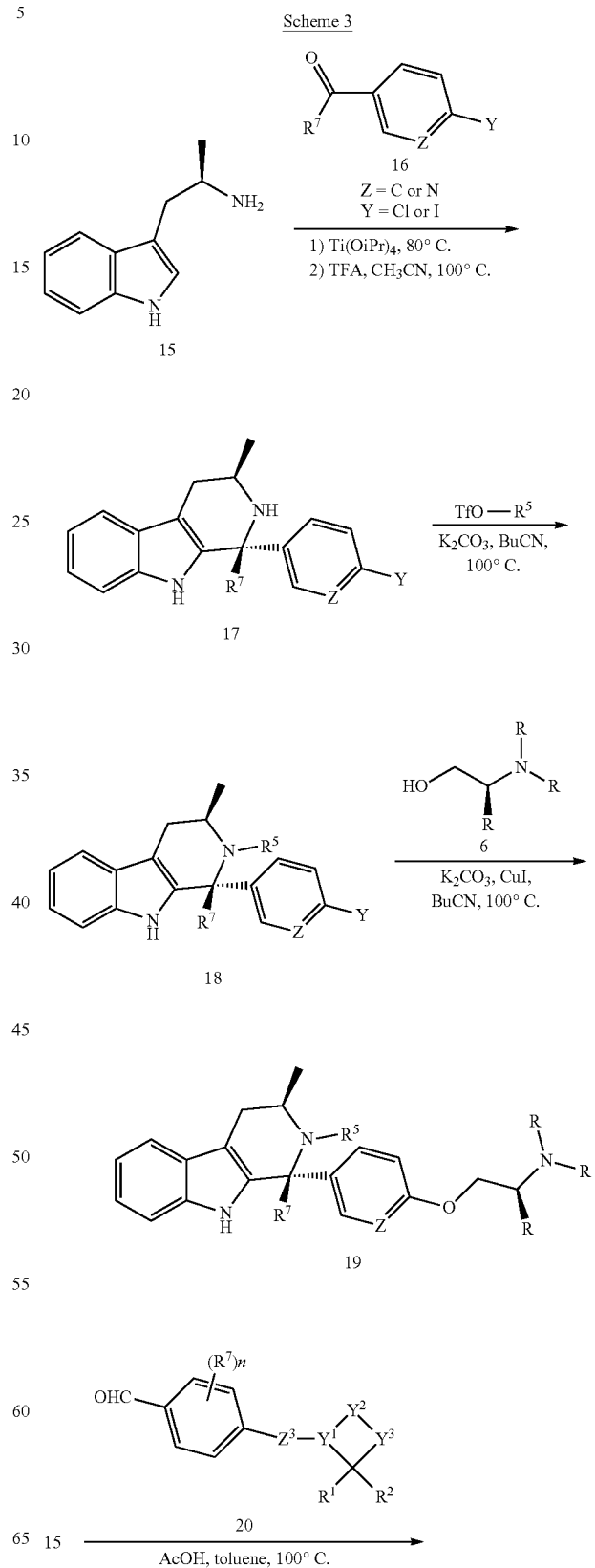

Synthesis of compound 14 is summarized in Scheme 2. Reaction of indole 9 with a cyclic alpha-Br ketone 10 led to compound 11. Reductive amination, followed by Pictet-

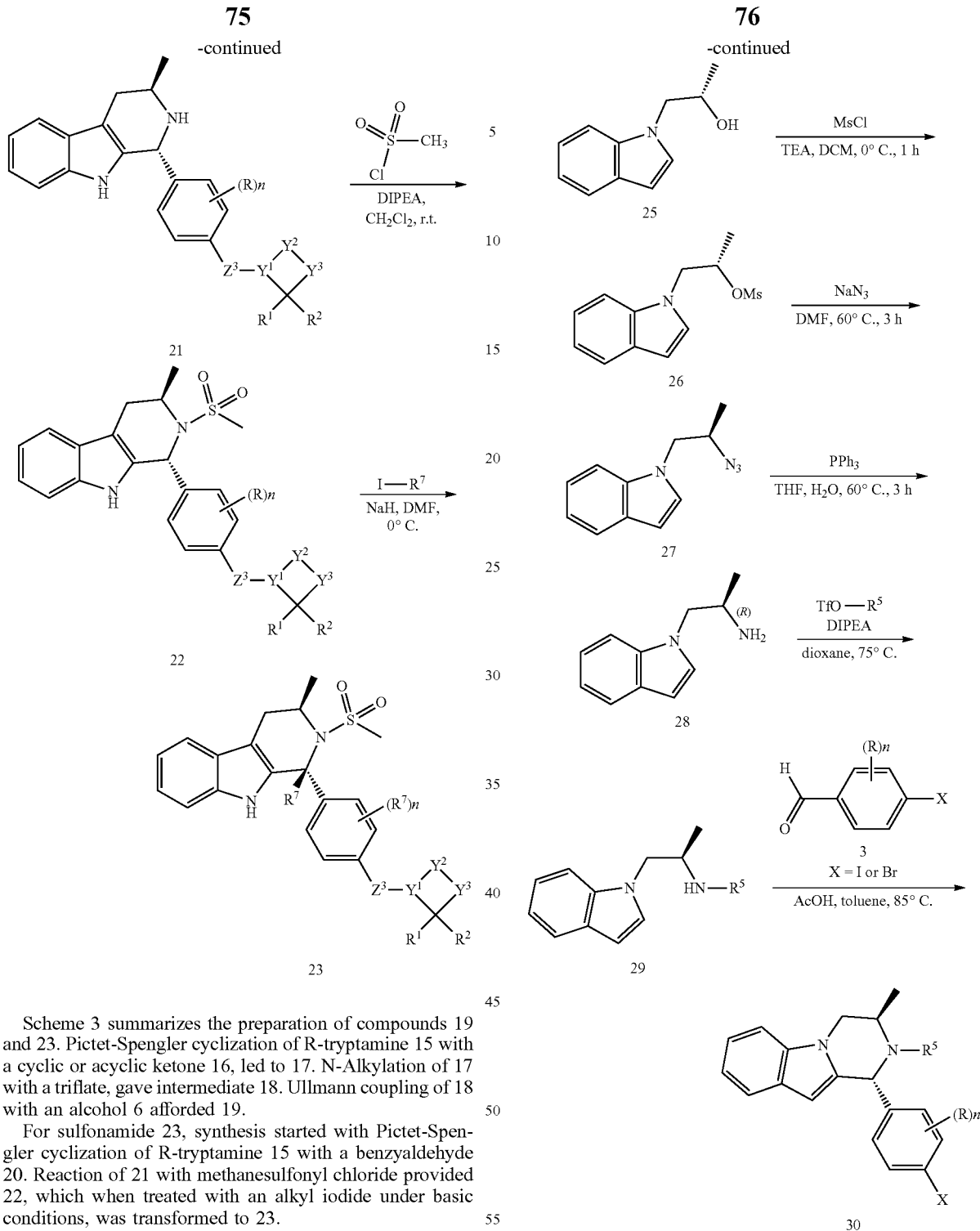

Scheme 3 summarizes the preparation of compounds 19 and 23. Pictet-Spengler cyclization of R-tryptamine 15 with a cyclic or acyclic ketone 16, led to 17. N-Alkylation of 17 with a triflate, gave intermediate 18. Ullmann coupling of 18 with an alcohol 6 afforded 19.

For sulfonamide 23, synthesis started with Pictet-Spengler cyclization of R-tryptamine 15 with a benzyaldehyde 20. Reaction of 21 with methanesulfonyl chloride provided 22, which when treated with an alkyl iodide under basic conditions, was transformed to 23.

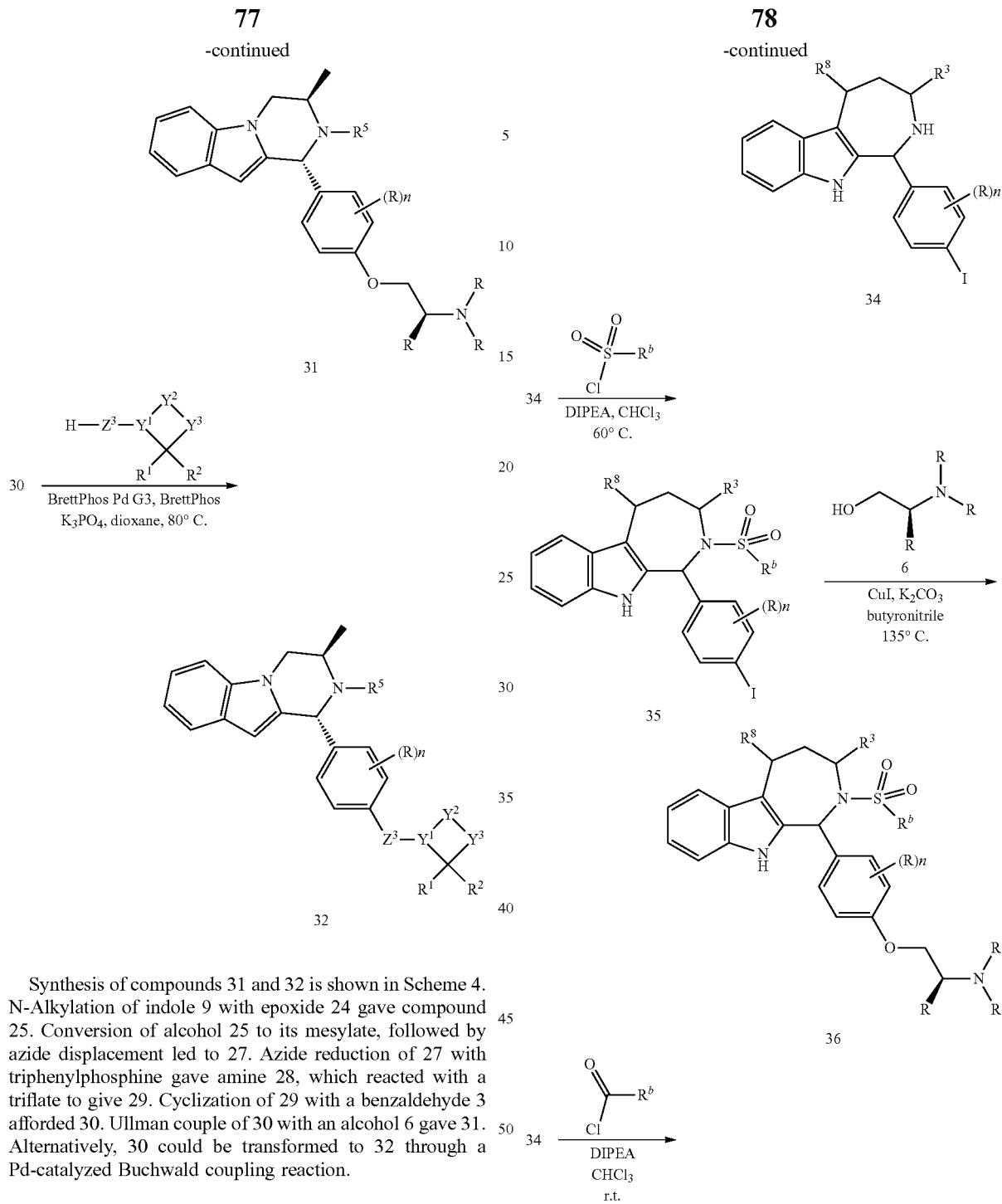

Synthesis of compounds 31 and 32 is shown in Scheme 4. N-Alkylation of indole 9 with epoxide 24 gave compound 25. Conversion of alcohol 25 to its mesylate, followed by azide displacement led to 27. Azide reduction of 27 with triphenylphosphine gave amine 28, which reacted with a triflate to give 29. Cyclization of 29 with a benzaldehyde 3 afforded 30. Ullman couple of 30 with an alcohol 6 gave 31. Alternatively, 30 could be transformed to 32 through a Pd-catalyzed Buchwald coupling reaction.

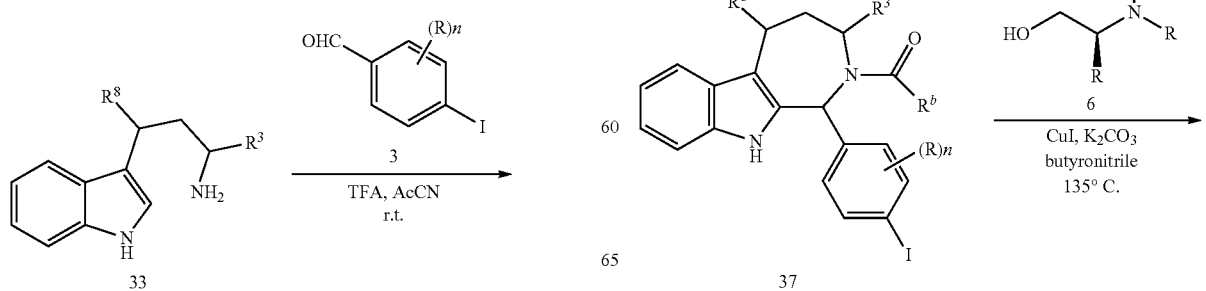

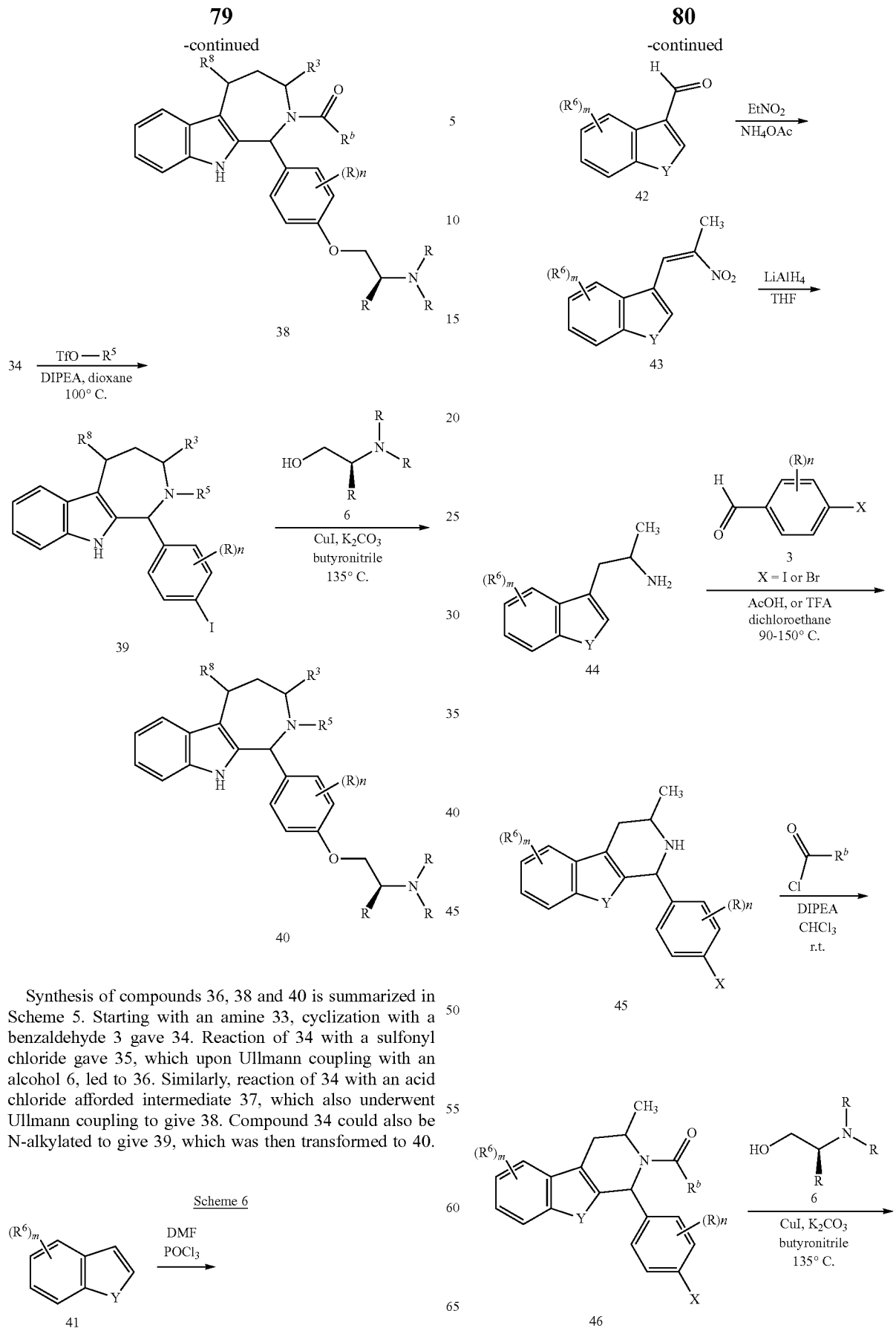

Synthesis of compounds 36, 38 and 40 is summarized in Scheme 5. Starting with an amine 33, cyclization with a benzaldehyde 3 gave 34. Reaction of 34 with a sulfonyl chloride gave 35, which upon Ullmann coupling with an alcohol 6, led to 36. Similarly, reaction of 34 with an acid chloride afforded intermediate 37, which also underwent Ullmann coupling to give 38. Compound 34 could also be N-alkylated to give 39, which was then transformed to 40.

led to 47. Alternatively, amine 44 could be N-alkylated with a triflate to provide 48. Cyclization of 48 with a benzaldehyde 3 afforded 49, which was subsequently converted to 50.

Scheme 7

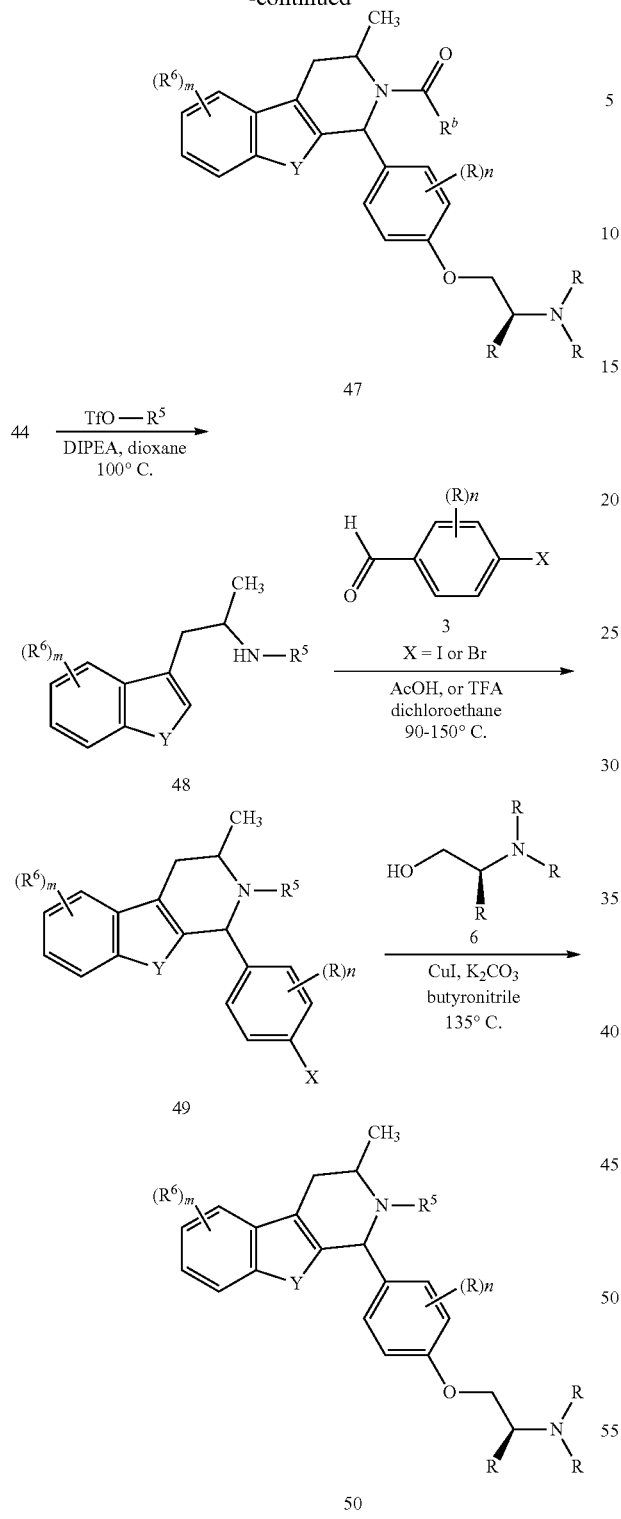
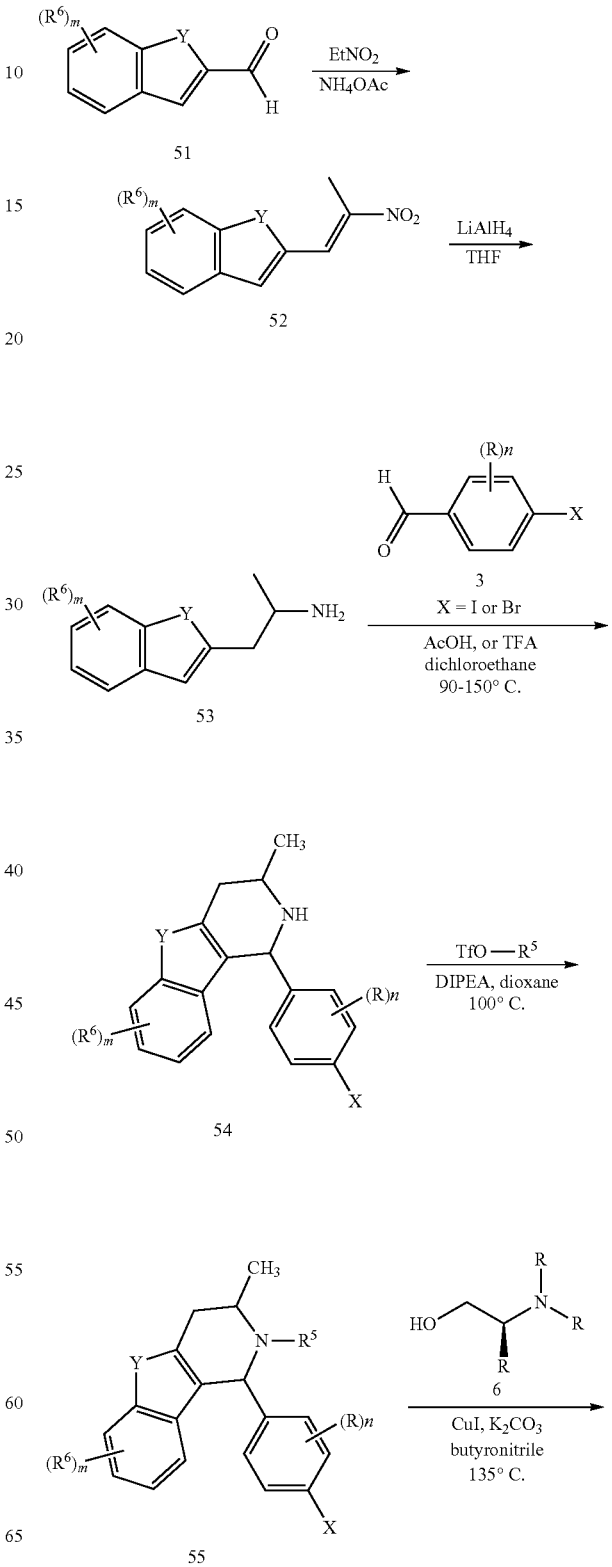

Y = O or S

Synthesis of amide 47 and 50 is summarized in Scheme 6. Vilsmeier reaction of a benzofuran (Y=O) or benzothiophene (Y=S) led to aldehyde 42. Aldol condensation of 42 with nitroethane afforded 43, which was reduced to an amine 44. Cyclization of 44 with a benzaldehyde 3 led to 45. Amide coupling, followed by Ullmann coupling reaction,

83

-continued

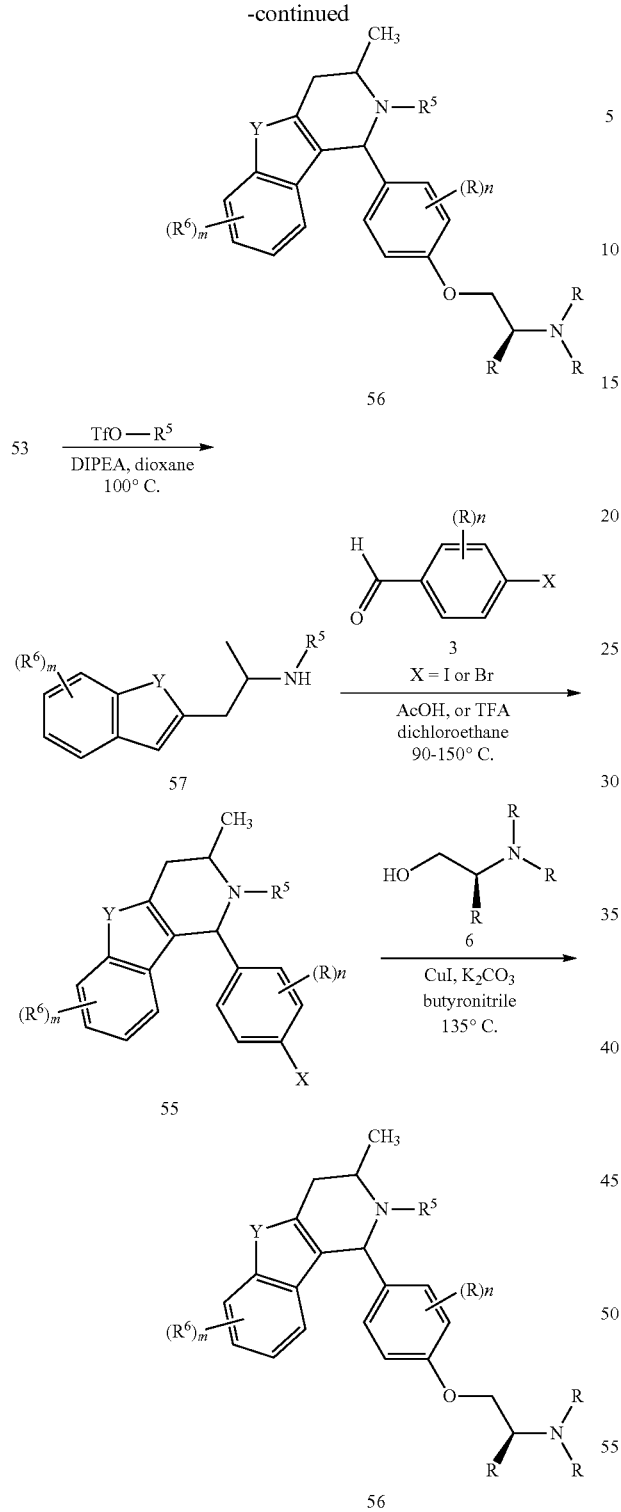

Y = S, NH

Synthesis of 56 is summarized in Scheme 7. Aldol condensation of aldehyde 51 with nitroethane provided intermediate 52, which was reduced to give 53. Reaction of 53 with a benzaldehyde 3 led to 54. N-alkylation, followed by Ullmann coupling reaction, led to 56. Alternatively, amine 53 could be N-alkylated with a triflate. Cyclization of 57

84 with a benzaldehyde 3 afforded 55, which was subsequently converted to 56 through Ullman coupling reaction with an alcohol 6.

Scheme 8

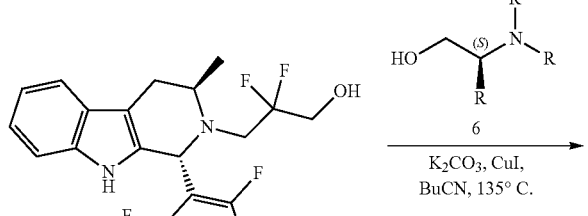

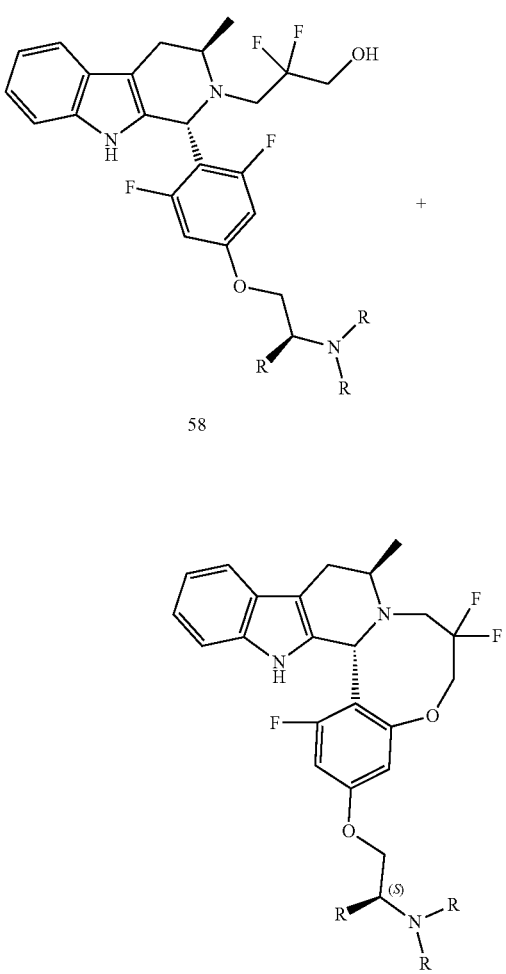

Synthesis of 59 is shown in Scheme 8. During Ullman coupling reaction of a bromide 57 with an alcohol 6, compound 59 was produced, together with 58.

EXAMPLES

Example 101 1-((1R,3R)-1-(2,6-difluoro-4-(2-(3-(fluoromethyl)azetidin-1-yl)ethoxy)phenyl)-3-methyl-3,4-dihydrobenzofuro[2,3-c]pyridin-2(1H)-yl)-2-methylpropan-1-one 101

Step 1: 3-(2-nitroprop-1-en-1-yl)benzofuran

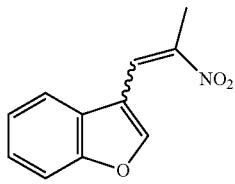

A mixture of benzofuran-3-carbaldehyde (0.973 g, 6.32 mmol) and ammonium acetate (268 mg, 3.48 mmol) in 1-nitroethane (19 mL) was heated at 100° C. for 3 hrs. At the end of reaction, the mixture was concentrated and the resulting residue was purified with flash column chromatography (0-30% iPrOAc/heptane). The product was crystallized from cyclopentyl methyl ether and heptane in two crops to give desired product as a tan to brown powder (0.814 g, yield 63%). $^1$H NMR (400 MHz, CDCl$_3$) δ 8.19 (s, 1H), 7.89 (s, 1H), 7.71 (d, J=7.6 Hz, 1H), 7.57 (d, J=8.0 Hz, 1H), 7.46-7.34 (m, 2H), 2.51 (s, 3H).

Step 2: 1-(benzofuran-3-yl)propan-2-amine

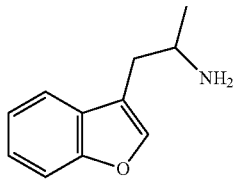

To a solution of lithium aluminum hydride in THF (2.4 M, 6.7 mL, 16 mmol) at 0° C. (icebath) was added a solution of 3-[(Z)-2-nitroprop-1-enyl]benzofuran (0.812 g, 4.00 mmol) in THF (5.0 mL) dropwise. The mixture was stirred at room temperature for 20 hrs. The reaction was then cooled with ice-bath, the mixture was carefully quenched with water (0.61 mL), 15% NaOH (0.61 mL), and water (1.8 mL). The solid was filtered off and the filter cake was washed with THF (4×). The combined filtrate was concentrated to give crude product which was used in the next step without further purification. $^1$H NMR (400 MHz, CDCl3) δ 7.57 (d, J=7.6 Hz, 1H), 7.50-7.45 (m, 2H), 7.35-7.20 (m, 2H), 3.41-3.23 (m, 1H), 2.80-2.76 (m, 1H), 2.65-2.59 (m, 1H), 1.18 (d, J=6.0 Hz, 3H).

Step 3: 1-(2,6-difluoro-4-iodophenyl)-3-methyl-1,2,3,4-tetrahydrobenzofuro[2,3-c]pyridine

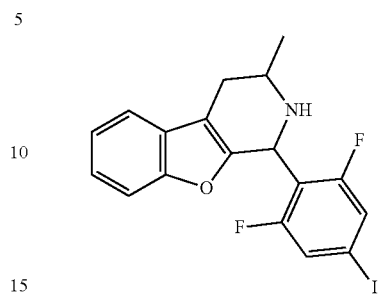

A mixture of 1-(benzofuran-3-yl)propan-2-amine (82.5 mg, 0.471 mmol), 2,6-difluoro-4-iodobenzaldehyde (129 mg, 0.471 mmol), and trifluoroacetic acid (0.0676 mL, 0.895 mmol) in 1,2-dichloroethane (2.82 mL, 35.8 mmol) was heated in a microwave at 120° C. for 0.5 hr. The reaction mixture was diluted with DCM and poured into a dilute Na$_2$CO$_3$ solution. The aqueous layer was extracted with DCM (2×). The combined DCM solutions were dried (Na$_2$SO$_4$) and concentrated. The crude product was purified with flash column chromatography (0-25% iPrOAc/heptane with 2.5% triethylamine) to yield the title product (119 mg, yield 59%).

Step 4: 1-(1-(2,6-difluoro-4-iodophenyl)-3-methyl-3,4-dihydrobenzofuro[2,3-c]pyridin-2(1H)-yl)-2-methylpropan-1-one

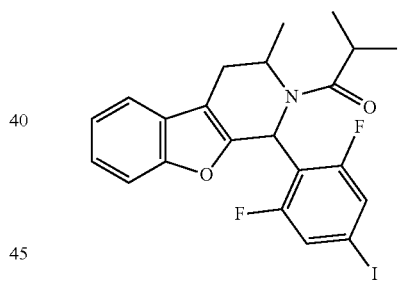

To a solution of 1-(2,6-difluoro-4-iodo-phenyl)-3-methyl-1,2,3,4-tetrahydrobenzothiopheno[2,3-c]pyridine (119 mg, 0.28 mmol) in DCM (1.4 mL) at 0° C. was added DIPEA (0.244 mL, 1.4 mmol), followed by isobutyryl chloride (0.18 mL, 0.70 mmol). The mixture was stirred at room temperature for 2 hrs and neutralized with a dilute NaHCO$_3$ solution. The aqueous layer was extracted with DCM (2×). The combined DCM solutions were dried (Na$_2$SO$_4$) and concentrated. The crude product was purified with flash column chromatography (0-20% iPrOAc/heptane) to yield a mixture both cis and trans-diastereoisomers (81 mg, yield 58%).

Step 5: 101

A mixture of 1-[1-(2,6-difluoro-4-iodo-phenyl)-3-methyl-3,4-dihydro-1H-benzofuro[2,3-c]pyridin-2-yl]-2-methyl-propan-1-one (81 mg, 0.16 mmol), 2-[3-(fluoromethyl)azetidin-1-yl]ethanol (44 mg, 0.33 mmol), CuI (16 mg, 0.082 mmol) and K$_2$CO$_3$ (68 mg, 0.49 mmol) in butyronitrile (0.98 mL) was heated under N$_2$ at 140° C. for 24 hrs. The reaction mixture was cooled to room temperature, diluted with EtOAc. The reaction mixture was filtered. The filtrate was concentrated to give crude product which was purified with by HPLC, followed by chiral SFC separation. Chiralpak OX (150×21.2 mm), 20% isocratic 0.1% NH$_4$OH in methanol at 70 mL/min, UV-220 nm, temp 40° C., cycle time 5.5 min to give 101, as the second eluting peak of 4 peaks (5.1 mg, yield 6.2%). $^1$H NMR (400 MHz, DMSO-d$_6$) δ 7.64-7.57 (m, 1H), 7.52-7.46 (m, 1H), 7.30-7.22 (m, 2H), 6.57 (d, J=11.8 Hz, 2H), 6.06 (s, 1H), 4.84 (s, 1H), 4.54 (d, J=6.3 Hz, 1H), 4.42 (d, J=6.2 Hz, 1H), 3.95-3.82 (m, 2H), 3.17-3.09 (m, 1H), 3.08-2.92 (m, 3H), 2.84 (d, J=15.7 Hz, 1H), 2.77-2.62 (m, 3H), 1.17 (d, J=6.5 Hz, 3H), 1.03-0.91 (m, 6H). LCMS: 501.2 [M+H]$^+$.

Example 102 1-((1,3-trans)-1-(2,6-difluoro-4-(2-(3-(fluoromethyl)azetidin-1-yl)ethoxy)phenyl)-3-methyl-3,4-dihydrobenzo[4,5]thieno[2,3-c]pyridin-2(1H)-yl)-2-methylpropan-1-one 102

Step 1: 3-(2-nitroprop-1-en-1-yl)benzo[b]thiophene

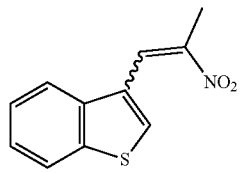

A mixture of benzothiophene-3-carbaldehyde (1.00 g, 6.16 mmol) and ammonium acetate (261 mg, 3.39 mmol) in 1-nitroethane (18.5 mL) was heated at 100° C. for 3 hrs. After concentration, the residue was crystallized from cyclopentyl methyl ether and heptane in two crops to give the title compound as yellow to brownish powder (0.925 g, yield 68.4%). $^1$H NMR (400 MHz, CDCl$_3$) δ 8.35 (s, 1H), 7.94-7.90 (m, 2H), 7.68 (s, 1H), 7.52-7.44 (m, 2H), 2.55 (s, 3H).

Step 2: 1-(benzo[b]thiophen-3-yl)propan-2-amine

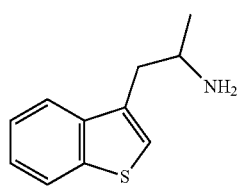

To a solution of lithium aluminum hydride in THF (2.4 M, 22 mL, 52.7 mmol) at 0° C. (icebath) was added a solution of 3-(2-nitroprop-1-enyl)benzothiophene (2.89 g, 13.2 mmol) in THF (19.8 mL) dropwise. The mixture was heated at 55° C. in an oil bath for 2 hrs. After being cooled with ice bath, the mixture was carefully quenched with water (2 mL), 15% NaOH (2 mL), and water (6 mL). The solid was filtered off (washed with THF 4×). The combined filtrate was concentrated to give the title compound as a tan oil which was used in the next step without further purification. $^1$H NMR (400 MHz, DMSO-d6) δ 7.99 (d, J=7.6 Hz, 1H), 7.94 (d, J=7.6 Hz, 1H), 7.57 (s, 1H), 7.45-7.36 (m, 2H), 3.46-3.38 (m, 1H), 3.24-3.19 (m, 1H), 2.98-2.93 (m, 1H), 1.15 (d, J=6.4 Hz, 3H).

Step 3: 1-(2,6-difluoro-4-iodophenyl)-3-methyl-1,2,3,4-tetrahydrobenzo[4,5]thieno[2,3-c]pyridine

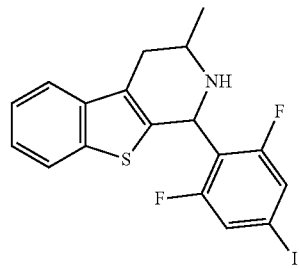 [SMILES: CC1Cc2c(sc3ccccc23)C(c2c(F)cc(I)cc2F)N1]

A mixture of 1-(1-benzothien-3-yl)-2-propanamine (0.211 g, 1.10 mmol), 2,6-difluoro-4-iodobenzaldehyde (0.302 g, 1.10 mmol), and trifluoroacetic acid (0.158 mL, 2.10 mmol) in 1,2-dichloroethane (6.62 mL) was heated under microwave at 120° C. for 1 h. The reaction mixture was diluted with DCM and poured into dilute aqueous Na$_2$CO$_3$. The contents were extracted with DCM (2×). The combined DCM solutions were dried (Na$_2$SO$_4$) and concentrated. The resulting residue was purified with flash column chromatography (0-20% iPrOAc/heptane with 2.5% trimethylamine) to yield the product (0.300 g, yield 61.6%).

Step 4: 1-(1-(2,6-difluoro-4-iodophenyl)-3-methyl-3,4-dihydrobenzo[4,5]thieno[2,3-c]pyridin-2(1H)-yl)-2-methylpropan-1-one

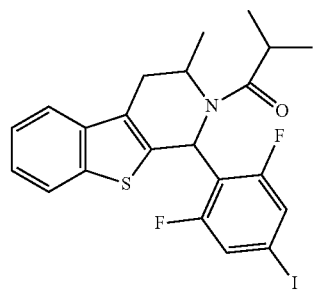 [SMILES: CC(C)C(=O)N1C(C)Cc2c(sc3ccccc23)C1c1c(F)cc(I)cc1F]

To a solution of 1-(2,6-difluoro-4-iodo-phenyl)-3-methyl-1,2,3,4-tetrahydrobenzothiopheno[2,3-c]pyridine (300 mg, 0.6798 mmol) in DCM (3.4 mL) at 0° C. was added DIPEA (0.59 mL, 3.4 mmol), followed by isobutyryl chloride (0.182 mL, 1.700 mmol). The mixture was stirred at room temperature for 2 hrs. The mixture was neutralized with dilute NaHCO$_3$, the aqueous layer was extracted with DCM (2×). The combined DCM solutions were dried (Na$_2$SO$_4$) and concentrated. The crude product was purified with flash column chromatography (0-20% iPrOAc/heptane) to give two products (cis-isomer: 157 mg, yield 45%; trans-isomer: 76 mg, yield 22%).

Step 5: 102

A mixture of 1-[(1,3-trans)-1-(2,6-difluoro-4-iodo-phenyl)-3-methyl-3,4-dihydro-1H-benzothiopheno[2,3-c]pyridin-2-yl]-2-methyl-propan-1-one (76 mg, 0.15 mmol), 2-[3-(fluoromethyl)azetidin-1-yl]ethanol (40 mg, 0.30 mmol), cuprous iodide (14 mg, 0.074 mmol) and potassium carbonate (62 mg, 0.45 mmol) in butyronitrile (0.89 mL) was heated under nitrogen at 140° C. for 24 hrs. The reaction mixture was cooled to room temperature, and diluted with EtOAc. Then the mixture was filtered. The filtrate was concentrated, and the resulting residue was purified with HPLC to give 102 (32 mg, yield 42%). $^1$H NMR (400 MHz, DMSO-$d_6$) δ 7.91-7.84 (m, 1H), 7.81-7.74 (m, 1H), 7.46-7.38 (m, 1H), 7.38-7.30 (m, 1H), 6.58 (d, J=11.2 Hz, 2H), 6.19 (s, 1H), 4.86 (s, 1H), 4.54 (d, J=6.2 Hz, 1H), 4.42 (d, J=6.2 Hz, 1H), 3.94-3.80 (m, 2H), 3.24-3.14 (m, 1H), 3.10-3.01 (m, 1H), 2.99-2.92 (m, 2H), 2.76-2.60 (m, 3H), 1.13 (d, J=6.5 Hz, 3H), 1.05-0.91 (m, 6H). LCMS: 517.2 [M+H]$^+$.

Example 103 (R)-1-(2,6-difluoro-4-(2-(3-(fluoromethyl)azetidin-1-yl)ethoxy)phenyl)-2-(2-fluoro-2-methylpropyl)-1,2,3,4,5,10-hexahydroazepino[3,4-b]indole 103

Step 1: 1-(2,6-difluoro-4-iodophenyl)-1,2,3,4,5,10-hexahydroazepino[3,4-b]indole

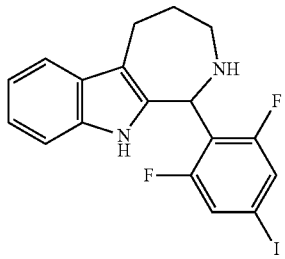 [SMILES: Fc1cc(I)cc(F)c1C1NCCCc2c1[nH]c1ccccc21]

A mixture of (1H-indol-3-yl)-1-propanamine (3.00 g, 17.2 mmol), 2,6-difluoro-4-iodo-benzaldehyde (4.61 g, 17.2 mmol) and trifluoroacetic acid (9.82 g, 86.1 mmol) in acetonitrile (98.4 mL) was stirred at room temperature for 3 days. The mixture was concentrated and the remaining residue was dissolved in DCM, washed with sat. NaHCO$_3$. The aqueous layer was back-extracted with DCM twice. The combined organics were dried over Na$_2$SO$_4$, filtered and concentrated. The crude product was purified by silica gel flash column chromatography (0-40% iPrOAc/heptane) to give the desired product (3.22 g, yield 44%) as a yellow solid. $^1$H NMR (400 MHz, Chloroform-d) δ 7.58-7.48 (m, 1H), 7.42-7.33 (m, 2H), 7.19-7.03 (m, 4H), 5.50 (s, 1H), 3.61-3.42 (m, 1H), 3.25-3.03 (m, 2H), 2.99-2.82 (m, 1H), 2.17-2.04 (m, 1H), 1.95-1.73 (m, 1H). LCMS: 425.0 [M+H]$^+$.

Step 2: 1-(2,6-difluoro-4-iodo-phenyl)-2-(2-fluoro-2-methyl-propyl)-3,4,5,10-tetrahydro-1H-azepino[3,4-b]indole

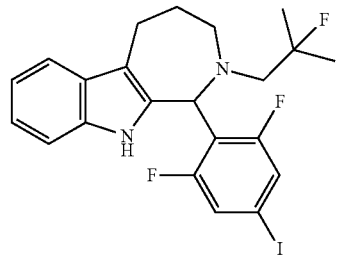 [SMILES: CC(C)(F)CN1CCCc2c([nH]c3ccccc23)C1c1c(F)cc(I)cc1F]

To a solution of 1-(2,6-difluoro-4-iodo-phenyl)-1,2,3,4,5,10-hexahydroazepino[3,4-b]indole (200 mg, 0.4715 mmol) and N,N-diisopropylethylamine (3 equiv., 1.414 mmol) in 1,4-dioxane (2 mL) under N$_2$, was added (2-fluoro-2-methyl-propyl) trifluoromethanesulfonate (2 equiv., 0.9430 mmol). The mixture was heated to 90° C. overnight. The next day, the mixture was partitioned between DCM and water. Organic layer was separated, dried over Na$_2$SO$_4$, and concentrated. The crude product was purified by flash column chromatography over silica gel, eluting with 0-20% iPrOAc/heptane to afford the title compound (125 mg, yield 53%). $^1$H NMR (400 MHz, Chloroform-d) δ 7.56-7.50 (m, 1H), 7.39 (s, 1H), 7.26 (d, J=1.9 Hz, 1H), 7.24 (s, 1H), 7.20-7.15 (m, 1H), 7.13-7.05 (m, 2H), 5.52 (s, 1H), 3.26-3.17 (m, 1H), 3.05 (dd, J=9.3, 5.8 Hz, 2H), 2.97 (ddd, J=14.7, 6.9, 4.5 Hz, 1H), 2.81 (dd, J=21.4, 14.7 Hz, 1H), 2.64 (dd, J=21.4, 14.7 Hz, 1H), 2.09-1.90 (m, 2H), 1.33 (d, J=2.3 Hz, 3H), 1.27 (d, J=2.5 Hz, 3H).

Step 3: 103

1-(2,6-difluoro-4-iodo-phenyl)-2-(2-fluoro-2-methyl-propyl)-3,4,5,10-tetrahydro-1H-azepino[3,4-b]indole (125 mg, 0.2509 mmol), 2-[3-(fluoromethyl)azetidin-1-yl]ethanol (2 equiv., 0.5017 mmol), cuprous iodide (0.4 equiv., 0.1003 mmol) and potassium carbonate (3 equiv., 0.7526 mmol) in butyronitrile (0.15 M, 19.2 mmol) was heated to 135° C. under N$_2$ atmosphere overnight. The next day, the reaction mixture was filtered and the filtrate was concentrated. The crude product was purified by chiral SFC (Column: PIC 100 Chiral. solvent A: Carbon Dioxide, solvent B: 0.1% Ammonium Hydroxide in Methanol, Isocratic 20% Ethanol. R.T. 0.553 min) to afford 103. $^1$H NMR (400 MHz, DMSO-$d_6$) δ 10.57 (s, 1H), 7.43 (dd, J=7.2, 1.5 Hz, 1H), 7.18-7.12 (m, 1H), 7.01-6.89 (m, 2H), 6.66 (d, J=10.8 Hz, 2H), 5.44 (s, 1H), 4.49 (dd, J=47.6, 6.2 Hz, 2H), 3.92 (t, J=5.5 Hz, 2H), 3.10-2.80 (m, 8H), 2.79-2.54 (m, 4H), 1.89 (d, J=41.3 Hz, 2H), 1.29 (d, J=4.9 Hz, 3H), 1.24 (d, J=4.9 Hz, 3H).

Example 104 (+)-1-(2,6-difluoro-4-(2-(3-(fluoromethyl)azetidin-1-yl)ethoxy)phenyl)-2-(methylsulfonyl)-1,2,3,4,5,10-hexahydroazepino[3,4-b]indole 104

Step 1: 1-(2,6-difluoro-4-iodophenyl)-2-(methylsulfonyl)-1,2,3,4,5,10-hexahydroazepino[3,4-b]indole

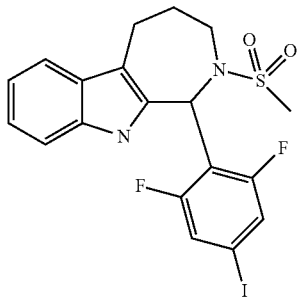 [SMILES: CS(=O)(=O)N1CCCc2c([nH]c3ccccc23)C1c1c(F)cc(I)cc1F]

To a solution of 1-(2,6-difluoro-4-iodo-phenyl)-1,2,3,4,5,5a,10,10a-octahydroazepino[3,4-b]indole (57 mg, 0.1337 mmol) in chloroform (0.15 M, 11.11 mmol), was added N,N-diisopropylethylamine (6 equiv., 0.8024 mmol) and methanesulfonyl chloride (6 equiv., 0.8024 mmol). The mixture was heated to 60° C. for 6 hrs. The reaction was quenched with the addition of saturated aq. NaHCO$_3$ solution, extracted with DCM (3×20 mL). The combined organic layers were dried over MgSO$_4$, filtered and concentrated. The crude material was purified flash column chromatography over silica gel with 0-50% iPrOAc/heptane to yield the desired product (51 mg, yield 76%).

Step 2: 104

To a microwave vial was added 1-(2,6-difluoro-4-iodo-phenyl)-2-methylsulfonyl-3,4,5,10-tetrahydro-1H-azepino[3,4-b]indole (50 mg, 0.09954 mmol), 2-[3-(fluoromethyl)azetidin-1-yl]ethanol (2 equiv., 0.1991 mmol), cuprous iodide (0.4 equiv., 0.03982 mmol), potassium carbonate (3 equiv., 0.2986 mmol) and butyronitrile (0.15 M, 7.61 mmol). The mixture was degassed for 5 min with nitrogen and then sealed. The vial was heated at 135° C. overnight. The next day, the mixture was cooled to room temperature, filtered, and concentrated. The crude product was purified by rp-HPLC to give 104 (35 mg, yield 69%). $^1$H NMR (400 MHz, DMSO-d$_6$) δ 10.79 (s, 1H), 7.48 (dd, J=7.6, 1.2 Hz, 1H), 7.22-7.18 (m, 1H), 7.03-6.96 (m, 2H), 6.77 (d, J=10.9 Hz, 2H), 6.71 (s, 1H), 4.49 (dd, J=47.6, 6.2 Hz, 2H), 3.96 (t, J=5.4 Hz, 2H), 3.89-3.77 (m, 1H), 3.29-3.14 (m, 4H), 3.10-2.94 (m, 4H), 2.85 (s, 3H), 2.83-2.65 (m, 4H). LCMS: 508.6 [M+H]$^+$.

Example 105 (1S,4R)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole 105

Step 1: N-(2-(1H-indol-3-yl)propyl)-2-fluoro-2-methylpropan-1-amine

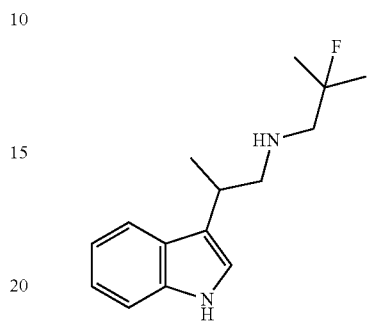

To a 250-mL RBF was added 2-(1H-indol-3-yl)propan-1-amine (566 mg, 3.2484 mmol; prepared according to published procedures from *J. Med. Chem.,* 2009, 52 (4), 904-907), 2-fluoro-2-methyl-propyl-trifluoromethanesulfonate (874 mg, 1.2 equiv., 3.8981 mmol), Hunig's Base (1.7 mL, 3 equiv., 9.7452 mmol), 1,4-dioxane (13 mL, 0.25 M). The reaction mixture was stirred overnight at 80° C. and the next day diluted with an aqueous saturated solution of ammonium chloride. The mixture was extracted with EtOAc. Organic layer was separated, dried with MgSO$_4$, filtered and concentrated. The crude material was purified from flash column chromatography on silica gel (0-100% EtOAc/hexane) to afford the title compound (225 mg, yield 28%). LCMS: 249.1 [M+1]$^+$.

Step 2: 1-(2,6-difluoro-4-iodophenyl)-2-(2-fluoro-2-methylpropyl)-4-methyl-2,3,4,9-tetrahydro-1H-pyrido[3,4-b]indole

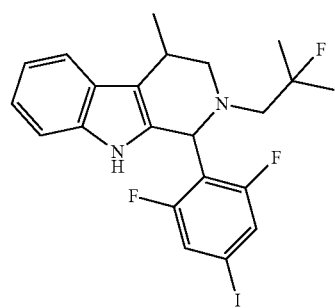 [SMILES: CC1CN(CC(C)(C)F)C(c2c(F)cc(I)cc2F)c2[nH]c3ccccc3c21]

To a sealed tube was added 2-fluoro-N-[2-(1H-indol-3-yl)propyl]-2-methyl-propan-1-amine (225 mg, 0.9062 mmol), 2,6-difluoro-4-iodo-benzaldehyde (291 mg, 1.2 equiv., 1.087 mmol), TFA (0.13 mL, 2 equiv., 1.812 mmol) and DCE (6 mL, 0.15 M). The reaction was stirred at room temperature for 4 days and then 3 hrs at 40° C. at which point all starting materials were consumed. The reaction mixture was quenched with an aqueous solution of NaHCO$_3$, and then extracted with DCM. The organic layer was separated, dried with MgSO$_4$, filtered and concentrated. The crude product was purified by flash column chromatography on silica gel (0-100% EtOAc/hexane) to provide the title compound (200 mg, yield 44%). LCMS: 499.1 [M+1]⁺.

Step 3: 105, 107, 108, 109

To a sealed tube was added (1-(2,6-difluoro-4-iodo-phenyl)-2-(2-fluoro-2-methyl-propyl)-4-methyl-1,3,4,9-tetrahydropyrido[3,4-b]indole (200 mg, 0.4014 mmol), 2-[3-(fluoromethyl)azetidin-1-yl]ethanol (107 mg, 2 equiv.), copper iodide (38 mg, 0.5 equiv., 0.2007 mmol), K₂CO₃ (166 mg, 3 equiv., 1.204 mmol), and butyronitrile (2.7 mL, 0.15 M). The reaction was degassed with nitrogen and stirred at 135° C. overnight. The next day, the reaction mixture was then concentrated and purified by chiral SFC (UPC—AD Column—10% EtOH) to give 4 diastereomers, arbitrarily assigned as 105, 107, 108, 109.

105: ¹H NMR (400 MHz, DMSO-d₆) δ 10.39 (s, 1H), 7.45-7.40 (m, 1H), 7.20-7.13 (m, 1H), 6.95 (dtd, J=17.2, 7.1, 1.3 Hz, 2H), 6.71-6.64 (m, 2H), 4.89 (s, 1H), 4.56 (d, J=6.2 Hz, 1H), 4.44 (d, J=6.2 Hz, 1H), 3.94 (t, J=5.4 Hz, 2H), 3.28 (d, J=7.7 Hz, 2H), 3.16 (dd, J=11.6, 2.7 Hz, 1H), 3.05 (dt, J=6.3, 3.4 Hz, 1H), 2.99 (t, J=6.5 Hz, 2H), 2.84 (dd, J=11.7, 3.8 Hz, 1H), 2.78-2.58 (m, 4H), 2.47-2.35 (m, 1H), 1.39 (d, J=6.7 Hz, 3H), 1.15 (dd, J=21.5, 10.9 Hz, 6H). LCMS: 504.2 [M+1]⁺.

Example 106 (R)-1-(1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-one 106

Step 1: 1-(1-(2,6-difluoro-4-iodophenyl)-3,4,5,10-tetrahydroazepino[3,4-b]indol-2(1H)-yl)-2-fluoro-2-methylpropan-1-one

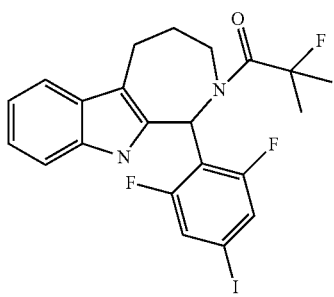 [SMILES: CC(C)(F)C(=O)N1CCCc2c([nH]c3ccccc23)C1c1c(F)cc(I)cc1F]

To a solution of 1-(2,6-difluoro-4-iodo-phenyl)-1,2,3,4,5,10-hexahydroazepino[3,4-b]indole (84 mg, 0.1980 mmol) in chloroform (0.1 M, 24.68 mmol) was added N,N-diisopropylethylamine (10 equiv., 1.980 mmol) and 2-fluoro-2-methyl-propanoyl chloride (5 equiv., 0.9901 mmol). After being stirred at room temperature for 1 hr, the reaction mixture was concentrated and the crude product was purified with flash column chromatography over silica gel (0-20% iPrOAc/heptane) to afford the title compound. ¹H NMR (400 MHz, Chloroform-d) δ 7.54 (ddt, J=7.0, 1.5, 0.8 Hz, 1H), 7.47 (s, 1H), 7.35-7.30 (m, 2H), 7.24-7.21 (m, 1H), 7.19-7.15 (m, 1H), 7.15-7.08 (m, 1H), 4.25 (d, J=15.2 Hz, 1H), 3.54 (s, 1H), 3.04-2.87 (m, 2H), 2.21 (ddt, J=15.9, 10.6, 5.3 Hz, 1H), 1.93 (ddd, J=11.5, 9.0, 5.8 Hz, 1H), 1.66 (d, J=22.3 Hz, 3H), 1.59-1.52 (m, 3H).

Step 2: 106

To a solution of 1-[1-(2,6-difluoro-4-iodo-phenyl)-3,4,5,10-tetrahydro-1H-azepino[3,4-b]indol-2-yl]-2-fluoro-2-methyl-propan-1-one (82 mg, 0.1601 mmol), 2-[3-(fluoromethyl)azetidin-1-yl]ethanol (2 equiv., 0.3201 mmol) in butyronitrile (0.15 M, 12.2 mmol), was added potassium carbonate (3 equiv., 0.4802 mmol) followed by cuprous iodide (0.4 equiv., 0.06402 mmol). The mixture was degassed for 5 min., then heated to 135° C. overnight. The next day, the reaction mixture was cooled to room temperature, filtered through Celite. The filtrate was concentrated and purified by SFC chiral separation (Column: PIC 100 Chiral. solvent A: Carbon Dioxide, solvent B: 0.1% Ammonium Hydroxide in Methanol, Isocratic 20% Ethanol. R.T. 0.584 min.) to afford 106. ¹H NMR (400 MHz, DMSO-d₆) δ 10.82 (s, 1H), 7.47-7.43 (m, 1H), 7.29 (s, 1H), 7.21 (dt, J=8.1, 0.9 Hz, 1H), 7.02 (ddd, J=8.1, 7.0, 1.3 Hz, 1H), 6.96 (ddd, J=8.0, 7.0, 1.2 Hz, 1H), 6.71 (d, J=11.3 Hz, 2H), 4.50 (dd, J=47.6, 6.2 Hz, 2H), 4.24 (d, J=15.2 Hz, 1H), 3.95 (t, J=5.4 Hz, 2H), 3.31-3.15 (m, 3H), 2.99 (dd, J=7.3, 5.9 Hz, 2H), 2.84 (s, 2H), 2.79-2.64 (m, 3H), 2.00 (d, J=21.6 Hz, 2H), 1.58 (d, J=14.9 Hz, 3H), 1.53 (d, J=13.7 Hz, 2H).

Example 107 (1R,4R)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole 107

Following the procedures of Example 105, 107 was prepared

107: ¹H NMR (400 MHz, DMSO-d₆) δ 10.43 (s, 1H), 7.54 (d, J=7.7 Hz, 1H), 7.17 (d, J=7.8 Hz, 1H), 7.04-6.88 (m, 2H), 6.74-6.59 (m, 2H), 4.96 (s, 1H), 4.56 (d, J=6.2 Hz, 1H), 4.44 (d, J=6.2 Hz, 1H), 3.94 (t, J=5.4 Hz, 2H), 3.30-3.14 (m, 4H), 2.99 (t, J=6.6 Hz, 2H), 2.79-2.57 (m, 4H), 2.45-2.30 (m, 2H), 1.33 (d, J=6.8 Hz, 3H), 1.16 (d, J=8.4 Hz, 3H), 1.11 (d, J=8.5 Hz, 3H). LCMS: 504.2 [M+1]⁺.

Example 108 (1R,4S)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole 108

Following the procedures of Example 105, 108 was prepared

108: ¹H NMR (400 MHz, DMSO-d₆) δ 10.43 (s, 1H), 7.57-7.50 (m, 1H), 7.17 (dd, J=7.5, 1.2 Hz, 1H), 6.94 (dtd, J=19.4, 7.2, 1.2 Hz, 2H), 6.72-6.61 (m, 2H), 4.96 (s, 1H), 4.56 (d, J=6.2 Hz, 1H), 4.44 (d, J=6.2 Hz, 1H), 3.94 (t, J=5.4 Hz, 2H), 3.39-3.33 (m, 2H), 3.20 (dddt, J=11.6, 7.1, 4.8, 1.9 Hz, 1H), 2.99 (t, J=6.5 Hz, 2H), 2.82-2.55 (m, 4H), 2.46-2.26 (m, 2H), 1.33 (d, J=6.7 Hz, 3H), 1.16 (d, J=8.4 Hz, 3H), 1.11 (d, J=8.5 Hz, 3H). LCMS: 504.3 [M+1]⁺.

Example 109 (1S,4S)-1-(2,6-difluoro-4-(2-(3-(fluoromethyl)azetidin-1-yl)ethoxy)phenyl)-2-(2-fluoro-2-methylpropyl)-4-methyl-2,3,4,9-tetrahydro-1H-pyrido[3,4-b]indole 109

Following the procedures of Example 105, 109 was prepared

109: ¹H NMR (400 MHz, DMSO-d₆) δ 10.39 (s, 1H), 7.46-7.39 (m, 1H), 7.21-7.13 (m, 1H), 6.95 (dtd, J=17.3, 7.1, 1.3 Hz, 2H), 6.72-6.62 (m, 2H), 4.89 (s, 1H), 4.56 (d, J=6.2 Hz, 1H), 4.44 (d, J=6.2 Hz, 1H), 3.94 (t, J=5.4 Hz, 2H), 3.16 (dd, J=11.8, 2.8 Hz, 1H), 3.10-2.95 (m, 3H), 2.94-2.58 (m, 5H), 2.47-2.30 (m, 1H), 1.39 (d, J=6.7 Hz, 3H), 1.15 (dd, J=21.5, 10.9 Hz, 6H). LCMS: 504.3 [M+1]⁺.

Example 110 (1R,3R)-1-(2,6-Difluoro-4-((1-(3-fluoropropyl)azetidin-3-yl)oxy)phenyl)-2-(2-fluoro-2-methylpropyl)-3-methyl-1,2,3,4-tetrahydropyrazino[1,2-a]indole 110

Step 1: tert-Butyl 3-(3,5-difluoro-4-((1R,3R)-2-(2-fluoro-2-methylpropyl)-3-methyl-1,2,3,4-tetrahydropyrazino[1,2-a]indol-1-yl)phenoxy)azetidine-1-carboxylate

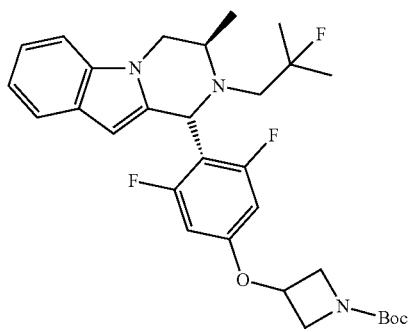

To a mixture of (R)-N-(1-(1H-indol-1-yl)propan-2-yl)-2-fluoro-2-methylpropan-1-amine (0.4 g, 1.61 mmol), tert-butyl 3-(3,5-difluoro-4-formyl-phenoxy)azetidine-1-carboxylate (0.51 g, 1.61 mmol) in toluene (6 mL) was added AcOH (0.18 mL, 3.22 mmol) and the mixture was stirred at 90° C. for 12 hours. After being cooling to 25° C., the reaction mixture was diluted with water (30 mL), extracted with EtOAc (30 mL×2). The combined organic layers were dried over anhydrous Na₂SO₄, filtered and concentrated. The crude residue was purified by silica gel column chromatography (20% EtOAc in petroleum ether) to afford the title compound (0.15 g, yield 17%) as a white solid. LCMS: 544.1 [M+H]⁺. ¹H NMR (400 MHz, CDCl₃) δ 7.48 (d, J=8.0 Hz, 1H), 7.32 (d, J=8.0 Hz, 1H), 7.19-7.15 (m, 1H), 7.10-7.08 (m, 1H), 6.25 (d, J=10.0 Hz, 2H), 5.95 (s, 1H), 5.41 (s, 1H), 4.83-4.80 (m, 1H), 4.32-4.28 (m, 3H), 4.01-3.98 (m, 3H), 3.86-3.84 (m, 1H), 2.97 (t, J=10.8 Hz, 1H), 2.35-2.20 (m, 1H), 1.46 (s, 9H), 1.29-1.13 (m, 9H).

Step 2: (1R,3R)-1-(4-(azetidin-3-yloxy)-2,6-difluorophenyl)-2-(2-fluoro-2-methylpropyl)-3-methyl-1,2,3,4-tetrahydropyrazino[1,2-a]indole

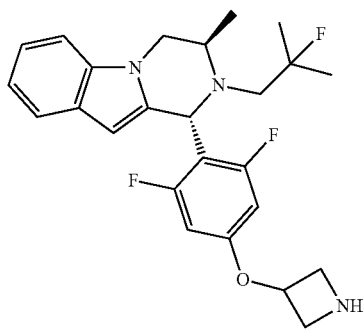 [SMILES: C[C@@H]1Cn2c(cc3ccccc32)[C@@H](c2c(F)cc(OC3CNC3)cc2F)N1CC(C)(C)F]

A mixture of tert-butyl 3-[3,5-difluoro-4-[(1R,3R)-2-isobutyl-3-methyl-1,3,4,9-tetrahydropyrido[3,4-b]indol-1-yl]phenoxy]azetidine-1-carboxylate (From step 1, 150 mg, 0.29 mmol) in DCM (0.6 mL) was added TFA (0.32 mL, 4.28 mmol). The reaction mixture was stirred at 20° C. for 1 hour. The solvent was removed in vacuo. The crude residue was used in next step directly. LCMS: 444.2 [M+H]⁺.

Step 3: 110

To a mixture of (1R,3R)-1-[4-(azetidin-3-yloxy)-2,6-difluoro-phenyl]-2-(2-fluoro-2-methyl-propyl)-3-methyl-3,4-dihydro-1H-pyrazino[1,2-a]indole (From step 2, 100 mg, 0.23 mmol) and DIPEA (0.12 mL, 0.68 mmol) in DMF (2 mL) was added 1-bromo-3-fluoropropane (0.04 mL, 0.34 mmol). The reaction mixture was stirred at 60° C. for 12 hours. After being cooled to room temperature, the reaction solution was diluted with water (20 mL), extracted with DCM (20 mL×2). The combined organic layers were dried over anhydrous Na₂SO₄, filtered and concentrated. The resulting residue was purified by reverse phase chromatography (acetonitrile 80-100/0.05% NH₄OH in water) to afford 110 (3.2 mg, yield 3%) as a yellow solid. LCMS: 504.3 [M+H]⁺. ¹H NMR (400 MHz, CD₃OD) δ 7.39 (d, J=8.0 Hz, 1H), 7.33 (d, J=8.0 Hz, 1H), 7.11-7.07 (m, 1H), 7.01-6.97 (m, 1H), 6.46 (d, J=10.4 Hz, 2H), 5.83 (s, 1H), 5.41 (s, 1H), 4.84-4.82 (m, 1H), 4.53-4.50 (m, 1H), 4.42-4.39 (m, 1H), 4.27-4.23 (m, 1H), 4.13-4.10 (m, 1H), 3.88-3.75 (m, 3H), 3.23-3.20 (m, 2H), 3.01 (t, J=10.8 Hz, 1H), 2.69 (t, J=7.6 Hz, 2H), 2.38-2.27 (m, 1H), 1.83-1.70 (m, 2H), 1.22-1.13 (m, 9H).

Example 111 (1S,3R)-1-(2,6-Difluoro-4-((1-(3-fluoropropyl)azetidin-3-yl)oxy)phenyl)-1,3-dimethyl-2-(methylsulfonyl)-2,3,4,9-tetrahydro-1H-pyrido[3,4-b]indole 111

Step 1: (R)-N-(1-(1H-Indol-3-yl)propan-2-yl)prop-2-en-1-amine

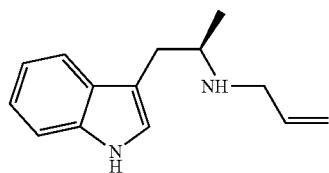 [SMILES: C=CCN[C@H](C)Cc1c[nH]c2ccccc12]

A mixture of ((R)-1-(1H-indol-3-yl)propan-2-amine (1.0 g, 5.74 mmol), allyl bromide (0.49 mL, 5.74 mmol) and DIPEA (2.04 mL, 11.48 mmol) in THF (20 mL) was stirred at 20° C. for 12 hours under N₂ atmosphere. The reaction mixture was diluted with water (40 mL) and the mixture was extracted with DCM (40 mL×2). The combined organic layers were dried over anhydrous Na₂SO₄, filtered and concentrated. The crude residue was purified by silica gel column chromatography (5% MeOH in DCM) to afford the title compound (620 mg, yield 50.4%) as a yellow solid. ¹H NMR (400 MHz, CDCl₃) δ 8.10 (s, 1H) 7.64 (d, J=8.0 Hz, 1H) 7.38 (d, J=8.0 Hz, 1H), 7.21 (t, J=7.6 Hz, 1H), 7.13 (d, J=7.6 Hz, 1H), 7.05 (s, 1H), 5.89-5.81 (m, 1H), 5.12 (d, J=16.8 Hz, 1H) 5.05 (d, J=10.4 Hz, 1H), 3.38-3.30 (m, 1H), 3.25-3.21 (m, 1H), 3.10-3.00 (m, 1H), 2.93-2.80 (m, 2H), 1.15 (d, J=6.0 Hz, 3H).

Step 2: tert-Butyl 3-(4-((1R,3R)-2-allyl-3-methyl-2,3,4,9-tetrahydro-1H-pyrido[3,4-b]indol-1-yl)-3,5-difluorophenoxy)azetidine-1-carboxylate

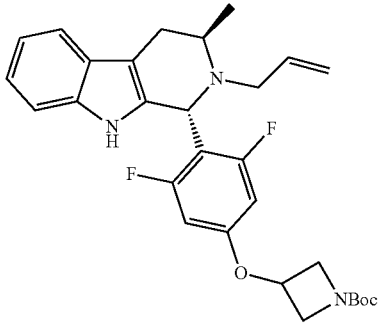 [SMILES: C=CCN1[C@H](c2c(F)cc(OC3CN(C(=O)OC(C)(C)C)C3)cc2F)c2[nH]c3ccccc3c2C[C@H]1C]

A mixture of (R)-N-(1-(1H-Indol-3-yl)propan-2-yl)prop-2-en-1-amine (From step 1, 500.0 mg, 2.33 mmol), tert-butyl 3-(3,5-difluoro-4-formyl-phenoxy)azetidine-1-carboxylate (730.95 mg, 2.33 mmol) and acetic acid (0.27 mL, 4.67 mmol) in toluene (2 mL) was stirred at 90° C. for 12 hours. After being cooled to 25° C., the reaction mixture was diluted with water (40 mL), extracted with EtOAc (100 mL×2). The combined organic layers were dried over anhydrous Na$_2$SO$_4$, filtered and concentrated. The crude residue was purified by silica gel column chromatography (20% EtOAc in petroleum ether) to afford the title compound (860 mg, yield 72.3%) as a yellow solid. The product was carried over to the next step directly.

Step 3: (1R,3R)-2-Allyl-1-(4-(azetidin-3-yloxy)-2,6-difluorophenyl)-3-methyl-2,3,4,9-tetrahydro-1H-pyrido[3,4-b]indole

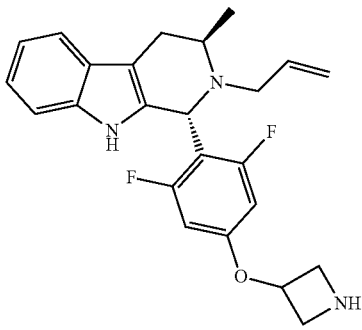 [SMILES: C=CCN1[C@H](c2c(F)cc(OC3CNC3)cc2F)c2[nH]c3ccccc3c2C[C@H]1C]

To a mixture of tert-butyl 3-(4-((1R,3R)-2-allyl-3-methyl-2,3,4,9-tetrahydro-1H-pyrido[3,4-b]indol-1-yl)-3,5-difluorophenoxy)azetidine-1-carboxylate (From step 2, 860.0 mg, 1.69 mmol) in dichloromethane (5 mL) under N$_2$ at −15° C. was added TFA (1.89 mL, 25.31 mmol) dropwise and the reaction mixture was shielded from light and was allowed to warm to 0° C. and stirred for 3 hours. The reaction mixture was diluted with DCM (100 mL) and saturated NaHCO$_3$ solution (20 mL) was added. The mixture was stirred for 5 minutes and two layers were separated. The organic layer was washed with saturated NaHCO$_3$ solution (20 mL) and brine, dried over Na$_2$SO$_4$, filtered, and concentrated in vacuo to afford the title compound (690 mg) as a yellow solid. LCMS: [M+H]$^+$ 410.0.

Step 4: (1R,3R)-2-Allyl-1-(2,6-difluoro-4-((1-(3-fluoropropyl)azetidin-3-yl)oxy)phenyl)-3-methyl-2,3,4,9-tetrahydro-1H-pyrido[3,4-b]indole

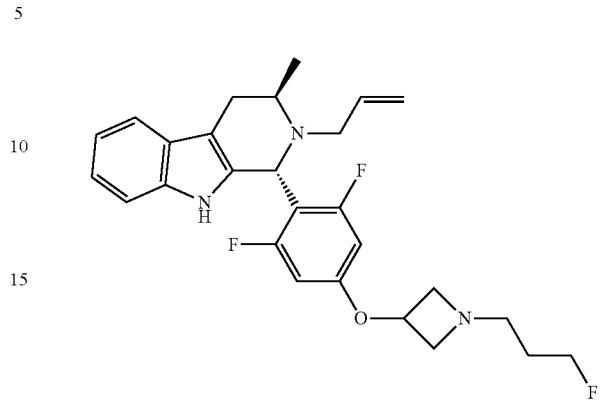

A mixture of (1R,3R)-2-allyl-1-(4-(azetidin-3-yloxy)-2,6-difluorophenyl)-3-methyl-2,3,4,9-tetrahydro-1H-pyrido[3,4-b]indole (From step 3, 690.0 mg, 1.69 mmol), 1-bromo-3-fluoropropane (0.03 mL, 1.69 mmol), and DIPEA (0.25 mL, 5.06 mmol) in DMF (5 mL) was stirred at 60° C. for 24 hours. The reaction mixture was diluted with water (50 mL), extracted with EtOAc (100 mL×2). The combined organic layers were dried over anhydrous Na$_2$SO$_4$, filtered and concentrated. The crude residue was purified by silica gel column chromatography (30% EtOAc in petroleum ether) to afford the title compound (500 mg, yield 63.2%) as a yellow solid. LCMS: [M+H]$^+$ 470.2.

Step 5: (1R,3R)-1-(2,6-Difluoro-4-((1-(3-fluoropropyl)azetidin-3-yl)oxy)phenyl)-3-methyl-2,3,4,9-tetrahydro-1H-pyrido[3,4-b]indole

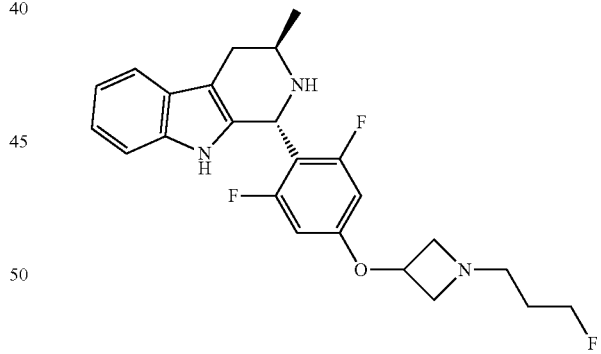

A mixture of (1R,3R)-2-allyl-1-(2,6-difluoro-4-((1-(3-fluoropropyl)azetidin-3-yl)oxy)phenyl)-3-methyl-2,3,4,9-tetrahydro-1H-pyrido[3,4-b]indole (From step 4, 500.0 mg, 1.06 mmol) and chlorotris(triphenylphosphine)rhodium(I) (492.62 mg, 0.530 mmol) in CH$_3$CN (2 mL) and water (0.40 mL) was stirred at 100° C. for 2 hours under N$_2$ atmosphere. The reaction mixture was cooled to 25° C. Solvent was removed and the mixture was purified by silica gel column chromatography (2%-5% MeOH in DCM) to afford the title compound (300 mg, yield 65.6%) as a yellow solid. $^1$H NMR (400 MHz, CDCl3) δ 7.59 (s, 1H), 7.52 (d, J=7.2 Hz, 1H), 7.27-7.23 (m, 1H), 7.16-7.09 (m, 2H), 6.32 (d, J=9.6 Hz, 2H), 5.60 (s, 1H), 4.80-4.72 (m, 1H), 4.56 (t, J=6.0 Hz, 1H), 4.44 (t, J=6.0 Hz, 1H), 3.90-3.80 (m, 2H), 3.52-4.98 (m, 1H), 3.16-3.09 (m, 2H), 3.02-2.98 (m, 1H), 2.67 (t, J=7.2 Hz, 2H), 2.54-2.50 (m, 1H), 1.85-1.71 (m, 2H), 1.30 (d, J=6.4 Hz, 3H).

Step 6: (1R,3R)-tert-Butyl 1-(2,6-difluoro-4-((1-(3-fluoropropyl)azetidin-3-yl)oxy)phenyl)-3-methyl-3,4-dihydro-1H-pyrido[3,4-b]indole-9(2H)-carboxylate

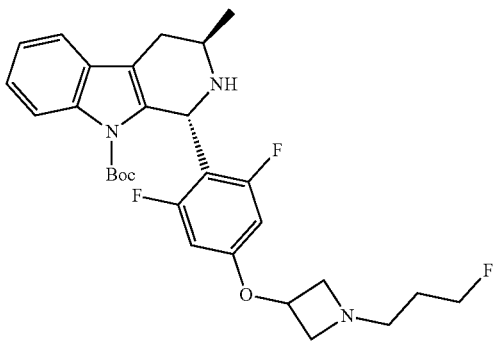 [SMILES: C[C@@H]1Cc2c(n(C(=O)OC(C)(C)C)c3ccccc23)[C@@H](c2c(F)cc(OC3CN(CCCF)C3)cc2F)N1]

To a mixture of (1R,3R)-1-[2,6-difluoro-4-[1-(3-fluoropropyl)azetidin-3-yl]oxy-phenyl]-3-methyl-2,3,4,9-tetrahydro-1H-pyrido[3,4-b]indole (0.7 g, 1.63 mmol) in acetonitrile (10 mL) was added Boc$_2$O (0.71 g, 3.26 mmol), TEA (0.91 mL, 6.52 mmol) and DMAP (40 mg, 0.33 mmol). The reaction mixture was stirred at 25° C. for 2 hours and was then concentrated. The residue was purified by chromatography on silica gel (0-5% MeOH in DCM) to afford the title compound (0.63 g, yield 73%) as a light yellow oil. LCMS: 530.1 [M+H]$^+$.

Step 7: (1R,3R)-tert-Butyl 1-(2,6-difluoro-4-((1-(3-fluoropropyl)azetidin-3-yl)oxy)phenyl)-3-methyl-2-(methylsulfonyl)-3,4-dihydro-1H-pyrido[3,4-b]indole-9(2H)-carboxylate

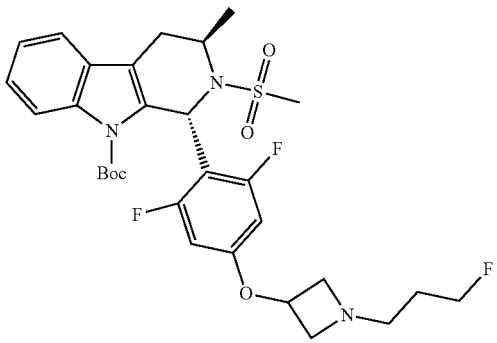 [SMILES: C[C@@H]1Cc2c(n(C(=O)OC(C)(C)C)c3ccccc23)[C@@H](c2c(F)cc(OC3CN(CCCF)C3)cc2F)N1S(C)(=O)=O]

To a mixture of N,N-diisopropylethylamine (0.34 mL, 1.89 mmol) in DCM (6 mL) was added (1R,3R)-tert-butyl 1-(2,6-difluoro-4-((1-(3-fluoropropyl)azetidin-3-yl)oxy)phenyl)-3-methyl-3,4-dihydro-1H-pyrido[3,4-b]indole-9(2H)-carboxylate (From step 6, 0.5 g, 0.94 mmol) and methanesulfonyl chloride (163 mg, 1.42 mmol) at 25° C. The reaction mixture was stirred at 40° C. for 16 hours and was then concentrated. The residue was purified by chromatography on silica gel (0-4% MeOH in DCM) to afford the title compound (140 mg, yield 24%) as a light yellow oil. LCMS: 608.1 [M+H]$^+$. $^1$H NMR (400 MHz, CDCl$_3$) δ 8.15 (d, J=8.0 Hz, 1H), 7.44 (d, J=7.2 Hz, 1H), 7.32-7.22 (m, 2H), 6.29-6.24 (m, 3H), 4.74-4.71 (m, 1H), 4.57-4.42 (m, 2H), 3.81-3.77 (m, 3H), 3.14-3.10 (m, 3H), 3.09 (s, 3H), 2.75-2.71 (m, 1H), 2.66-2.63 (m, 2H), 1.82-1.78 (m, 2H), 1.69 (d, J=7.2 Hz, 3H), 1.45 (s, 9H).

Step 8: (1S,3R)-tert-Butyl 1-(2,6-difluoro-4-((1-(3-fluoropropyl)azetidin-3-yl)oxy)phenyl)-1,3-dimethyl-2-(methylsulfonyl)-3,4-dihydro-1H-pyrido[3,4-b]indole-9(2H)-carboxylate

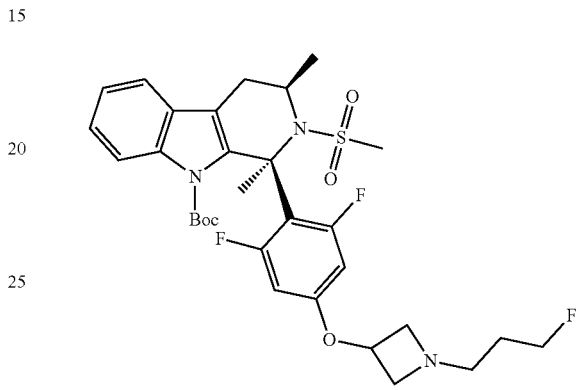

To a mixture of (1R,3R)-tert-butyl 1-(2,6-difluoro-4-((1-(3-fluoropropyl)azetidin-3-yl)oxy)phenyl)-3-methyl-2-(methylsulfonyl)-3,4-dihydro-1H-pyrido[3,4-b]indole-9(2H)-carboxylate (From step 7, 140 mg, 0.23 mmol) in N,N-dimethylformamide (3 mL) was added NaH (60% in mineral oil, 28 mg, 0.69 mmol) at 0° C. The reaction mixture was stirred at 0° C. for 30 minutes. CH$_3$I (0.1 mL, 0.23 mmol) was added dropwise. The reaction mixture was stirred at 0° C. for another hour. Saturated aqueous NH$_4$Cl solution (10 mL) was added to the reaction mixture and the mixture was extracted with DCM (10 mL×2). The combined organic layers were dried over Na$_2$SO$_4$ and were concentrated. The residue was purified by chromatography on silica (0-50% EtOAc in petroleum ether) to afford the title compound (30 mg, yield 21%). LCMS: 622.2 [M+H]$^+$. $^1$H NMR (400 MHz, CDCl$_3$): 8.15 (d, J=8.0 Hz, 1H), 7.44 (d, J=8.0 Hz, 1H), 7.33-7.23 (m, 2H), 6.50-6.47 (m, 2H), 4.57-4.54 (m, 1H), 4.45-4.42 (m, 2H), 3.78-3.72 (m, 3H), 3.15-3.11 (m, 1H), 3.07 (m, 3H), 2.80-2.60 (m, 3H), 2.58-2.51 (m, 2H), 2.32 (s, 3H), 1.88-1.81 (m, 2H), 1.69 (d, J=7.2 Hz, 3H), 1.45 (s, 9H).

Step 9: 111

To a mixture of (1S,3R)-tert-butyl 1-(2,6-difluoro-4-((1-(3-fluoropropyl)azetidin-3-yl)oxy)phenyl)-1,3-dimethyl-2-(methylsulfonyl)-3,4-dihydro-1H-pyrido[3,4-b]indole-9(2H)-carboxylate (From step 8, 30 mg, 0.05 mmol) in DCM (1 mL) was added TFA (83 mg, 0.72 mmol) at 25° C. The reaction mixture was stirred at 25° C. for 3 hours and the mixture was poured into saturated aqueous NaHCO$_3$ solution (10 mL) and was extracted with DCM (10 mL×2). The combined organic layers were dried over Na$_2$SO$_4$ and were concentrated. The residue was purified by TLC (9% MeOH in DCM) to give 111 (2.5 mg, yield 10%) as a light yellow solid. LCMS: 522.1 [M+H]$^+$. $^1$H NMR (400 MHz, CDCl$_3$): δ 7.62-7.61 (m, 1H), 7.52 (d, J=7.2 Hz, 1H), 7.19-7.11 (m, 2H), 6.55-6.52 (d, J=12.0 Hz, 2H), 6.28 (s, 1H), 4.59-4.41 (m, 3H), 3.78-3.71 (m, 3H), 3.23-3.20 (m, 1H), 2.88-2.60 (m, 6H), 2.33 (s, 3H), 1.88-1.81 (m, 2H), 1.45 (d, J=6.0 Hz, 3H).

Example 112 (10R,16bR)-1,7,7-Trifluoro-3-(2-(3-(fluoromethyl)azetidin-1-yl)ethoxy)-10-methyl-7,8,10,11,16,16b-hexahydro-6H-benzo[2',3'][1,5]oxazocino[5',4':1,2]pyrido[3,4-b]indole 112

Step 1: 3-((1R,3R)-1-(4-Bromo-2,6-difluorophenyl)-3-methyl-3,4-dihydro-1H-pyrido[3,4-b]indol-2(9H)-yl)-2,2-difluoropropan-1-ol

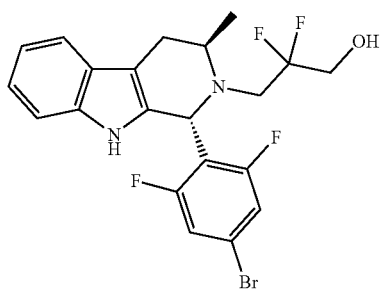 [SMILES: C[C@@H]1Cc2c([nH]c3ccccc23)[C@@H](c2c(F)cc(Br)cc2F)N1CC(F)(F)CO]

A mixture of (R)-3-((1-(1H-indol-3-yl)propan-2-yl)amino)-2,2-difluoropropan-1-ol (0.7 g, 2.61 mmol), 4-bromo-2,6-difluorobenzaldehyde (0.58 g, 2.61 mmol) and AcOH (0.45 mL, 7.83 mmol) in toluene (10 mL) was stirred at 90° C. for 12 hours. After being cooled to 25° C., the reaction mixture was diluted with water (50 mL), extracted with EtOAc (50 mL×2). The combined organic layers were dried over anhydrous Na$_2$SO$_4$, filtered and concentrated. The crude residue was purified by silica gel column chromatography (20% petroleum ether in EtOAc) to afford the title compound (0.8 g, 65%) as light yellow solid. LCMS: 471.0 [M+H]$^+$.

Step 2: 112

A mixture of 3-((1R,3R)-1-(4-bromo-2,6-difluorophenyl)-3-methyl-3,4-dihydro-1H-pyrido[3,4-b]indol-2(9H)-yl)-2,2-difluoropropan-1-ol (From step 1, 0.7 g, 1.49 mmol), 2-[3-(fluoromethyl)azetidin-1-yl]ethanol (0.99 g, 7.43 mmol), CuI (0.28 g, 1.49 mmol) and K$_2$CO$_3$ (0.62 g, 4.46 mmol) in n-butyronitrile (10 mL) was stirred at 135° C. under N$_2$ atmosphere for 12 hours. After being cooled to 25° C., the reaction mixture was diluted with water (50 mL), extracted with DCM (50 mL×2). The combined organic layers were dried over anhydrous Na$_2$SO$_4$, filtered and concentrated. The resulting residue was purified by reverse phase chromatography (acetonitrile 50-80/0.05% NH$_4$OH in water) to afford 3-((1R,3R)-1-(2,6-difluoro-4-(2-(3-(fluoromethyl)azetidin-1-yl)ethoxy)phenyl)-3-methyl-3,4-dihydro-1H-pyrido[3,4-b]indol-2(9H)-yl)-2,2-difluoropropan-1-ol (59 mg, 8%), having the structure:

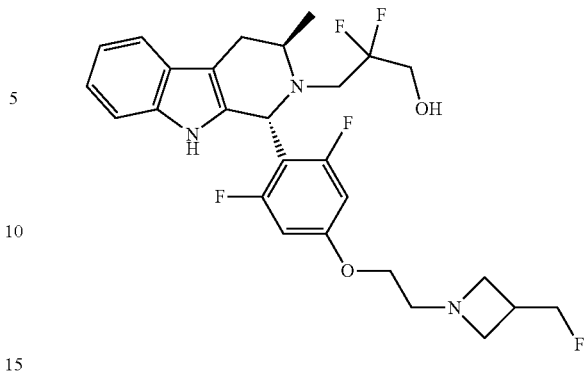

and 112 (41 mg, 6%) both as white solids. LCMS: 504.1 [M+H]$^+$. $^1$H NMR (400 MHz, CD$_3$OD) δ 7.40 (d, J=7.6 Hz, 1H), 7.20 (d, J=7.6 Hz, 1H), 7.01-6.96 (m, 2H), 6.67 (s, 1H), 6.52 (dd, J=12.0, 2.4 Hz, 1H), 5.71 (s, 1H), 4.54-4.42 (dd, J=47.6, 5.2 Hz, 2H), 4.45-4.38 (m, 1H), 4.17-4.10 (m, 1H), 4.00 (t, J=5.2 Hz, 2H), 3.54-3.43 (m, 3H), 3.23-3.19 (m, 3H), 3.01-2.81 (m, 5H), 2.69-2.63 (m, 1H), 1.26 (d, J=6.4 Hz, 3H).

Example 113 (1R,3'R)-2'-(2-fluoro-2-methylpropyl)-5-(2-(3-(fluoromethyl)azetidin-1-yl)ethoxy)-3'-methyl-2,2',3,3',4',9'-hexahydrospiro[indene-1,1'-pyrido[3,4-b]indole] 113

Step 1: (1R,3'R)-5-iodo-3'-methyl-2,2',3,3',4',9'-hexahydrospiro[indene-1,1'-pyrido[3,4-b]indole]

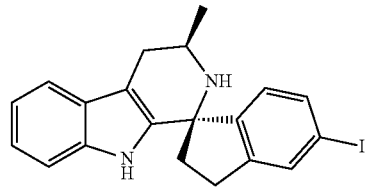 [SMILES: C[C@@H]1Cc2c([nH]c3ccccc23)[C@]2(CCc3cc(I)ccc32)N1]

To a suspension of (2R)-1-(1H-indol-3-yl)propan-2-amine (479 mg, 2.74 mmol) and 5-iodo-indan-1-one (617 mg, 2.39 mmol) under argon was added titanium(IV)isopropoxide (1.02 g, 3.58 mmol) and the reaction mixture was stirred at 80° C. for 3 h. The reaction mixture was allowed to cool to RT, acetonitrile (12 mL) was added followed by trifluoroacetic acid dropwise (0.58 mL, 7.65 mmol). The resulting mixture was further stirred at 110° C. for 18 h and then cooled to 0° C. The mixture was diluted with EtOAc and washed with saturated aqueous sodium bicarbonate solution (×3). The organic phase was washed further with brine, dried over sodium sulfate, filtered and concentrated in vacuo. The crude product was purified by silica gel chromatography (mobile phase: cyclohexane/ethyl acetate, gradient 0% to 50%). Appropriate fractions were combined and evaporated to afford the title compound as a yellowish foam (310 mg, yield 31%). $^1$H NMR (300 MHz, CDCl$_3$): δ 7.67 (br. s, 1H), 7.56-7.51 (m, 2H), 7.41 (d, J=7.9 Hz, 1H), 7.25-7.08 (m, 3H), 6.68 (d, J=7.8 Hz, 1H), 3.35-3.21 (m, 2H), 3.03-2.89 (m, 2H), 2.71-2.45 (m, 2H), 2.37-2.28 (m, 1H), 1.43 (s, 1H), 1.21 (d, J=6.4 Hz, 3H); LCMS: 415.1 [M+H]$^+$.

Step 2: (1R,3'R)-2'-(2-fluoro-2-methylpropyl)-5-iodo-3'-methyl-2,2',3,3',4',9'-hexahydrospiro[indene-1,1'-pyrido[3,4-b]indole]

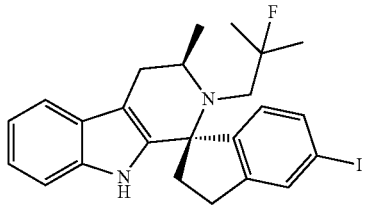 [SMILES: C[C@@H]1Cc2c([nH]c3ccccc23)[C@]2(CCc3cc(I)ccc32)N1CC(C)(C)F]

To a solution of (1R,3'R)-5-iodo-3'-methyl-2,2',3,3',4',9'-hexahydrospiro[indene-1,1'-pyrido[3,4-b]indole] 5a (290 mg, 0.70 mmol) in acetonitrile (2.1 mL) under argon was added potassium carbonate (773 mg, 5.6 mmol) and trifluoro-methanesulfonic acid 2-fluoro-2-methyl-propyl ester (CAS. 145349-17-3, 1.25 g, 5.60 mmol). On complete addition the mixture was stirred at 100° C. for 40 h. The reaction mixture was allowed to cool to RT, partitioned between EtOAc and water. The organic phase was washed further with water and brine, dried over sodium sulfate, filtered and concentrated in vacuo. The crude product was adsorbed onto HMN diatomaceous earth (Isolute®, Biotage) and purified by silica gel chromatography (mobile phase: cyclohexane/ethyl acetate, gradient 0% to 10%). Appropriate fractions were combined and evaporated to afford the title compound as a yellowish foam (104 mg, yield 30%). $^1$H NMR (300 MHz, CDCl$_3$): δ 7.64 (d, J=1.1 Hz, 1H), 7.53-7.39 (m, 2H), 7.18-7.06 (m, 3H), 6.98 (s, 1H), 6.86-6.82 (m, 1H), 3.97-3.88 (m, 1H), 3.24-2.92 (m, 4H), 2.72-2.60 (m, 2H), 2.25 (ddd, J=5.3, 9.0, 14.2 Hz, 1H), 2.10-1.92 (m, 1H), 1.30-1.08 (m, 9H); LCMS: 489.1 [M+H]$^+$.

Step 3: 113

The title compound was prepared from (1R,3'R)-2'-(2-fluoro-2-methylpropyl)-5-iodo-3'-methyl-2,2',3,3',4',9'-hexahydrospiro[indene-1,1'-pyrido[3,4-b]indole] (31 mg, 0.06 mmol) and 2-(3-fluoromethyl-azetidin-1-yl)-ethanol (51 mg, 0.038 mmol) following the procedure used for the preparation of Example 101 Step 5. The crude product was purified onto a C18 cartridge (mobile phase: 10% to 95% acetonitrile in water, 25 mins, 0.1% aq. ammonia buffer) followed by purification by chiral HPLC (ChiralPak IC, mobile phase: 10% IPA in heptane, 0.1% diethylamine, over 30 min) to give 113 as a white solid (3.6 mg, yield 11%). $^1$H NMR (400 MHz, CDCl$_3$): δ 7.53-7.48 (m, 1H), 7.15-7.01 (m, 4H), 6.95 (d, J=9.4 Hz, 1H), 6.77-6.74 (m, 1H), 6.68-6.63 (m, 1H), 4.57 (d, J=5.7 Hz, 1H), 4.47-4.44 (m, 1H), 3.97-3.92 (m, 3H), 3.53-3.46 (m, 2H), 3.21-2.80 (m, 8H), 2.71-2.61 (m, 2H), 2.31-2.21 (m, 1H), 2.07 (dd, J=14.4, 35.0 Hz, 1H), 1.25 (d, J=22.5 Hz, 3H), 1.16-1.10 (m, 6H); LCMS: 494.4 [M+H]$^+$.

Example 116 (1R,3R)-1-(2,6-difluoro-4-(2-(3-(fluoromethyl)azetidin-1-yl)ethoxy)phenyl)-2-(2-fluoro-2-methylpropyl)-3-methyl-1,2,3,4,5,10-hexahydroazepino[3,4-b]indole 116

Step 1: 4-(1H-indol-3-yl)butan-2-amine

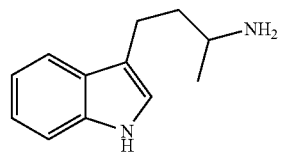

To a solution of 4-(1H-indol-3-yl)butan-2-one (900 mg, 4.81 mmol) in methanol (0.25 M, 475 mmol) was added ammonium acetate (5 equiv., 24.033 mmol) and sodium cyanoborohydride (2 equiv., 9.6133 mmol). The mixture was heated to 40° C. for 4 h. The reaction mixture was concentrated to remove solvent. The residue was partitioned between ethyl acetate and water, and 15% NaOH (4 m L) was added to adjust pH to 10. The organic layer was dried over Na$_2$SO$_4$, concentrated to give crude title compound (1.0 g, yield 99%). LCMS: 189.4 [M+H]$^+$.

Step 2: 1-(2,6-difluoro-4-iodo-phenyl)-3-methyl-1,2,3,4,5,10-hexahydroazepino[3,4-b]indole

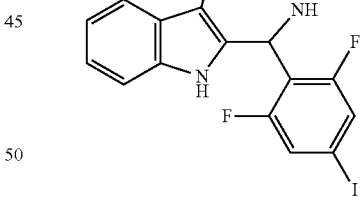

A mixture of 4-(1H-indol-3-yl)butan-2-amine (400 mg, 2.1246 mmol), 2,6-difluoro-4-iodo-benzaldehyde (2.2308 mmol, 597.86 mg) and 1,1,1-trifluoroacetone (466.31 mg, 4.0368 mmol) in acetonitrile (0.5 M, 81.3 mmol) was stirred at room temperature overnight. The reaction was quenched with sat. NaHCO$_3$ solution, extracted with DCM (3×5 mL). The combined organics were dried (Na$_2$SO$_4$), filtered and concentrated. The crude product was purified by silica gel flash column chromatography (0-30% iPrOAc/Heptane) to give the title compound (280 mg, yield 30%) as white solid. LCMS: 439.2 [M+H]$^+$.

Step 3: 1-(2,6-difluoro-4-iodo-phenyl)-2-(2-fluoro-2-methyl-propyl)-3-methyl-3,4,5,10-tetrahydro-1H-azepino[3,4-b]indole

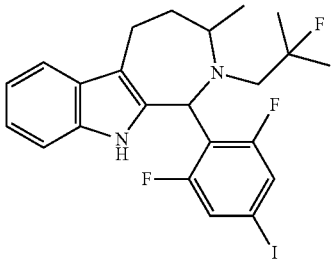 [SMILES: CC1CCc2c([nH]c3ccccc23)C(c2c(F)cc(I)cc2F)N1CC(C)(C)F]

To a solution of 1-(2,6-difluoro-4-iodo-phenyl)-3-methyl-1,2,3,4,5,10-hexahydroazepino[3,4-b]indole (350 mg, 0.7987 mmol)), N,N-diisopropylethylamine (5 equiv., 3.994 mmol) in 1,4-dioxane (1.2 mL) under $N_2$, was added (2-fluoro-2-methyl-propyl) trifluoromethanesulfonate (5 equiv., 3.994 mmol). The mixture was heated to 100° C. overnight. Additional potassium carbonate (5 equiv., 3.994 mmol) was added and the reaction mixture was heated at 100° C. for 1 week. The reaction was cooled to room temperature, partitioned between DCM and water. Organic layer was separated, dried over $Na_2SO_4$, and concentrated. The crude product was purified by flash column chromatography on silica gel (0-10% iPrOAc in heptane) to give the title compound (260 mg, yield 64%). LCMS: 513.5 [M+H]$^+$.

Step 4: 116

1-(2,6-difluoro-4-iodo-phenyl)-2-(2-fluoro-2-methyl-propyl)-3-methyl-3,4,5,10-tetrahydro-1H-azepino[3,4-b]indole (350 mg, 0.6831 mmol), 2-[3-(fluoromethyl)azetidin-1-yl]ethanol (3 equiv., 2.049 mmol), cuprous iodide (0.4 equiv., 0.2732 mmol) and potassium carbonate (3 equiv., 2.049 mmol) in butyronitrile (0.15 M, 52.2 mmol) was heated to 135° C. under $N_2$ atmosphere overnight. The reaction mixture was filtered, concentrated to dryness. Crude product was purified by chiral SFC purification (Column: PIC 100 Chiral. solvent A: Carbon Dioxide, solvent B: 0.1% Ammonium Hydroxide in Methanol, Isocratic 20% Ethanol. R.T. 0.588 min.) to obtain 116 (21 mg, yield 6%). $^1$H NMR (400 MHz, DMSO-d$_6$) δ 10.63 (s, 1H), 7.46-7.39 (m, 1H), 7.19-7.13 (m, 1H), 7.00-6.90 (m, 2H), 6.68-6.60 (m, 2H), 5.70 (d, J=3.8 Hz, 1H), 4.49 (dd, J=47.6, 6.2 Hz, 2H), 3.93 (t, J=5.4 Hz, 2H), 3.25-3.17 (m, 1H), 2.99 (t, J=6.3 Hz, 3H), 2.81-2.54 (m, 6H), 1.78 (q, J=12.9, 11.9 Hz, 1H), 1.64 (dd, J=12.2, 6.8 Hz, 1H), 1.32 (d, J=21.7 Hz, 3H), 1.22 (d, J=21.1 Hz, 3H), 0.97 (d, J=6.8 Hz, 3H). LCMS: 518.6 [M+H]$^+$.

Example 117 (S)-3-((R)-1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-ol 117

Step 1: tert-butyl-[3-[1-(2,6-difluoro-4-iodo-phenyl)-3,4,5,10-tetrahydro-1H-azepino[3,4-b]indol-2-yl]-2-fluoro-2-methyl-propoxy]-diphenyl-silane

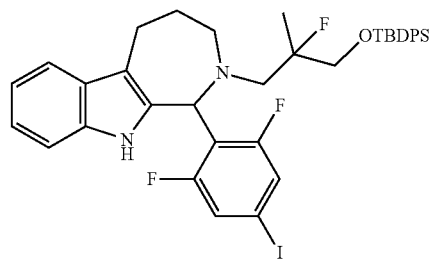

To a solution of 1-(2,6-difluoro-4-iodo-phenyl)-1,2,3,4,5,10-hexahydroazepino[3,4-b]indole (600 mg, 1.414 mmol) and N,N-diisopropylethylamine (3 equiv., 4.243 mmol) in 1,4-dioxane (3 mL) under $N_2$, was added [3-[tert-butyl(diphenyl)silyl]oxy-2-fluoro-2-methyl-propyl]trifluoromethanesulfonate (2 equiv., 2.829 mmol). The mixture was heated to 90° C. for 2 days. The mixture was cooled to room temperature and partitioned between DCM and water. Organic layer was separated, dried over $Na_2SO_4$, and then concentrated to dryness. The crude product was purified by flash column chromatography on silica gel (0-5% iPrOAc/heptane) to give the title compound (800 mg, yield 75%) as light yellow foam. LCMS: 753.1 [M+H]$^+$.

Step 2: 3-[1-(2,6-difluoro-4-iodo-phenyl)-3,4,5,10-tetrahydro-1H-azepino[3,4-b]indol-2-yl]-2-fluoro-2-methyl-propan-1-ol

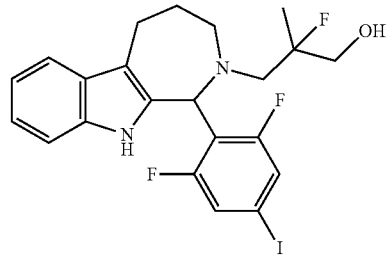 [SMILES: CC(F)(CO)CN1CCCc2c([nH]c3ccccc23)C1c1c(F)cc(I)cc1F]

To a solution of tert-butyl-[3-[1-(2,6-difluoro-4-iodo-phenyl)-3,4,5,10-tetrahydro-1H-azepino[3,4-b]indol-2-yl]-2-fluoro-2-methyl-propoxy]-diphenyl-silane (800 mg, 1.063 mmol) in tetrahydrofuran (0.25 M, 52.2 mmol) was added tetrabutylammonium fluoride (TBAF) in THF (1.0 equiv., 1.063 mmol). The reaction mixture was stirred at room temperature for 6 hrs. Monitoring the reaction by LCMS showed incomplete conversion. Therefore, another eq. of TBAF was added and the mixture was stirred overnight. The next day, the reaction mixture was partitioned between ethyl acetate and brine. Organic layer was separated, dried over $Na_2SO_4$, and then concentrated to dryness. The crude product was purified by silica gel flash column chromatography (0-30% iPrOAc/heptane) to give the title compound (322 mg, yield 59%) as white solid. LCMS: 515.0 [M+H]+.

Step 3: 117, 118, 119

A mixture of 3-[1-(2,6-difluoro-4-iodo-phenyl)-3,4,5,10-tetrahydro-1H-azepino[3,4-b]indol-2-yl]-2-fluoro-2-methyl-propan-1-ol (322 mg, 0.6261 mmol), 2-[3-(fluoromethyl)azetidin-1-yl]ethanol (3 equiv., 1.878 mmol), potassium carbonate (3 equiv., 1.878 mmol), and cuprous iodide (0.4 equiv., 0.2504 mmol) in butyronitrile (0.15 M, 47.8 mmol) was degassed for 5 min. Then the reaction mixture was heated to 125° C. for 6 hrs. The reaction mixture was cooled to room temperature and filtered. Filtrate was concentrated and submitted for chiral SFC separation (Column: PIC 100 Chiral. solvent A: Carbon Dioxide, solvent B: 0.1% Ammonium Hydroxide in Methanol, Isocratic 30% Ethanol) to afford 118 (8.7 mg, yield 2.7%), 117 (7.1 mg, yield 2.2%) and 119 (7.2 mg, yield 2.2%).

117: RT=0.701 min. 1H NMR (400 MHz, DMSO-d6) δ 10.57 (s, 1H), 7.47-7.38 (m, 1H), 7.17-7.10 (m, 1H), 7.00-6.86 (m, 2H), 6.66 (d, J=10.9 Hz, 2H), 5.45 (s, 1H), 4.85 (t, J=5.7 Hz, 1H), 4.49 (dd, J=47.6, 6.2 Hz, 2H), 3.93 (t, J=5.5 Hz, 2H), 3.50 (ddd, J=17.7, 11.7, 5.7 Hz, 1H), 3.40-3.34 (m, 2H), 3.30-3.21 (m, 3H), 3.00-2.95 (m, 2H), 2.94-2.80 (m, 2H), 2.78-2.57 (m, 4H), 2.03-1.78 (m, 2H), 1.22 (d, J=22.0 Hz, 3H).

Example 118 (R)-3-((R)-1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-ol 118

Following the procedures of Example 117, 118 was prepared (8.7 mg, yield 2.7%). 118: RT=1.096 min. 1H NMR (400 MHz, DMSO-d6) δ 10.56 (s, 1H), 7.43 (dd, J=7.4, 1.5 Hz, 1H), 7.14 (dt, J=8.0, 0.9 Hz, 1H), 7.00-6.89 (m, 2H), 6.65 (d, J=10.9 Hz, 2H), 5.41 (s, 1H), 4.87 (t, J=5.7 Hz, 1H), 4.49 (dd, J=47.6, 6.2 Hz, 2H), 3.92 (t, J=5.5 Hz, 2H), 3.51-3.33 (m, 2H), 3.28 (s, 1H), 3.10-2.81 (m, 7H), 2.78-2.53 (m, 4H), 1.88 (d, J=41.4 Hz, 2H), 1.21 (d, J=22.2 Hz, 3H).

Example 119 3-((S)-1-(2,6-difluoro-4-(2-(3-(fluoromethyl)azetidin-1-yl)ethoxy)phenyl)-3,4,5,10-tetrahydroazepino[3,4-b]indol-2(1H)-yl)-2-fluoro-2-methylpropan-1-ol 119

Following the procedures of Example 117, 119 was prepared (7.2 mg, yield 2.2%). 119: RT=0.787 min. 1H NMR (400 MHz, DMSO-d6) δ 10.57 (s, 1H), 7.46-7.39 (m, 1H), 7.20-7.09 (m, 1H), 7.01-6.86 (m, 2H), 6.66 (d, J=10.9 Hz, 2H), 5.45 (s, 1H), 4.85 (t, J=5.7 Hz, 1H), 4.49 (dd, J=47.6, 6.2 Hz, 2H), 3.92 (t, J=5.4 Hz, 2H), 3.55-3.45 (m, 2H), 3.28-3.25 (m, 2H), 3.13-2.56 (m, 11H), 2.02-1.78 (m, 2H), 1.22 (d, J=22.0 Hz, 3H).

Example 120 (6R,8R)-8-(2,6-difluoro-4-((1-(3-fluoropropyl)azetidin-3-yl)oxy)phenyl)-7-(2-fluoro-2-methylpropyl)-6-methyl-6,7,8,9-tetrahydro-5H-pyrrolo[2,3-b:5,4-c']dipyridine 120

Step 1: (2-Fluoro-2-methyl-propyl)-[1-methyl-2-(1H-pyrrolo[2,3-b]pyridin-3-yl)-ethyl]-amine

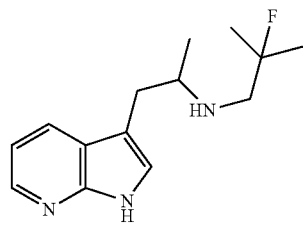 [SMILES: CC(Cc1c[nH]c2ncccc12)NCC(C)(C)F]

Sodium triacetoxyborohydride (4.33 g, 20.5 mmol) was added portion-wise to a mixture of 1-(1H-pyrrolo[2,3-b]pyridin-3-yl)-propan-2-one (2.36 g, 13.6 mmol) and 2-fluoro-2-methyl-propylamine hydrochloride (2.25 g, 17.6 mmol) in dichloromethane (40 mL). On complete addition the mixture was allowed to stir at RT for 18 h. The mixture was diluted with dichloromethane and washed with saturated sodium hydrogen carbonate solution. The organic layer was dried over anhydrous sodium sulfate, filtered and evaporated to afford a racemic mixture of the title compound as a brown oil which solidified on standing (3.1 g, yield 93%). 1H NMR (400 MHz, CDCl3): δ 9.36 (s, 1H), 8.30 (dd, J=1.6, 4.8 Hz, 1H), 7.94 (dd, J=1.3, 7.9 Hz, 1H), 7.17 (d, J=1.9 Hz, 1H), 7.07 (dd, J=4.7, 7.8 Hz, 1H), 3.03-2.97 (m, 1H), 2.90-2.65 (m, 4H), 1.34 (d, J=23.8 Hz, 6H), 1.10-1.08 (m, 3H); LCMS: 250.2 [M+H]+.

Step 2: 8-(2,6-Difluoro-4-iodo-phenyl)-7-(2-fluoro-2-methyl-propyl)-6-methyl-6,7,8,9-tetrahydro-5H-dipyrido[2,3-b;4',3'-d]pyrrole

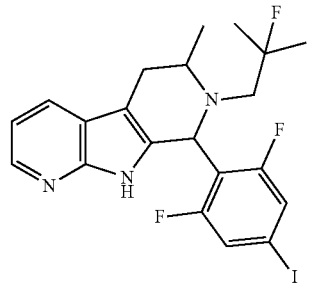 [SMILES: CC1Cc2c([nH]c3ncccc23)C(c2c(F)cc(I)cc2F)N1CC(C)(C)F]

To a solution of (2-fluoro-2-methyl-propyl)-[1-methyl-2-(1H-pyrrolo[2,3-b]pyridin-3-yl)-ethyl]-amine (2.0 g, 8.0 mmol) in toluene (66 mL) under argon were added 2,6-difluoro-4-iodo-benzaldehyde (4.36 g, 16.2 mmol) and acetic acid (16.4 mL). The mixture was heated at 100° C. for 48 h. The mixture was allowed to cool to RT and concentrated in vacuo. The residue was purified by silica gel chromatography (mobile phase: ethyl acetate in dichloromethane, gradient 0% to 20%) to afford a (6R,8R)- and (6S,8S)- mixture of diastereoisomers of the title compound as a beige solid (2.0 g, yield 50%). 1H NMR (400 MHz, CDCl3): δ 9.61 (s, 1H), 8.39-8.35 (m, 1H), 8.13-8.10 (m, 1H), 8.03 (dd, J=1.5, 4.9 Hz, 1H), 7.84-7.81 (m, 1H), 7.70-7.64 (m, 1H), 7.05-7.01 (m, 1H), 5.28-5.27 (m, 1H), 3.67-3.63 (m, 1H), 3.19-3.01 (m, 1H), 2.94-2.81 (m, 1H), 2.64-2.55 (m, 1H), 2.44-2.32 (m, 1H), 1.29-1.15 (m, 6H), 1.10 (d, J=6.5 Hz, 3H); LCMS: 500.1 [M+H]$^+$.

Step 3: 8-(2,6-Difluoro-4-iodo-phenyl)-7-(2-fluoro-2-methyl-propyl)-6-methyl-9-(2-trimethylsilanyl-ethoxymethyl)-6,7,8,9-tetrahydro-5H-dipyrido[2,3-b;4',3'-d]pyrrole & 8-(2,6-difluoro-4-iodo-phenyl)-7-(2-fluoro-2-methyl-propyl)-6-methyl-1-(2-trimethylsilanyl-ethoxymethyl)-5,6,7,8-tetrahydro-1H-dipyrido[2,3-b;4',3'-d]pyrrole

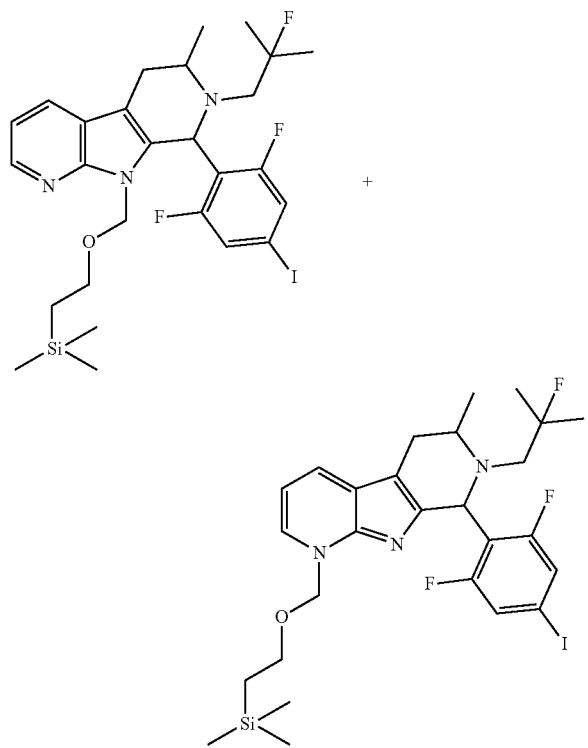

Sodium hydride (52 mg, 1.3 mmol, 60% suspension in oil) was added to a solution of 8-(2,6-difluoro-4-iodo-phenyl)-7-(2-fluoro-2-methyl-propyl)-6-methyl-6,7,8,9-tetrahydro-5H-dipyrido[2,3-b;4',3'-d]pyrrole (500 mg, 1.0 mmol) in DMF (10 mL). On complete addition the mixture was allowed to stir at RT for 20 min, (trimethylsilyl) ethoxymethyl chloride (154 μL, 221 mg, 1.33 mmol) was added and stirring continued for 2 h. The mixture was quenched by the addition of saturated aqueous sodium hydrogen carbonate solution, diluted with brine and extracted with ethyl acetate. The organic phase was dried over anhydrous sodium sulfate, filtered and evaporated to afford an oil. The residual oil was purified by reverse phase chromatography (15 mm, C18 Puriflash cartridge, mobile phase: 10-98% acetonitrile in water (+0.1% formic acid)). Appropriate fractions were collected and evaporated to afford two products. First eluting product 8-(2,6-difluoro-4-iodo-phenyl)-7-(2-fluoro-2-methyl-propyl)-6-methyl-1-(2-trimethylsilanyl-ethoxymethyl)-5,6,7,8-tetrahydro-1H-dipyrido[2,3-b;4',3'-d]pyrrole was obtained as an orange oil (300 mg, 47%). $^1$H NMR (400 MHz, CDCl$_3$) 8.18-8.14 (3H, m), 8.06-8.04 (1H, m), 6.06-6.05 (2H, m), 5.37 (1H, s), 5.30-5.30 (2H, m), 3.68-3.63 (3H, m), 3.19-3.11 (1H, m), 2.96-2.88 (1H, m), 2.66-2.61 (1H, m), 2.34 (1H, dd, J=15.1, 28.0 Hz), 1.26-1.14 (6H, m), 1.10-1.07 (3H, m), 0.98-0.93 (2H, m), −0.04 (s, 9H); LCMS: 630.2 [M+H]$^+$. Second eluting product 8-(2,6-difluoro-4-iodo-phenyl)-7-(2-fluoro-2-methyl-propyl)-6-methyl-9-(2-trimethylsilanyl-ethoxymethyl)-6,7,8,9-tetrahydro-5H-dipyrido[2,3-b;4',3'-d]pyrrole was obtained a colourless oil (144 mg, yield 23%). $^1$H NMR (400 MHz, CDCl$_3$): δ 8.25 (dd, J=1.6, 4.8 Hz, 1H), 7.79 (dd, J=1.6, 7.8 Hz, 1H), 7.07 (dd, J=4.8, 7.7 Hz, 1H), 5.50-5.47 (m, 2H), 5.30 (s, 2H), 5.14 (d, J=10.9 Hz, 1H), 3.55-3.50 (m, 1H), 3.30-3.25 (m, 2H), 2.91-2.70 (m, 2H), 2.62-2.45 (m, 2H), 1.35 (d, J=21.4 Hz, 3H), 1.25-1.18 (m, 3H), 1.10 (d, J=6.6 Hz, 3H), 0.68-0.62 (m, 2H), −0.11 (s, 9H); LCMS: 630.2 [M+H]$^+$.

Step 4: 8-{2,6-Difluoro-4-[2-(3-fluoromethyl-azetidin-1-yl)-ethoxy]-phenyl}-7-(2-fluoro-2-methyl-propyl)-6-methyl-9-(2-trimethylsilanyl-ethoxymethyl)-6,7,8,9-tetrahydro-5H-dipyrido[2,3-b;4',3'-d]pyrrole

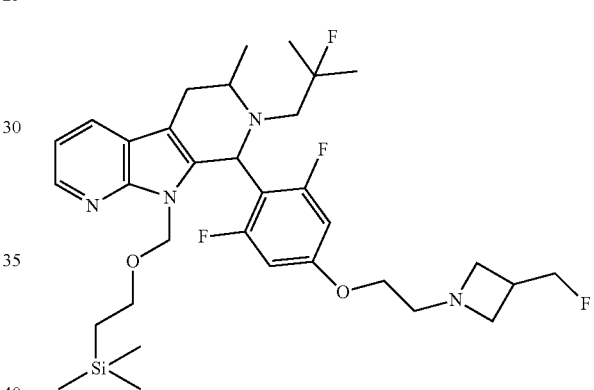

A mixture of 8-(2,6-difluoro-4-iodo-phenyl)-7-(2-fluoro-2-methyl-propyl)-6-methyl-1-(2-trimethylsilanyl-ethoxymethyl)-5,6,7,8-tetrahydro-1H-dipyrido[2,3-b;4',3'-d]pyrrole (144 mg, 0.22 mmol), 2-(3-fluoromethyl-azetidin-1-yl)-ethanol, prepared according to WO 2013/090836, page 124 (160 mg, 1.20 mmol; CAS No.: 1443984-69-7, WO 2013/090836), copper iodide (9.5 mg, 0.05 mmol), and potassium carbonate (99 mg, 0.72 mmol) in butyronitrile (2 mL) was degassed with three vacuum/argon cycles. The reaction mixture was heated at 140° C. for 24 h, allowed to cool to room temperature and diluted with ethyl acetate. The solid was removed from the reaction mixture by filtration through Celite and the solid was washed with ethyl acetate. The combined filtrate was washed with water and brine, dried over Na$_2$SO$_4$, filtered, and concentrated under reduced pressure. The crude product was purified by silica gel chromatography (mobile phase: 0-10% 2N methanol in ammonia/dichloromethane). Appropriate fractions were collected and evaporated to afford a (6R,8R)- and (6S,8S)- mixture of diastereoisomers of the title compound as an orange oil (17.2 mg, yield 21%). $^1$H NMR (400 MHz, CDCl$_3$): δ 8.23 (dd, J=1.6, 4.8 Hz, 1H), 7.79-7.76 (m, 1H), 7.04 (dd, J=4.8, 7.8 Hz, 1H), 5.61 (d, J=10.8 Hz, 1H), 5.43 (s, 1H), 5.29-5.28 (m, 1H), 4.93 (d, J=10.8 Hz, 1H), 4.55 (d, J=5.7 Hz, 1H), 4.43 (d, J=5.7 Hz, 1H), 3.90-3.86 (m, 2H), 3.59-3.43 (m, 3H), 3.35-3.23 (m, 2H), 3.15-3.10 (m, 2H), 2.95-2.75 (m, 4H), 2.60-2.43 (m, 2H), 1.32 (d, J=21.4 Hz, 3H), 1.24-1.17 (m, 3H), 1.10-1.07 (m, 3H), 0.82-0.64 (m, 2H), −0.13 (s, 9H); LCMS: 635.4 [M+H]⁺.

Step 5: 120 and 121

To a mixture of 8-{2,6-difluoro-4-[2-(3-fluoromethyl-azetidin-1-yl)-ethoxy]-phenyl}-7-(2-fluoro-2-methyl-propyl)-6-methyl-9-(2-trimethylsilanyl-ethoxymethyl)-6,7,8,9-tetrahydro-5H-dipyrido[2,3-b;4',3'-d]pyrrole (100 mg, 0.16 mmol) in dichloromethane (1 mL) under argon was added TFA (1 mL) and the mixture was stirred at RT for 2 h. The reaction mixture was concentrated in vacuo and the resultant residue was treated with saturated sodium hydrogen carbonate solution and extracted with dichloromethane (×2). The combined organic extract was dried over anhydrous sodium sulfate, filtered and the filtrate evaporated to afford a yellow oil. The resultant oil was purified by silica gel chromatography (mobile phase: 0-20% 2N ammonia in methanol/dichloromethane). Appropriate fractions were combined and evaporated. The resultant residue was purified by reverse phase chiral chromatography (ChiralPak IC column 21.2× 250 mm, C18, 15 micron, mobile phase: 20% IPA/Heptane, 0.1% diethylamine). Appropriate fractions were combined and evaporated to afford two products. First eluting trans-diastereoisomer 120 was obtained as a white solid (13 mg, yield 16%). ¹H NMR (400 MHz, DMSO-d₆): δ 11.11 (s, 1H), 8.08 (dd, J=1.5, 4.7 Hz, 1H), 7.79 (dd, J=4.6, 4.6 Hz, 1H), 6.99 (dd, J=4.8, 7.8 Hz, 1H), 6.62 (d, J=11.1 Hz, 2H), 5.14 (s, 1H), 4.55 (d, J=6.2 Hz, 1H), 4.44 (d, J=6.2 Hz, 1H), 3.93 (t, J=5.4 Hz, 2H), 3.51-3.44 (m, 1H), 3.30-3.29 (m, 1H), 2.98 (t, J=6.4 Hz, 2H), 2.88-2.64 (m, 6H), 2.59-2.54 (m, 1H), 2.43-2.30 (m, 1H), 1.25-1.11 (m, 6H), 1.05 (d, J=6.5 Hz, 3H); LCMS: 505.3 [M+H]⁺.

Example 121 (6R,8S)-8-(2,6-difluoro-4-((1-(3-fluoropropyl)azetidin-3-yl)oxy)phenyl)-7-(2-fluoro-2-methylpropyl)-6-methyl-6,7,8,9-tetrahydr-5H-pyrrolo[2,3-b:5,4-c']dipyridine 121

Following the procedures of Example 120, 121 was isolated as the second eluting trans-diastereoisomer as a white solid (13 mg, yield 16%). ¹H NMR (400 MHz, CDCl₃): δ 8.78 (s, 1H), 8.07 (dd, J=1.5, 4.8 Hz, 1H), 7.77 (dd, J=1.3, 7.8 Hz, 1H), 7.01 (dd, J=4.7, 7.6 Hz, 1H), 6.41-6.36 (m, 2H), 5.20 (s, 1H), 4.56 (d, J=5.7 Hz, 1H), 4.44 (d, J=5.7 Hz, 1H), 3.92-3.87 (m, 2H), 3.73-3.65 (m, 1H), 3.48 (t, J=7.2 Hz, 2H), 3.17-3.05 (m, 3H), 2.93-2.79 (m, 4H), 2.62-2.54 (m, 1H), 2.37 (dd, J=14.9, 26.8 Hz, 1H), 1.25-1.13 (m, 6H), 1.10 (d, J=6.8 Hz, 3H); LCMS: 505.3 [M+H]⁺.

Example 122 3-((1R,3R)-1-(2,6-Difluoro-4-((1-(3-fluoropropyl)azetidin-3-yl)oxy)phenyl)-3-methyl-3,4-dihydropyrazino[1,2-a]indol-2(1H)-yl)-2-fluoro-2-methylpropan-1-ol 122

Step 1: (S)-1-(1H-Indol-1-yl)propan-2-ol

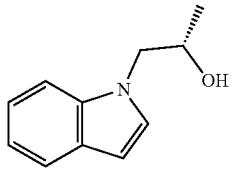

To a stirred solution of 1H-indole (5.0 g, 42.68 mmol) in THF (75 mL) was added NaH (60% in mineral oil, 2.05 g, 51.22 mmol) in an ice bath and the mixture was stirred for 30 minutes. To the reaction mixture was added (S)-2-methyloxirane (4.96 g, 85.36 mmol) dropwise and mixture was stirred at 20° C. for 4 hours. Water (100 mL) was added to the reaction mixture and the mixture was washed with EtOAc (100 mL×2). The combined organic layers were dried over anhydrous Na₂SO₄, filtered and concentrated. The crude residue was purified by silica gel column chromatography (20% EtOAc in petroleum ether) to afford the title compound (6.5 g, yield 87%) as a light yellow oil. ¹H NMR (400 MHz, CDCl₃) δ 7.65 (d, J=8.0 Hz, 1H), 7.38 (d, J=8.0 Hz, 1H), 7.25-7.21 (m, 1H), 7.15-7.11 (m, 2H), 6.54 (d, J=3.2 Hz, 1H), 4.22-4.20 (m, 3H), 1.26 (d, J=6.8 Hz, 3H).

Step 2: (S)-1-(1H-Indol-1-yl)propan-2-yl methanesulfonate

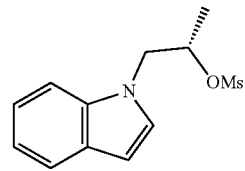 [SMILES: C[C@@H](Cn1ccc2ccccc21)OS(C)(=O)=O]

To a stirred solution of (S)-1-(1H-indol-1-yl)propan-2-ol (From step 1, 6.5 g, 34.24 mmol) and TEA (14.32 mL, 102.72 mmol) in DCM (120 mL) was added methanesulfonyl chloride (5.3 mL, 68.48 mmol) dropwise in an ice bath. The reaction mixture was stirred at 20° C. for 2 hours. The mixture was diluted with DCM (100 mL), washed with 1 N HCl (100 mL), saturated aqueous NaHCO₃ (100 mL) and brine (100 mL). The organic layer was dried over anhydrous Na₂SO₄, filtered and concentrated to afford the title compound (8 g, yield 92%) as yellow oil, which was used for the next step directly. LCMS: 253.8 [M+H]⁺.

Step 3: (R)-1-(2-Azidopropyl)-1H-indole

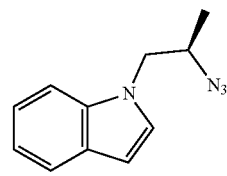

To a mixture of NaN₃ (4.71 g, 72.45 mmol) in DMF (120 mL) was added [(1S)-2-indol-1-yl-1-methyl-ethyl]methanesulfonate (From step 2, 8 g, 31.58 mmol) and the reaction mixture was stirred at 60° C. for 2 hours. After being cooling to 25° C., the reaction mixture was diluted with EtOAc (500 mL), washed with brine (500 mL×3). The combined organic layers were dried over anhydrous Na₂SO₄, filtered and concentrated to afford the crude title compound (5.8 g, yield 92%) as a yellow oil, which was used in next step directly. LCMS: 200.9 [M+H]⁺.

Step 4: (R)-1-(1H-Indol-1-yl)propan-2-amine

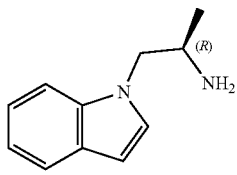

A mixture of (R)-1-(2-azidopropyl)-1H-indole (From step 3, 5.8 g, 28.97 mmol) and PPh$_3$ (11.4 g, 43.45 mmol) in THF (100 mL) was stirred at 60° C. for 1 hour. Water (50 mL) was added to the reaction mixture and the mixture was stirred at 60° C. for 4 hours. After being cooling to 25° C., the reaction mixture was diluted with water (100 mL), extracted with DCM (100 mL×2). The combined organic layers were dried over anhydrous Na$_2$SO$_4$, filtered and concentrated. The residue was purified by silica gel column chromatography (10% MeOH in DCM) to afford the title compound (3.2 g, yield 63%) as a yellow oil. LCMS: 174.8 [M+H]$^+$. $^1$HNMR (400 MHz, CDCl$_3$) δ 7.65 (d, J=8.0 Hz, 1H), 7.38 (d, J=8.0 Hz, 1H), 7.24-7.20 (m, 1H), 7.14-7.10 (m, 2H), 6.52 (d, J=2.4 Hz, 1H), 4.14-4.09 (m, 1H), 3.94-3.90 (m, 1H), 3.48-3.45 (m, 1H), 1.15 (d, J=6.0 Hz, 3H).

Step 5: N-((R)-1-(1H-Indol-1-yl)propan-2-yl)-3-((tert-butyldiphenylsilyl)oxy)-2-fluoro-2-methylpropan-1-amine

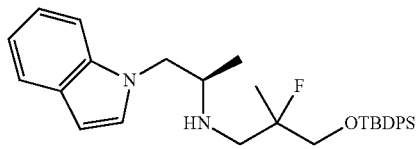

A mixture of [3-[tert-butyl(diphenyl)silyl]oxy-2-fluoro-2-methyl-propyl]trifluoromethanesulfonate (1.37 g, 2.87 mmol), DIPEA (1.02 mL, 5.74 mmol) and (2R)-1-indol-1-ylpropan-2-amine (Intermediate 6 in Scheme 1, 500 mg, 2.87 mmol) in 1,4-dioxane (15 mL) was stirred at 90° C. for 12 hours. The reaction mixture was diluted with water (50 mL), extracted with DCM (50 mL×2). The combined organic layers were dried over anhydrous Na$_2$SO$_4$, filtered and concentrated. The crude residue was purified by silica gel column chromatography (25% EtOAc in petroleum ether) to afford the title compound (1.1 g, yield 76%) as a colorless oil. LCMS: 503.2 [M+H]$^+$.

Step 6: tert-Butyl 3-(4-((1R,3R)-2-(3-((tert-butyldiphenylsilyl)oxy)-2-fluoro-2-methylpropyl)-3-methyl-1,2,3,4-tetrahydropyrazino[1,2-a]indol-1-yl)-3,5-difluorophenoxy)azetidine-1-carboxylate

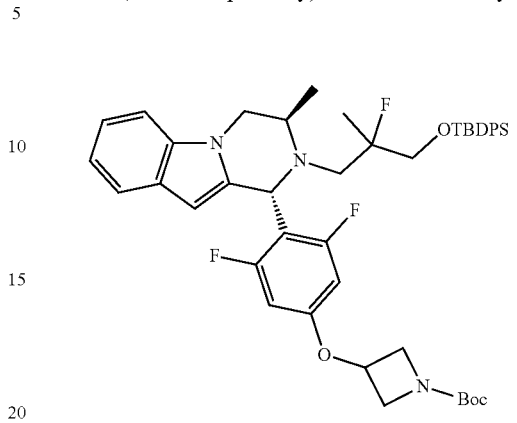

A mixture of N-((R)-1-(1H-indol-1-yl)propan-2-yl)-3-((tert-butyldiphenylsilyl)oxy)-2-fluoro-2-methylpropan-1-amine (From step 1, 1.0 g, 1.99 mmol), HOAc (0.34 mL, 5.97 mmol) and tert-butyl 3-(3,5-difluoro-4-formyl-phenoxy)azetidine-1-carboxylate (1.21 mL, 1.99 mmol) in toluene (18 mL) was stirred at 110° C. for 12 hours. After being cooled to 25° C., the reaction mixture was diluted with water (50 mL), extracted with EtOAc (50 mL×2). The combined organic layers were dried over anhydrous Na$_2$SO$_4$, filtered and concentrated. The crude residue was purified by silica gel column chromatography (20% petroleum ether in EtOAc) to afford the title compound (750 mg, yield 47%) as a light yellow solid. LCMS: 798.2 [M+H]$^+$.

Step 7: tert-Butyl 3-(3,5-difluoro-4-((1R,3R)-2-(2-fluoro-3-hydroxy-2-methylpropyl)-3-methyl-1,2,3,4-tetrahydropyrazino[1,2-a]indol-1-yl)phenoxy)azetidine-1-carboxylate

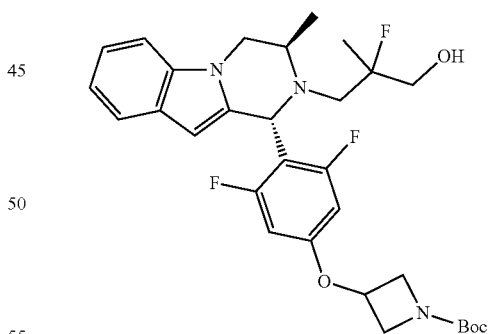

A mixture of tert-butyl 3-(4-((1R,3R)-2-(3-((tert-butyldiphenylsilyl)oxy)-2-fluoro-2-methylpropyl)-3-methyl-1,2,3,4-tetrahydropyrazino[1,2-a]indol-1-yl)-3,5-difluorophenoxy)azetidine-1-carboxylate (From step 2, 0.65 g, 0.81 mmol) and TBAF (1.63 mL, 1.63 mmol) in THF (10 mL) was stirred at 25° C. for 12 hours. The reaction mixture was diluted with water (50 mL), extracted with EtOAc (50 mL×2). The combined organic layers were dried over anhydrous Na$_2$SO$_4$, filtered and concentrated. The crude residue was purified by silica gel column chromatography (60% EtOAc in petroleum ether) to afford the title compound (350 mg, yield 77%) as a light yellow oil. LCMS (5-95 AB/1.5 min): RT=0.886 min, [M+H]+ 560.1.

Step 8: 3-((1R,3R)-1-(4-(Azetidin-3-yloxy)-2,6-difluorophenyl)-3-methyl-3,4-dihydropyrazino[1,2-a]indol-2(1-yl)-2-fluoro-2-methylpropan-1-ol

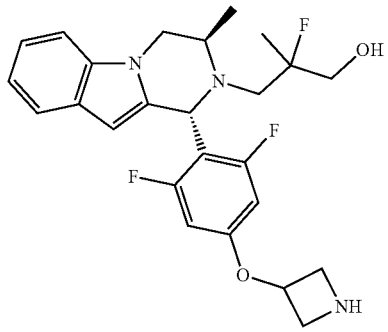 [SMILES: C[C@@H]1Cn2c(cc3ccccc32)[C@@H](c2c(F)cc(OC3CNC3)cc2F)N1CC(C)(F)CO]

A solution of tert-butyl 3-(3,5-difluoro-4-((1R,3R)-2-(2-fluoro-3-hydroxy-2-methylpropyl)-3-methyl-1,2,3,4-tetrahydropyrazino[1,2-a]indol-1-yl)phenoxy)azetidine-1-carboxylate (From step 3, 350 mg, 0.63 mmol) in 1,4-dioxane (2 mL) was added concentrated H$_2$SO$_4$ (0.17 mL, 3.13 mmol) in an ice bath. The reaction mixture was stirred at 25° C. for 0.5 hours. The reaction mixture was poured into sat Na$_2$CO$_3$ (10 mL), extracted with DCM (20 mL×2). The combined organic layers were dried over anhydrous Na$_2$SO$_4$, filtered and concentrated to afford the title compound (240 mg, yield 84%) as a yellow solid. LCMS: 460.2 [M+H]$^+$.

Step 9: 122

A mixture of 3-((1R,3R)-1-(4-(azetidin-3-yloxy)-2,6-difluorophenyl)-3-methyl-3,4-dihydropyrazino[1,2-a]indol-2(1H)-yl)-2-fluoro-2-methylpropan-1-ol (From step 4, 240 mg, 0.52 mmol), DIPEA (0.28 mL, 1.57 mmol) and 1-iodo-3-fluoropropane (1.21 mL, 0.52 mmol) in DMF (5 mL) was stirred at 25° C. for 12 hours. The reaction mixture was diluted with water (20 mL), extracted with EtOAc (20 mL×2). The combined organic layers were dried over anhydrous Na$_2$SO$_4$, filtered and concentrated. The resulting residue was purified by reverse phase chromatography (acetonitrile 55-85/0.05% NH$_4$OH in water) to afford 122 (32 mg, yield 12%) as a light yellow solid. LCMS: 520.2 [M+H]$^+$.
$^1$H NMR (400 MHz, CD$_3$OD) δ 7.38-7.36 (d, J=8.0 Hz, 1H), 7.31-7.30 (d, J=8.0 Hz, 1H), 7.10 (m, 1H), 6.96 (m, 1H), 6.46-6.41 (m, 2H), 5.82 (s, 1H), 5.40-5.39 (m, 1H), 4.82-4.79 (m, 1H), 4.51-4.49 (m, 1H), 4.39-4.36 (m, 1H), 4.25-4.06 (m, 2H), 3.85-3.75 (m, 4H), 3.39-3.34 (m, 1H), 3.21-3.01 (m, 3H), 2.65 (t, J=7.6 Hz, 2H), 2.51-2.42 (m, 1H), 1.78-1.70 (m, 2H), 1.16-1.10 (m, 6H).

Example 123 (1R,5R)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole 123

Step 1: 3-(1H-indol-3-yl)butanamide

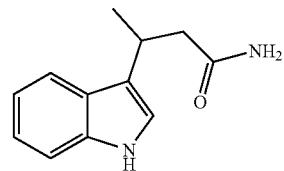

To a solution of 3-(1H-indol-3-yl)butanoic acid (0.5 g, 2 mmol) in diethyl ether (0.5 M, 40 mmol) was added thionyl chloride (1.1 equiv., 3 mmol). The reaction mixture was stirred at room temperature for 1 hr. To this mixture was added dropwise ammonium hydroxide in H$_2$O (5 equiv., 10 mmol, 25% v/v) at 0° C. The mixture was stirred for 30 min and then diluted with water (25 mL), and then extracted with DCM (2×25 mL). Combined organic layers were dried over sodium sulfate, and then concentrated to give the title compound (350 mg, yield 70%). LCMS: 203.1 [M+H]$^+$.

Step 2: 3-(1H-indol-3-yl)butan-1-amine

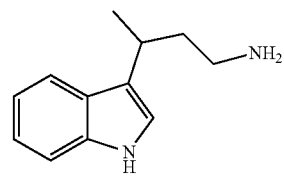

A solution of 3-(1H-indol-3-yl)butanamide (A, 350 mg, 1.7305 mmol) in tetrahydrofuran (0.2 M, 106 mmol) was added to lithium aluminum hydride (2 M) in THF (3 equiv., 5.1916 mmol) at room temperature under N$_2$. The reaction mixture was then heated to reflux for 3 hrs. The mixture was then cooled to 0° C., quenched by slowly adding 0.3 mL of water, followed by 0.3 mL of 15% NaOH solution. The mixture was filtered through Celite, and the filtrate was dried over Na$_2$SO$_4$. Removal of solvents via rotavap afforded the crude title compound (290 mg, yield 89%). LCMS: 189.1 [M+H]$^+$.

Step 3: 1-(2,6-difluoro-4-iodo-phenyl)-5-methyl-1,2,3,4,5,10-hexahydroazepino[3,4-b]indole

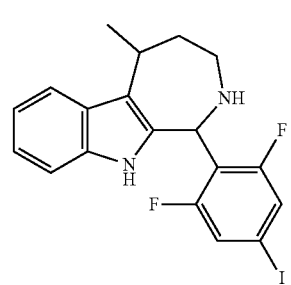 [SMILES: CC1CCNC(c2c(F)cc(I)cc2F)c2[nH]c3ccccc3c21]

A mixture of 3-(1H-indol-3-yl)butan-1-amine (1200 mg, 6.3738 mmol), 2,6-difluoro-4-iodo-benzaldehyde (1793.6 mg, 6.6925 mmol) and trifluoroacetic acid (1380.8 mg, 12.110 mmol) in acetonitrile (1 M, 122 mmol) was heated to 80° C. overnight. The mixture was partitioned between DCM and sat. NaHCO₃. The aqueous layer was separated and then extracted with DCM (3×50 mL). The combined organics were dried (Na₂SO₄), filtered and concentrated. The crude product was purified by silica gel flash column chromatography (0-50% iPrOAc/heptane) to give the title compound (1260 mg, yield 45%) as light yellow solid. LCMS: 439.2 [M+H]⁺.

Step 4: 1-(2,6-difluoro-4-iodo-phenyl)-2-(2-fluoro-2-methyl-propyl)-5-methyl-3,4,5,10-tetrahydro-1H-azepino[3,4-b]indole

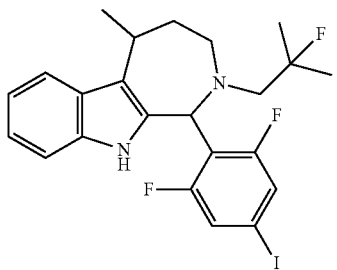 [SMILES: CC1CCN(CC(C)(C)F)C(c2c(F)cc(I)cc2F)c2[nH]c3ccccc3c21]

To a solution of 1-(2,6-difluoro-4-iodo-phenyl)-5-methyl-1,2,3,4,5,10-hexahydroazepino[3,4-b]indole (500 mg, 1.141 mmol) and N,N-diisopropylethylamine (4 equiv., 4.564 mmol) in 1,4-dioxane (5 mL) under N₂, was added (2-fluoro-2-methyl-propyl) trifluoromethanesulfonate (4 equiv., 4.564 mmol). The mixture was heated to 80° C. overnight when monitoring the reaction by LCMS showed incomplete conversion. Therefore, additional (2-fluoro-2-methyl-propyl) trifluoromethanesulfonate (4 equiv., 4.564 mmol) and N,N-diisopropylethylamine (4 equiv., 4.564 mmol) were introduced. The mixture was then heated to 100° C. for 20 hrs. The mixture was partitioned between DCM and water. Organic layer was separated, dried over Na₂SO₄, and concentrated to dryness. The crude product was purified by flash column chromatography (0-20% iPrOAc/heptane) to give the title compound (427 mg, yield 73%).

Step 5: 123, 124, 125, 126

1-(2,6-difluoro-4-iodo-phenyl)-2-(2-fluoro-2-methyl-propyl)-5-methyl-3,4,5,10-tetrahydro-1H-azepino[3,4-b]indole (420 mg, 0.8197 mmol), 2-[3-(fluoromethyl)azetidin-1-yl]ethanol (3 equiv., 2.459 mmol), cuprous iodide (0.4 equiv., 0.3279 mmol) and potassium carbonate (3 equiv., 2.459 mmol) in butyronitrile (0.15 M, 62.6 mmol) was heated to 135° C. under N₂ atmosphere overnight. The reaction mixture was cooled to room temperature, and filtered. The filtrate was concentrated to give crude products (300 mg, yield 71%). The mixture was further purified by SFC purification (Column: PIC 100 Chiral. solvent A: Carbon Dioxide, solvent B: 0.1% Ammonium Hydroxide in Methanol, Isocratic 20% Ethanol) to give 126 (24.7 mg, yield 4.8%), 125 (23.2 mg, yield 4.5%), 124 (17.8 mg, yield 3.4%), and 123 (18.9 mg, yield 3.7%).

123: R.T. 0.376 min. ¹H NMR (400 MHz, DMSO-d₆) δ 10.28 (s, 1H), 7.60-7.52 (m, 1H), 7.22-7.11 (m, 1H), 6.92 (dddd, J=21.3, 8.1, 7.0, 1.2 Hz, 2H), 6.74-6.64 (m, 2H), 5.37 (s, 1H), 4.50 (dd, J=47.6, 6.2 Hz, 2H), 3.94 (t, J=5.4 Hz, 2H), 3.59 (q, J=6.9 Hz, 1H), 3.29 (s, 2H), 3.10-3.01 (m, 1H), 2.99 (t, J=6.6 Hz, 2H), 2.92 (ddd, J=14.0, 9.2, 4.7 Hz, 1H), 2.84-2.65 (m, 4H), 2.41 (dd, J=24.4, 14.6 Hz, 1H), 2.18-2.04 (m, 1H), 1.72 (dd, J=12.8, 7.1 Hz, 1H), 1.49 (d, J=7.1 Hz, 3H), 1.18 (dd, J=21.6, 1.9 Hz, 6H).

Example 124 (1S,5S)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole 124

Following the procedures of Example 123, 124 was prepared (24.7 mg, yield 4.8%). 124: R.T. 0.565 min. 1H NMR (400 MHz, DMSO-d6) δ 10.28 (s, 1H), 7.60-7.50 (m, 1H), 7.16 (ddd, J=8.0, 1.3, 0.7 Hz, 1H), 6.92 (dddd, J=21.3, 8.1, 7.0, 1.2 Hz, 2H), 6.74-6.63 (m, 2H), 5.37 (s, 1H), 4.50 (dd, J=47.6, 6.2 Hz, 2H), 3.94 (t, J=5.4 Hz, 2H), 3.59 (q, J=6.9 Hz, 1H), 3.29 (s, 2H), 3.11-2.87 (m, 4H), 2.85-2.62 (m, 4H), 2.48-2.27 (m, 1H), 2.10 (ddd, J=14.1, 9.4, 4.8 Hz, 1H), 1.72 (dd, J=13.4, 7.7 Hz, 1H), 1.49 (d, J=7.1 Hz, 3H), 1.18 (dd, J=21.5, 1.9 Hz, 6H).

Example 125 (1R,5S)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole 125

Following the procedures of Example 123, 125 was prepared (23.2 mg, yield 4.5%). 125: R.T. 0.588 min. 1H NMR (400 MHz, DMSO-d₆) δ 10.37 (s, 1H), 7.49-7.40 (m, 1H), 7.17-7.10 (m, 1H), 7.01-6.87 (m, 2H), 6.65 (d, J=10.9 Hz, 2H), 5.41 (s, 1H), 4.49 (dd, J=47.6, 6.2 Hz, 2H), 3.93 (t, J=5.4 Hz, 2H), 3.51-3.35 (m, 1H), 3.29-3.20 (m, 2H), 3.02-2.95 (m, 2H), 2.94-2.79 (m, 2H), 2.78-2.52 (m, 4H), 2.42-2.29 (m, 1H), 1.70-1.59 (m, 1H), 1.31 (d, J=7.2 Hz, 3H), 1.26 (dd, J=21.4, 3.7 Hz, 6H).

Example 126 (1S,5R)-1-(2,6-difluoro-4-(2-(3-(fluoromethyl)azetidin-1-yl)ethoxy)phenyl)-2-(2-fluoro-2-methylpropyl)-5-methyl-1,2,3,4,5,10-hexahydroazepino[3,4-b]indole 126

Following the procedures of Example 123, 126 was prepared (24.7 mg, yield 4.8%). 126: R.T. 0.789 min. ¹H NMR (400 MHz, DMSO-d₆) δ 10.37 (s, 1H), 7.49-7.39 (m, 1H), 7.19-7.09 (m, 1H), 7.01-6.87 (m, 2H), 6.65 (d, J=10.8 Hz, 2H), 5.42 (s, 1H), 4.49 (dd, J=47.6, 6.2 Hz, 2H), 3.93 (t, J=5.4 Hz, 2H), 3.46-3.41 (m, 1H), 3.26-3.20 (m, 2H), 2.98 (dd, J=7.3, 6.0 Hz, 2H), 2.94-2.78 (m, 2H), 2.77-2.52 (m, 4H), 2.41-2.28 (m, 0H), 1.63 (d, J=14.1 Hz, 0H), 1.31 (d, J=7.2 Hz, 3H), 1.26 (dd, J=21.5, 3.7 Hz, 6H).

Example 127 N-(3,5-Difluoro-4-((1R,3R)-2-(2-fluoro-2-methylpropyl)-3-methyl-1,2,3,4-tetrahydropyrazino[1,2-a]indol-1-yl)phenyl)-1-(3-fluoropropyl)azetidin-3-amine 127

Step 1: (R)-N-(1-(1H-Indol-1-yl)propan-2-yl)-2-fluoro-2-methylpropan-1-amine

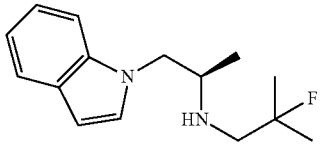 [SMILES: C[C@H](Cn1ccc2ccccc21)NCC(C)(C)F]

To a solution of (2R)-1-indol-1-ylpropan-2-amine (1.0 g, 5.74 mmol) in 1,4-dioxane (10 mL) was added (2-fluoro-2-methyl-propyl) trifluoromethanesulfonate (1.42 g, 6.31 mmol) followed by the addition of N,N-diisopropylethylamine (2.85 mL, 17.22 mmol). The reaction mixture was stirred at 80° C. for 16 hours. The mixture was then concentrated and the residue was purified by column chromatography on silica gel (DCM) to give the title compound (1.1 g, 77%) as a light yellow oil. $^1$H NMR (400 MHz, CDCl$_3$) δ 7.63 (d, J=8.0 Hz, 1H), 7.38 (d, J=8.0 Hz, 1H), 7.24-7.17 (m, 1H), 7.16-7.06 (m, 2H), 6.50 (d, J=3.2 Hz, 1H), 4.16-3.98 (m, 2H), 3.21-3.11 (m, 1H), 2.82-2.71 (m, 1H), 2.60-2.47 (m, 1H), 1.36-1.26 (m, 6H), 1.08 (d, J=6.4 Hz, 3H).

Step 2: (1R,3R)-1-(4-Bromo-2,6-difluorophenyl)-2-(2-fluoro-2-methylpropyl)-3-methyl-1,2,3,4-tetrahydropyrazino[1,2-a]indole

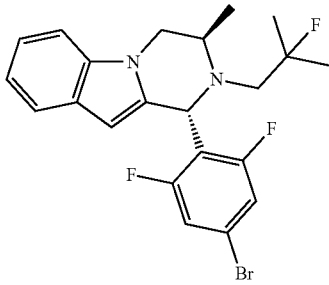 [SMILES: C[C@@H]1Cn2c(cc3ccccc32)[C@@H](c2c(F)cc(Br)cc2F)N1CC(C)(C)F]

To a solution of 4-bromo-2,6-difluorobenzaldehyde (1.6 g, 7.24 mmol) and (R)-N-(1-(1H-indol-1-yl)propan-2-yl)-2-fluoro-2-methylpropan-1-amine (1.8 g, 7.24 mmol) in toluene (18 mL) was added AcOH (1.04 mL, 18.1 mmol). The reaction mixture was stirred at 110° C. for 16 hours. After being cooled to 30° C., the reaction mixture was diluted with EtOAc (100 mL), washed with saturated Na$_2$CO$_3$ (30 mL), water (30 mL) and brine (30 mL). The mixture was dried over anhydrous Na$_2$SO$_4$, filtered and concentrated. The residue was purified by column chromatography on silica gel (0-9% EtOAc in petroleum ether) followed by prep. TLC (9% EtOAc in petroleum ether) to give the title compound (0.4 g, yield 12%) as a light yellow solid. LCMS: 451.3 [M+H]$^+$. $^1$H NMR (400 MHz, CDCl$_3$) δ 7.50 (d, J=7.6 Hz, 1H), 7.33 (d, J=8.0 Hz, 1H), 7.22-7.16 (m, 1H), 7.12-7.01 (m, 3H), 5.96 (s, 1H), 5.46 (s, 1H), 4.36-4.32 (m, 1H), 4.07-4.04 (m, 1H), 3.95-3.82 (m, 1H), 3.03 (t, J=14.8 Hz, 1H), 2.35-2.18 (m, 1H), 1.27-1.10 (m, 9H).

Step 3: tert-Butyl 3-((3,5-difluoro-4-((1R,3R)-2-(2-fluoro-2-methylpropyl)-3-methyl-1,2,3,4-tetrahydropyrazino[1,2-a]indol-1-yl)phenyl)amino)azetidine-1-carboxylate

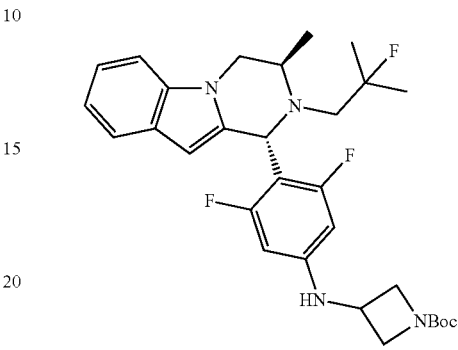

To a solution of (1R,3R)-1-(4-bromo-2,6-difluoro-phenyl)-2-(2-fluoro-2-methyl-propyl)-3-methyl-3,4-dihydro-1H-pyrazino[1,2-a]indole (0.35 g, 0.78 mmol) and tert-butyl 3-aminoazetidine-1-carboxylate (0.20 g, 1.2 mmol) in toluene (4 mL) was added (R)-(+)-2,2'-bis(diphenylphosphino)-1,1'-binaphthyl (0.097 g, 0.16 mmol), tris(dibenzylideneacetone) dipalladium(0) (71 mg, 0.08 mmol) and sodium tert-butoxide (0.22 g, 2.33 mmol). The reaction mixture was stirred at 80° C. for 16 hours under N$_2$ atmosphere. The mixture was filtered and concentrated. The residue was purified by column chromatography on silica gel (0-50% EtOAc in petroleum ether) to give the title compound (0.40 g, yield 95%) as a light yellow solid. $^1$H NMR (400 MHz, CDCl$_3$) δ 7.48 (d, J=7.6 Hz, 1H), 7.32 (d, J=8.0 Hz, 1H), 7.20-7.13 (m, 1H), 7.10-7.04 (m, 1H), 6.00-5.92 (m, 3H), 5.34 (s, 1H), 4.35-4.24 (m, 4H), 4.18-4.09 (m, 1H), 4.03 (dd, J=11.2, 3.2 Hz, 1H), 3.92-3.82 (m, 1H), 3.73 (dd, J=9.2, 4.4 Hz, 2H), 2.95 (t, J=14.4 Hz, 1H), 2.39-2.24 (m, 1H), 1.45 (s, 9H), 1.26-1.10 (m, 9H).

Step 4: N-(3,5-Difluoro-4-((1R,3R)-2-(2-fluoro-2-methylpropyl)-3-methyl-1,2,3,4-tetrahydropyrazino[1,2-a]indol-1-yl)phenyl)azetidin-3-amine

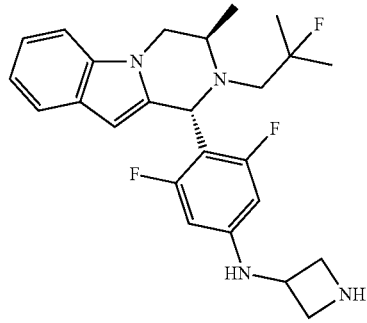 [SMILES: C[C@@H]1Cn2c(cc3ccccc32)[C@@H](c2c(F)cc(NC3CNC3)cc2F)N1CC(C)(C)F]

To a solution of tert-butyl 3-[3,5-difluoro-4-[(1R,3R)-2-(2-fluoro-2-methyl-propyl)-3-methyl-3,4-dihydro-1H-pyrazino[1,2-a]indol-1-yl]anilino]azetidine-1-carboxylate (From step 2, 0.35 g, 0.65 mmol) in 1,4-dioxane (4 mL) was added sulfuric acid (0.34 mL, 6.45 mmol) at 0° C. The mixture was stirred at 18° C. for 30 minutes. Saturated aqueous NaHCO$_3$ (20 mL) was added to the mixture and the mixture was extracted with EtOAc (40 mL×2). The combined organic layers were washed with brine (20 mL×2), dried over anhydrous Na$_2$SO$_4$, filtered and concentrated. The residue was purified by column chromatography on silica gel (0-10% MeOH (0.5% TEA) in DCM) to give the title compound (0.2 g, yield 70%) as a light yellow solid. LCMS: 443.2 [M+H]$^+$.

Step 5: 127

To a solution of N-[3,5-difluoro-4-[(1R,3R)-2-(2-fluoro-2-methyl-propyl)-3-methyl-3,4-dihydro-1H-pyrazino[1,2-a]indol-1-yl]phenyl]azetidin-3-amine (0.20 g, 0.45 mmol) in N,N-dimethylformamide (1.5 mL) was added N,N-diisopropylethylamine (0.22 mL, 1.36 mmol) followed by the addition of 1-iodo-3-fluoropropane (85 mg, 0.45 mmol). The reaction mixture was stirred at 25° C. for 16 hours. The mixture was filtered and concentrated. The residue was purified by reverse phase chromatography (acetonitrile 63-93%/0.05% NH$_4$OH in water) to give 127 (20.2 mg, yield 9%) as a light yellow solid. LCMS: 503.3 [M+H]$^+$. $^1$H NMR (400 MHz, CD$_3$OD) δ 7.38 (d, J=7.6 Hz, 1H), 7.31 (d, J=7.6 Hz, 1H), 7.11-7.04 (m, 1H), 7.01-6.93 (m, 1H), 6.08 (d, J=11.2 Hz, 2H), 5.82 (s, 1H), 5.30 (s, 1H), 4.56-4.35 (m, 2H), 4.22 (dd, J=11.6, 4.0 Hz, 1H), 4.09 (dd, J=11.2, 3.2 Hz, 1H), 4.06-4.00 (m, 1H), 3.91-3.83 (m, 1H), 3.82-3.74 (m, 2H), 3.00-2.87 (m, 3H), 2.66 (t, J=7.6 Hz, 2H), 2.43-2.27 (m, 1H), 1.83-1.68 (m, 2H), 1.22-1.09 (m, 9H).

Example 128 (1R,3R)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine 128

As described below, the trans-isomer from Example 130, Step 3 was converted to the final product and the enantiomers 128 and 129 were separated by chiral SFC (stationary phase: AD; mobile phase: MeOH w/0.1% NH$_4$OH).

128: 14.5 mg; $^1$H NMR (400 MHz, DMSO-d$_6$) δ 7.92 (ddd, J=7.9, 1.3, 0.7 Hz, 1H), 7.26 (ddd, J=8.0, 7.1, 1.3 Hz, 1H), 7.20 (ddd, J=8.2, 7.1, 1.2 Hz, 1H), 7.10-7.04 (m, 3H), 6.80 (d, J=8.7 Hz, 2H), 5.12 (s, 1H), 4.49 (dd, J=47.6, 6.2 Hz, 2H), 3.85 (t, J=5.4 Hz, 2H), 3.37-3.25 (m, 2H), 3.24-3.15 (m, 1H), 2.98 (brs, 2H), 2.84-2.64 (m, 6H), 2.44 (t, J=14.7 Hz, 1H), 1.43 (d, J=21.8 Hz, 3H), 1.28 (d, J=21.6 Hz, 3H), 1.03 (d, J=6.7 Hz, 3H); LCMS: 485.2 [M+H]$^+$.

Example 129 (1S,3S)-2-(2-Fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine 129

Following the procedures of Example 128, 129 was prepared

129: 9.9 mg; $^1$H NMR (400 MHz, DMSO-d$_6$) δ 7.92 (ddd, J=8.0, 1.2, 0.7 Hz, 1H), 7.69 (d, J=11.8 Hz, 1H), 7.29-7.23 (m, 1H), 7.23-7.16 (m, 1H), 7.10-7.05 (m, 2H), 5.12 (s, 1H), 4.49 (dd, J=47.6, 6.2 Hz, 2H), 3.85 (t, J=5.6 Hz, 2H), 3.31 (s, 4H), 3.25-3.13 (m, 1H), 2.98 (t, J=6.5 Hz, 2H), 2.83-2.54 (m, 6H), 2.48-2.41 (m, 1H), 1.43 (d, J=21.7 Hz, 3H), 1.28 (d, J=21.6 Hz, 3H), 1.03 (d, J=6.7 Hz, 3H); LCMS: 485.2 [M+H]$^+$.

Example 130 (1S,3R)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine 130

Step 1: 2-(2-Nitroprop-1-en-1-yl)benzo[b]thiophene

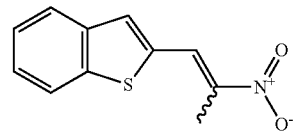

A mixture of benzothiophene-2-carboxaldehyde (3.80 g, 24.4 mmol), ammonium acetate (1.63 g, 21.3 mmol) in nitroethane (20 mL) was heated at 100° C. for 5 hrs. The reaction mixture was cooled and was diluted with isopropyl acetate (IPAC). The solution was washed with water, brine, dried over sodium sulfate and was concentrated. The residue was triturated with heptane/IPAC and the solid was collected by filtration to obtain 2-(2-nitroprop-1-en-1-yl)benzo[b]thiophene (2.90) as an orange solid. $^1$HNMR (400 MHz, Chloroform-d) δ 8.35 (q, J=1.0 Hz, 1H), 7.93-7.82 (m, 2H), 7.66 (s, 1H), 7.52-7.31 (m, 2H), 2.64 (d, J=1.0 Hz, 3H).

Step 2: 1-(Benzo[b]thiophen-2-yl)propan-2-amine

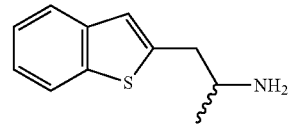

A solution of 2-(2-nitroprop-1-en-1-yl)benzo[b]thiophene (2.90 g, 23.4 mmol) in dry THF (50 mL) was cooled in an ice-bath and LAH (19.2 mL of 2M solution in THF) was added slowly and the resulting mixture was stirred at ambient temperature for 1 hr, then refluxed for 2 hrs and was allowed to stir overnight at ambient temperature. The resulting suspension was cooled in an ice-bath and was quenched with a few cubes of ice followed by 2N NaOH (5 mL, 2 N). The suspension was filtered through Celite while washing with IPAC. The filtrate was dried over sodium sulfate and was concentrated. The residue was purified by flash chromatography (silica gel, 0-10% MeOH/DCM) to obtain an orange oil (1.10 g). $^1$H NMR (400 MHz, Chloroform-d) δ 7.80-7.74 (m, 1H), 7.72-7.66 (m, 1H), 7.35-7.23 (m, 2H), 7.09-7.02 (m, 1H), 3.34-3.20 (m, 1H), 3.02-2.93 (m, 1H), 2.86-2.77 (m, 1H), 1.18 (d, J=6.3 Hz, 3H). LCMS: 192.05 [M+H]$^+$.

Step 3: cis- and trans-1-(4-Iodophenyl)-3-methyl-1,2,3,4-tetrahydrobenzo[4,5]thieno[3,2-c]pyridine

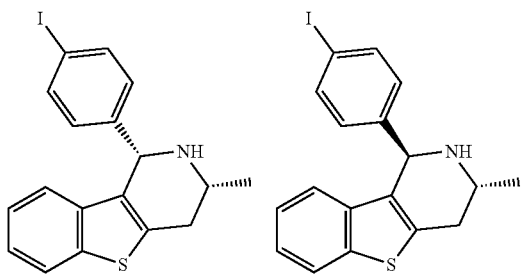

A mixture of 1-(benzo[b]thiophen-2-yl)propan-2-amine (150 mg, 0.84 mmol), 4-iodobenzaldehyde (182 mg, 0.84 mmol) and TFA (1.07 mL) in dichloroethane (1.5 mL) was heated at 150° C. for 50 min. in a microwave reactor. The reaction mixture was cooled and was concentrated. The residue was dissolved in IPAC and stirred over saturated sodium bicarbonate. The organic layer was separated, washed with water, brine, dried over sodium sulfate and was concentrated. The residue was purified by flash chromatography (silica gel, 0-10% MeOH/DCM) and the cis- and trans-diastereomers were separated.

cis-isomer: 150 mg; $^1$H NMR (400 MHz, Chloroform-d) δ 7.74 (ddd, J=8.0, 1.1, 0.7 Hz, 1H), 7.67-7.62 (m, 2H), 7.18 (ddd, J=8.1, 7.2, 1.2 Hz, 1H), 7.10-7.01 (m, 3H), 6.85-6.70 (m, 1H), 5.25-5.13 (m, 1H), 3.31-3.19 (m, 1H), 2.93 (ddd, J=16.1, 3.5, 2.0 Hz, 1H), 2.73 (ddd, J=16.2, 10.3, 2.9 Hz, 1H), 1.30 (d, J=6.3 Hz, 3H); LCMS: 405.9 [M+H]$^+$.

trans-isomer: 60 mg; $^1$H NMR (400 MHz, Chloroform-d)$^1$H NMR (400 MHz, Chloroform-d) δ 7.80-7.76 (m, 1H), 7.62-7.58 (m, 2H), 7.23 (ddd, J=8.1, 7.1, 1.4 Hz, 1H), 7.16 (ddd, J=8.2, 7.1, 1.1 Hz, 1H), 7.08-7.05 (m, 1H), 6.97-6.92 (m, 2H), 5.28 (d, J=1.5 Hz, 1H), 3.19-3.11 (m, 1H), 2.96 (dd, J=16.7, 4.0 Hz, 1H), 2.66 (ddd, J=16.7, 10.0, 1.6 Hz, 1H), 1.18 (d, J=6.3 Hz, 3H); LCMS: 405.9 [M+H]$^+$.

Step 4: cis-2-(2-Fluoro-2-methylpropyl)-1-(4-iodophenyl)-3-methyl-1,2,3,4-tetrahydrobenzo[4,5]thieno[3,2-c]pyridine

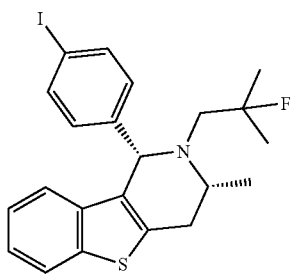 [SMILES: C[C@@H]1Cc2sc3ccccc3c2[C@H](c2ccc(I)cc2)N1CC(C)(C)F]

The cis-isomer from step 3 (150 mg, 0.37 mmol) was dissolved in dichloroethane (2 mL) and 2-fluoro-2-methylpropyl trifluoromethanesulfonate (131 mg. 0.56 mmol) and potassium carbonate (102 mg, 0.74 mmol) were added and the mixture was heated at 90° C. for 2 weeks. The reaction mixture was cooled, diluted with IPAC, washed with water, brine, dried over sodium sulfate and was concentrated. The residue was purified by flash column chromatography (silica gel, 0-30% IPAC/heptane) to obtain the title compound (130 mg): $^1$H NMR (400 MHz, Chloroform-d) δ 7.83 (ddd, J=8.0, 1.2, 0.7 Hz, 1H), 7.54-7.50 (m, 2H), 7.30-7.24 (m, 1H), 7.21 (ddd, J=8.2, 7.1, 1.2 Hz, 1H), 7.16-7.10 (m, 3H), 5.08 (s, 1H), 3.37-3.22 (m, 2H), 2.90 (t, J=15.5 Hz, 1H), 2.72-2.54 (m, 2H), 1.53 (d, J=21.3 Hz, 3H), 1.34 (d, J=21.4 Hz, 3H), 0.88 (d, J=7.0 Hz, 3H); LCMS: 480.0 [M+H]$^+$.

Step 5: (1S,3R)-, and (1R,3S)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine

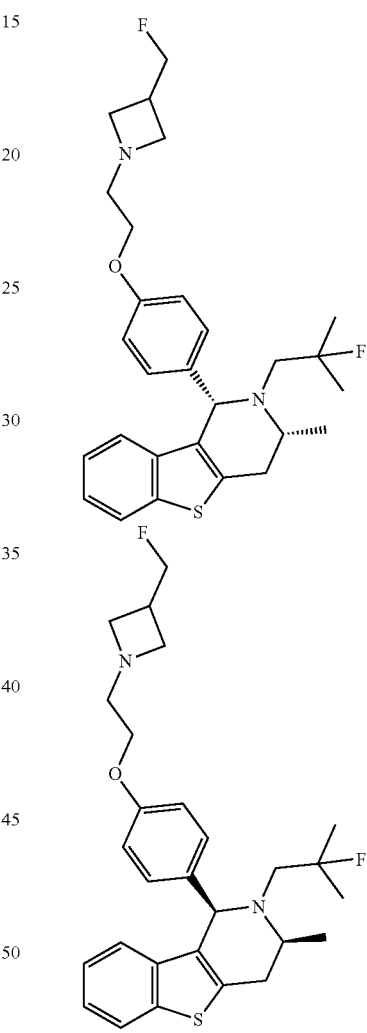

A mixture of cis-2-(2-Fluoro-2-methylpropyl)-1-(4-iodophenyl)-3-methyl-1,2,3,4-tetrahydrobenzo[4,5]thieno[3,2-c]pyridine (130 mg, 0.27 mmol), 2-(3-(fluoromethyl)azetidin-1-yl)ethan-1-ol (74 mg, 0.56 mmol), curpous iodide (23 mg, 0.11 mmol) and potassium carbonate (102 mg, 0.74 mmol) in butyronitrile (1 mL) was degassed by purging with nitrogen followed by evacuation three times. The resulting mixture was heated at 135° C. for 20 hrs. The reaction was cooled, diluted with IPAC and was filtered through celite. The filtrate was washed with water, brine, dried over sodium sulfate and was concentrated. The enantiomers 130 and 131 were separated by chiral SFC (stationary phase: AD; mobile phase: EtOH w/0.1% NH$_4$OH):

130: 15 mg; RT=0.534; $^1$H NMR (400 MHz, DMSO-d$_6$) δ 7.93 (ddd, J=8.0, 1.2, 0.7 Hz, 1H), 7.32-7.11 (m, 4H), 7.03 (ddd, J=7.9, 1.3, 0.7 Hz, 1H), 6.80-6.68 (m, 2H), 5.05 (d, J=1.6 Hz, 1H), 4.49 (dd, J=47.6, 6.3 Hz, 2H), 3.84 (t, J=5.6 Hz, 2H), 3.31 (s, 4H), 2.98 (dd, J=7.3, 5.8 Hz, 2H), 2.87-2.55 (m, 6H), 1.43 (d, J=21.4 Hz, 3H), 1.27 (d, J=21.6 Hz, 3H), 0.85 (d, J=7.0 Hz, 3H); LCMS: 485.2 [M+H]$^+$.

Example 131 (1R,3S)-2-(2-fluoro-2-methylpropyl)-1-(4-(2-(3-(fluoromethyl)azetidin-1-yl)ethoxy)phenyl)-3-methyl-1,2,3,4-tetrahydrobenzo[4,5]thieno[3,2-c]pyridine 131

Following the procedures of Example 130, 131 was prepared

131: 16 mg; $^1$H NMR (400 MHz, DMSO-d$_6$) δ 7.93 (ddd, J=7.9, 1.2, 0.7 Hz, 1H), 7.23 (dddd, J=27.3, 8.2, 7.1, 1.2 Hz, 2H), 7.17-7.09 (m, 2H), 7.06-7.00 (m, 1H), 6.80-6.69 (m, 2H), 5.05 (s, 1H), 4.49 (dd, J=47.6, 6.3 Hz, 2H), 3.84 (t, J=5.6 Hz, 2H), 3.31 (s, 4H), 2.98 (dd, J=7.2, 5.9 Hz, 2H), 2.88-2.53 (m, 6H), 1.43 (d, J=21.5 Hz, 3H), 1.28 (d, J=21.6 Hz, 3H), 0.85 (d, J=7.0 Hz, 3H); LCMS: 485.2 [M+H]$^+$.

Example 132 (6S,8S)-8-{2,6-Difluoro-4-[2-(3-fluoromethyl-azetidin-1-yl)-ethoxy]-phenyl}-7-(2-fluoro-2-methyl-propyl)-6-methyl-6,7,8,9-tetrahydro-5H-dipyrido[2,3-b;4',3'-d]pyrrole 132

Following the procedures of Examples 120 and 121, 132 was prepared.

Example 133 (6R,8R)-6-{2,6-Difluoro-4-[2-(3-fluoromethyl-azetidin-1-yl)-ethoxy]-phenyl}-7-(2-fluoro-2-methyl-propyl)-8-methyl-6,7,8,9-tetrahydro-5H-dipyrido[3,2-b;4',3'-d]pyrrole 133

Following the procedures of Examples 120 and 121, 133 was prepared.

Example 135 (1R,3R)-2-(2-Fluoro-2-methylpropyl)-1-(4-(2-(3-(fluoromethyl)azetidin-1-yl)ethoxy)phenyl)-1,3-dimethyl-2,3,4,9-tetrahydro-1H-pyrido[3,4-b]indole 135

Step 1: (1R,3R)-1-(4-Iodophenyl)-1,3-dimethyl-2,3,4,9-tetrahydro-1H-pyrido[3,4-b]indole

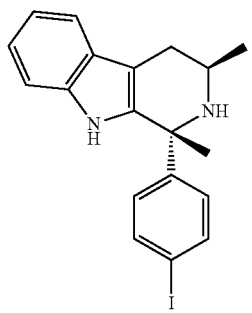 [SMILES: C[C@@H]1Cc2c([nH]c3ccccc23)[C@@](C)(c2ccc(I)cc2)N1]

To a solution of trifluoroacetic acid (1.07 mL, 14.35 mmol) and (2R)-1-(1H-indol-3-yl)propan-2-amine (1.0 g, 5.74 mmol) in 1,2-dichloroethane (3 mL) was added 1-(4-iodophenyl)ethanone (1.41 g, 5.74 mmol). The mixture was stirred in a microware reactor vial at 150° C. for 1 hour. The reaction mixture was diluted with EtOAc (40 mL), washed with saturated Na$_2$CO$_3$ (15 mL), water (15 mL) and brine (15 mL). The solution was dried over anhydrous Na$_2$SO$_4$, filtered and concentrated. The residue was purified by column chromatography on silica gel (0-25% EtOAc in petroleum ether) to give the title compound (2 g, yield 87%) as light yellow solid. $^1$H NMR (400 MHz, CDCl$_3$) δ 7.84 (s, 1H), 7.59 (d, J=8.4 Hz, 2H), 7.54 (d, J=8.0 Hz, 1H), 7.37 (d, J=8.0 Hz, 1H), 7.25-7.12 (m, 2H), 7.02 (d, J=8.4 Hz, 2H), 2.89-2.75 (m, 2H), 2.49-2.36 (m, 1H), 1.78 (s, 3H), 1.20 (d, J=6.0 Hz, 3H).

Step 2: (1R,3R)-2-(2-Fluoro-2-methylpropyl)-1-(4-iodophenyl)-1,3-dimethyl-2,3,4,9-tetrahydro-1H-pyrido[3,4-b]indole

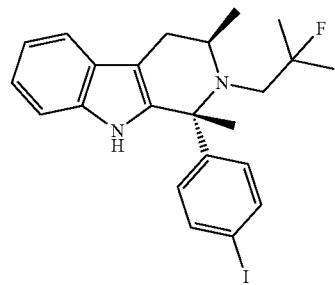 [SMILES: C[C@@H]1Cc2c([nH]c3ccccc23)[C@@](C)(c2ccc(I)cc2)N1CC(C)(C)F]

To a solution of potassium carbonate (1.37 g, 9.94 mmol) in n-butyronitrile (5 mL) was added (1R,3R)-1-(4-iodophenyl)-1,3-dimethyl-2,3,4,9-tetrahydropyrido[3,4-b]indole (From step 1, 0.5 g, 1.24 mmol) and (2-fluoro-2-methylpropyl)trifluoromethane sulfonate (1.39 g, 6.21 mmol). The mixture was stirred at 130° C. for 16 hours. After being cooled to 25° C., the reaction mixture was filtered and concentrated. The residue was purified by column chromatography on silica gel (0-10% EtOAc in petroleum ether) to give the title compound (150 mg, yield 25%) as a light yellow solid. $^1$H NMR (400 MHz, DMSO-d$_6$) δ 10.84 (s, 1H), 7.61 (d, J=8.4 Hz, 2H), 7.40 (d, J=8.0 Hz, 1H), 7.29 (d, J=8.0 Hz, 1H), 7.17-7.00 (m, 3H), 6.97-6.90 (m, 1H), 2.82-2.50 (m, 5H), 1.67 (s, 3H), 1.38-1.20 (m, 6H), 1.03 (d, J=6.4 Hz, 3H).

Step 3: 135

To a solution of (1R,3R)-2-(2-fluoro-2-methyl-propyl)-1-(4-iodophenyl)-1,3-dimethyl-4,9-dihydro-3H-pyrido[3,4-b]indole (From step 2, 0.1 g, 0.21 mmol) and 2-[3-(fluoromethyl)azetidin-1-yl]ethanol (0.14 g, 1.05 mmol) in n-butyronitrile (2 mL) was added copper(I) iodide (0.12 g, 0.63 mmol) and potassium carbonate (0.15 g, 1.1 mmol). The reaction mixture was stirred at 130° C. for 3 hours under N$_2$ atmosphere. After being cooled to 25° C., the mixture was concentrated to dryness. The residue was purified by reverse phase chromatography (acetonitrile 70-100%/0.05% NH$_4$OH in water) to give 135 (13 mg, yield 13%) as a light yellow solid. LCMS: 482.3 [M+H]$^+$. $^1$H NMR (400 MHz, CD$_3$OD) δ 7.41 (d, J=7.6 Hz, 1H), 7.30-7.15 (m, 3H), 7.06-6.92 (m, 2H), 6.76 (d, J=8.4 Hz, 2H), 4.55-4.38 (dd, J=47.6, 5.6 Hz, 2H), 4.00 (t, J=4.8 Hz, 2H), 3.65-3.43 (m, 3H), 3.24-3.15 (m, 2H), 2.90-2.72 (m, 5H), 2.69-2.53 (m, 2H), 1.75 (s, 3H), 1.34-1.05 (m, 9H).

Example 136 (1R,3S)-1-(2,6-difluoro-4-(2-(3-(fluoromethyl)azetidin-1-yl)ethoxy)phenyl)-2-(2-fluoro-2-methylpropyl)-3-methyl-2,3,4,5-tetrahydro-1H-pyrido[4,3-b]indole 136

Step 1: 1-(1H-indol-2-yl)propan-2-amine

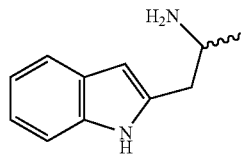

1H-Indole-2-carbaldehyde (2.0 g, 13.8 mmol) was converted to 2-(2-nitroprop-1-enyl)-1H-indole (2.5 g) as described for Example 37 and 38 Step 1. $^1$H NMR (400 MHz, Chloroform-d) δ 8.32 (s, 1H), 8.14-8.07 (m, 1H), 7.73-7.66 (m, 1H), 7.45-7.40 (m, 1H), 7.32 (ddd, J=8.2, 7.0, 1.2 Hz, 1H), 7.21-7.14 (m, 1H), 7.02-6.92 (m, 1H), 2.63 (d, J=1.0 Hz, 3H).

Then 2-(2-Nitroprop-1-enyl)-1H-indole (2.5 g, 12.4 mmol) was converted to 1-(1H-indol-2-yl)propan-2-amine (1.50 g) as described for Example 37 and 38 Step 2. $^1$H NMR (400 MHz, Chloroform-d) δ 9.10 (brs, 1H), 7.59-7.46 (m, 1H), 7.36-7.28 (m, 1H), 7.15-7.03 (m, 2H), 6.31-6.16 (m, 1H), 3.37-3.21 (m, 1H), 2.95-2.75 (m, 1H), 2.73-2.56 (m, 1H), 1.16 (d, J=6.3 Hz, 4H); LCMS: 175.1[M+H]$^+$.

Step 2: N-(1-(1H-indol-2-yl)propan-2-yl)-2-fluoro-2-methylpropan-1-amine

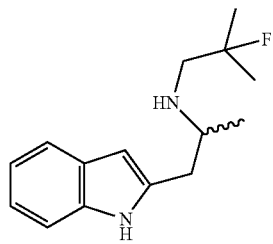 [SMILES: CC(Cc1cc2ccccc2[nH]1)NCC(C)(C)F]

A mixture of 1-(1H-indol-2-yl)propan-2-amine (1.0 g, 5.74 mmol), 2-fluoro-2-methylpropyl trifluoromethanesulfonate (1.42 g, 6.31 mmol) and DIPEA (2.0 mL, 11.5 mmol) in 1,4-dioxane (20 mL) was heated at 90° C. for 20 hrs. The reaction mixture was cooled, diluted with IPAC, washed with water, brine, dried over sodium sulfate and was concentrated. The residue was purified by flash column chromatography on silica gel (0-5% MeOH/DCM) to obtain the title compound (1.2 g). $^1$H NMR (400 MHz, Chloroform-d) δ 9.72 (s, 1H), 7.55-7.50 (m, 1H), 7.30-7.26 (m, 1H), 7.15-7.07 (m, 1H), 7.07-6.99 (m, 1H), 6.22 (dd, J=1.0, 2.0 Hz, 1H), 3.09-2.99 (m, 1H), 2.99-2.84 (m, 2H), 2.81-2.58 (m, 2H), 1.49 (d, J=21.4 Hz, 3H), 1.43 (d, J=21.3 Hz, 3H), 1.13 (d, J=6.3 Hz, 3H); LCMS: 249.1 [M+H]$^+$.

Step 3: 1-(2,6-difluoro-4-iodophenyl)-2-(2-fluoro-2-methylpropyl)-3-methyl-2,3,4,5-tetrahydro-1H-pyrido[4,3-b]indole

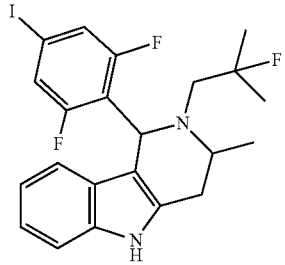 [SMILES: CC1Cc2[nH]c3ccccc3c2C(c2c(F)cc(I)cc2F)N1CC(C)(C)F]

A mixture of N-(1-(1H-indol-2-yl)propan-2-yl)-2-fluoro-2-methylpropan-1-amine (0.40 g, 1.6 mmol), 2,6-difluoro-4-iodobenzaldehyde (0.40 g, 1.61 mmol) and acetic acid (0.20 mL) in toluene (5 mL) was heated at 90° C. overnight. The reaction mixture was cooled, concentrated and was purified by flash column chromatography over silica gel (0-20% IPAC/heptane) to obtain the title compound (0.30 g). $^1$H NMR (400 MHz, Chloroform-d) δ 7.81 (s, 1H), 7.31-7.27 (m, 1H), 7.21-7.15 (m, 2H), 7.05 (ddd, J=8.2, 7.1, 1.2 Hz, 1H), 6.90 (ddd, J=8.0, 7.1, 1.0 Hz, 1H), 6.83-6.77 (m, 1H), 5.24 (d, J=1.7 Hz, 1H), 3.82-3.72 (m, 1H), 3.31 (ddd, J=15.6, 5.4, 2.1 Hz, 1H), 2.97 (t, J=15.2 Hz, 1H), 2.53 (ddd, J=15.4, 2.9, 1.4 Hz, 1H), 2.33 (dd, J=30.4, 14.9 Hz, 1H), 1.21 (d, J=20.0 Hz, 3H), 1.16 (d, J=20.0 Hz, 3H), 1.08 (d, J=6.5 Hz, 3H); LCMS: 499.0 [M+H]$^+$.

Step 4: 136 and 137

Ullmann coupling of 1-(2,6-difluoro-4-iodophenyl)-2-(2-fluoro-2-methylpropyl)-3-methyl-2,3,4,5-tetrahydro-1H-pyrido[4,3-b]indole with 2-[3-(fluoromethyl)azetidin-1-yl]ethanol followed procedures as described for Example 101, Step 5. The two trans-enantiomers 136 and 137 were separated by chiral SFC (stationary phase: AD mobile phase: EtOH w/0.1% NH$_4$OH).

136: RT=0.543; $^1$H NMR (400 MHz, DMSO-d$_6$) δ δ 10.81 (s, 1H), 7.26-7.2 (m, 1H), 6.91 (ddd, J=8.1, 7.1, 1.2 Hz, 1H), 6.73 (ddd, J=8.0, 7.0, 1.0 Hz, 1H), 6.58 (d, J=9.0 Hz, 3H), 5.08 (s, 1H), 4.49 (dd, J=47.6, 6.2 Hz, 2H), 3.90 (dq, J=7.7, 4.8 Hz, 2H), 3.69-3.55 (m, 1H), 3.31-3.25 (m, 2H), 3.17-3.08 (m, 1H), 3.00-2.85 (m, 3H), 2.77-2.65 (m, 3H), 2.56 (dd, J=16.1, 2.8 Hz, 1H), 2.39-2.23 (m, 1H), 1.14 (d, J=21.4 Hz, 3H), 1.11 (d, J=21.4 Hz, 3H), 1.03 (d, J=6.5 Hz, 3H); LCMS: 504.3 [M+H]$^+$.

Example 137 (1S,3R)-1-(2,6-difluoro-4-(2-(3-(fluoromethyl)azetidin-1-yl)ethoxy)phenyl)-2-(2-fluoro-2-methylpropyl)-3-methyl-2,3,4,5-tetrahydro-1H-pyrido[4,3-b]indole 137

Following the procedures of Example 136, 137 was prepared

137: RT=0.423; $^1$H NMR (400 MHz, DMSO-d$_6$) δ 10.81 (s, 1H), 7.26-7.22 (m, 1H), 6.91 (ddd, J=8.1, 7.0, 1.2 Hz, 1H), 6.73 (ddd, J=8.0, 7.1, 1.0 Hz, 1H), 6.58 (d, J=9.0 Hz, 3H), 5.08 (s, 1H), 4.49 (dd, J=47.6, 6.2 Hz, 2H), 3.90 (dq, J=7.3, 4.8 Hz, 2H), 3.62 (d, J=8.2 Hz, 1H), 3.30-3.27 (m, 2H), 3.17-3.09 (m, 1H), 3.00-2.84 (m, 3H), 2.76-2.64 (m, 3H), 2.56 (dd, J=16.2, 2.8 Hz, 1H), 2.31 (dd, J=28.7, 14.9

Hz, 1H), 1.14 (d, J=21.5 Hz, 3H), 1.11 (d, J=21.5 Hz, 3H), 1.03 (d, J=6.4 Hz, 3H); LCMS: 504.3 [M+H]⁺.

Example 138 (2aR,4R,9cR)-4-(2,6-difluoro-4-(2-(3-(fluoromethyl)azetidin-1-yl)ethoxy)phenyl)-3-(2-fluoro-2-methylpropyl)-2,2a,3,4,5,9c-hexahydro-1H-cyclobuta[5,6]pyrido[3,4-b]indole 138

Step 1: 2-(1H-Indol-3-yl)-cyclobutanone

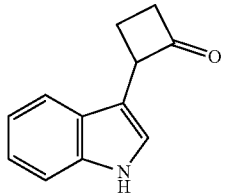 [SMILES: O=C1CCC1c1c[nH]c2ccccc12]

To a mixture of indole (CAS No.: 120-72-9, 10.8 g, 92.3 mmol) in 2,2,2-trifluoroethanol (185 mL) under argon was added 2-bromocyclobutanone (CAS No.: 1192-01-4, 13.75 g, 92.3 mmol) prepared from cyclobutanone according to the procedure described in WO 2014/045156 and sodium carbonate (11.74 g, 110.7 mmol). The resulting mixture was stirred at RT for 18 h, filtered through a pad of Celite® and the filtrate concentrated in vacuo. The crude product was adsorbed onto HMN diatomaceous earth (Isolute®, Biotage) and purified by silica gel chromatography (mobile phase: cyclohexane/ethyl acetate, gradient 0% to 20%) to afford the title compound as a colorless oil (3.04 g, yield 18%). ¹H NMR (300 MHz, CDCl₃): δ 8.04 (br. s, 1H), 7.57 (dd, J=0.8, 7.9 Hz, 1H), 7.35-7.38 (m, 1H), 7.21 (dt, J=1.3, 7.7 Hz, 1H), 7.16-7.10 (m, 2H), 4.78-4.72 (m, 1H), 3.34-3.23 (m, 1H), 3.18-3.09 (m, 1H), 2.67-2.58 (m, 1H), 2.25-2.16 (m, 1H); LCMS: 186.2 [M+H]⁺.

Step 2: (2-Fluoro-2-methyl-propyl)-[2-(1H-indol-3-yl)-cyclobutyl]-amine

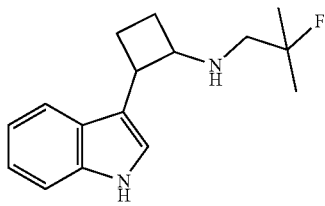 [SMILES: CC(C)(F)CNC1CCC1c1c[nH]c2ccccc12]

A solution of 2-(1H-indol-3-yl)-cyclobutanone (1.08 g, 7.76 mmol) in MeOH (37 mL) and 2-fluoro-2-methyl-propylamine hydrochloride (CAS: 879121-42-3, 926 mg, 9.71 mmol) under argon was stirred for 10 min. Sodium cyanoborohydride (CAS No.: 25895-60-7, 398 mg, 8.54 mmol) was added in two portions at 0° C. and the reaction mixture was allowed to warm to RT and stirred for 72 h. The mixture was concentrated in vacuo and the resultant residue was purified by silica gel chromatography (mobile phase: DCM/MeOH, gradient 0% to 5%). Appropriate fractions were collected and evaporated to afford an enantiomeric mixture of the title compound as a yellowish oil (1.04 g, yield 54%). ¹H NMR (400 MHz, CDCl₃): δ 8.70 (s, 1H), 7.58-7.56 (m, 1H), 7.48 (dd, J=8.0, 23.4 Hz, 2H), 7.25-7.21 (m, 1H), 7.16 (ddd, J=0.9, 7.1, 7.9 Hz, 1H), 5.16-5.10 (m, 1H), 4.29-4.22 (m, 1H), 4.10-4.02 (m, 1H), 2.85 (dd, J=13.0, 17.3 Hz, 1H), 2.61-2.38 (m, 5H), 1.09 (d, J=21.3 Hz, 3H), 0.74 (d, J=21.5 Hz, 3H); LCMS: 261.3 [M+H]⁺.

Step 3: (2aR,4R,9cR)-4-(2,6-difluoro-4-iodophenyl)-3-(2-fluoro-2-methylpropyl)-2,2a,3,4,5,9c-hexahydro-1H-cyclobuta[5,6]pyrido[3,4-b]indole and (2aS,4S,9cS)-4-(2,6-difluoro-4-iodophenyl)-3-(2-fluoro-2-methylpropyl)-2,2a,3,4,5,9c-hexahydro-1H-cyclobuta[5,6]pyrido[3,4-b]indole

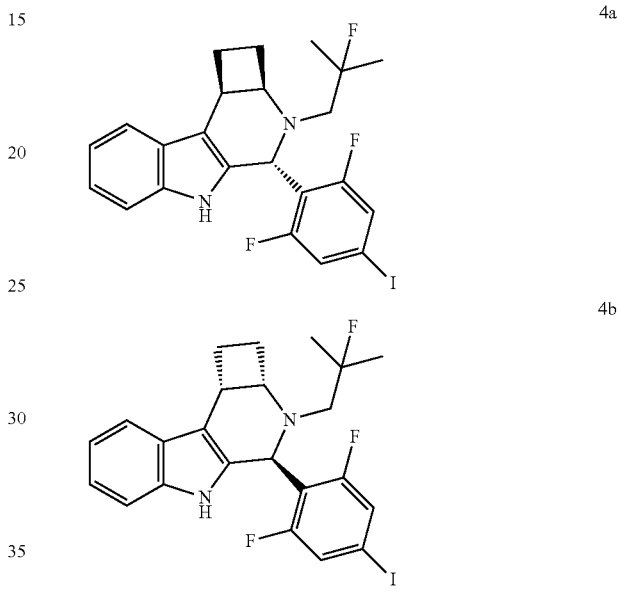

The title compound was prepared from (2-fluoro-2-methyl-propyl)-[2-(1H-indol-3-yl)-cyclobutyl]-amine (320 mg, 1.23 mmol) and 2,6-difluoro-4-iodo-benzaldehyde (610 mg, 2.27 mmol) following the procedure outlined for Example 112 step 1. The crude product was purified and purified by silica gel chromatography (mobile phase: cyclohexane/ethyl acetate, gradient 0% to 20%) followed by a purification by chiral HPLC (ChiralPak IC, mobile phase: 10% DCM in heptane, 0.1% diethylamine over 30 min). Appropriate fractions were collected and evaporated to afford two diastereoisomers. First product isolated 4a (rt=8.0 mins, de>99%) as a white solid (130 mg, yield 21%). ¹H NMR (400 MHz, CDCl₃): δ 7.50 (d, J=7.6 Hz, 1H), 7.32-7.21 (m, 4H), 7.17-7.07 (m, 2H), 5.17 (s, 1H), 4.27-4.20 (m, 1H), 3.84-3.78 (m, 1H), 2.88 (t, J=14.0 Hz, 1H), 2.30-2.01 (m, 4H), 1.70-1.64 (m, 1H), 1.15 (dd, J=21.3, 24.7 Hz, 6H); LCMS: 511.2 [M+H]⁺. Second product isolated 4b (rt=9.0 mins, de>99%) as a white solid (80 mg, yield 13%). ¹H NMR (400 MHz, CDCl₃): δ 7.50 (d, J=7.6 Hz, 1H), 7.32-7.21 (m, 4H), 7.17-7.07 (m, 2H), 5.18 (s, 1H), 4.27-4.20 (m, 1H), 3.85-3.79 (m, 1H), 2.88 (t, J=14.0 Hz, 1H), 2.30-2.00 (m, 4H), 1.70-1.64 (m, 1H), 1.15 (dd, J=21.4, 24.8 Hz, 6H); LCMS: 511.2 [M+H]⁺.

Step 4: (2aR,4R,9cR)-4-(2,6-difluoro-4-(2-(3-(fluoromethyl)azetidin-1-yl)ethoxy)phenyl)-3-(2-fluoro-2-methylpropyl)-2,2a,3,4,5,9c-hexahydro-1H-cyclobuta[5,6]pyrido[3,4-b]indole

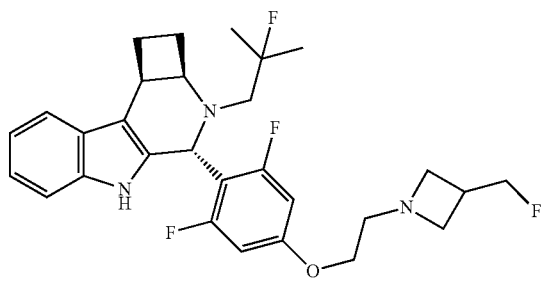 [SMILES: CC(C)(F)CN1[C@H](c2c(F)cc(OCCN3CC(CF)C3)cc2F)c2[nH]c3ccccc3c2[C@H]2CC[C@H]21]

The title compound was prepared from (2aR,4R,9cR)-4-(2,6-difluoro-4-iodophenyl)-3-(2-fluoro-2-methylpropyl)-2,2a,3,4,5,9c-hexahydro-1H-cyclobuta[5,6]pyrido[3,4-b]indole 4a and 2-(3-fluoromethyl-azetidin-1-yl)-ethanol (CAS No.: 1443984-69-7, WO 2013090836) following the procedure outlined for Example 101 step 5. The crude product was purified by silica gel chromatography (mobile phase: dichloromethane/2N ammonia in methanol, gradient 0% to 3%). Appropriate fractions were collected and evaporated to afford 138 as a yellow solid (75 mg, yield 71%). $^1$H NMR (400 MHz, CDCl$_3$): δ 7.49 (d, J=7.6 Hz, 1H), 7.31-7.21 (m, 4H), 7.26 (s, 4H), 7.15-7.05 (m, 2H), 6.47-6.40 (m, 2H), 5.11 (s, 1H), 4.57 (d, J=5.6 Hz, 1H), 4.45 (d, J=5.6 Hz, 1H), 4.29-4.20 (m, 1H), 3.95-3.91 (m, 2H), 3.82 (t, J=7.0 Hz, 1H), 3.49 (dd, J=6.8, 7.5 Hz, 2H), 3.15 (t, J=7.1 Hz, 2H), 2.90-2.81 (m, 4H), 2.33-2.03 (m, 4H), 1.14 (dd, J=15.9, 21.3 Hz, 6H); LCMS: 516.3 [M+H]$^+$.

Example 139 (+)-1-(2,6-difluoro-4-(2-(3-(fluoromethyl)azetidin-1-yl)ethoxy)phenyl)-2-(2-fluoro-2-methylpropyl)-3,5-dimethyl-2,3,4,5-tetrahydro-1H-pyrido[4,3-b]indole 139

Step 1: 1-(2,6-Difluoro-4-iodo-phenyl)-2-(2-fluoro-2-methyl-propyl)-3,5-dimethyl-3,4-dihydro-1H-pyrido[4,3-b]indole

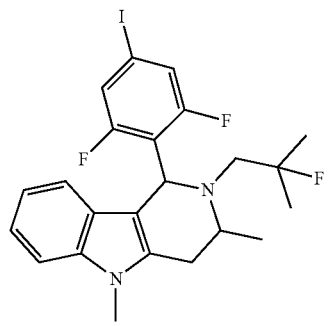 [SMILES: CC1Cc2c(c3ccccc3n2C)C(c2c(F)cc(I)cc2F)N1CC(C)(C)F]

To a solution of 1-(2,6-difluoro-4-iodophenyl)-2-(2-fluoro-2-methylpropyl)-3-methyl-2,3,4,5-tetrahydro-1H-pyrido[4,3-b]indole (300 mg, 0.60 mmol) in DMF (3 mL) was added sodium hydride (29 mg, 60% in mineral oil) and the mixture was stirred for 10 min. To the resulting mixture was added iodomethane (171 mg, 1.30 mmol) and the reaction was stirred at ambient temperature for 20 hrs. The reaction mixture was quenched with water and was extracted with IPAC. The organic layer was separated, washed with brine, dried over sodium sulfate and was concentrated. The residue was purified by flash column chromatography on silica gel (0-20% IPAC/heptane) to obtain the title compound (115 mg). $^1$H NMR (400 MHz, Chloroform-d) δ 7.27-7.23 (m, 1H), 7.19-7.13 (m, 2H), 7.08 (ddd, J=8.2, 7.0, 1.2 Hz, 1H), 6.89 (ddd, J=8.0, 7.0, 1.0 Hz, 1H), 6.80 (d, J=7.9 Hz, 1H), 5.26 (s, 1H), 3.86-3.74 (m, 1H), 3.66 (s, 3H), 3.24-3.17 (m, 1H), 2.95 (t, J=15.4 Hz, 1H), 2.56 (ddd, J=15.6, 3.1, 1.4 Hz, 1H), 2.33 (dd, J=30.1, 14.9 Hz, 1H), 1.22 (d, J=19.6 Hz, 3H), 1.16 (d, J=20.0 Hz, 3H), 1.08 (d, J=6.5 Hz, 3H).

Step 2: 139

1-(2,6-Difluoro-4-iodo-phenyl)-2-(2-fluoro-2-methylpropyl)-3,5-dimethyl-3,4-dihydro-1H-pyrido[4,3-b]indole was converted to 139 via Ullmann coupling reaction as described for Example 101 Step 5. $^1$H NMR (400 MHz, DMSO-d$_6$) δ 7.37-7.31 (m, 1H), 6.99 (ddd, J=8.2, 7.1, 1.2 Hz, 1H), 6.77 (ddd, J=8.0, 7.1, 1.0 Hz, 1H), 6.63-6.54 (m, 3H), 5.10 (s, 1H), 4.49 (dd, J=47.6, 6.2 Hz, 2H), 3.90 (h, J=5.3, 4.9 Hz, 2H), 3.61-3.62 (m, 1H), 3.65 (s, 3H), 3.31 (s, 2H), 3.15-2.83 (m, 4H), 2.66 (d, J=16.0 Hz, 4H), 2.43-2.21 (m, 1H), 1.16 (d, J=21.5 Hz, 3H), 1.12 (d, J=21.5 Hz, 3H), 1.04 (d, J=6.5 Hz, 3H); LCMS: 518.3 [M+H]$^+$.

Example 141 (1R,3R)-1-(2,6-difluoro-4-((1-(3-fluoropropyl)azetidin-3-yl)oxy)phenyl)-3-methyl-2-(2,2,2-trifluoroethyl)-1,2,3,4-tetrahydropyrazino[1,2-a]indole 141

Step 1: (R)-1-(1H-Indol-1-yl)-N-(2,2,2-trifluoroethyl)propan-2-amine

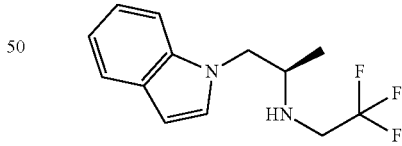

A mixture of (2R)-1-indol-1-ylpropan-2-amine (Intermediate 6 in Scheme 1, 1.8 g, 10.33 mmol), N,N-diisopropylethylamine (3.7 mL, 20.66 mmol) and 2,2,2-trifluoroethyl trifluoromethanesulfonate (2.4 g, 10.33 mmol) in 1,4-dioxane (30 mL) was stirred at 90° C. for 12 hours. The reaction mixture was diluted with water (50 mL), extracted with DCM (50 mL×2). Combined organic layers were dried over anhydrous Na$_2$SO$_4$, filtered and concentrated. The crude residue was purified by silica gel column chromatography (25% EtOAc in petroleum ether) to afford (2R)-1-indol-1-yl-N-(2,2,2-trifluoroethyl)propan-2-amine (2.3 g, yield 87%) as a colorless oil. LCMS: 256.9 [M+H]$^+$.

Step 2: tert-Butyl 3-(3,5-difluoro-4-((1R,3R)-3-methyl-2-(2,2,2-trifluoroethyl)-1,2,3,4-tetrahydropyrazino[1,2-a]indol-1-yl)phenoxy)azetidine-1-carboxylate

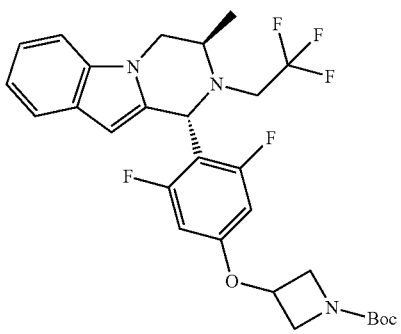 [SMILES: C[C@@H]1Cn2c(cc3ccccc32)[C@@H](c2c(F)cc(OC3CN(C(=O)OC(C)(C)C)C3)cc2F)N1CC(F)(F)F]

A mixture of (2R)-1-indol-1-yl-N-(2,2,2-trifluoroethyl)propan-2-amine (From step 1, 2.0 g, 7.8 mmol), tert-butyl 3-(3,5-difluoro-4-formyl-phenoxy)azetidine-1-carboxylate (2445 mg, 7.8 mmol) and acetic acid (4.7 g, 78.04 mmol) in toluene (40 mL) was stirred at 110° C. under $N_2$ atmosphere for 16 hours. The reaction mixture was concentrated and purified by silica gel column chromatography (0-20% EtOAc in petroleum ether) to give the title compound (0.35 g, yield 8%) (Containing about 20% cis mixture) as a light yellow oil. LCMS: 552.0 [M+H]$^+$. $^1$H NMR (400 MHz, CDCl$_3$) δ 7.49 (d, J=8.0 Hz, 1H), 7.31 (d, J=8.0 Hz, 1H), 7.21-7.17 (m, 1H), 7.11-7.07 (m, 1H), 6.31-6.25 (d, J=10.4 Hz, 2H), 6.00 (s, 1H), 5.53 (s, 1H), 4.81 (m, 1H), 4.35-4.15 (m, 3H), 4.08-3.95 (m, 3H), 3.75-3.65 (m, 1H), 3.40-3.10 (m, 1H), 2.97-2.94 (m, 1H), 1.45 (m, 9H), 1.21 (d, J=6.4 Hz, 3H).

Step 3: (1R,3R)-1-(4-(Azetidin-3-yloxy)-2,6-difluorophenyl)-3-methyl-2-(2,2,2-trifluoroethyl)-1,2,3,4-tetrahydropyrazino[1,2-a]indole

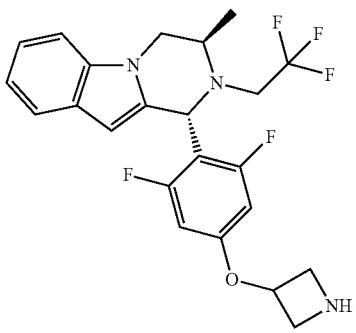 [SMILES: C[C@@H]1Cn2c(cc3ccccc32)[C@@H](c2c(F)cc(OC3CNC3)cc2F)N1CC(F)(F)F]

To a solution of tert-butyl 3-(3,5-difluoro-4-((1R,3R)-3-methyl-2-(2,2,2-trifluoroethyl)-1,2,3,4-tetrahydropyrazino[1,2-a]indol-1-yl)phenoxy)azetidine-1-carboxylate (From step 2, 100 mg, 0.18 mmol, containing about 20% cis isomer) and 2,6-lutidine (97 mg, 0.91 mmol) in DCM (0.5 mL) was added tert-butyldimethylsilyl trifluoromethanesulfonate (144 mg, 0.54 mmol) slowly at 25° C. The reaction mixture was stirred at 25° C. for 16 hours. The reaction mixture was diluted with DCM (5 mL) to the mixture was added saturated aqueous NaHCO$_3$ solution (2 mL). The organic phase was separated and dried over Na$_2$SO$_4$, filtered and concentrated to dryness. The residue was purified by pre-TLC (5% MeOH in DCM) to afford the title compound (50 mg, yield 61%), containing about 20% cis isomer, as a light yellow solid. LCMS: 452.2 [M+H]$^+$. $^1$H NMR (400 MHz, CDCl$_3$) δ 7.49-7.47 (d, J=7.6 Hz, 1H), 7.30 (d, J=8.0 Hz, 1H), 7.17 (t, J=7.2 Hz, 1H), 7.08 (t, J=7.2 Hz, 1H), 6.32-6.25 (d, J=10.0 Hz, 2H), 6.00-5.85 (m, 1H), 5.68-5.51 (m, 1H), 4.96-4.93 (m, 1H), 4.36-4.20 (m, 1H), 4.10-3.97 (m, 3H), 3.84 (m, 2H), 3.75-3.71 (m, 1H), 3.27-3.15 (m, 1H), 3.00-2.88 (m, 1H), 1.38-1.20 (m, 3H).

Step 4: 141

To the mixture of (1R,3R)-1-(4-(azetidin-3-yloxy)-2,6-difluorophenyl)-3-methyl-2-(2,2,2-trifluoroethyl)-1,2,3,4-tetrahydropyrazino[1,2-a]indole (From step 3, 400 mg, 0.89 mmol), N,N-diisopropylethylamine (343 mg, 2.66 mmol) in DMF (4 mL) was added 1-iodo-3-fluoropropane (166 mg, 0.89 mmol). The reaction mixture was stirred at 15° C. for 16 hours. The reaction mixture was concentrated and purified by pre-TLC (50% EtOAc in DCM) to afford a crude mixture (trans:cis=4:1). The crude product was purified by SFC (AD 250 mm*30 mm, 10 um), Base-IPA, 30%) to afford 141 (177 mg, yield 39%) as a white solid. LCMS: 512.3 [M+H]$^+$. $^1$H NMR (400 MHz, CD$_3$OD) δ 7.40 (d, J=8.0 Hz, 1H), 7.34 (d, J=8.0 Hz, 1H), 7.11 (t, J=8.0 Hz, 1H), 7.05-6.96 (m, 1H), 6.47 (d, J=10.8 Hz, 2H), 5.90 (s, 1H), 5.55 (s, 1H), 4.86-4.80 (m, 1H), 4.52 (t, J=6.0 Hz, 1H), 4.40 (t, J=6.0 Hz, 1H), 4.27-4.23 (m, 1H), 4.15-4.10 (m, 1H), 3.84-3.68 (m, 3H), 3.51-3.36 (m, 1H), 3.27-3.17 (m, 2H), 3.03-2.87 (m, 1H), 2.67 (t, J=7.2 Hz, 2H), 1.84-1.66 (m, 2H), 1.21 (d, J=6.4 Hz, 3H).

Example 142 (R)-3-(1-(2,6-difluoro-4-(1-(3-fluoropropyl)azetidin-3-ylamino)phenyl)-4,4-dimethyl-3,4-dihydro-1H-pyrido[3,4-b]indol-2(9H)-yl)-2,2-difluoropropan-1-ol 142

Following the same procedures as in Example 103, racemic 3-(1-(2,6-difluoro-4-((1-(3-fluoropropyl)azetidin-3-yl)amino)phenyl)-4,4-dimethyl-1,3,4,9-tetrahydro-2H-pyrido[3,4-b]indol-2-yl)-2,2-difluoropropan-1-ol was prepared from the commercially available 2-(1H-Indol-3-yl)-2-methylpropan-1-amine (CAS 15467-31-9), and separated by chiral SFC (column: OJ, MeOH w/0.1% NH$_4$OH).

142: $^1$H NMR (400 MHz, DMSO-d$_6$) δ 10.37 (s, 1H), 7.55 (d, J=7.7 Hz, 1H), 7.16 (d, J=7.8 Hz, 1H), 6.98-6.87 (m, 2H), 6.77 (d, J=6.8 Hz, 1H), 6.14 (d, J=12.5 Hz, 2H), 5.26 (t, J=6.1 Hz, 1H), 4.91 (s, 1H), 4.46 (dt, J=47.5, 6.1 Hz, 2H), 4.01-3.88 (m, 1H), 3.74-3.60 (m, 3H), 3.33-3.22 (m, 1H), 2.95 (d, J=11.5 Hz, 1H), 2.90-2.66 (m, 4H), 2.62 (d, J=11.4 Hz, 1H), 2.46 (t, J=7.0 Hz, 2H), 1.65 (dp, J=25.7, 6.5 Hz, 2H), 1.39 (s, 3H), 1.38 (s, 3H); LCMS: 537.2 [M+H]$^+$.

Example 143 (S)-3-(1-(2,6-difluoro-4-(1-(3-fluoropropyl)azetidin-3-ylamino)phenyl)-4,4-dimethyl-3,4-dihydro-1H-pyrido[3,4-b]indol-2(9H)-yl)-2,2-difluoropropan-1-ol 143

Following the procedures of Example 142, 143 was prepared

143: $^1$H NMR (400 MHz, DMSO-d$_6$) δ 10.37 (s, 1H), 7.55 (d, J=7.8 Hz, 1H), 7.16 (d, J=7.8 Hz, 1H), 6.93 (dt, J=19.4, 7.2 Hz, 2H), 6.77 (d, J=6.9 Hz, 1H), 6.14 (d, J=12.5 Hz, 2H), 5.26 (t, J=6.1 Hz, 1H), 4.91 (s, 1H), 4.46 (dt,

J=47.5, 6.0 Hz, 2H), 4.01-3.90 (m, 1H), 3.74-3.61 (m, 3H), 3.32-3.22 (m, 1H), 2.95 (d, J=11.5 Hz, 1H), 2.90-2.65 (m, 4H), 2.62 (d, J=11.5 Hz, 1H), 2.46 (t, J=7.1 Hz, 2H), 1.66 (dq, J=25.4, 6.6 Hz, 2H), 1.39 (s, 3H), 1.38 (s, 3H); LCMS: 537.2 [M+H]$^+$.

Example 145 N-(3,5-Difluoro-4-((1S,3R)-3-methyl-2-(2,2,2-trifluoroethyl)-1,2,3,4-tetrahydropyrazino[1,2-a]indol-1-yl)phenyl)-1-(3-fluoropropyl)azetidin-3-amine 145

Step 1: (1R,3R)-1-(4-Bromo-2,6-difluorophenyl)-3-methyl-2-(2,2,2-trifluoroethyl)-1,2,3,4-tetrahydropyrazino[1,2-a]indole

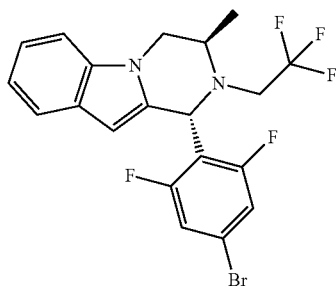 [SMILES: C[C@@H]1Cn2c(cc3ccccc32)[C@@H](c2c(F)cc(Br)cc2F)N1CC(F)(F)F]

To a solution of (2R)-1-indol-1-yl-N-(2,2,2-trifluoroethyl)propan-2-amine (From 1 of Example 6, 2.80 g, 5.57 mmol), 4-bromo-2,6-difluorobenzaldehyde (1.23 g, 5.57 mmol) in toluene (60 mL) were added acetic acid (3.33 g, 55.69 mmol). The solution was stirred at 90° C. for 16 hours. After being cooled to room temperature, the reaction mixture was concentrated to dryness and was then purified by flash column chromatography (0-10% EtOAc in petroleum ether) to afford the title compound (1.2 g, yield 42%, contaminated with ~10% cis isomer) as a solid. $^1$H NMR (400 MHz, CDCl$_3$) δ 7.54-7.47 (m, 1H), 7.36-7.29 (m, 1H), 7.24-7.17 (m, 1H), 7.15-7.05 (m, 3H), 6.02 (s, 1H), 5.59 (s, 1H), 4.38-4.34 (m, 1H), 4.07-4.04 (m, 1H), 3.79-3.69 (m, 1H), 3.38-3.22 (m, 1H), 3.01-2.87 (m, 1H), 1.22 (d, J=6.4 Hz, 3H).

Step 2: tert-Butyl 3-((3,5-difluoro-4-((1R,3R)-3-methyl-2-(2,2,2-trifluoroethyl)-1,2,3,4-tetrahydropyrazino[1,2-a]indol-1-yl)phenyl)amino)azetidine-1-carboxylate

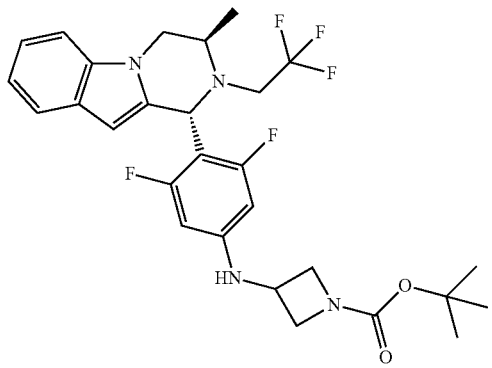 [SMILES: C[C@@H]1Cn2c(cc3ccccc32)[C@@H](c2c(F)cc(NC3CN(C(=O)OC(C)(C)C)C3)cc2F)N1CC(F)(F)F]

To a solution of (1R,3R)-1-(4-bromo-2,6-difluorophenyl)-3-methyl-2-(2,2,2-trifluoroethyl)-1,2,3,4-tetrahydropyrazino[1,2-a]indole (From step 1, 1.0 g, 2.2 mmol) and potassium phosphate (1.39 g, 6 mmol), Brettphos Pd G3 (0.1 g, 0.11 mmol), Brettphos (0.23 g, 0.44 mmol) in 1,4-dioxane (10 mL) was added tert-butyl 3-aminoazetidine-1-carboxylate (0.56 g, 3.27 mmol). The reaction mixture was stirred at 80° C. for 16 hours under N$_2$. The reaction mixture was diluted with EtOAc (100 mL), washed with water (30 mL×2), dried over anhydrous sodium sulfate, and concentrated in vacuo. The crude product was purified by flash column chromatography (0-30% EtOAc in petroleum ether) to afford the title compound (1.0 g, yield 83%, contaminated with ~10% cis isomer) as a yellow solid. $^1$H NMR (400 MHz, CDCl$_3$) δ 7.50 (d, J=7.6 Hz, 1H), 7.32 (d, J=8.0 Hz, 1H), 7.18 (t, J=7.6 Hz, 1H), 7.09 (t, J=7.6 Hz, 1H), 6.04-5.95 (m, 3H), 5.48 (s, 1H), 4.39-4.19 (m, 4H), 4.14-4.12 (m, 1H), 4.05-4.01 (m, 1H), 3.79-3.70 (m, 3H), 3.28-3.15 (m, 1H), 3.05-2.92 (m, 1H), 1.45 (s, 9H), 1.21 (d, J=6.4 Hz, 3H).

Step 3: (1R,3R)-1-[4-(Azetidin-3-yloxy)-2,6-difluoro-phenyl]-2-(2-fluoro-2-methyl-propyl)-3-methyl-2,3,4,9-tetrahydro-1H-beta-carboline

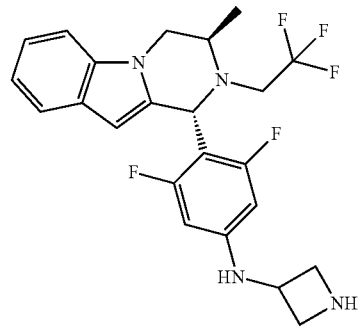 [SMILES: C[C@@H]1Cn2c(cc3ccccc32)[C@@H](c2c(F)cc(NC3CNC3)cc2F)N1CC(F)(F)F]

To a mixture of 2,6-lutidine (0.85 mL, 7 mmol), tert-butyl 3-((3,5-difluoro-4-((1R,3R)-3-methyl-2-(2,2,2-trifluoroethyl)-1,2,3,4-tetrahydropyrazino[1,2-a]indol-1-yl)phenyl)amino)azetidine-1-carboxylate (From step 2, 800 mg, 1.45 mmol, contaminated with ~10% cis isomer) in dichloromethane (10 mL) was added trimethylsilyl trifluoromethanesulfonate (0.79 mL, 4.36 mmol) and the reaction mixture was stirred at 15° C. for 16 hours under N$_2$. The reaction mixture was diluted with DCM (30 mL) and was washed with saturated aqueous NaHCO$_3$ solution (20 mL), dried over anhydrous sodium sulfate, and concentrated in vacuo. The residue was purified on silica gel column chromatography (0-10% MeOH in DCM) to afford the title compound (0.65 g, yield 99%, contaminated with ~10% cis isomer) as light green solid. LCMS: 451.0 [M+H]$^+$. $^1$H NMR (400 MHz, CD$_3$OD) δ 7.39 (d, J=8.0 Hz, 1H), 7.31 (d, J=8.0 Hz, 1H), 7.09 (m, 1H), 7.03-6.95 (m, 1H), 6.07 (d, J=12.0 Hz, 2H), 5.88 (s, 1H), 5.44 (s, 1H), 4.34-4.17 (m, 2H), 4.10-4.06 (m, 1H), 3.88-3.78 (m, 2H), 3.77-3.66 (m, 1H), 3.55-3.45 (m, 2H), 3.39-3.33 (m, 1H), 3.04-2.90 (m, 1H), 1.19 (d, J=6.4 Hz, 3H).

Step 4: 145 and 146

To a stirred solution of N,N-Diisopropylethylamine (0.71 mL, 4 mmol) and (1R,3R)-1-[4-(azetidin-3-yloxy)-2,6-difluoro-phenyl]-2-(2-fluoro-2-methyl-propyl)-3-methyl-2,3, 4,9-tetrahydro-1H-beta-carboline (From step 3, 600 mg, 1.33 mmol, contaminated with ~10% cis isomer) in N,N-dimethylformamide (10 mL) was added 1-iodo-3-fluoropropane (0.25 g, 1.33 mmol). The reaction mixture was stirred at 15° C. for 16 hours. The reaction mixture was diluted with EtOAc (30 mL), washed with brine (10 mL×5), dried over anhydrous sodium sulfate, concentrated in vacuo and was then purified by flash chromatography on silica gel (0-50% DCM in EtOAc) to give the title compound (400 mg, 58%, contaminated with ~10% cis isomer) as a yellow solid. The solid was further purified by SFC (AD250 mm*30 mm, 5 um), supercritical $CO_2$/EtOH (0.1% $NH_3.H_2O$)=40% to give 146 (0.28 g, yield 70%) as a white solid, and 145 (27 mg, 6%) as a white solid. 145: $^1$H NMR (400 MHz, $CD_3OD$) δ 7.38 (d, J=8.0 Hz, 1H), 7.32 (d, J=8.4 Hz, 1H), 7.12-7.08 (m, 1H), 7.00-6.96 (m, 1H), 6.08 (d, J=11.6 Hz, 2H), 5.74 (s, 1H), 5.49 (s, 1H), 4.54-4.41 (m, 2H), 4.30-4.26 (m, 1H), 4.10-4.05 (m, 1H), 3.80-3.75 (m, 3H), 3.47-3.40 (m, 2H), 3.31-3.22 (m, 1H), 3.02-2.95 (m, 2H), 2.66 (t, J=6.8 Hz, 2H), 1.78-1.62 (m, 2H), 1.35 (d, J=6.4 Hz, 3H). SFC (AD-3 150×4.6 mm, 5-40% EtOH (0.05% DEA) in $CO_2$/10 min), RT=4.019 min.

Example 146 N-(3,5-Difluoro-4-((1R,3R)-3-methyl-2-(2,2,2-trifluoroethyl)-1,2,3,4-tetrahydropyrazino[1,2-a]indol-1-yl)phenyl)-1-(3-fluoropropyl)azetidin-3-amine 146

Following the procedures of Example 145, 146 was obtained: $^1$H NMR (400 MHz, $CD_3OD$) δ 7.38 (d, J=7.6 Hz, 1H), 7.28 (d, J=8.4 Hz, 1H), 7.12-7.06 (m, 1H), 7.01-6.95 (m, 1H), 6.08 (d, J=11.2 Hz, 2H), 5.88 (s, 1H), 5.44 (s, 1H), 4.51-4.46 (m, 1H), 4.40-4.31 (m, 1H), 4.19-4.15 (m, 1H), 4.03-3.98 (m, 2H), 3.76-3.61 (m, 3H), 3.35-3.22 (m, 1H), 3.02-2.86 (m, 3H), 2.58 (t, J=7.2 Hz, 2H), 1.78-1.62 (m, 2H), 1.13 (d, J=6.0 Hz, 3H). SFC (AD-3 150×4.6 mm, 5-40% EtOH (0.05% DEA) in $CO_2$/10 min), RT=4.722 min.

Example 147 (1S,3R)-1-(2,6-difluoro-4-(2-(3-(fluoromethyl)azetidin-1-yl)ethoxy)phenyl)-2-(2-fluoro-2-methylpropyl)-3-methyl-2,3,4,5-tetrahydro-1H-pyrido[4,3-b]indole 147

Step 1: 3-[tert-butyl(diphenyl)silyl]oxy-2,2-difluoro-N-[2-(1H-indol-2-yl)-1-methyl-ethyl]propan-1-amine

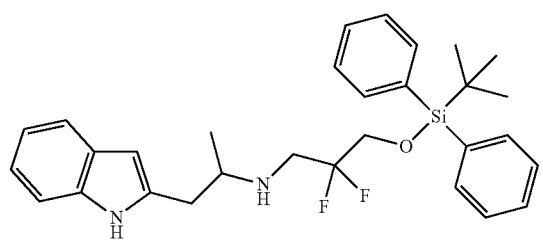 [SMILES: CC(Cc1cc2ccccc2[nH]1)NCC(F)(F)CO[Si](c1ccccc1)(c1ccccc1)C(C)(C)C]

1-(1H-Indol-2-yl)propan-2-amine (0.50 g, 2.7 mmol) was mixed with [3-[tert-butyl(diphenyl)silyl]oxy-2,2-difluoropropyl]trifluoromethanesulfonate (1.40 g, 3.0 mmol) and DIPEA (0.95 mL, 5.5 mmol) in 1,4-dioxane (5 mL) and was heated at 90° C. for 20 hrs. The reaction mixture was cooled, diluted with IPAC, washed with water and brine, dried over sodium sulfate and was concentrated. The residue was purified by column chromatography (silica gel, 0-50% IPAC/heptane) to obtain the title compound (0.48 g). LCMS: 507.25 $[M+H]^+$.

Step 2: tert-butyl-[3-[1-(2,6-difluoro-4-iodo-phenyl)-3-methyl-1,3,4,5-tetrahydropyrido[4,3-b]indol-2-yl]-2,2-difluoro-propoxy]-diphenyl-silane

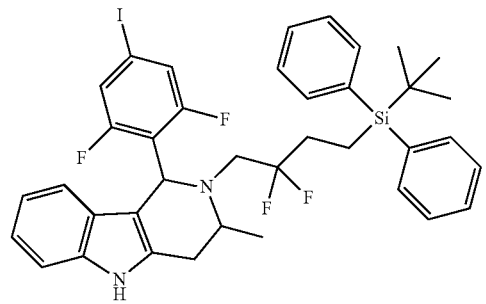 [SMILES: CC1Cc2[nH]c3ccccc3c2C(c2c(F)cc(I)cc2F)N1CC(F)(F)CC[Si](c1ccccc1)(c1ccccc1)C(C)(C)C]

A mixture of 3-[tert-butyl(diphenyl)silyl]oxy-2,2-difluoro-N-[2-(1H-indol-2-yl)-1-methyl-ethyl]propan-1-amine (0.48 g, 0.95 mmol) and 2,6-difluoro-4-iodobenzaldehyde (230 mg, 0.85 mmol) and acetic acid (0.22 mL, 3.8 mmol) in toluene (3 mL) was heated at 90° C. for 20 hrs. The reaction mixture was cooled and concentrated to give an oil. The oil was purified by flash column chromatography on silica gel (0-20% IPAC/heptane) to obtain the title compound (0.51 g).

Step 3: 147 and 148

Ullmann reaction of tert-Butyl-[3-[1-(2,6-difluoro-4-iodo-phenyl)-3-methyl-1,3,4,5-tetrahydropyrido[4,3-b]indol-2-yl]-2,2-difluoro-propoxy]-diphenyl-silane with 2-(3-(fluoromethyl)azetidin-1-yl)ethan-1-ol, followed by treatment with TBAF gave the racemic mixture, which was separated by chiral SFC (mobile phase: AD; mobile phase: MeOH w/0.1% $NH_4OH$) to provide the enantiomers 147 and 148:

147: 13.6 mg; RT=0.925 min; $^1$H NMR (400 MHz, DMSO-$d_6$) δ 10.84 (s, 1H), 7.31-7.13 (m, 1H), 6.92 (ddd, J=8.2, 7.1, 1.2 Hz, 1H), 6.74 (ddd, J=8.0, 7.1, 1.0 Hz, 1H), 6.62-6.53 (m, 3H), 5.29-5.19 (m, 1H), 5.14 (s, 1H), 4.49 (dd, J=47.6, 6.3 Hz, 2H), 3.97-3.83 (m, 2H), 3.74-3.51 (m, 2H), 3.30-3.26 (m, 2H), 3.23-3.07 (m, 2H), 3.03-2.90 (m, 2H), 2.77-2.54 (m, 6H), 1.07 (d, J=6.5 Hz, 3H); LCMS: 524.2 $[M+H]^+$.

Example 148 (1S,3R)-1-(2,6-difluoro-4-(2-(3-(fluoromethyl)azetidin-1-yl)ethoxy)phenyl)-2-(2-fluoro-2-methylpropyl)-3-methyl-2,3,4,5-tetrahydro-1H-pyrido[4,3-b]indole 148

Following the procedures of Example 147, 148 was prepared

148: 18.8 mg, RT=1.118 min; $^1$H NMR (400 MHz, DMSO-$d_6$) δ 10.84 (s, 1H), 7.28-7.15 (m, 1H), 6.92 (ddd, J=8.1, 7.1, 1.2 Hz, 1H), 6.74 (ddd, J=8.0, 7.1, 1.0 Hz, 1H), 6.63-6.53 (m, 3H), 5.23 (t, J=6.1 Hz, 1H), 5.14 (s, 1H), 4.49 (dd, J=47.6, 6.3 Hz, 2H), 3.98-3.82 (m, 2H), 3.72-3.52 (m, 2H), 3.40-3.32 (m, 2H), 3.19-3.04 (m, 2H), 3.01-2.94 (m, 2H), 2.77-2.55 (m, 6H), 1.07 (d, J=6.4 Hz, 3H); LCMS: 524.2 $[M+H]^+$.

Example 154 3-((1R,3S)-1-(2,6-difluoro-4-((1-(3-fluoropropyl)azetidin-3-yl)amino)phenyl)-3-methyl-1,3,4,5-tetrahydro-2H-pyrido[4,3-b]indol-2-yl)-2,2-difluoropropan-1-ol 154

Step 1: tert-butyl 3-(4-(2-(3-(tert-butyldiphenylsilyloxy)-2,2-difluoropropyl)-3-methyl-2,3,4,5-tetrahydro-1H-pyrido[4,3-b]indol-1-yl)-3,5-difluorophenylamino)azetidine-1-carboxylate

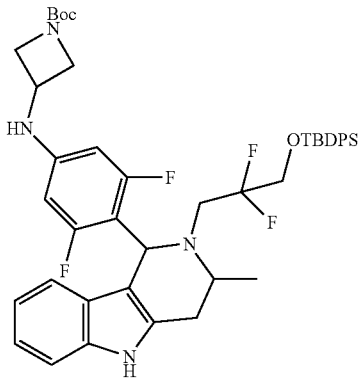

A mixture of tert-butyl-[3-[1-(2,6-difluoro-4-iodo-phenyl)-3-methyl-1,3,4,5-tetrahydropyrido[4,3-b]indol-2-yl]-2,2-difluoro-propoxy]-diphenyl-silane (200 mg, 0.26 mmol), tert-butyl 3-aminoazetidine-1-carboxylate (72 mg, 0.40 mmol), Pd$_2$(dba)$_3$ (24 mg, 0.026 mmol), Xanthphos (30.6 mg, 0.053 mmol) and cesium carbonate (230 mg, 0.79 mmol) in 1,4-dioxane (3 mL) was degassed for 5 min. The resulting red mixture was heated in a sealed tube at 100° C. for 20 hrs. The resulting mixture was diluted with IPAC and filtered through Celite. The filtrate was washed with water, brine, dried over sodium sulfate and was concentrated. The residue was purified by flash column chromatography on silica gel (0-100% IPAC/heptane) to obtain the title compound (120 mg). $^1$H NMR (400 MHz, Chloroform-d) δ 7.77 (s, 1H), 7.66-7.59 (m, 4H), 7.46-7.33 (m, 5H), 7.28-7.25 (m, 2H), 7.03 (ddd, J=8.2, 7.0, 1.3 Hz, 1H), 6.91-6.75 (m, 2H), 5.76 (d, J=11.3 Hz, 2H), 5.19 (s, 1H), 4.24-4.16 (m, 2H), 4.04-3.91 (m, 3H), 3.70-3.60 (m, 3H), 3.51 (q, J=12.2 Hz, 1H), 3.22-3.07 (m, 2H), 2.84 (q, J=14.8 Hz, 1H), 2.49-2.43 (m, 1H), 1.44 (s, 9H), 1.23 (d, J=6.3 Hz, 3H), 1.03 (s, 9H). LCMS: 802.5 [M+H]$^+$.

Step 2: N-(4-(2-(3-(tert-butyldiphenylsilyloxy)-2,2-difluoropropyl)-3-methyl-2,3,4,5-tetrahydro-1H-pyrido[4,3-b]indol-1-yl)-3,5-difluorophenyl)azetidin-3-amine

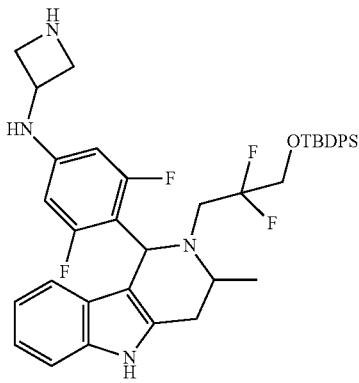

tert-butyl 3-(4-(2-(2,2-difluoro-3-hydroxypropyl)-3-methyl-2,3,4,5-tetrahydro-1H-pyrido[4,3-b]indol-1-yl)-3,5-difluorophenylamino)azetidine-1-carboxylate (120 mg, 0.15 mmol) was dissolved in DCM (2 mL) and 2,6-lutidine (85 mg, 0.79 mmol) and TBSOTf (140 mg, 0.53 mmol) were added. The mixture was stirred for 1 hr. The resulting mixture was concentrated and diluted with methanol/THF (2 mL, 1:1 mixture) and 2 N NaOH (1 ml) was added and stirred for 1 hr. The reaction mixture was extracted with IPAC. The organic layer was washed with water, brine, dried over sodium sulfate and was concentrated to give the crude title compound. LCMS: 701.3 [M+H]$^+$.

Step 3: N-(4-(2-(3-(tert-butyldiphenylsilyloxy)-2,2-difluoropropyl)-3-methyl-2,3,4,5-tetrahydro-1H-pyrido[4,3-b]indol-1-yl)-3,5-difluorophenyl)-1-(3-fluoropropyl)azetidin-3-amine

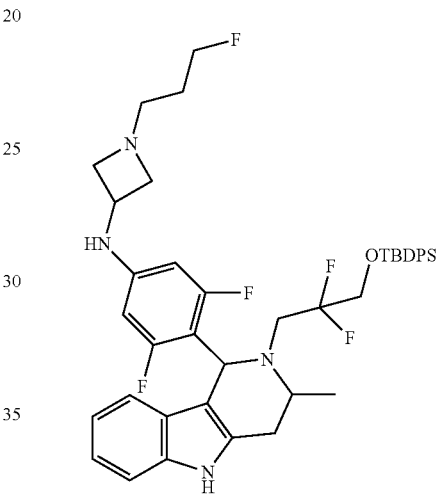

To the crude N-(4-(2-(3-(tert-butyldiphenylsilyloxy)-2,2-difluoropropyl)-3-methyl-2,3,4,5-tetrahydro-1H-pyrido[4,3-b]indol-1-yl)-3,5-difluorophenyl)azetidin-3-amine dissolved in DMF (1 mL) were added 1-fluoro-3-iodopropane (40 mg) and DIPEA (23 mg) and the mixture was stirred at ambient temperature for 20 hrs. The reaction mixture was diluted with IPAC, washed with water, brine, dried over sodium sulfate and was concentrated. The crude product was purified by flash column chromatography to obtain the title compound (70 mg). LCMS: 761.4 [M+H]$^+$.

Step 4: 154 and 155

N-(4-(2-(3-(tert-butyldiphenylsilyloxy)-2,2-difluoropropyl)-3-methyl-2,3,4,5-tetrahydro-1H-pyrido[4,3-b]indol-1-yl)-3,5-difluorophenyl)-1-(3-fluoropropyl)azetidin-3-amine (70 mg) was dissolved in THF (1 mL). TBAF (0.12 mL, 1 M) was added and the mixture was stirred at ambient temperature for 2 hrs. The reaction mixture was diluted with IPAC, washed with water, brine, dried over sodium sulfate and was concentrated. The residue was purified by flash column chromatography on silica gel (0-5% MeOH/DCM) to obtain the title compound as a racemic mixture (32 mg), which was further separated by chiral SFC (column: cel-1; mobile phase: MeOH w/0.1% NH$_4$OH) to give two pure enantiomers 154 and 155.
154: RT=0.732 min; 6 $^1$H NMR (400 MHz, DMSO-d$_6$) δ 10.77 (s, 1H), 7.23 (d, J=8.1 Hz, 1H), 6.91 (ddd, J=8.1, 7.0, 1.2 Hz, 1H), 6.73 (td, J=7.4, 7.0, 0.9 Hz, 1H), 6.61 (dd, J=17.1, 7.3 Hz, 2H), 6.05 (d, J=12.3 Hz, 2H), 5.19 (t, J=6.2 Hz, 1H), 5.04 (s, 1H), 4.44 (dt, J=47.4, 6.1 Hz, 2H), 3.91 (q, J=6.5 Hz, 1H), 3.70-3.51 (m, 4H), 3.31 (s, 2H), 3.17-2.96 (m, 2H), 2.78-2.54 (m, 4H), 2.45 (t, J=7.0 Hz, 1H), 1.64 (dp, J=25.7, 6.5 Hz, 2H), 1.05 (d, J=6.5 Hz, 3H). LCMS: 523.2 [M+H]$^+$.

Example 155 3-((1S,3R)-1-(2,6-difluoro-4-((1-(3-fluoropropyl)azetidin-3-yl)amino)phenyl)-3-methyl-1,3,4,5-tetrahydro-2H-pyrido[4,3-b]indol-2-yl)-2,2-difluoropropan-1-ol 155

Following the procedures of Example 154, 155 was prepared

155: RT=1.212 min; $^1$H NMR (400 MHz, DMSO-d$_6$) δ 10.77 (s, 1H), 7.23 (d, J=8.1 Hz, 1H), 6.91 (ddd, J=8.1, 7.0, 1.2 Hz, 1H), 6.73 (td, J=7.4, 6.9, 1.0 Hz, 1H), 6.62 (dd, J=14.2, 7.3 Hz, 2H), 6.06 (d, J=12.3 Hz, 2H), 5.19 (t, J=6.2 Hz, 1H), 5.04 (s, 1H), 4.45 (dt, J=47.4, 6.0 Hz, 2H), 3.92 (q, J=6.6 Hz, 1H), 3.60 (ddd, J=42.2, 12.2, 5.9 Hz, 4H), 3.31 (s, 2H), 3.13-2.98 (m, 2H), 2.81-2.53 (m, 4H), 2.49 (s, 1H), 1.65 (dp, J=25.7, 6.6 Hz, 2H), 1.05 (d, J=6.5 Hz, 3H). LCMS: 523.2 [M+H]$^+$.

Example 156 3-[(1R,3R)-1-[2,6-difluoro-4-[[1-(3-fluoropropyl)azetidin-3-yl]amino]phenyl]-3-methyl-3,4-dihydro-1H-pyrazino[1,2-a]indol-2-yl]-2,2-difluoro-propan-1-ol 156

Step 1: N-[4-(diethoxymethyl)-3,5-difluoro-phenyl]-1-(3-fluoropropyl)azetidin-3-amine

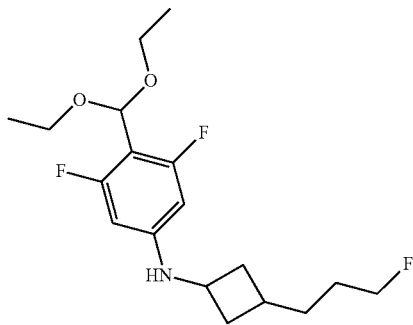 [SMILES: CCOC(OCC)c1c(F)cc(NC2CC(CCCF)C2)cc1F]

A mixture of 1-(3-fluoropropyl)azetidin-3-amine (CAS No.: 1538772-53-0) (2.55 g, 19.3 mmol), 5-bromo-2-(diethoxymethyl)-1,3-difluoro-benzene (CAS No.: 1206630-22-9) (4.96 g, 16.1 mmol), XANTPHOS Pd G3 (0.40 g, 0.40 mmol), cesium carbonate (13.1 g, 40.3 mmol) and Toluene (25 mL) under argon was heated at 100° C. overnight. The reaction mixture was allowed to cool to RT and quenched with water (15 mL). The layers were separated and the organic layer evaporated to afford crude title product (3.69 g, yield 68%) as a pale brown gum. $^1$H NMR (400 MHz, CDCl$_3$) δ 6.03-5.98 (m, 2H), 5.59 (s, 1H), 4.56-4.52 (m, 1H), 4.43 (t, J=5.9 Hz, 1H), 4.24 (d, J=6.7 Hz, 1H), 4.04-3.98 (m, 1H), 3.77-3.67 (m, 4H), 3.58-3.49 (m, 2H), 2.90-2.85 (m, 2H), 2.58 (t, J=7.1 Hz, 2H), 1.82-1.66 (m, 2H), 1.24 (t, J=7.1 Hz, 6H); LCMS: 347.1 [M+H]$^+$.

Step 2: 3-[tert-Butyl(diphenyl)silyl]oxy-2,2-difluoro-N-[(1R)-2-indol-1-yl-1-methyl-ethyl]propan-1-amine

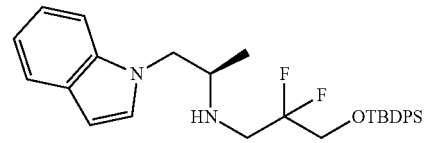

To a solution of (2R)-1-indol-1-ylpropan-2-amine (From step 4, 5.42 g, 31.1 mmol) in 1,4-dioxane (90 mL) was added [3-[tert-butyl(diphenyl)silyl]oxy-2,2-difluoro-propyl]trifluoromethanesulfonate (15 g, 31.09 mmol) and N,N-diisopropylethylamine (6.77 mL, 38.86 mmol). The reaction mixture was stirred at 85° C. for 16 h. The mixture was concentrated, the residue was dissolved in EtOAc (200 mL) and washed with saturated aqueous NaHCO$_3$ solution (100 mL), water (100 mL) and brine (100 mL). The organic layer was dried (MgSO4), filtered and concentrated. The residue was purified by column chromatography on silica gel (DCM). Appropriate fractions were combined and evaporated to give the title compound (13.1 g, yield 83%) as a light yellow oil. $^1$H NMR (400 MHz, CDCl$_3$) δ 7.66-7.60 (m, 6H), 7.45-7.31 (m, 6H), 7.18 (dt, J=1.1, 7.6 Hz, 1H), 7.11-7.06 (m, 2H), 6.47 (d, J=2.6 Hz, 1H), 4.09 (dd, J=6.5, 14.2 Hz, 1H), 3.97 (dd, J=6.2, 14.2 Hz, 1H), 3.84-3.76 (m, 2H), 3.26-2.98 (m, 3H), 1.05-1.04 (m, 12H); LCMS: 507.3 [M+H]$^+$.

Step 3: 4-{(1R,3R)-2-[3-(tert-Butyl-diphenyl-silanyloxy)-2,2-difluoro-propyl]-3-methyl-1,2,3,4-tetrahydro-pyrazino[1,2-a]indol-1-yl}-3,5-difluoro-phenyl)-[1-(3-fluoropropyl)-azetidin-3-yl]-amine

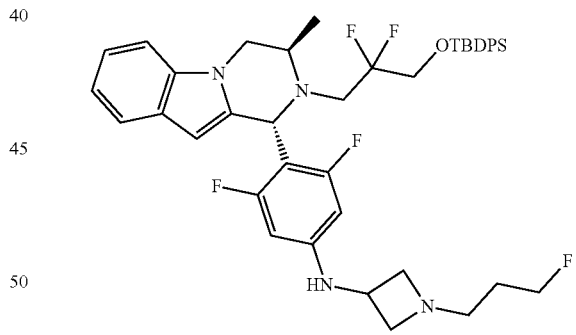

A mixture of 3-[tert-butyl(diphenyl)silyl]oxy-2,2-difluoro-N-[(1R)-2-indol-1-yl-1-methyl-ethyl]propan-1-amine (From step 2, 0.88 g, 1.73 mmol), HOAc (0.25 mL, 4.33 mmol), N-[4-(diethoxymethyl)-3,5-difluoro-phenyl]-1-(3-fluoropropyl)azetidin-3-amine (from step 1, 0.6 g, 1.73 mmol) and toluene (12 mL) was stirred at 110° C. for 5.75 h. The reaction mixture was allowed to cool to RT, diluted with EtOAc and washed with saturated aqueous sodium hydrogen carbonate solution and brine, dried over anhydrous Na$_2$SO$_4$, filtered and concentrated. The crude residue was purified by silica gel column chromatography (0-10% 2M ammonia in methanol/DCM) and by reverse phase chromatography (C18, eluent acetonitrile/water (+0.1% formic acid)). Appropriate fractions were combined and evaporated to afford the title compound (69 mg, yield 5%) as a light yellow solid. $^1$H NMR (400 MHz, CDCl$_3$) δ 7.65-7.58 (m, 4H), 7.49-7.34 (m, 6H), 7.28 (d, J=8.8 Hz, 2H), 7.18-7.04 (m, 2H), 5.96-5.86 (m, 3H), 5.41-5.38 (m, 1H), 4.55 (t, J=5.6 Hz, 1H), 4.43 (t, J=5.6 Hz, 1H), 4.11-4.04 (m, 2H), 3.96-3.88 (m, 2H), 3.82-3.68 (m, 3H), 3.65-3.44 (m, 3H), 3.20-3.10 (m, 1H), 2.89-2.82 (m, 3H), 2.81-2.79 (m, 3H), 1.92-1.79 (m, 2H), 1.31-1.25 (m, 1H), 1.04-1.02 (m, 9H); LCMS: 761.2 [M+H]$^+$.

Step 4: 156

To a solution of 4-{(1R,3R)-2-[3-(tert-butyl-diphenyl-silanyloxy)-2,2-difluoro-propyl]-3-methyl-1,2,3,4-tetrahydro-pyrazino[1,2-a]indol-1-yl}-3,5-difluoro-phenyl)-[1-(3-fluoropropyl)-azetidin-3-yl]-amine (From step 3, 69 mg, 0.09 mmol) and 1M TBAF in THF (0.18 mL, 0.18 mmol) in THF (3 mL) was stirred at 25° C. for 46 h. The reaction mixture was diluted with water (50 mL) and extracted with EtOAc. The combined organic layer was dried over anhydrous Na$_2$SO$_4$, filtered and concentrated. The crude residue was purified by SFC (LUX CELLULOSE-4 25/75 MeOH (0.1% DEA)/CO2, 15 ml/min, 120 bar, 40 C, SYSTEM 190 Bar, DAD 250 nm) to afford 156 (5 mg, yield 11%) as a light yellow oil. $^1$H NMR (400 MHz, CDCl$_3$) δ 7.50-7.46 (m, 1H), 7.20-7.15 (m, 1H), 7.10-7.05 (m, 1H), 6.06-5.96 (m, 3H), 5.33 (s, 1H), 4.55 (t, J=5.9 Hz, 1H), 4.43 (t, J=5.9 Hz, 1H), 4.33-4.22 (m, 2H), 4.10-3.98 (m, 2H), 3.90-3.82 (m, 1H), 3.74-3.63 (m, 4H), 3.18 (ddd, J=6.4, 8.5, 16.1 Hz, 1H), 2.98-2.86 (m, 4H), 2.59 (t, J=7.1 Hz, 2H), 1.82-1.68 (m, 2H), 1.22-1.19 (m, 3H); LCMS: 523.4 [M+H]$^+$.

Example 157 3-((1R,3R)-1-(2,6-Difluoro-4-((1-(3-fluoropropyl)azetidin-3-yl)amino)phenyl)-3-methyl-3,4-dihydrobenzofuro[2,3-c]pyridin-2(1H)-yl)-2,2-difluoropropan-1-ol 157

Step 1: N-(1-(Benzofuran-3-yl)propan-2-yl)-3-((tert-butyldiphenylsilyl)oxy)-2,2-difluoropropan-1-amine

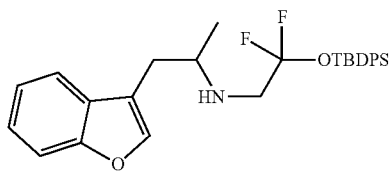

A mixture of 1-(benzofuran-3-yl)propan-2-amine (From step 2 of Example 57, 2.0 g, 11.4 mmol), [3-[tert-butyl(diphenyl)silyl]oxy-2,2-difluoro-propyl]trifluoromethanesulfonate (5.5 g, 11.4 mmol) and N,N-diisopropylethylamine (3.8 mL, 23.0 mmol) in 1,4-dioxane (20 mL) was stirred at 90° C. for 3 hrs. The reaction mixture was concentrated and purified by silica gel flash column chromatography (0-30% EtOAc in petroleum ether) to afford the title compound (4.1 g, yield 71%) as a colorless oil. $^1$H NMR (400 MHz, CDCl$_3$) δ 7.66 (d, J=7.2 Hz, 4H), 7.53-7.47 (m, 1H), 7.46-7.34 (m, 8H), 7.31-7.15 (m, 2H), 3.90-3.76 (m, 2H), 3.29-3.07 (m, 3H), 2.87-2.78 (m, 1H), 2.73-2.62 (m, 1H), 1.11 (d, J=6.0 Hz, 3H), 1.04 (s, 9H).

Step 2: 3-((1-(Benzofuran-3-yl)propan-2-yl)amino)-2,2-difluoropropan-1-ol

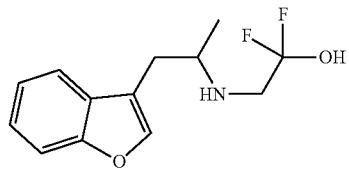 [SMILES: CC(Cc1coc2ccccc12)NCC(O)(F)F]

To a solution of N-[2-(benzofuran-3-yl)-1-methyl-ethyl]-3-[tert-butyl(diphenyl)silyl]oxy-2,2-difluoro-propan-1-amine (3.0 g, 5.91 mmol) in THF (30 mL) was added tetrabutylammoniumfluoride (1M in THF, 8.86 mL, 8.86 mmol). The reaction mixture was stirred at 20° C. for 3 hours. The reaction mixture was diluted with EtOAc (80 mL), washed with aqueous 1 N NaOH solution (20 mL×5). The organic layer was dried over anhydrous Na$_2$SO$_4$, filtered, concentrated and purified by silica gel flash column chromatography (0-10% MeOH in DCM) to afford the title compound (1.3 g, yield 82%) as a light yellow oil. $^1$H NMR (400 MHz, CDCl$_3$) δ 7.58-7.43 (m, 3H), 7.34-7.22 (m, 2H), 3.85 (t, J=12.4 Hz, 2H), 3.27-3.02 (m, 3H), 2.86-2.68 (m, 2H), 1.15 (d, J=6.4 Hz, 3H).

Step 3: 3-((1,3-trans)-1-(4-Bromo-2,6-difluorophenyl)-3-methyl-3,4-dihydrobenzofuro[2,3-c]pyridin-2(1H)-yl)-2,2-difluoropropan-1-ol

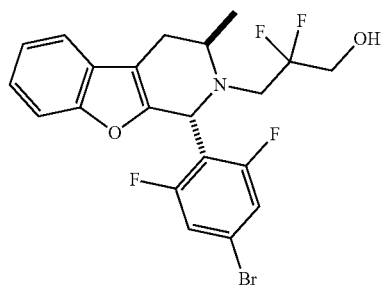 [SMILES: C[C@@H]1Cc2c(oc3ccccc23)[C@@H](c2c(F)cc(Br)cc2F)N1CC(F)(F)CO]

A mixture of 3-[[2-(benzofuran-3-yl)-1-methyl-ethyl]amino]-2,2-difluoro-propan-1-ol (100 mg, 0.37 mmol), 4-bromo-2,6-difluorobenzaldehyde (82 mg, 0.37 mmol) and trifluoroacetic acid (42 mg, 0.37 mmol) in 1,2-dichloroethane (4 mL) was stirred at 120° C. for 30 minutes in a microwave reactor. To the reaction mixture was added aqueous NaHCO$_3$ solution (5 mL) and the mixture was extracted with EtOAc (10 mL×2). The combined organic layers were dried over anhydrous Na$_2$SO$_4$, filtered and concentrated. The crude product was purified by silica gel flash column chromatography (0-30% EtOAc in petroleum ether) to afford the title compound (80 mg, yield 46%). $^1$H NMR (400 MHz, CDCl$_3$) δ 7.52-7.46 (m, 1H), 7.39-7.33 (m, 1H), 7.28-7.21 (m, 2H), 7.11 (d, J=8.4 Hz, 2H), 5.23 (s, 1H), 3.81-3.58 (m, 3H), 3.34-3.15 (m, 1H), 3.08-2.95 (m, 1H), 2.92-2.73 (m, 2H), 2.66-2.56 (m, 1H), 1.20 (d, J=6.8 Hz, 3H).

Step 4: tert-Butyl 3-((4-((1,3-trans)-2-(2,2-difluoro-3-hydroxypropyl)-3-methyl-1,2,3,4-tetrahydrobenzofuro[2,3-c]pyridin-1-yl)-3,5-difluorophenyl)amino)azetidine-1-carboxylate

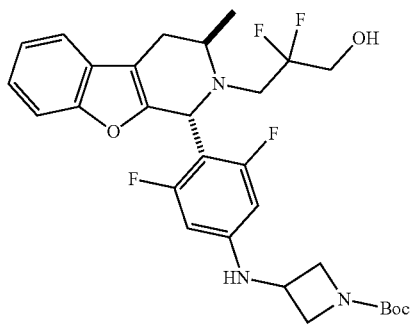 [SMILES: C[C@@H]1Cc2c(oc3ccccc23)[C@@H](c2c(F)cc(NC3CN(C(=O)OC(C)(C)C)C3)cc2F)N1CC(F)(F)CO]

A mixture of 3-((1,3-trans)-1-(4-bromo-2,6-difluorophenyl)-3-methyl-3,4-dihydrobenzofuro[2,3-c]pyridin-2(1H)-yl)-2,2-difluoropropan-1-ol (300 mg, 0.64 mmol), Pd$_2$(dba)$_3$ (58 mg, 0.06 mmol), Cs$_2$CO$_3$ (621 mg, 1.91 mmol), 1-Boc-3-(amino)azetidine (165 mg, 0.96 mmol) and 4,5-bis(diphenylphosphino)-9,9-dimethylxanthene (73 mg, 0.13 mmol) in 1,4-dioxane (4 mL) was stirred at 80° C. for 2 hours under N$_2$. The mixture was filtered, concentrated and purified by silica gel flash column chromatography (0-50% EtOAc in hexanes) to afford the title compound (262 mg, yield 73%) as a light yellow solid. $^1$H NMR (400 MHz, CDCl$_3$) δ 7.52-7.43 (m, 1H), 7.37-7.33 (m, 1H), 7.24-7.17 (m, 2H), 6.03 (d, J=11.2 Hz, 2H), 5.11 (s, 1H), 4.41-4.39 (m, 1H), 4.32-4.23 (m, 2H), 4.19-4.06 (m, 1H), 3.75-3.70 (m, 3H), 3.40-3.31 (m, 1H), 3.24-3.20 (m, 1H), 3.10-2.84 (m, 2H), 2.60-2.55 (m, 1H), 1.44 (s, 9H), 1.19 (d, J=6.4 Hz, 3H).

Step 5: N-(4-((1,3-trans)-2-(2,2-Difluoro-3-((trimethylsilyl)oxy)propyl)-3-methyl-1,2,3,4-tetrahydrobenzofuro[2,3-c]pyridin-1-yl)-3,5-difluorophenyl)azetidin-3-amine

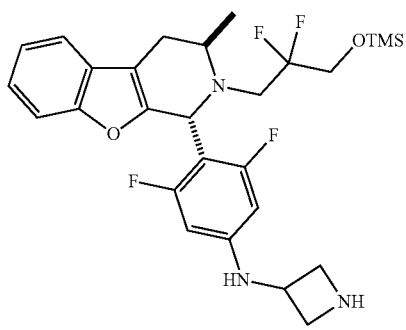

To a solution of tert-butyl 3-((4-((1,3-trans)-2-(2,2-difluoro-3-hydroxypropyl)-3-methyl-1,2,3,4-tetrahydrobenzofuro[2,3-c]pyridin-1-yl)-3,5-difluorophenyl)amino)azetidine-1-carboxylate (350 mg, 0.62 mmol) and 2,6-lutidine (0.36 mL, 3.07 mmol) in dichloromethane (15 mL) was added trimethylsilyl trifluoromethanesulfonate (0.23 mL, 1.24 mmol) slowly at 0° C. under N$_2$. The reaction mixture was stirred at 0° C. for 10 minutes. Saturated aqueous NaHCO$_3$ solution (10 mL) was added to the reaction mixture and the mixture was extracted with DCM (50 mL). The organic layer was concentrated to give the crude title compound (330 mg, yield 99%) as a brown oil which was used in next step directly without purification.

Step 6: 3-((1,3-trans)-1-(4-(Azetidin-3-ylamino)-2,6-difluorophenyl)-3-methyl-3,4-dihydrobenzofuro[2,3-c]pyridin-2(1H)-yl)-2,2-difluoropropan-1-ol

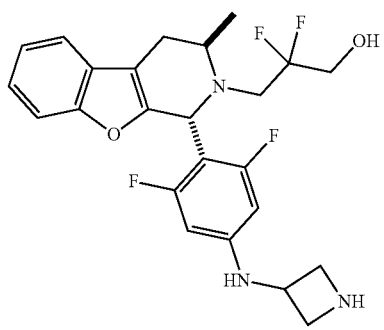 [SMILES: C[C@@H]1Cc2c(oc3ccccc23)[C@@H](c2c(F)cc(NC3CNC3)cc2F)N1CC(F)(F)CO]

To a solution of N-(4-((1,3-trans)-2-(2,2-difluoro-3-((trimethylsilyl)oxy)propyl)-3-methyl-1,2,3,4-tetrahydrobenzofuro[2,3-c]pyridin-1-yl)-3,5-difluorophenyl)azetidin-3-amine (330 mg, 0.62 mmol) in tetrahydrofuran (4 mL) was added tetrabutylammoniumfluoride (1 M in THF, 0.92 mL, 0.92 mmol). The reaction mixture was stirred at 20° C. for 10 minutes. The reaction mixture was diluted with EtOAc (100 mL), washed with aqueous 1 N NaOH solution (40 mL×3). The organic layer was dried over Na$_2$SO$_4$, filtered, concentrated and purified by silica gel flash column chromatography (0-15% MeOH (10% TEA) in DCM) to afford the title compound (200 mg, yield 70%) as a white solid. $^1$H NMR (400 MHz, CDCl$_3$) δ 7.49-7.42 (m, 1H), 7.38-7.31 (m, 1H), 7.24-7.16 (m, 2H), 6.03 (d, J=11.2 Hz, 2H), 5.10 (s, 1H), 4.56-4.54 (m, 1H), 4.35-4.25 (m, 1H), 4.04-3.87 (m, 2H), 3.74-3.58 (m, 3H), 3.55-3.45 (m, 2H), 3.23-3.20 (m, 1H), 3.06-2.88 (m, 2H), 2.85-2.62 (m, 2H), 2.60-2.50 (m, 1H), 1.18 (d, J=6.4 Hz, 3H).

Step 7: 157 and 158

To a mixture of 3-((1,3-trans)-1-(4-(azetidin-3-ylamino)-2,6-difluorophenyl)-3-methyl-3,4-dihydrobenzofuro[2,3-c]pyridin-2(1H)-yl)-2,2-difluoropropan-1-ol (From step 6, 200 mg, 0.43 mmol) and N,N-diisopropylethylamine (0.23 mL, 1.29 mmol) in N,N-dimethylformamide (3 mL) was added 1-iodo-3-fluoropropane (81 mg, 0.43 mmol). The reaction mixture was stirred at 20° C. for 16 urs. The reaction mixture was diluted with EtOAc (200 mL), washed with brine (20 mL×5). The organic layer was dried over anhydrous Na$_2$SO$_4$, filtered, concentrated and purified by prep—TLC (10% MeOH in DCM) to afford the title compound (120 mg, yield 53%) as a white solid, which was further separated by chiral SFC (AD (250 mm*30 mm, 5 um) 0.1% NH$_3$H$_2$O, CO$_2$/EtOH=40%) to give two pure enantiomers 157 and 158, structures arbitrarily assigned.

157: Analytical SFC column, Second peak, RT=5.385 min. $^1$H NMR (400 MHz, CD$_3$OD) δ 7.53-7.47 (m, 1H), 7.39-7.30 (m, 1H), 7.26-7.18 (m, 2H), 6.12 (d, J=12.0 Hz, 2H), 5.12 (s, 1H), 4.58-4.38 (m, 2H), 4.07-4.05 (m 1H), 3.89-3.72 (m, 3H), 3.67-3.59 (m, 1H), 3.55-3.50 (m, 1H), 3.23-3.10 (m, 1H), 3.03-2.89 (m, 3H), 2.82-2.70 (m, 1H), 2.70-2.50 (m, 3H), 1.85-1.70 (m, 2H), 1.19 (d, J=6.8 Hz, 3H). LCMS: 524.2 [M+H]⁺.

Example 158 3-((1S,3S)-1-(2,6-Difluoro-4-((1-(3-fluoropropyl)azetidin-3-yl)amino)phenyl)-3-methyl-3,4-dihydrobenzofuro[2,3-c]pyridin-2(1H)-yl)-2,2-difluoropropan-1-ol 158

Following the procedures of Example 157, 158 was prepared.

158: Analytical SFC column, First peak, RT=4.667 min. ¹H NMR (400 MHz, CD₃OD) δ 7.53-7.47 (m, 1H), 7.39-7.30 (m, 1H), 7.26-7.18 (m, 2H), 6.12 (d, J=12.0 Hz, 2H), 5.12 (s, 1H), 4.58-4.38 (m, 2H), 4.07-4.05 (m 1H), 3.89-3.72 (m, 3H), 3.67-3.59 (m, 1H), 3.55-3.50 (m, 1H), 3.23-3.10 (m, 1H), 3.03-2.89 (m, 3H), 2.82-2.70 (m, 1H), 2.70-2.50 (m, 3H), 1.85-1.70 (m, 2H), 1.19 (d, J=6.8 Hz, 3H). LCMS: 524.2 [M+H]⁺.

Example 159 3-((1R,3R)-1-(2,6-difluoro-4-((1-(3-fluoropropyl)azetidin-3-yl)amino)phenyl)-3-methyl-3,4-dihydrobenzo[4,5]thieno[2,3-c]pyridin-2(1H)-yl)-2,2-difluoropropan-1-ol 159

Step 1: N-(1-(Benzo[b]thiophen-3-yl)propan-2-yl)-3-((tert-butyldiphenylsilyl)oxy)-2,2-difluoropropan-1-amine

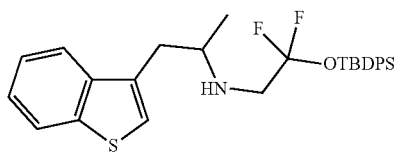

A mixture of 1-(benzothiophen-3-yl)propan-2-amine (From step 2 of Example 54, 8.0 g, 41.82 mmol), [3-[tert-butyl(diphenyl)silyl]oxy-2,2-difluoropropyl]trifluoromethanesulfonate (20.18 g, 41.82 mmol) and DIPEA (14.8 mL, 84.74 mmol) in 1,4-dioxane (120 mL) was stirred at 90° C. for 16 hrs. The reaction mixture was concentrated and the residue was triturated with EtOAc (150 mL), washed with brine (40 mL×2). The mixture was then dried over anhydrous Na₂SO₄, filtered and concentrated. The residue was purified by silica gel column (0-18% EtOAc in petroleum ether) to give the title compound (9.1 g, yield 42%) as a yellow syrup. ¹H NMR (400 MHz, CDCl₃) δ 7.88-7.84 (m, 1H), 7.76-7.72 (m, 1H), 7.68-7.65 (m, 4H), 7.46-7.33 (m, 8H), 7.14 (s, 1H), 3.90-3.80 (m, 2H), 3.25-3.09 (m, 3H), 3.05-2.97 (m, 1H), 2.86-2.80 (m, 1H), 1.11 (d, J=6.0 Hz, 3H), 1.05 (s, 9H). LCMS: 524.1 [M+H]⁺.

Step 2: (1,3-trans)-1-(4-Bromo-2,6-difluorophenyl)-2-(3-((tert-butyldiphenylsilyl)oxy)-2,2-difluoropropyl)-3-methyl-1,2,3,4-tetrahydrobenzo[4,5]thieno[2,3-c]pyridine

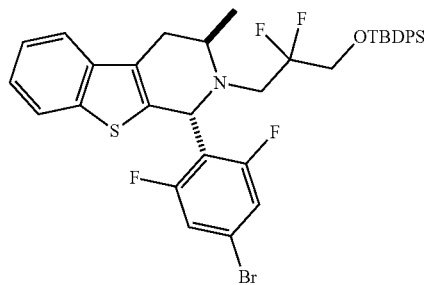

A mixture of N-(1-(benzo[b]thiophen-3-yl)propan-2-yl)-3-((tert-butyldiphenylsilyl)oxy)-2,2-difluoropropan-1-amine (2.25 g, 4.3 mmol), acetic acid (0.49 mL, 8.59 mmol) and 4-bromo-2,6-difluorobenzaldehyde (0.95 g, 4.3 mmol) in 1,2-dichloroethane (15 mL) was stirred at 120° C. for 1.5 hrs under microwave irradiation. The reaction mixture was diluted with DCM (50 mL), washed with saturated aqueous NaHCO₃ (20 mL), dried over Na₂SO₄, filtered and concentrated. The residue was purified by flash chromatography on silica gel (0-6% EtOAc in petroleum ether) to afford the title compound (1.84 g, yield 59%) as a light-yellow solid. ¹H NMR (400 MHz, CDCl₃) δ 7.75-7.70 (m, 1H), 7.67-7.58 (m, 5H), 7.48-7.35 (m, 7H), 7.33-7.26 (m, 1H), 6.93 (d, J=8.4 Hz, 2H), 5.37 (s, 1H), 3.98-3.87 (m, 1H), 3.73-3.54 (m, 2H), 3.32-3.18 (m, 1H), 3.02-2.97 (m, 1H), 2.84-2.72 (m, 1H), 2.68-2.63 (m, 1H), 1.15 (d, J=6.4 Hz, 3H), 1.04 (s, 9H). LCMS: 726.0 [M+H]⁺.

Step 3: tert-Butyl 3-((4-((1,3-trans)-2-(3-((tert-butyldiphenylsilyl)oxy)-2,2-difluoropropyl)-3-methyl-1,2,3,4-tetrahydrobenzo[4,5]thieno[2,3-c]pyridin-1-yl)-3,5-difluorophenyl)amino)azetidine-1-carboxylate

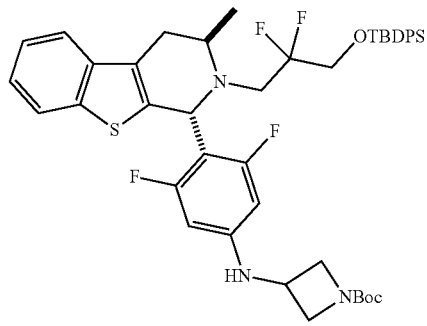

A mixture of (1,3-trans)-1-(4-bromo-2,6-difluorophenyl)-2-(3-((tert-butyldiphenylsilyl)oxy)-2,2-difluoropropyl)-3-methyl-1,2,3,4-tetrahydrobenzo[4,5]thieno[2,3-c]pyridine (500.0 mg, 0.69 mmol), 1-Boc-3-(amino)azetidine (177.73 mg, 1.03 mmol), Cs₂CO₃ (672.5 mg, 2.06 mmol), Xantphos (79.62 mg, 0.14 mmol) and Pd₂(dba)₃ (63.0 mg, 0.07 mmol) in 1,4-dioxane (15 mL) was stirred at 110° C. for 3 hrs under N₂ atmosphere. The reaction mixture was diluted with EtOAc (60 mL), filtered and the filter cake was washed with EtOAc (40 mL). The filtrate was concentrated and the residue was purified by flash chromatography on silica gel (0-25% EtOAc in petroleum ether) to afford the title compound (378 mg, yield 65%) as a light-yellow solid. ¹H NMR (400 MHz, CDCl₃) δ 7.75-7.70 (m, 1H), 7.66-7.59 (m, 5H), 7.44-7.30 (m, 7H), 7.29-7.25 (m, 1H), 5.83 (d, J=10.8 Hz, 2H), 5.26 (s, 1H), 4.27-4.19 (m, 2H), 4.04-3.92 (m, 2H), 3.72-3.64 (m, 3H), 3.58-3.50 (m, 1H), 3.25-3.15 (m, 1H), 3.00-2.94 (m, 1H), 2.85-2.75 (m, 1H), 2.65-2.55 (m, 1H), 1.44 (s, 9H), 1.14 (d, J=6.4 Hz, 3H), 1.04 (s, 9H). LCMS: 818.3, [M+H]⁺.

Step 4: N-(4-((1,3-trans)-2-(3-((tert-Butyldiphenyl-silyl)oxy)-2,2-difluoropropyl)-3-methyl-1,2,3,4-tetrahydrobenzo[4,5]thieno[2,3-c]pyridin-1-yl)-3,5-difluorophenyl)azetidin-3-amine

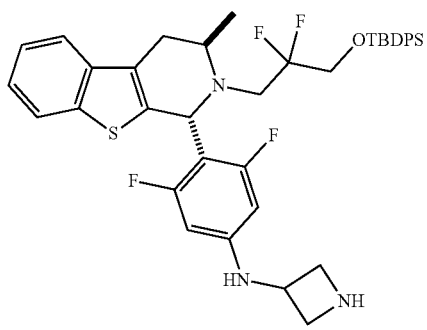

To a solution of tert-butyl 3-((4-((1,3-trans)-2-(3-((tert-butyldiphenylsilyl)oxy)-2,2-difluoropropyl)-3-methyl-1,2,3,4-tetrahydrobenzo[4,5]thieno[2,3-c]pyridin-1-yl)-3,5-difluorophenyl)amino)azetidine-1-carboxylate (375.0 mg, 0.46 mmol) and 2,6-lutidine (0.27 mL, 2.29 mmol) in DCM (20 mL) was added trimethylsilyl trifluoromethanesulfonate (0.25 mL, 1.38 mmol) slowly at 5° C. The reaction mixture was stirred at 5° C. for 10 minutes. The reaction mixture was diluted with DCM (30 mL) and to the mixture was added aqueous NaHCO₃ solution (20 mL) and two layers were separated. The organic phase was washed with brine (10 mL), dried over Na₂SO₄, filtered and concentrated. The residue was purified by flash chromatography on silica gel (MeOH in DCM (0.1% NEt₃)) to give the title compound (286 mg, yield 85%) as a light-yellow solid. ¹H NMR (400 MHz, CDCl₃) δ 7.75-7.69 (m, 1H), 7.67-7.58 (m, 5H), 7.46-7.33 (m, 7H), 7.28-7.24 (m, 1H), 5.85 (d, J=10.8 Hz, 2H), 5.25 (s, 1H), 4.28-4.23 (m, 1H), 4.21-4.14 (m, 1H), 4.04-3.93 (m, 1H), 3.89-3.80 (m, 2H), 3.73-3.65 (m, 1H), 3.63-3.54 (m, 1H), 3.48-3.43 (m, 2H), 3.25-3.10 (m, 1H), 3.01-2.93 (m, 1H), 2.64-2.59 (m, 1H), 1.14 (d, J=6.4 Hz, 3H), 1.04 (s, 9H). LCMS: 718.2 [M+H]⁺.

Step 5: N-(4-((1,3-trans)-2-(3-((tert-Butyldiphenyl-silyl)oxy)-2,2-difluoropropyl)-3-methyl-1,2,3,4-tetrahydrobenzo[4,5]thieno[2,3-c]pyridin-1-yl)-3,5-difluorophenyl)-1-(3-fluoropropyl)azetidin-3-amine

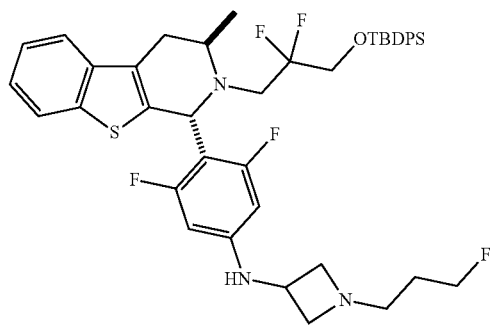

A mixture of N-(4-((1,3-trans)-2-(3-((tert-butyldiphenyl-silyl)oxy)-2,2-difluoropropyl)-3-methyl-1,2,3,4-tetrahydrobenzo[4,5]thieno[2,3-c]pyridin-1-yl)-3,5-difluorophenyl) azetidin-3-amine (285.0 mg, 0.40 mmol), 1-iodo-3-fluoropropane (75.0 mg, 0.40 mmol) and DIPEA (0.22 mL, 1.24 mmol) in DMF (5 mL) was stirred at 25° C. for 4 hours. The reaction mixture was diluted with EtOAc (40 mL), washed with brine (20 mL×6). The organic layer was dried over anhydrous Na₂SO₄, filtered, concentrated. The residue was purified by flash chromatography on silica gel (0-6% MeOH in DCM) to give the title compound (250 mg, yield 76%) as a light-yellow solid. ¹H NMR (400 MHz, CDCl₃) δ 7.75-7.70 (m, 1H), 7.65-7.58 (m, 5H), 7.44-7.33 (m, 7H), 7.28-7.24 (m, 1H), 5.85 (d, J=11.2 Hz, 2H), 5.25 (s, 1H), 4.60-4.40 (m, 2H), 4.15-4.08 (m, 1H), 4.03-3.85 (m, 2H), 3.71-3.64 (m, 3H), 3.58-3.50 (m, 1H), 3.25-3.10 (m, 1H), 2.86-2.78 (m, 3H), 2.65-2.55 (m, 3H), 1.80-1.65 (m, 2H), 1.13 (d, J=6.4 Hz, 3H), 1.04 (s, 9H). LCMS: 778.3 [M+H]⁺.

Step 6: 159 and 160

To a solution of N-(4-((1,3-trans)-2-(3-((tert-butyldiphe-nylsilyl)oxy)-2,2-difluoropropyl)-3-methyl-1,2,3,4-tetrahydrobenzo[4,5]thieno[2,3-c]pyridin-1-yl)-3,5-difluorophe-nyl)-1-(3-fluoropropyl)azetidin-3-amine (250.0 mg, 0.32 mmol) in THF (5 mL) was added TBAF (1 M in THF, 0.48 mL, 0.48 mmol). The reaction mixture was stirred at 15° C. for 2 hours. The reaction mixture was concentrated and the residue was dissolved in EtOAc (20 mL) and washed with brine (10 mL×5). The organic phase was dried over anhydrous Na₂SO₄, concentrated and purified by flash column chromatography on silica gel (0-6% MeOH in DCM) to afford the title compound (140 mg, 76%) as a light yellow solid. The racemic trans-mixture was subjected to chiral SFC separation (OJ (250 mm*30 mm, 10 um), 0.1% NH₄OH in EtOH at 80 mL/min) to give two enantiomers 159 and 160:

159: 55 mg, yield 40%, Analytical SFC column, Second peak, RT=6.547 min. ¹H NMR (400 MHz, CDCl₃) δ 7.71 (d, J=7.6 Hz, 1H), 7.61 (d, J=7.6 Hz, 1H), 7.40-7.33 (m, 1H), 7.31-7.26 (m, 1H), 6.04 (d, J=11.2 Hz, 2H), 5.19 (s, 1H), 4.60-4.40 (m, 3H), 4.08-4.00 (m 1H), 3.82-3.61 (m, 5H), 3.26-3.18 (m, 1H), 3.16-3.08 (m, 1H), 2.99-2.86 (m, 3H), 2.75-2.68 (m, 1H), 2.63-2.55 (m, 2H), 1.83-1.70 (m, 2H), 1.17 (d, J=6.4 Hz, 3H). LCMS: 540.1, [M+H]⁺.

Example 160 3-((1S,3S)-1-(2,6-difluoro-4-((1-(3-fluoropropyl)azetidin-3-yl)amino)phenyl)-3-methyl-3,4-dihydrobenzo[4,5]thieno[2,3-c]pyridin-2(1H)-yl)-2,2-difluoropropan-1-ol 160

Following the procedures of Example 159, 160 was prepared
160: 50 mg, yield 37%, Analytical SFC column, First peak, RT=4.240 min. $^1$H NMR (400 MHz, CDCl$_3$) δ 7.71 (d, J=7.6 Hz, 1H), 7.61 (d, J=7.6 Hz, 1H), 7.40-7.33 (m, 1H), 7.31-7.26 (m, 1H), 6.04 (d, J=11.2 Hz, 2H), 5.19 (s, 1H), 4.60-4.40 (m, 3H), 4.08-4.00 (m 1H), 3.82-3.61 (m, 5H), 3.26-3.18 (m, 1H), 3.16-3.08 (m, 1H), 2.99-2.86 (m, 3H), 2.75-2.68 (m, 1H), 2.63-2.55 (m, 2H), 1.83-1.70 (m, 2H), 1.17 (d, J=6.4 Hz, 3H). LCMS: 540.1, [M+H]$^+$.

Example 161 3-((1R,3R)-1-(2,6-Difluoro-4-((1-(3-fluoropropyl)azetidin-3-yl)amino)phenyl)-6-methoxy-3-methyl-3,4-dihydro-1H-pyrrolo[2,3-c:5,4-c']dipyridin-2(9H)-yl)-2,2-difluoropropan-1-ol 161

Following the procedures of Example 162, 161 was prepared: Rt=4.09 min. $^1$H NMR (400 MHz, CD$_3$OD) δ 8.05 (s, 1H), 6.80 (s, 1H), 6.14 (d, J=12.0 Hz, 2H), 5.17 (s, 1H), 4.57-4.42 (m, 2H), 4.21-4.04 (m, 3H), 3.89 (s, 3H), 3.82-3.71 (m, 1H), 3.63-3.59 (m, 1H), 3.51-3.35 (m, 3H), 3.16-3.09 (m, 1H), 2.97-2.93 (m, 3H), 2.76-2.56 (m, 2H), 1.90-1.78 (m, 2H), 1.14 (d, J=6.4 Hz, 3H). LCMS: 554.2 [M+H]$^+$.

Example 162 3-((1S,3S)-1-(2,6-Difluoro-4-((1-(3-fluoropropyl)azetidin-3-yl)amino)phenyl)-6-methoxy-3-methyl-3,4-dihydro-1H-pyrrolo[2,3-c:5,4-c']dipyridin-2(9H)-yl)-2,2-difluoropropan-1-ol 162

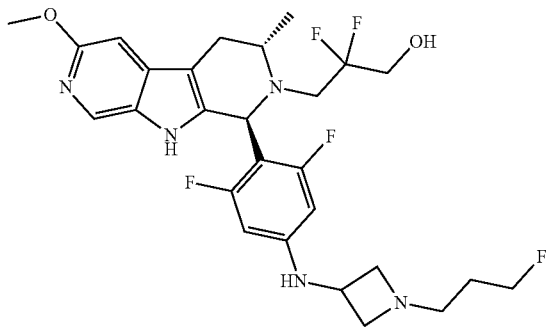 [SMILES: COc1cc2c3c([nH]c2cn1)[C@H](c1c(F)cc(NC2CN(CCCF)C2)cc1F)N(CC(F)(F)CO)[C@@H](C)C3]

Step 1: (E)-2-(2-Methoxy-5-nitro-4-pyridyl)-N,N-dimethyl-ethenamine

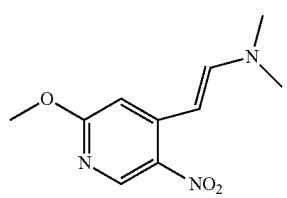

A mixture of 2-methoxy-4-methyl-5-nitro-pyridine (20.0 g, 119 mmol) in DMF-DMA (300 mL) was stirred at 120° C. for 36 hours. Solvent was removed in vacuo. The crude residue was purified by silica gel column chromatography (30% EtOAc in petroleum ether) to afford the title compound (14.5 g, yield 55%) as a brown solid. $^1$H NMR (400 MHz, CDCl$_3$) δ 8.78 (s, 1H), 7.17 (d, J=13.2 Hz, 1H), 6.58 (s, 1H), 5.92 (d, J=13.2 Hz, 1H), 3.94 (s, 3H), 2.97 (s, 6H).

Step 2: 5-Methoxy-1H-pyrrolo[2,3-c]pyridine

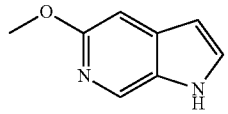

A mixture of (E)-2-(2-methoxy-5-nitro-4-pyridyl)-N,N-dimethyl-ethenamine (From step 1, 14.5 g, 65 mmol) and 10 wt % Pd on carbon (3.46 g) in ethanol (300 mL) was stirred at 20° C. for 3 hours under H$_2$ (15 psi). The reaction mixture was filtered over a Celite pad. The filtrate was concentrated in vacuo. The crude residue was purified by silica gel column chromatography (60% EtOAc in petroleum ether) to afford the title compound (8.8 g, 91%) as a light yellow solid. $^1$H NMR (400 MHz, CDCl$_3$) δ 8.97 (s, 1H), 8.42 (s, 1H), 7.38 (d, J=3.2 Hz, 1H), 6.95 (s, 1H), 6.46 (d, J=3.2 Hz, 1H), 3.98 (s, 3H).

Step 3: 5-Methoxy-1H-pyrrolo[2,3-c]pyridine-3-carbaldehyde

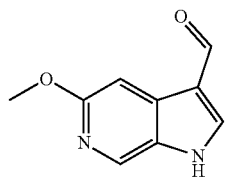

A mixture of 5-methoxy-1H-pyrrolo[2,3-c]pyridine (From step 2, 12.5 g, 84.37 mmol) and hexamethylenetetramine (17.74 g, 126.55 mmol) in HOAc (200 mL) was stirred at 100° C. for 4 hours. Water (300 mL) was added to the reaction mixture and the solution was extracted with EtOAc (300 mL×2). The combined organic layers were dried over anhydrous Na$_2$SO$_4$ and concentrated. The residue was purified by chromatography on silica gel (0-4% MeOH in DCM) to afford the title compound (12.6 g, yield 85%) as a white solid. $^1$H NMR (400 MHz, CD$_3$OD) δ 9.89 (s, 1H), 8.37 (s, 1H), 8.26 (s, 1H), 7.45 (s, 1H), 3.93 (s, 3H).

Step 4: 5-Methoxy-3-[2-nitroprop-1-enyl]-1H-pyrrolo[2,3-c]pyridine

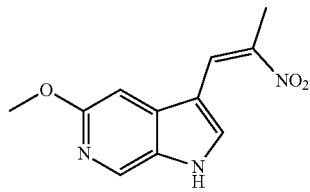 [SMILES: COc1cc2c(/C=C(/C)[N+](=O)[O-])c[nH]c2cn1]

A mixture of 5-methoxy-1H-pyrrolo[2,3-c]pyridine-3-carbaldehyde (From step 3, 12.6 g, 71.52 mmol) and NH₄OAc (2.75 g, 35.76 mmol) in nitroethane (150 mL) was stirred at 80° C. for 3 hours. The solvent was removed in vacuo and water (300 mL) was added. The mixture was filtered, washed with water (100 mL×2) and the cake was dried to afford the title compound (12.1 g, yield 73%) as a yellow solid. ¹H NMR (400 MHz, CD₃OD) δ 8.44 (s, 1H), 8.41 (s, 1H), 8.03 (s, 1H), 7.16 (s, 1H), 3.98 (s, 3H), 2.55 (s, 3H).

Step 5: 1-(5-Methoxy-1H-pyrrolo[2,3-c]pyridin-3-yl)propan-2-amine

To a stirred solution of 5-methoxy-3-[2-nitroprop-1-enyl]-1H-pyrrolo[2,3-c]pyridine (From step 4, 12.1 g, 51.88 mmol) in THF (180 mL) was added LiAlH₄ (9.8 g, 259.41 mmol) in an ice bath. The reaction mixture was heated to 70° C. and stirred for 3 hours. The reaction mixture was cooled to 0° C. and to the mixture was added H₂O (10 mL), followed by 15% aqueous NaOH solution (10 mL) and water (30 mL). The mixture was dried over anhydrous MgSO₄ and filtered. The filtrate was concentrated to dryness to afford the title compound (10.8 g, quantitative yield) as a yellow solid. LCMS: 206.1 [M+H]⁺.

Step 6: 3-[tert-Butyl(diphenyl)silyl]oxy-2,2-difluoro-N-[2-(5-methoxy-1H-pyrrolo[2,3-c]pyridin-3-yl)-1-methyl-ethyl]propan-1-amine

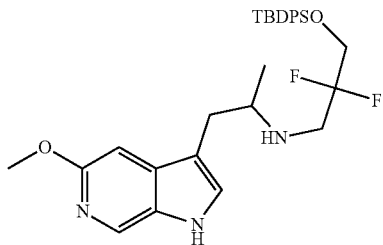

A mixture of [3-[tert-butyl(diphenyl)silyl]oxy-2,2-difluoro-propyl]trifluoromethanesulfonate (25.39 g, 52.62 mmol), DIPEA (24.52 mL, 157.85 mmol) and 1-(5-methoxy-1H-pyrrolo[2,3-c]pyridin-3-yl)propan-2-amine (From step 5, 10.8 g, 52.62 mmol) in dioxane (200 mL) was stirred at 90° C. for 16 hours. The reaction mixture was diluted in water (200 mL) and extracted with EtOAc (200 mL×2). The combined organic layers were dried over anhydrous Na₂SO₄, filtered and concentrated. The crude residue was purified by silica gel column chromatography (20% EtOAc in petroleum ether) to afford the title compound (12.4 g, yield 44%) as a light yellow solid. LCMS: 538.1 [M+H]⁺.

Step 7: (1,3-trans)-1-(4-Bromo-2,6-difluorophenyl)-2-(3-((tert-butyldiphenylsilyl)oxy)-2,2-difluoropropyl)-6-methoxy-3-methyl-2,3,4,9-tetrahydro-1H-pyrrolo[2,3-c:5,4-c']dipyridine

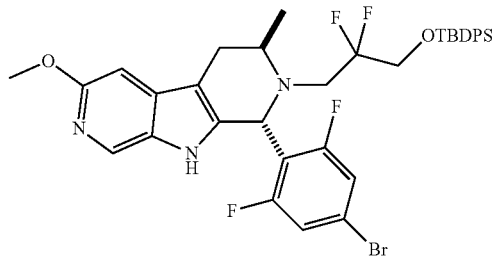

A mixture of 3-[tert-butyl(diphenyl)silyl]oxy-2,2-difluoro-N-[2-(5-methoxy-1H-pyrrolo[2,3-c]pyridin-3-yl)-1-methyl-ethyl]propan-1-amine (From step 6, 12.4 g, 23.06 mmol), 4-bromo-2,6-difluorobenzaldehyde (5.1 g, 23.06 mmol) and HOAc (6.66 mL, 115.3 mmol) in toluene (200 mL) was stirred at 110° C. for 48 hours. The reaction mixture was diluted in water (200 mL), extracted with EtOAc (300 mL×2). The combined organic layers were dried over anhydrous Na₂SO₄, filtered and concentrated. The crude residue was purified by silica gel column chromatography (30% EtOAc in petroleum ether) to afford the title compound (3.5 g, yield 21%) as a yellow solid. ¹H NMR (400 MHz, CDCl₃) δ 8.18 (s, 1H), 7.71-7.59 (m, 5H), 7.50-7.37 (m, 6H), 6.93 (d, J=9.2 Hz, 2H), 6.77 (s, 1H), 5.26 (s, 1H), 3.93-3.89 (m, 4H), 3.68-3.57 (m, 2H), 3.28-3.21 (m, 1H), 2.90-2.85 (m, 1H), 2.78-2.72 (m, 1H), 2.51-2.47 (m, 1H), 1.14 (d, J=6.4 Hz, 3H), 1.04 (s, 9H).

Step 8: tert-Butyl 3-((4-((1,3-trans)-2-(3-((tert-butyldiphenylsilyl)oxy)-2,2-difluoropropyl)-6-methoxy-3-methyl-2,3,4,9-tetrahydro-1H-pyrrolo[2,3-c:5,4-c']dipyridin-1-yl)-3,5-difluorophenyl)amino)azetidine-1-carboxylate

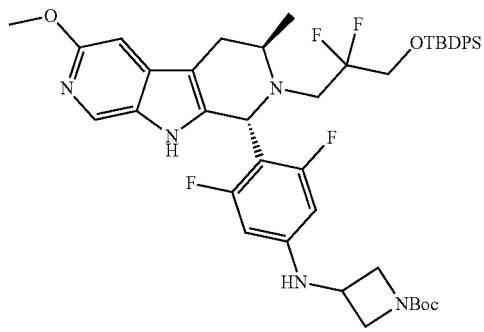

A mixture of (1,3-trans)-1-(4-bromo-2,6-difluorophenyl)-2-(3-((tert-butyldiphenylsilyl)oxy)-2,2-difluoropropyl)-6-methoxy-3-methyl-2,3,4,9-tetrahydro-1H-pyrrolo[2,3-c:5,4-c']dipyridine (From step 7, 700 mg, 0.95 mmol), 1-Boc-3-(amino)azetidine (326 mg, 1.89 mmol), Cs₂CO₃ (924 mg, 2.84 mmol), Pd₂(dba)₃ (87 mg, 0.09 mmol) and Xantphos (109 mg, 0.19 mmol) in dioxane (14 mL) was stirred at 110° C. under N₂ atmosphere for 3 hours. After being cooled to 25° C., the reaction mixture was diluted in water (100 mL), extracted with EtOAc (100 mL×2). The combined organic layers were dried over anhydrous Na₂SO₄, filtered and concentrated. The crude residue was purified by silica gel column chromatography (50% EtOAc in petroleum ether) to afford the title compound (380 mg, yield 48%) as a light yellow solid. LCMS: 832.3 [M+H]⁺.

Step 9: N-(4-((1,3-trans)-2-(3-((tert-Butyldiphenylsilyl)oxy)-2,2-difluoropropyl)-6-methoxy-3-methyl-2,3,4,9-tetrahydro-1H-pyrrolo[2,3-c:5,4-c']dipyridin-1-yl)-3,5-difluorophenyl)azetidin-3-amine

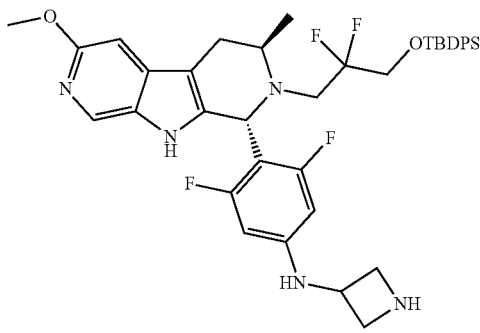

A stirred solution tert-butyl 3-((4-((1,3-trans)-2-(3-((tert-butyldiphenylsilyl)oxy)-2,2-difluoropropyl)-6-methoxy-3-methyl-2,3,4,9-tetrahydro-1H-pyrrolo[2,3-c:5,4-c']dipyridin-1-yl)-3,5-difluorophenyl)amino)azetidine-1-carboxylate (From step 8, 380 mg, 0.46 mmol) and 2,6-lutidine (0.27 mL, 2.28 mmol) in DCM (4 mL) was added TMSOTf (0.25 mL, 1.37 mmol) in an ice bath. The reaction mixture was stirred at 0° C. for 10 min. The reaction mixture was diluted in saturated aqueous NaHCO₃ solution (50 mL), extracted with DCM (50 mL×3). The combined organic layer were dried over anhydrous Na₂SO₄, filtered and concentrated. The crude residue was purified by silica gel column chromatography (10% MeOH in DCM) to afford the title compound (240 mg, yield 72%) as a light yellow solid. LCMS: 732.3 [M+H]⁺.

Step 10: N-(4-((1,3-trans)-2-(3-((tert-Butyldiphenylsilyl)oxy)-2,2-difluoropropyl)-6-methoxy-3-methyl-2,3,4,9-tetrahydro-1H-pyrrolo[2,3-c:5,4-c']dipyridin-1-yl)-3,5-difluorophenyl)-1-(3-fluoropropyl)azetidin-3-amine

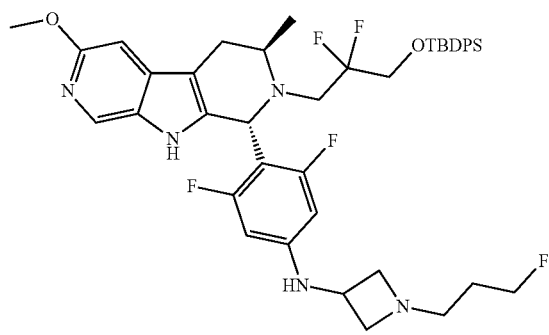

A mixture of N-(4-((1,3-trans)-2-(3-((tert-butyldiphenylsilyl)oxy)-2,2-difluoropropyl)-6-methoxy-3-methyl-2,3,4,9-tetrahydro-1H-pyrrolo[2,3-c:5,4-c']dipyridin-1-yl)-3,5-difluorophenyl)azetidin-3-amine (From step 9, 240 mg, 0.33 mmol), 1-iodo-3-fluoropropane (62 mg, 0.33 mmol) and DIPEA (0.15 mL, 0.98 mmol) in DMF (4 mL) was stirred at 25° C. for 16 hours. The reaction mixture was diluted in EtOAc (30 mL), washed with brine (30 mL×2). The organic layer was dried over anhydrous Na₂SO₄, filtered and concentrated. The crude residue was purified by silica gel column chromatography (5% MeOH in DCM) to afford the title compound (150 mg, yield 58%) as a light yellow solid. LCMS: 792.3 [M+H]⁺.

Step 11: 161 and 162

A mixture of N-(4-((1,3-trans)-2-(3-((tert-butyldiphenylsilyl)oxy)-2,2-difluoropropyl)-6-methoxy-3-methyl-2,3,4,9-tetrahydro-1H-pyrrolo[2,3-c:5,4-c']dipyridin-1-yl)-3,5-difluorophenyl)-1-(3-fluoropropyl)azetidin-3-amine (From step 10, 150 mg, 0.19 mmol) in THF (3 mL) was added TBAF (1.0 M in THF, 0.57 mL, 0.57 mmol). The reaction mixture was stirred at 25° C. for 1 hour. The reaction mixture was diluted in saturated aqueous NaHCO₃ solution (20 mL), extracted with EtOAc (20 mL×3). The combined organic layers were dried over anhydrous Na₂SO₄, filtered and concentrated. The crude residue was purified by silica gel column chromatography (10% MeOH in DCM) to afford the racemic products (40 mg, yield 38%) which was purified by chiral SFC (AD 250 mm*30 mm, 10 um; supercritical CO₂/EtOH (0.1% NH₃H₂O)=40/40 at 80 mL/min) to afford 161 (8 mg, yield 20%) and 162 (8 mg, yield 20%) both as white solids. 162: Rt=5.20 min. ¹H NMR (400 MHz, CD₃OD) δ 8.04 (s, 1H), 6.78 (s, 1H), 6.11 (d, J=12.0 Hz, 2H), 5.15 (s, 1H), 4.52-4.38 (m, 2H), 4.05-4.02 (m, 1H), 3.88 (s, 3H), 3.79-3.72 (m, 3H), 3.63-3.40 (m, 2H), 3.15-3.09 (m, 1H), 2.96-2.93 (m, 3H), 2.77-2.55 (m, 4H), 1.81-1.68 (m, 2H), 1.13 (d, J=6.4 Hz, 3H). LCMS: 554.2 [M+H]⁺.

Example 163 3-[(1R,3R)-1-[2,6-difluoro-4-[(S)-[1-(3-fluoropropyl)azetidin-3-yl]-hydroxy-methyl]phenyl]-3-methyl-3,4-dihydro-1H-pyrazino[1,2-a]indol-2-yl]-2,2-difluoro-propan-1-ol 163

Following the procedures of Example 164, 163 was prepared, the first eluting peak (rt=10.5 mins, de>99%) as a white solid (10 mg, 27%): ¹H NMR (400 MHz, CDCl₃): δ 7.48 (d, J=7.6 Hz, 1H), 7.21-7.16 (m, 1H), 7.11-7.06 (m, 1H), 6.92 (d, J=10.5 Hz, 2H), 5.96 (s, 1H), 5.50 (s, 1H), 4.88 (d, J=5.0 Hz, 1H), 4.53 (t, J=5.7 Hz, 1H), 4.41 (t, J=6.0 Hz, 1H), 4.29 (dd, J=4.0, 11.6 Hz, 1H), 4.14-4.05 (m, 1H), 3.87-3.80 (m, 1H), 3.63 (t, J=12.5 Hz, 2H), 3.33-3.08 (m, 6H), 2.93-2.78 (m, 2H), 2.65-2.53 (m, 4H), 1.78-1.67 (m, 2H), 1.22-1.19 (m, 3H); LCMS: 538.2 [M+H]⁺.

Example 164 3-[(1R,3R)-1-[2,6-difluoro-4-[(R)-[1-(3-fluoropropyl)azetidin-3-yl]-hydroxy-methyl]phenyl]-3-methyl-3,4-dihydro-1H-pyrazino[1,2-a]indol-2-yl]-2,2-difluoro-propan-1-ol 164

Step 1: 3-[tert-butyl(diphenyl)silyl]oxy-2,2-difluoro-N-[(1R)-2-indol-1-yl-1-methyl-ethyl]propan-1-amine

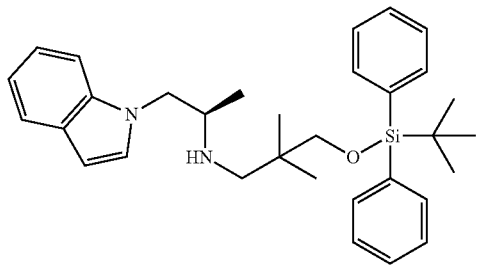 [SMILES: C[C@H](Cn1ccc2ccccc21)NCC(C)(C)CO[Si](c1ccccc1)(c1ccccc1)C(C)(C)C]

[3-[tert-butyl(diphenyl)silyl]oxy-2,2-difluoro-propyl]trifluoromethanesulfonate (16.7 g, 34.61 mmol) was added over 5 min to a solution of (2R)-1-indol-1-ylpropan-2-amine (5.97 g, 34.26 mmol) and N,N-diisopropylethylamine (7.46 mL, 42.83 mmol) in 1,4-dioxane (95 mL). The reaction mixture was stirred at 90° C. for 4 h, allowed to cool to RT, concentrated in vacuo. The residue was dissolved in EtOAc and washed with saturated NaHCO₃ solution, water and brine. The organic layer was dried (Na₂SO₄), filtered and concentrated in vacuo. The residue was purified by column chromatography on silica gel (0-80% DCM in Cyclohexane) to give the title compound (15.1 g, yield 87%) as a colorless gum. ¹H NMR (400 MHz, CDCl₃) δ 7.67-7.61 (m, 6H), 7.52-7.31 (m, 6H), 7.18 (t, J=7.6 Hz, 1H), 7.12-7.07 (m, 2H), 6.48 (d, J=3.2 Hz, 1H), 4.10 (dd, J=6.6, 14.3 Hz, 1H), 3.98 (dd, J=6.2, 14.3 Hz, 1H), 3.84-3.76 (m, 2H), 3.26-2.96 (m, 3H), 1.05-1.04 (m, 12H).

Step 2: tert-butyl 3-[[4-[(1R,3R)-2-[3-[tert-butyl(diphenyl)silyl]oxy-2,2-difluoro-propyl]-3-methyl-3,4-dihydro-1H-pyrazino[1,2-a]indol-1-yl]-3,5-difluoro-phenyl]-hydroxy-methyl]azetidine-1-carboxylate

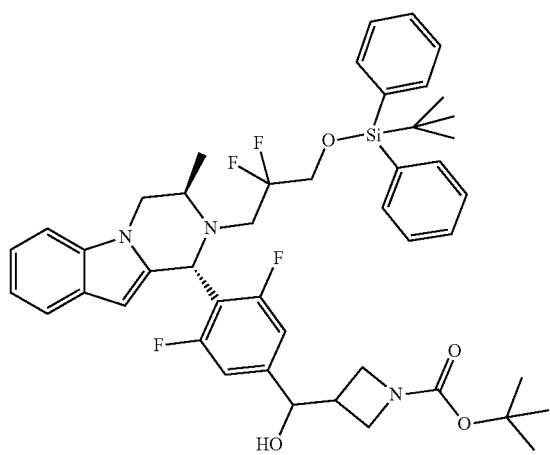 [SMILES: C[C@@H]1Cn2c(cc3ccccc32)[C@@H](c2c(F)cc(C(O)C3CN(C(=O)OC(C)(C)C)C3)cc2F)N1CC(F)(F)CO[Si](c1ccccc1)(c1ccccc1)C(C)(C)C]

A degassed mixture of 3-[tert-butyl(diphenyl)silyl]oxy-2,2-difluoro-N-[(1R)-2-indol-1-yl-1-methyl-ethyl]propan-1-amine (1.05 g, 2.07 mmol), tert-butyl 3-[(3,5-difluoro-4-formyl-phenyl)-hydroxy-methyl]azetidine-1-carboxylate (747. mg, 2.28 mmol) and acetic acid (297 µl, 5.19 mmol) in Toluene (2.7 mL) in a dried sealed microwave vial was stirred on a heating block at 120° C. for 4 h. The mixture was allowed to cool to RT and diluted with EtOAc (200 mL). The organic layer was washed with saturated NaHCO₃ (30 mL), water (30 mL) and brine (30 mL), dried over anhydrous Na₂SO₄, filtered and concentrated in-vacuo. The residue was purified by column chromatography on silica gel (0-10% EtOAc in Cyclohexane) followed by purification on a KP-NH cartridge (0-80% EtOAc in Cyclohexane) and column chromatography on silica gel (15 µm cartridge, 0-70% tBME in Cyclohexane) to give a diastereoisomeric mixture of the title compound (110 mg, yield 6.5%) as a yellow oil. LCMS: 817.3 [M+H]⁺. ¹H NMR (400 MHz, CDCl₃) δ 7.65-7.05 (m, 14H), 6.83-6.67 (m, 2H), 5.95 (s, 1H), 5.54 (s, 1H), 4.64-4.58 (m, 1H), 4.18-4.09 (m, 1H), 3.97-3.51 (m, 11H), 3.21-2.54 (m, 4H), 1.47-1.37 (m, 9H), 1.21-1.13 (m, 3H), 1.10-1.00 (m, 9H).

Step 3: azetidin-3-yl-[4-[(1R,3R)-2-[3-[tert-butyl(diphenyl)silyl]oxy-2,2-difluoro-propyl]-3-methyl-3,4-dihydro-1H-pyrazino[1,2-a]indol-1-yl]-3,5-difluoro-phenyl]methanol

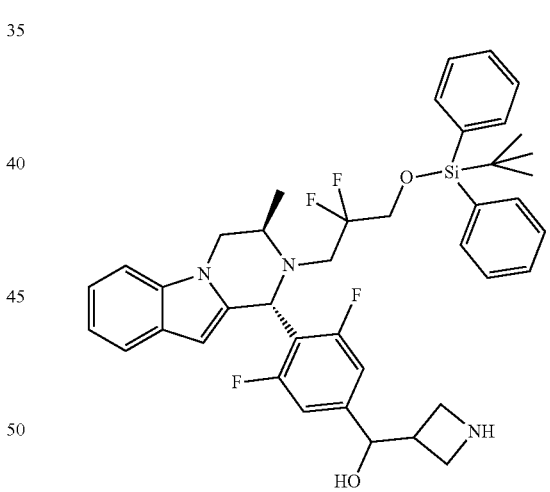

TFA (123 uL, 1.59 mmol) was added dropwise to a cooled (−10° C.) solution of tert-butyl 3-[[4-[(1R,3R)-2-[3-[tert-butyl(diphenyl)silyl]oxy-2,2-difluoro-propyl]-3-methyl-3,4-dihydro-1H-pyrazino[1,2-a]indol-1-yl]-3,5-difluoro-phenyl]-hydroxy-methyl]azetidine-1-carboxylate (52 mg, 0.06 mmol) in DCM (300 µL) under argon. The reaction mixture was stirred at 0° C. for 1.75 h, EtOAc (50 mL) and sat. NaHCO₃ (8 mL) were added and stirring for 5 min, extraction. The organic layer was further washed with sat. NaHCO₃ (8 mL), brine, dried over Na₂SO₄, filtered, and concentrated in vacuo to afford a diastereoisomeric mixture of the title compound as a pale yellow oil (48 mg, yield 105%). The crude residue was used in next step directly. LCMS: 716.2 [M+H]⁺.

Step 4: [4-[(1R,3R)-2-[3-[tert-butyl(diphenyl)silyl]oxy-2,2-difluoro-propyl]-3-methyl-3,4-dihydro-1H-pyrazino[1,2-a]indol-1-yl]-3,5-difluoro-phenyl]-[1-(3-fluoropropyl)azetidin-3-yl]methanol

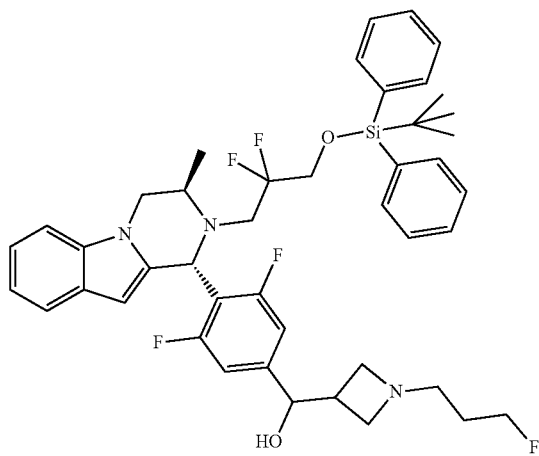 [SMILES: C[C@@H]1Cn2c(cc3ccccc32)[C@@H](c2c(F)cc(C(O)C3CN(CCCF)C3)cc2F)N1CC(F)(F)CO[Si](c1ccccc1)(c1ccccc1)C(C)(C)C]

A mixture of azetidin-3-yl-[4-[(1R,3R)-2-[3-[tert-butyl(diphenyl)silyl]oxy-2,2-difluoro-propyl]-3-methyl-3,4-dihydro-1H-pyrazino[1,2-a]indol-1-yl]-3,5-difluoro-phenyl]methanol (114.5 mg, 0.16 mmol), potassium carbonate (110.6 mg, 0.80 mmol) and 1-fluoro-3-iodo-propane (16.54 μL, 0.18 mmol) in acetonitrile (3.7 mL) was stirred at RT for 18 h. The solid was removed by filtration through a pad of Celite®, the filtercake rinsed with acetonitrile and the filtrate concentrated in-vacuo. The crude residue was purified by silica gel column chromatography (15 μm Si cartridge, 0 to 10% 2N ammonia in MeOH in DCM) to afford the title compound (47 mg, yield 38%) as a yellow foam. LCMS: 777.5 [M+H]$^+$. $^1$H NMR (400 MHz, CDCl3) δ 7.65-7.59 (m, 4H), 7.50-7.23 (m, 8H), 7.20-6.99 (m, 2H), 6.83-6.73 (m, 2H), 5.96 (d, J=2.9 Hz, 1H), 5.55 (d, J=3.4 Hz, 1H), 4.82-4.76 (m, 1H), 4.54-4.50 (m, 1H), 4.43-4.38 (m, 1H), 4.15-4.10 (m, 1H), 3.98-3.88 (m, 2H), 3.75-3.73 (m, 2H), 3.62-3.52 (m, 1H), 3.28-3.13 (m, 4H), 3.01 (q, J=7.3 Hz, 1H), 2.84-2.72 (m, 1H), 2.53-2.47 (m, 3H), 1.38-1.28 (m, 1H), 1.16 (d, J=6.6 Hz, 3H), 1.05-1.03 (m, 9H).

Step 5: The title compounds were prepared from [4-[(1R,3R)-2-[3-[tert-butyl(diphenyl)silyl]oxy-2,2-difluoro-propyl]-3-methyl-3,4-dihydro-1H-pyrazino[1,2-a]indol-1-yl]-3,5-difluoro-phenyl]-[1-(3-fluoropropyl)azetidin-3-yl]methanol (From step 4, 40.0 mg, 0.05 mmol) and a solution of tetrabutylammonium fluoride 1.0 M in THF (56.7 uL, 0.06 mmol) following the procedure outlined for the preparation of example 117 Step 2. The crude product was purified by silica gel chromatography (mobile phase: dichloromethane/2N ammonia in methanol, gradient 0% to 5%) followed by a purification by chiral HPLC (ChiralPak IC, mobile phase: 7% EtOH in heptane, 0.1% Diethylamine, 16 min run, multiple injections). Appropriate fractions were collected to give two diastereoisomers.

First eluting peak 163 (rt=10.5 mins, de>99%) as a white solid (10 mg, 27%).

Second eluting peak 164 (rt=16 mins, de>99%) as a white solid (10 mg, 27%). $^1$H NMR (400 MHz, CDCl3): δ 7.48 (d, J=7.6 Hz, 1H), 7.21-7.16 (m, 1H), 7.11-7.06 (m, 1H), 6.92 (d, J=10.5 Hz, 2H), 5.96 (s, 1H), 5.50 (s, 1H), 4.88 (d, J=5.0 Hz, 1H), 4.53 (t, J=5.7 Hz, 1H), 4.41 (t, J=6.0 Hz, 1H), 4.29 (dd, J=4.0, 11.6 Hz, 1H), 4.14-4.05 (m, 1H), 3.87-3.80 (m, 1H), 3.63 (t, J=12.5 Hz, 2H), 3.33-3.08 (m, 6H), 2.93-2.78 (m, 2H), 2.65-2.53 (m, 4H), 1.78-1.67 (m, 2H), 1.22-1.19 (m, 3H); LCMS: 538.2 [M+H]$^+$.

Example 901 Breast Cancer Cell ERa High Content Fluorescence Imaging Degradation Assay MCF7 breast cancer cells were seeded on day 1 at a density of 10,000 cells per well in 384 well poly-lysine coated tissue culture plate (Greiner # T-3101-4), in 50 μL/well RPMI (phenol red free), 10% FBS (Charcoal stripped), containing L-glutamine. On day 2, compounds were prepared at 2 compound source concentrations: 100 μM and 1 μM (ultimately to give 2 overlapping titration curves), in a Labcyte low dead volume plate, 10 μL/well, and 10 μL of DMSO in designated wells for backfill, and 5 μM Fulvestrant (control compound) in designated wells. Compounds and controls were dispensed using a Labcyte Echo acoustic dispenser to dispense compounds with a predefined serial dilution (1.8×, 10 point, in duplicate) and appropriate backfill and control compounds (final total volume transferred was 417.5 nL and compound dispense volume ranges from 2.5 nL to 417.5 nL; 0.84% DMSO (v/v) final), ultimately producing a concentration range from 0.05 nM to 835 nM. Cell plates were incubated at 37° C., for 4 hours. Fixation and permeabilization were carried out using a Biotek EL406 plate washer and dispenser as follows. Cells were fixed by addition of 15 μL of 16% paraformaldehyde (Electron Microscopy Sciences #15710-S) directly to the 50 μL cell culture medium in each well using the peristaltic pump 5 μL cassette on a Biotek EL406 (final concentration of formaldehyde was 3.7% w/v). Samples were incubated 30 minutes. Well contents was aspirated and 50 μL/well of Phosphate Buffered Saline (PBS) containing 0.5% w/v bovine serum albumen, 0.5% v/v Triton X-100 (Antibody Dilution Buffer) was added to each well. Samples were incubated for 30 minutes. Well contents were aspirated and washed 3 times with 100 μL/well of PBS. Immunofluorescence staining of estrogen receptor alpha (ESR1) was carried out using a Biotek EL406 plate washer and dispenser as follows. The well supernatant was aspirated from the wells and 25 μL/well of anti-ESR1 mAb (F10) (Santa Cruz sc-8002) diluted 1:1000 in Antibody Dilution Buffer was dispensed. Samples were incubated for 2 hours at room temperature. Samples were washed 4 times with 100 μL/well of PBS. 25 uL (microliters)/well of secondary antibody solution (Alexafluor 488 conjugate anti-mouse IgG (LifeTechnologies # A21202) diluted 1:1000 and Hoechst 33342 1 μg/ml diluted in Antibody Dilution Buffer) were dispensed into each well. Samples were incubated for 2 hours at room temperature. Samples were washed 3 times with 100 μL/well of PBS using a Biotek EL406. Quantitative fluorescence imaging of ESR1 was carried out using a Cellomics Arrayscan V (Thermo). Fluorescence images of the samples (Channel 1: XF53 Hoechst (DNA stain); Channel 2: XF53 FITC (ESR1 stain)) were acquired using a Cellomics VTI Arrayscan using the Bioapplication "Compartmental Analysis" using the auto-exposure (based on DMSO control wells) setting "peak target percentile" set to 25% target saturation for both channels. Channel 1 (DNA stain) was used to define the nuclear region (Circ). Measurements of "Mean_CircAvgIntCh2", which is the Alexafluor 488 fluorescence intensity (ESR1) within the nuclear region, was measured on a per cell basis and averaged over all the measured cells. Data analysis was carried out using Genedata Screener Software, with DMSO and 5 nM Fulvestrant treated samples being used to define the 0% and 100% changes in ESR1. The "Robust Fit" method was used to define the inflexion point of curve ($EC_{50}$) and the plateau of the maximal effect (Sinf). Degradation data for exemplary Formula I, II, and III compounds is reported as ER-alpha MCF7 HCS $S_{inf}$ (%) values in Table 1.

Example 902 In Vitro Cell Proliferation Assay

Efficacy of estrogen receptor modulator compounds and chemotherapeutic compounds are measured by a cell proliferation assay employing the following protocol (Mendoza et al (2002) Cancer Res. 62:5485-5488).

The CellTiter-Glo® Luminescent Cell Viability Assay is a homogeneous method to determine the number of viable cells in culture based on quantitation of the ATP present, which signals the presence of metabolically active cells. The CellTiter-Glo® Assay is designed for use with multiwell plate formats, making it ideal for automated high-throughput screening (HTS), cell proliferation and cytotoxicity assays. The homogeneous assay procedure involves adding a single reagent (CellTiter-Glo® Reagent) directly to cells cultured in serum-supplemented medium. Cell washing, removal of medium or multiple pipetting steps are not required. The Cell Titer-Glo® Luminescent Cell Viability Assay, including reagents and protocol are commercially available (Promega Corp., Madison, Wis., Technical Bulletin TB288).

The assay assesses the ability of compounds to enter cells and inhibit cell proliferation. The assay principle is based on the determination of the number of viable cells present by quantitating the ATP present in a homogenous assay where addition of the Cell Titer-Glo® reagent results in cell lysis and generation of a luminescent signal through the luciferase reaction. The luminescent signal is proportional to the amount of ATP present.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate O/N (overnight) at 37° C., 5% $CO_2$.

Day 2—Add Drug to Cells, Compound Dilution, DMSO Plates (serial 1:2 for 9 points). Add 20 µl of compound at 10 mM in the 2nd column of 96 well plate. Perform serial 1:2 across the plate (10 µl+20 µl 100% DMSO) for a total of 9 points using Precision Media Plates 96-well conical bottom polypropylene plates from Nunc (cat. #249946) (1:50 dilution). Add 147 µl of Media into all wells. Transfer 3 µl of DMSO+compound from each well in the DMSO Plate to each corresponding well on Media Plate using Rapidplate® (Caliper, a Perkin-Elmer Co.). For 2 drug combination studies, transfer one drug 1.5 µl of DMSO+compound from each well in the DMSO Plate to each corresponding well on Media Plate using Rapidplate. Then, transfer another drug 1.5 µl to the medium plate.

Drug Addition to Cells, Cell Plate (1:10 dilution): Add 6 µl of media+compound directly to cells (54 µl of media on the cells already). Incubate 3 days at 37° C., 5% $CO_2$ in an incubator that will not be opened often.

Day 5—Develop Plates, Thaw Cell Titer Glo Buffer at room temperature: Remove Cell Plates from 37° C. and equilibrate to room temperature for about 30 minutes. Add Cell Titer-Glo® Buffer to Cell Titer-Glo® Substrate (bottle to bottle). Add 30 µl Cell Titer-Glo® Reagent (Promega cat. # G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions were made in DMSO in a 96 well plate. The compounds were further diluted into growth media using a Rapidplate® robot (Zymark Corp., Hopkinton, Mass.). The diluted compounds were then added to quadruplicate wells in 384-well cell plates and incubated at 37° C. and 5% $CO_2$. After 4 days, relative numbers of viable cells were measured by luminescence using Cell Titer-Glo® (Promega) according to the manufacturer's instructions and read on a Wallac Multilabel Reader® (PerkinElmer, Foster City). EC50 values were calculated using Prism® 4.0 software (GraphPad, San Diego). Drugs in combination assays were dosed starting at 4× $EC_{50}$ concentrations. If cases where the EC50 of the drug was >2.5 µM, the highest concentration used was 10 µM. Estrogen receptor modulator compounds and chemotherapeutic agents were added simultaneously or separated by 4 hours (one before the other) in all assays.

An additional exemplary in vitro cell proliferation assay includes the following steps:

1. An aliquot of 100 µl of cell culture containing about $10^4$ cells (see Table 3 for cell lines and tumor type) in medium was deposited in each well of a 384-well, opaque-walled plate.

2. Control wells were prepared containing medium and without cells.

3. The compound was added to the experimental wells and incubated for 3-5 days.

4. The plates were equilibrated to room temperature for approximately 30 minutes.

5. A volume of CellTiter-Glo® Reagent equal to the volume of cell culture medium present in each well was added.

6. The contents were mixed for 2 minutes on an orbital shaker to induce cell lysis.

7. The plate was incubated at room temperature for 10 minutes to stabilize the luminescence signal.

8. Luminescence was recorded and reported in graphs as RLU=relative luminescence units.

9. Analyze using the Chou and Talalay combination method and Dose-Effect Analysis with CalcuSyn® software (Biosoft, Cambridge, UK) in order to obtain a Combination Index.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Alternatively, Proliferation/Viability was analyzed after 48 hr of drug treatment using Cell Titer-Glo® reagent (Promega Inc., Madison, Wis.). DMSO treatment was used as control in all viability assays. $IC_{50}$ values were calculated using XL fit software (IDBS, Alameda, Calif.)

The cell lines were obtained from either ATCC (American Type Culture Collection, Manassas, Va.) or DSMZ (Deutsche Sammlung von Mikroorganismen und Zellkulturen GmbH, Braunschweig, DE). Cells were cultured in RPMI 1640 medium supplemented with 10% fetal bovine serum, 100 units/ml penicillin, 2 mM L-glutamine, and 100 mg/ml streptomycin (Life Technology, Grand Island, N.Y.) at 37° C. under 5% $CO_2$.

Example 903 MCF7 In Vitro Cell Proliferation Assay

MCF7 cells were washed with PBS and plated in RPMI 1640 (Gibco 11835-030 [−phenol+glutamine]) and 10% Charcoal Stripped FBS (Gibco 12676-029), in poly-lysine coated 384 well tissue culture plates (Greiner), at 25,000 cells/ml, 40 ul/well, and incubated overnight. Compounds were prepared in serial dilution in DMSO at 500-fold the final desired concentration using a Biomek-FX and diluted 50-fold in RPMI 1640. The control compound fulvestrant and negative control dimethylsulfoxide were also prepared in a similar manner. 5 ul of each individual compound concentration and each control compound was transferred to the cell plate. Fulvestrant was added to control wells at a final concentration of 100 nM). DMSO was added to negative control wells (0.2% v/v). Five microliters (5 µl) of 1 nM Estradiol (in phenol red free RPMI 1640 (Gibco 11835-030) was added to each well of the cell plate (except no estradiol control wells). Cells were incubated for 72 hours then lysed using Cell TiterGlo reagent (Promega # G7572) 40 ul/well and the luminescence was measured on an Envision (Perkin Elmer) plate reader. Data were analyzed using Genedata Screener software, using DMSO and Fulvestrant treated samples to define 0% and 100% inhibition and EC50 values were calculated using curve fitting using Robust method.

Example 904 ERa Co-Activator Peptide Antagonist Assay

Test compounds were prepared at 1 mM in DMSO and serially diluted in a 12 point, 1 to 3-fold titration using a Biomek FX in 384 well clear V-bottom polypropylene plates (Greiner cat #781280). A 3× compound intermediate dilution was prepared by mixing 1 mL of each concentration of the compound serial dilution with 32.3 mL of TR-FRET Coregulator Buffer E (Life Technologies PV4540). 2 mL of the 3× compound intermediate dilution was transferred to a 1536-well (Aurora. Biotechnologies MaKO 1536 Black Plate, #00028905) using a Biomek FX. A Bioraptr Dispenser® (Beckman Coulter) was used to dispense: 2 mL per well of "3× ERa solution": 22 nM ERa (human estrogen receptor alpha, GST-tagged ESR1 ligand binding domain, spanning residues S282-V595, either wild-type sequence or containing the mutations: Y537S or D538G) in TR-FRET Coregulator Buffer E containing 7.5 mM dithiothreitol (DTT); and 2 mL of 3× Assay mix (750 nM Fluorescein-PGC1a peptide sequence; Life Technologies PV4421), 12 nM Estradiol, 15 nM Anti-GST Tb-labeled antibody in TR-FRET Coregulator Buffer E (with 7.5 mM DTT). "No receptor" control wells received buffer without GST-ERa protein. Plates were centrifuged at 1800 rpm for 20 seconds in V-spin centrifuge and incubated for 2 hours at room temperature with the plates covered. Measurements were made using a Perkin Elmer EnVision Fluorescence Reader using TR-FRET setting (Top mirror: Perkin Elmer Lance/DELFIA Dual emission (PE #2100-4160): Excitation filter: Perkin Elmer UV (TFR) 340 nm (PE #2100-5010); Emission filters: Chroma 495 nmr/10 nm and 520 nm/25 nm (Chroma # PV003 filters for LanthaScreen, 25 mm diameter for EnVision) Excitation light: 100%; Delay: 100 us; Window time: 200; Number of sequential windows: 1; Time between flashes: 2000 us; Number of flashes: 100: Number of flashes ($2^{nd}$ detector): 100. Percentage inhibition values were calculated relative to no compound (DMSO only) controls and a "no ERa controls". Curve fitting and $IC_{50}$ calculations were carried out using Genedata Screener software.

Example 905 In Vivo Mouse Tumor Xenograft Efficacy

Mice: Female severe combined immunodeficiency mice (Fox Chase SCID®, C.B-17/IcrHsd, Harlan) or nude mice (Taconic Farms, Harlan) are 8 to 9 weeks old and had a BW range of 15.1 to 21.4 grams on Day 0 of the study. The animals are fed ad libitum water (reverse osmosis, 1 ppm Cl) and NIH 31 Modified and Irradiated Lab Diet® consisting of 18.0% crude protein, 5.0% crude fat, and 5.0% crude fiber. The mice are housed on irradiated ALPHA-Dri® Bed-O'Cobs® Laboratory Animal Bedding in static microisolators on a 12-hour light cycle at 21-22° C. (70-72° F.) and 40-60% humidity. PRC specifically complies with the recommendations of the Guide for Care and Use of Laboratory Animals with respect to restraint, husbandry, surgical procedures, feed and fluid regulation, and veterinary care. The animal care and use program at PRC is accredited by the Association for Assessment and Accreditation of Laboratory Animal Care International (AAALAC), which assures compliance with accepted standards for the care and use of laboratory animals.

Tumor Implantation: Xenografts are initiated with cancer cells. Cells are cultured in RPMI 1640 medium supplemented with 10% fetal bovine serum, 2 mM glutamine, 100 units/mL penicillin, 100 µg/mL streptomycin sulfate and 25 µg/mL gentamicin. The cells are harvested during exponential growth and resuspended in phosphate buffered saline (PBS) at a concentration of $5 \times 10^6$ or $10 \times 10^6$ cells/mL depending on the doubling time of the cell line. Tumor cells are implanted subcutaneously in the right flank, and tumor growth is monitored as the average size approached the target range of 100 to 150 mm3. Twenty-one days after tumor implantation, designated as Day 0 of the study, the mice are placed into four groups each consisting of ten mice with individual tumor volumes ranging from 75-172 mm3 and group mean tumor volumes from 120-121 mm3 (see Appendix A). Volume is calculated using the formula:

$$\text{Tumor Volume (mm}^3) = (w^2 \times 1)/2,$$

where w=width and l=length in mm of a tumor. Tumor weight may be estimated with the assumption that 1 mg is equivalent to 1 mm3 of tumor volume.

Therapeutic Agents: Estrogen receptor modulator compounds and chemotherapeutic agents are typically prepared from dry powders, stored at room temperature, and protected from light. Drug doses are prepared weekly in 0.5% methylcellulose: 0.2% Tween 80 in deionized water ("Vehicle") and stored at 4° C. Vehicle (+) is solvent/buffer with ethynyl estradiol (ethinyl estradiol, EE2) at 0.1 mg/kg. Vehicle (−) is solvent/buffer without ethynyl estradiol. Doses of compounds are prepared on each day of dosing by diluting an aliquot of the stock with sterile saline (0.9% NaCl). All doses are formulated to deliver the stated mg/kg dosage in a volume of 0.2 mL per 20 grams of body weight (10 mL/kg).

Treatment: All doses are scaled to the body weights of the individual animals and provided by the route indicated.

Endpoint: Tumor volume is measured in 2 dimensions (length and width), using Ultra Cal IV calipers (Model 54 10 111; Fred V. Fowler Company), as follows: tumor volume $(\text{mm}^3) = (\text{length} \times \text{width}^2) \times 0.5$ and analyzed using Excel version 11.2 (Microsoft Corporation). A linear mixed effect (LME) modeling approach is used to analyze the repeated measurement of tumor volumes from the same animals over time (Pinheiro J, et al. nlme: linear and nonlinear mixed effects models. R package version 3.1 92. 2009; Tan N, et al. Clin. Cancer Res. 2011; 17(6): 1394-1404). This approach addresses both repeated measurements and modest dropouts due to any non-treatment-related death of animals before study end. Cubic regression splines are used to fit a nonlinear profile to the time courses of log 2 tumor volume at each dose level. These nonlinear profiles are then related to dose within the mixed model. Tumor growth inhibition as a percentage of vehicle control (% TGI) is calculated as the percentage of the area under the fitted curve (AUC) for the respective dose group per day in relation to the vehicle, using the following formula: % TGI=100× $(1-AUC_{dose}/AUC_{veh})$. Using this formula, a TGI value of 100% indicates tumor stasis, a TGI value of >1% but <100% indicates tumor growth delay, and a TGI value of >100% indicates tumor regression. Partial response (PR) for an animal is defined as a tumor regression of >50% but <100% of the starting tumor volume. Complete response (CR) was defined as 100% tumor regression (i.e., no measurable tumor) on any day during the study.

Toxicity: Animals are weighed daily for the first five days of the study and twice weekly thereafter. Animal body weights are measured using an Adventurer Pro® AV812 scale (Ohaus Corporation). Percent weight change is calculated as follows: body weight change (%)=[(weight$_{day\ new}$−weight$_{day\ 0}$)/weight$_{day\ 0}$]×100. The mice are observed frequently for overt signs of any adverse, treatment-related side effects, and clinical signs of toxicity recorded when observed. Acceptable toxicity is defined as a group mean body weight (BW) loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy, or may also be classified as TR if due to unknown causes during the dosing period or within 10 days of the last dose. A death is classified as NTR if there is no evidence that death was related to treatment side effects.

In-Vivo Xenograft Breast Cancer Model; (MCF-7; Tamoxifen-Sensitive):

Time release pellets containing 0.72 mg 17-0 Estradiol are subcutaneously implanted into nu/nu mice. MCF-7 cells were grown in RPMI containing 10% FBS at 5% $CO_2$, 37° C. Trypsinized cells are pelleted and re-suspended in 50% RPMI (serum free) and 50% Matrigel at 1×10$^7$ cells/mL. MCF-7 cells are subcutaneously injected (100 µL/animal) on the right flank 2-3 days post pellet implantation. Tumor volume (length×width$^2$/2) is monitored bi-weekly. When tumors reach an average volume of ~200 mm$^3$ animals are randomized and treatment is started. Animals are treated with vehicle or compound daily for 4 weeks. Tumor volume and body weight are monitored bi-weekly throughout the study.

In-Vivo Xenograft Breast Cancer Model; (Tamoxifen-Resistant Model):

Female nu/nu mice (with supplemental 17-0 Estradiol pellets; 0.72 mg; 60 day slow release) bearing MCF-7 tumors (mean tumor volume 200 mm$^3$) are treated with tamoxifen (citrate) by oral gavage. Tumor volume (length×width$^2$/2) and body weight are monitored twice weekly. Following a significant anti-tumor response in which tumor volume remained static, evident tumor growth is first observed at approximately 100 days of treatment. At 120 days of treatment, tamoxifen dose is increased. Rapidly growing tumors are deemed tamoxifen resistant and selected for in vivo passage into new host animals. Tumor Fragments (~100 mm$^3$/animal) from the tamoxifen resistant tumors are subcutaneously implanted into the right flank of female nu/nu mice (with 17-0 (beta) Estradiol pellets (0.72 mg; 60 day slow release)). Passaged tumors are maintained under constant Tamoxifen selection, and tumor volume (length×width$^2$/2) is monitored weekly. When tumor volume reached ~150-250 mm$^3$, animals are randomized into treatment groups (mean tumor volume 200 mm$^3$) and tamoxifen treatment is terminated. Animals are treated with vehicle or compound daily for 4 weeks. Tumor volume and body weight are Monitored Twice Weekly for the Duration of the Study.

Example 906 Immature Uterine Wet Weight Assay

Female immature CD-IGS rats (21 days old upon arrival) are treated for three days. Animals are dosed daily for three days. For Antagonist Mode, Vehicle or test compound is administered orally by gavage followed 15 minutes later by an oral dose of 0.1 mg/kg Ethynyl Estradiol. For Agonist Mode, Vehicle or test compound is administered orally by gavage. On the fourth day 24 hours after dose, plasma is collected for pharmacokinetic analysis. Immediately following plasma collection, the animals are euthanized and the uterus removed and weighed.

Uteri and ovaries from 2 animals per group are fixed in 10% neutral buffered formalin and paraffin embedded, sectioned and stained for H&E (SDPath). Stained tissues are analyzed and read by a board certified pathologist. Uteri and ovaries from 4 animals per group are flash frozen in liquid $N_2$ for transcriptional analysis, examining a select set of genes modulated by the estrogen receptor.

Example 907 Adult Uterine Wet Weight-10 Day Assay

Female CD-IGS rats (69 days old, Charles River Laboratories) are purchased and split into groups. Group 1 is ovariectomized at the vendor (Charles River Laboratories) at 60 days of age and the study is started 2 weeks after surgery, while groups 2-8 were intact. Vehicle or test compound is administered orally for 10 days. Two hours after the 10$^{th}$ and final dose, cardiac punctures are performed and serum is collected for pharmacokinetic and estradiol analyses. Immediately following serum collection, the animals are euthanized and the uterus and ovaries removed and weighed.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:
1. A compound having the structure:
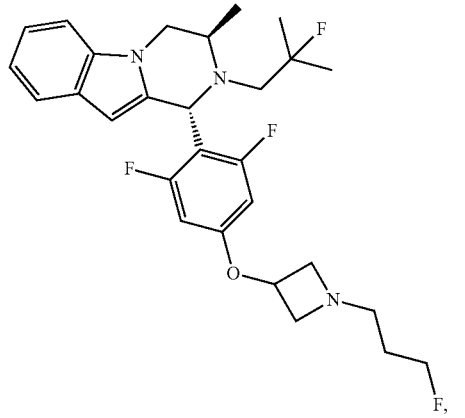
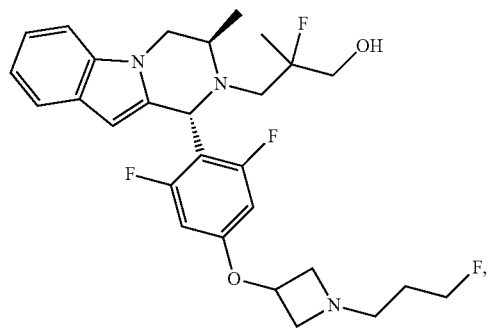
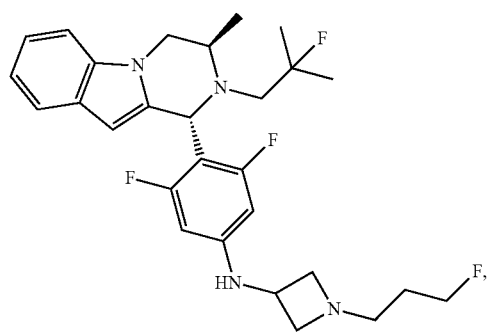
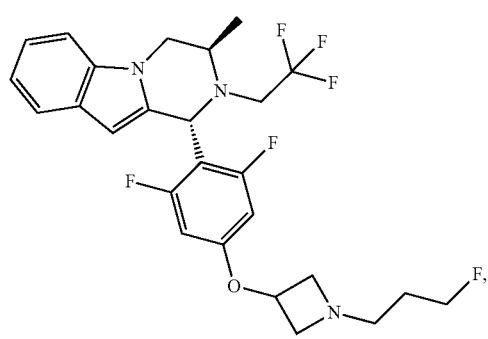
-continued
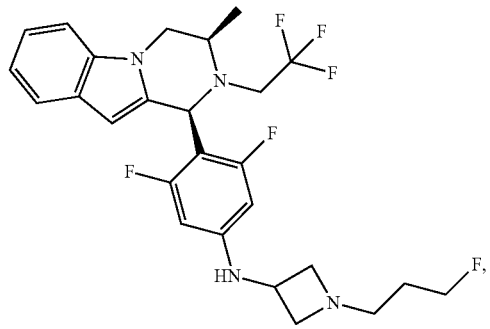
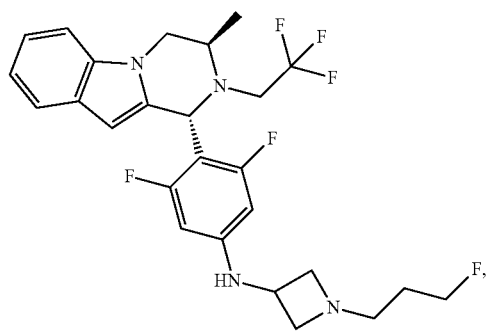
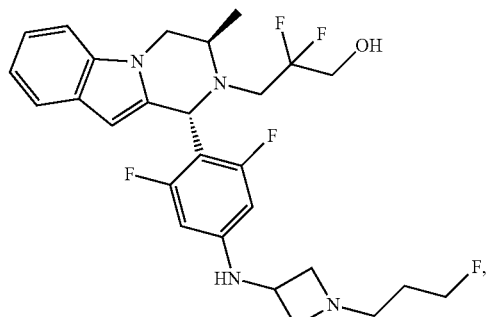
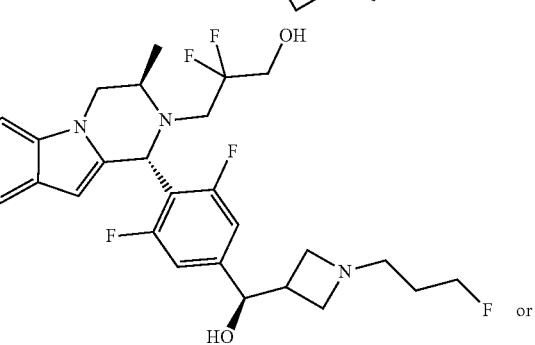 or
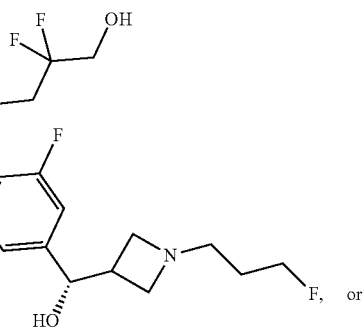, or

169
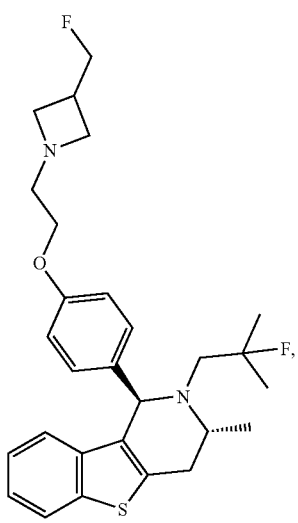
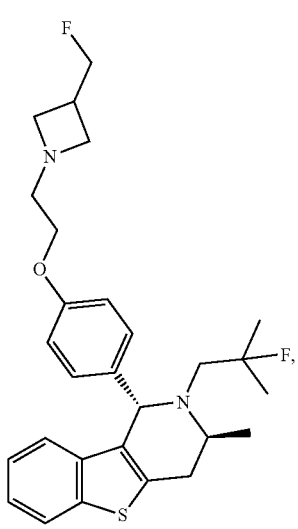
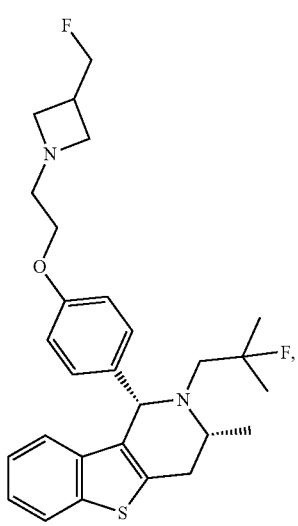
170
-continued
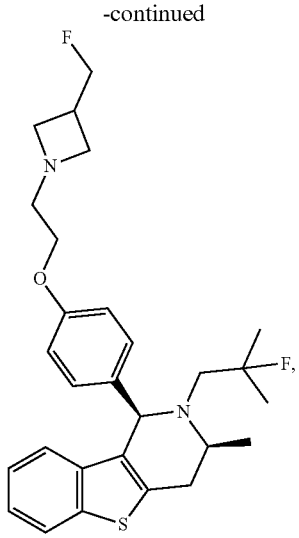
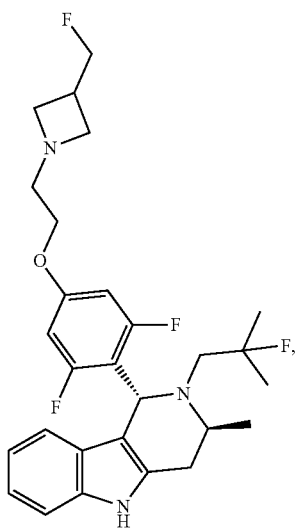
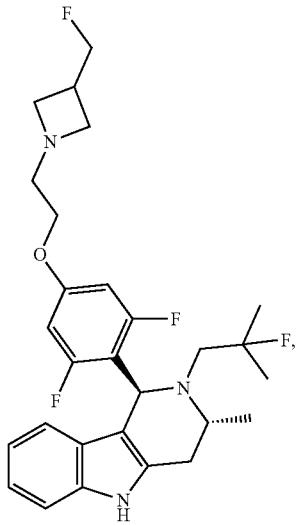

171
-continued
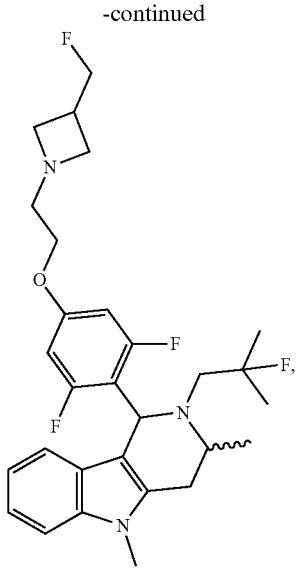
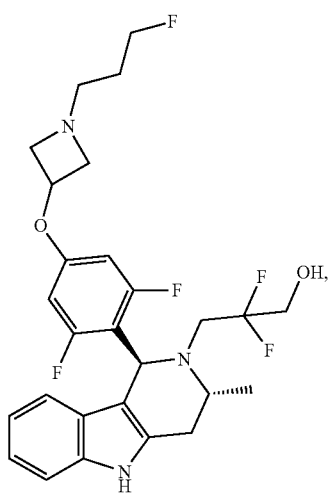
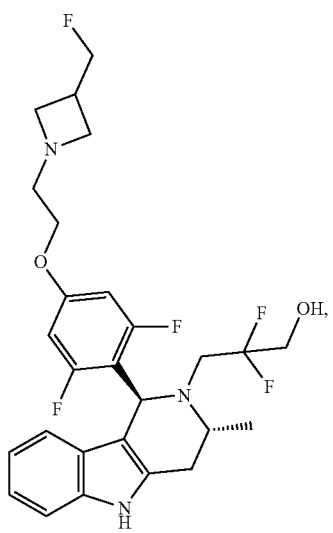
172
-continued
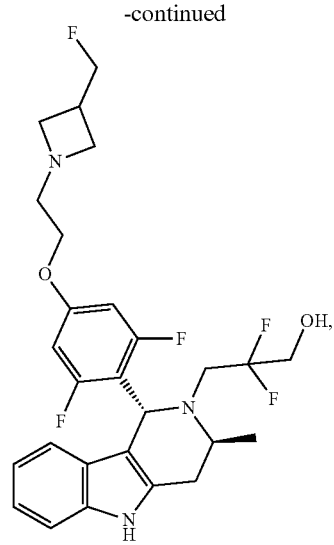
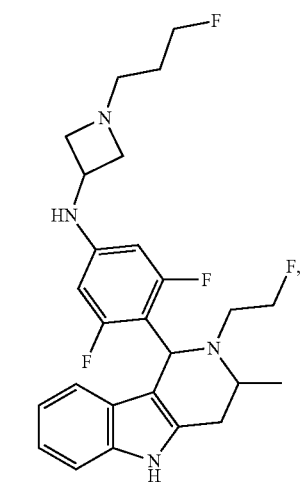
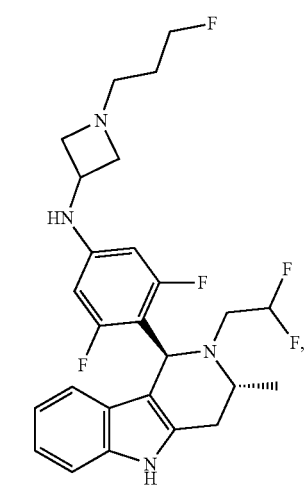

-continued
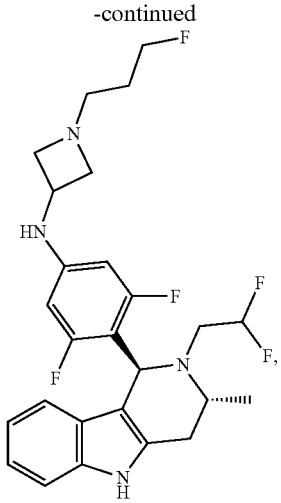
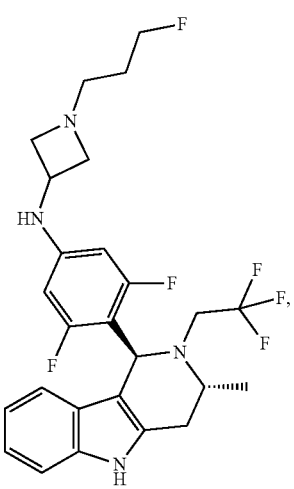
-continued
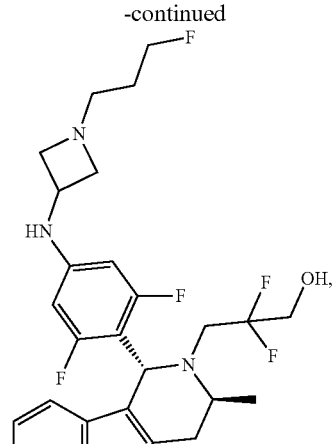
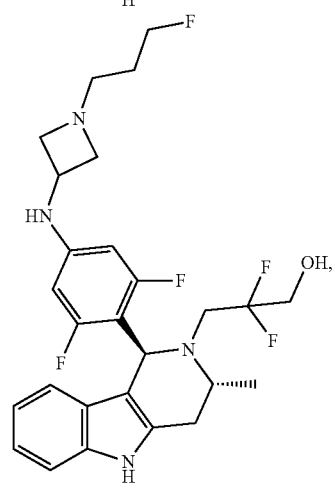
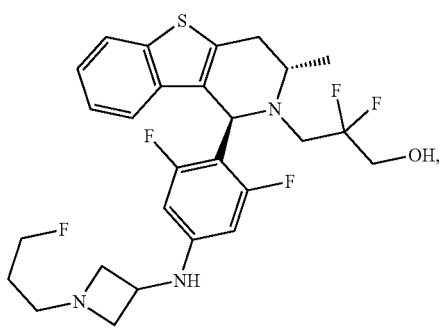
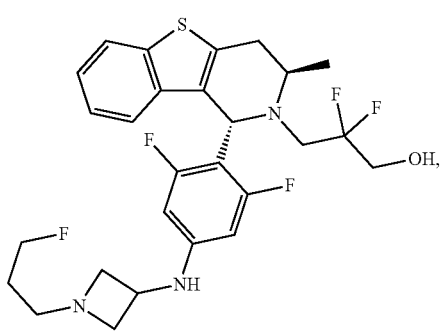

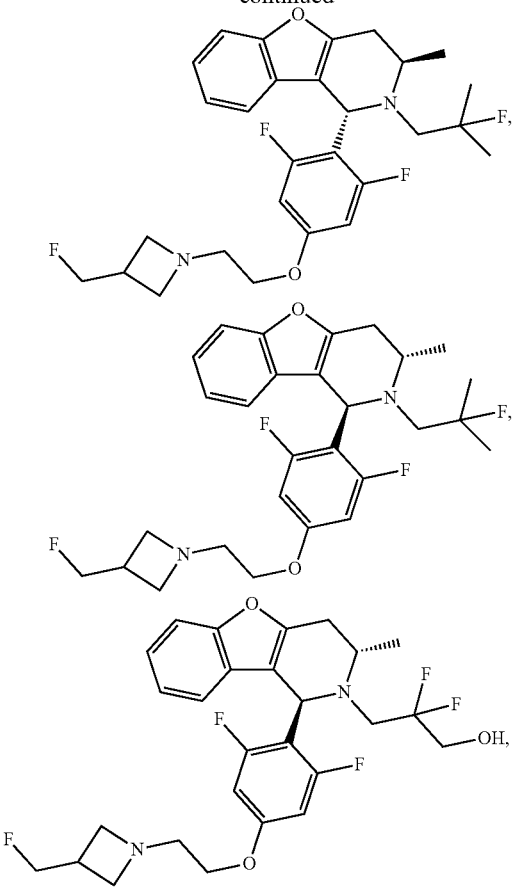

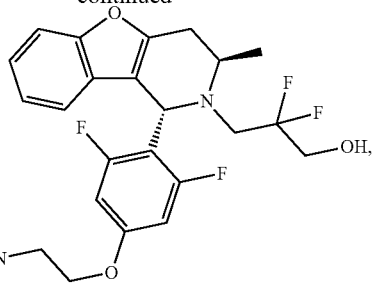

or a pharmaceutically acceptable salt thereof.

2. A pharmaceutical composition comprising a compound of claim 1 and at least one pharmaceutically acceptable excipient.

3. A method of treating breast cancer in a patient having such cancer, the method comprising administering a therapeutically effective amount of a compound of claim 1.

4. The method of claim 3, further comprising administering an additional therapeutic agent selected from the group consisting of paclitaxel, anastrozole, exemestane, cyclophosphamide, epirubicin, fulvestrant, letrozole, palbociclib, gemcitabine, trastuzumab (HERCEPTIN®, Genentech), trastuzumab emtansine (KADCYLA®, Genentech), pegfilgrastim, filgrastim, tamoxifen, docetaxel, toremifene, vinorelbine, capecitabine, and ixabepilone.

5. The method of claim 3, further comprising administering a CDK 4/6 inhibitor comprising palbociclib (PD-0332991), ribociclib (LEE011), or abemaciclib (LY283519).

* * * * *